United States Patent
Fangrow

(10) Patent No.: US 10,697,570 B2
(45) Date of Patent: *Jun. 30, 2020

(54) AXIALLY ENGAGING MEDICAL CONNECTOR SYSTEM WITH DIMINISHED FLUID REMNANTS

(71) Applicant: ICU Medical, Inc., San Clemente, CA (US)

(72) Inventor: Thomas F. Fangrow, Mission Viejo, CA (US)

(73) Assignee: ICU Medical, Inc., San Clemente, CA (US)

( * ) Notice: Subject to any disclaimer, the term of this patent is extended or adjusted under 35 U.S.C. 154(b) by 85 days.

This patent is subject to a terminal disclaimer.

(21) Appl. No.: 16/185,579

(22) Filed: Nov. 9, 2018

(65) Prior Publication Data

US 2019/0078712 A1    Mar. 14, 2019

Related U.S. Application Data

(63) Continuation of application No. 15/900,658, filed on Feb. 20, 2018, now Pat. No. 10,156,306, which is a
(Continued)

(51) Int. Cl.
*A61M 39/26* (2006.01)
*A61M 39/18* (2006.01)
(Continued)

(52) U.S. Cl.
CPC .......... *F16L 29/00* (2013.01); *A61M 39/1011* (2013.01); *A61M 39/18* (2013.01);
(Continued)

(58) Field of Classification Search
CPC ...... A61M 39/18; A61M 39/22; A61M 39/26; A61M 2039/1027; A61M 2039/267;
(Continued)

(56) References Cited

U.S. PATENT DOCUMENTS 2,254,997 A   9/1941 Fisher
2,456,045 A   12/1948 Brock
(Continued)

FOREIGN PATENT DOCUMENTS

CA   2747283 A1   7/2002
CN   1137241 A    12/1996
(Continued)

OTHER PUBLICATIONS

Air Embolism and Exsanguination from Separation of Two-Piece Side Port/Hemostasis Valve Cardiac Catheter Introducers, ECRI Institute, Jan. 1995, in 2 pages, http://www.mdsr.ecri.org/summary/detail.aspx?doc_id=8098.
(Continued)

*Primary Examiner* — Kevin F Murphy
*Assistant Examiner* — Jonathan J Waddy
(74) *Attorney, Agent, or Firm* — Knobbe Martens Olson & Bear, LLP

(57) ABSTRACT

A connector system for medical fluid includes a male connector and a female connector that have a closed configuration when detached from one another. The first end of the male connector is configured to mate with a first end of the female connector. When the male connector is coupled with the female connector, complementary structures engage to move seals away from ports in the male connector and the female connector, opening a fluid pathway through the connectors. The mating ends of the connectors are not exposed to the medical fluid when the connectors are coupled so that when the connectors are disconnected, the mating ends are substantially free of residual medical fluid.

24 Claims, 99 Drawing Sheets

Related U.S. Application Data continuation of application No. 14/199,836, filed on Mar. 6, 2014, now Pat. No. 9,933,094, which is a continuation of application No. PCT/US2012/054289, filed on Sep. 7, 2012.

(60) Provisional application No. 61/533,138, filed on Sep. 9, 2011, provisional application No. 61/557,793, filed on Nov. 9, 2011, provisional application No. 61/579,582, filed on Dec. 22, 2011, provisional application No. 61/607,429, filed on Mar. 6, 2012, provisional application No. 61/692,516, filed on Aug. 23, 2012.

(51) Int. Cl.
| | |
|---|---|
| *F16L 37/35* | (2006.01) |
| *F16L 29/04* | (2006.01) |
| *F16L 37/34* | (2006.01) |
| *F16L 29/00* | (2006.01) |
| *A61M 39/10* | (2006.01) |

(52) U.S. Cl.
CPC ..... *A61M 39/26* (2013.01); *A61M 2039/1027* (2013.01); *A61M 2039/1033* (2013.01); *A61M 2039/1066* (2013.01); *A61M 2039/262* (2013.01); *A61M 2039/263* (2013.01); *A61M 2039/267* (2013.01); *F16L 29/04* (2013.01); *F16L 37/34* (2013.01); *F16L 37/35* (2013.01)

(58) Field of Classification Search
CPC ... A61M 2039/268; F16L 29/02; F16L 29/04; F16L 37/33; F16L 37/34; F16L 37/35; F16L 37/36; F16L 37/367; F16L 37/407; F16L 37/413; F16L 37/42; F16L 37/44
USPC .......... 137/614, 614.04; 251/149.1
See application file for complete search history.

(56) References Cited

U.S. PATENT DOCUMENTS

| | | |
|---|---|---|
| 2,457,052 A | 12/1948 | Le Clair |
| 2,485,006 A * | 10/1949 | Main, Jr. ........... F16L 29/04 137/614.03 |
| 2,842,382 A | 7/1958 | Franck |
| 2,931,668 A | 4/1960 | Baley |
| 2,968,497 A | 1/1961 | Treleman |
| 3,127,892 A | 4/1964 | Bellamy, Jr. et al. |
| 3,191,972 A | 6/1965 | Collar |
| 3,304,047 A | 2/1967 | Martin |
| 3,334,860 A | 8/1967 | Bolton, Jr. |
| 3,538,950 A | 11/1970 | Porteners |
| 3,707,972 A | 1/1973 | Villari et al. |
| 3,729,031 A | 4/1973 | Baldwin |
| 3,824,556 A | 7/1974 | Berkovits et al. |
| 3,986,508 A | 10/1976 | Barrington |
| 4,055,179 A | 10/1977 | Manschot et al. |
| 4,066,067 A | 1/1978 | Micheli |
| 4,076,285 A | 2/1978 | Martinez |
| 4,080,965 A | 3/1978 | Phillips |
| 4,084,606 A | 4/1978 | Mittleman |
| 4,121,585 A | 10/1978 | Becker, Jr. |
| 4,133,441 A | 1/1979 | Mittleman et al. |
| 4,143,853 A | 3/1979 | Abramson |
| 4,150,845 A | 4/1979 | Kopacz et al. |
| 4,187,848 A | 2/1980 | Taylor |
| 4,195,632 A | 4/1980 | Parker et al. |
| 4,233,982 A | 11/1980 | Bauer et al. |
| 4,245,635 A | 1/1981 | Kontos |
| 4,324,239 A | 4/1982 | Gordon et al. |
| 4,334,551 A | 6/1982 | Pfister |
| 4,340,049 A | 7/1982 | Munsch |
| 4,379,458 A | 4/1983 | Bauer et al. |
| 4,387,879 A | 6/1983 | Tauschinski |
| 4,397,442 A | 8/1983 | Larkin |
| 4,430,073 A | 2/1984 | Bemis et al. |
| 4,436,125 A | 3/1984 | Blenkush |
| 4,452,473 A | 6/1984 | Ruschke |
| 4,457,749 A | 7/1984 | Bellotti et al. |
| 4,511,359 A | 4/1985 | Vaillancourt |
| 4,538,836 A | 9/1985 | Kruetten |
| 4,541,457 A | 9/1985 | Blenkush |
| 4,576,359 A | 3/1986 | Oetiker |
| 4,610,469 A | 9/1986 | Wolff-Mooij |
| 4,619,640 A | 10/1986 | Potolsky et al. |
| 4,623,332 A | 11/1986 | Lindmayer et al. |
| 4,629,159 A | 12/1986 | Wellenstam |
| 4,660,803 A | 4/1987 | Johnston et al. |
| 4,662,878 A | 5/1987 | Lindmayer |
| 4,673,400 A | 6/1987 | Martin |
| 4,700,744 A | 10/1987 | Rutter et al. |
| 4,723,603 A | 2/1988 | Plummer |
| 4,723,948 A | 2/1988 | Clark et al. |
| 4,728,075 A | 3/1988 | Paradis |
| 4,745,950 A | 5/1988 | Mathieu |
| 4,758,023 A | 7/1988 | Vermillion |
| 4,774,964 A | 10/1988 | Bonaldo |
| 4,774,965 A | 10/1988 | Rodriguez et al. |
| 4,781,702 A | 11/1988 | Herrli |
| 4,804,015 A | 2/1989 | Albinsson |
| 4,816,024 A | 3/1989 | Sitar et al. |
| 4,819,692 A | 4/1989 | Olson et al. |
| 4,834,271 A | 5/1989 | Litwin |
| 4,844,512 A | 7/1989 | Gahwiler |
| 4,862,913 A | 9/1989 | Wildfang |
| 4,863,201 A | 9/1989 | Carstens |
| 4,883,483 A | 11/1989 | Lindmayer |
| 4,915,687 A | 4/1990 | Sivert |
| 4,917,669 A | 4/1990 | Bonaldo |
| 4,935,010 A | 6/1990 | Cox et al. |
| 4,949,745 A | 8/1990 | McKeon |
| 4,950,260 A | 8/1990 | Bonaldo |
| 4,969,879 A | 11/1990 | Lichte |
| D313,277 S | 12/1990 | Haining |
| D314,050 S | 1/1991 | Sone |
| 5,006,114 A | 4/1991 | Rogers et al. |
| 5,021,059 A | 6/1991 | Kensey et al. |
| 5,047,021 A | 9/1991 | Utterberg |
| 5,053,015 A | 10/1991 | Gross |
| 5,065,783 A | 11/1991 | Ogle, II |
| 5,066,286 A | 11/1991 | Ryan |
| 5,070,885 A | 12/1991 | Bonaldo |
| 5,083,819 A | 1/1992 | Bynum |
| 5,098,385 A | 3/1992 | Walsh |
| 5,108,376 A | 4/1992 | Bonaldo |
| 5,122,123 A | 6/1992 | Vaillancourt |
| 5,139,483 A | 8/1992 | Ryan |
| 5,147,333 A | 9/1992 | Raines |
| 5,154,703 A | 10/1992 | Bonaldo |
| 5,176,406 A | 1/1993 | Straghan |
| RE34,223 E | 4/1993 | Bonaldo |
| 5,199,948 A | 4/1993 | McPhee |
| 5,201,717 A | 4/1993 | Wyatt et al. |
| 5,201,725 A | 4/1993 | Kling |
| 5,203,775 A | 4/1993 | Frank et al. |
| 5,211,634 A | 5/1993 | Vaillancourt |
| 5,215,537 A | 6/1993 | Lynn et al. |
| 5,215,538 A | 6/1993 | Larkin |
| 5,224,939 A | 7/1993 | Holman et al. |
| 5,242,393 A | 9/1993 | Brimhall et al. |
| 5,242,425 A | 9/1993 | White et al. |
| 5,251,873 A | 10/1993 | Atkinson et al. |
| 5,269,771 A | 12/1993 | Thomas et al. |
| 5,273,533 A | 12/1993 | Bonaldo |
| 5,279,571 A | 1/1994 | Larkin |
| 5,281,206 A | 1/1994 | Lopez |
| 5,284,475 A | 2/1994 | Mackal |
| 5,295,657 A | 3/1994 | Atkinson |
| 5,301,686 A | 4/1994 | Newman |
| 5,306,243 A | 4/1994 | Bonaldo |
| 5,312,377 A | 5/1994 | Dalton |
| 5,322,518 A | 6/1994 | Schneider et al. |

(56) References Cited

U.S. PATENT DOCUMENTS

| | | |
|---|---|---|
| 5,324,270 A | 6/1994 | Kayan et al. |
| 5,330,235 A | 7/1994 | Wagner et al. |
| 5,330,450 A | 7/1994 | Lopez |
| 5,334,159 A | 8/1994 | Turkel |
| 5,344,414 A | 9/1994 | Lopez et al. |
| 5,360,413 A | 11/1994 | Leason et al. |
| 5,370,636 A | 12/1994 | Von Witzleben |
| 5,380,306 A | 1/1995 | Brinon |
| 5,385,372 A | 1/1995 | Utterberg |
| 5,390,898 A | 2/1995 | Smedley et al. |
| 5,391,150 A | 2/1995 | Richmond |
| 5,395,348 A | 3/1995 | Ryan |
| 5,397,314 A | 3/1995 | Farley et al. |
| 5,400,500 A | 3/1995 | Behnke et al. |
| 5,401,245 A | 3/1995 | Haining |
| 5,402,826 A | 4/1995 | Molnar et al. |
| 5,402,982 A | 4/1995 | Atkinson et al. |
| 5,405,323 A | 4/1995 | Rogers et al. |
| 5,405,331 A | 4/1995 | Behnke et al. |
| 5,405,333 A | 4/1995 | Richmond |
| 5,411,499 A | 5/1995 | Dudar et al. |
| 5,417,673 A | 5/1995 | Gordon |
| 5,423,791 A | 6/1995 | Bartlett |
| 5,425,465 A | 6/1995 | Healy |
| 5,433,330 A | 7/1995 | Yatsko et al. |
| 5,439,451 A | 8/1995 | Collinson et al. |
| 5,441,487 A | 8/1995 | Vedder |
| 5,445,623 A | 8/1995 | Richmond |
| 5,447,177 A | 9/1995 | Ricken et al. |
| 5,456,668 A | 10/1995 | Ogle, II |
| 5,456,675 A | 10/1995 | Wolbring et al. |
| 5,462,255 A | 10/1995 | Rosen et al. |
| 5,464,399 A | 11/1995 | Boettger |
| 5,470,319 A | 11/1995 | Mayer |
| 5,470,327 A | 11/1995 | Helgren et al. |
| 5,474,536 A | 12/1995 | Bonaldo |
| 5,480,393 A | 1/1996 | Bommarito |
| 5,489,274 A | 2/1996 | Chu et al. |
| 5,492,147 A | 2/1996 | Challender et al. |
| 5,501,426 A | 3/1996 | Atkinson et al. |
| 5,507,744 A | 4/1996 | Tay et al. |
| 5,514,177 A | 5/1996 | Kurz et al. |
| 5,518,026 A | 5/1996 | Benjey |
| 5,520,665 A | 5/1996 | Fleetwood |
| 5,520,666 A | 5/1996 | Choudhury et al. |
| 5,527,284 A | 6/1996 | Ohnemus et al. |
| 5,533,708 A | 7/1996 | Atkinson et al. |
| 5,533,983 A | 7/1996 | Haining |
| 5,533,996 A | 7/1996 | Murphey et al. |
| 5,535,785 A | 7/1996 | Werge et al. |
| 5,540,661 A | 7/1996 | Tomisaka et al. |
| 5,549,566 A | 8/1996 | Elias et al. |
| 5,549,577 A | 8/1996 | Siegel et al. |
| 5,549,651 A | 8/1996 | Lynn |
| 5,552,118 A | 9/1996 | Mayer |
| 5,555,908 A | 9/1996 | Edwards et al. |
| 5,569,235 A | 10/1996 | Ross et al. |
| 5,573,516 A | 11/1996 | Tyner |
| 5,575,769 A | 11/1996 | Vaillancourt |
| 5,578,059 A | 11/1996 | Patzer |
| 5,584,819 A | 12/1996 | Kopfer |
| 5,591,137 A | 1/1997 | Stevens |
| 5,591,143 A | 1/1997 | Trombley, III et al. |
| 5,597,536 A | 1/1997 | Mayer |
| 5,616,129 A | 4/1997 | Mayer |
| 5,616,130 A | 4/1997 | Mayer |
| RE35,539 E | 6/1997 | Bonaldo |
| 5,643,224 A | 7/1997 | Szapiro et al. |
| 5,645,538 A | 7/1997 | Richmond |
| 5,651,776 A | 7/1997 | Appling et al. |
| 5,658,260 A | 8/1997 | Desecki et al. |
| 5,674,206 A | 10/1997 | Allton et al. |
| 5,676,346 A | 10/1997 | Leinsing |
| 5,685,866 A | 11/1997 | Lopez |
| 5,685,868 A | 11/1997 | Lundquist |
| 5,699,821 A | 12/1997 | Paradis |
| 5,700,248 A | 12/1997 | Lopez |
| 5,702,374 A | 12/1997 | Johnson |
| 5,709,243 A | 1/1998 | Wells et al. |
| 5,735,826 A | 4/1998 | Richmond |
| 5,738,144 A | 4/1998 | Rogers |
| 5,741,084 A | 4/1998 | Del Rio et al. |
| 5,749,861 A | 5/1998 | Guala et al. |
| RE35,841 E | 7/1998 | Frank et al. |
| 5,776,116 A | 7/1998 | Lopez |
| 5,782,816 A | 7/1998 | Werschmidt et al. |
| 5,784,750 A | 7/1998 | Sankovic et al. |
| 5,785,693 A | 7/1998 | Haining |
| 5,788,215 A | 8/1998 | Ryan |
| 5,806,831 A | 9/1998 | Paradis |
| 5,810,398 A | 9/1998 | Matkovich |
| 5,810,792 A | 9/1998 | Fangrow, Jr. et al. |
| 5,814,024 A | 9/1998 | Thompson et al. |
| 5,820,601 A | 10/1998 | Mayer |
| 5,820,614 A | 10/1998 | Erksine et al. |
| 5,830,189 A | 11/1998 | Chang |
| 5,830,195 A | 11/1998 | Peters et al. |
| 5,839,715 A | 11/1998 | Leinsing |
| 5,848,994 A | 12/1998 | Richmond |
| 5,855,568 A | 6/1999 | Battiato et al. |
| 5,947,954 A | 9/1999 | Bonaldo |
| 5,984,373 A | 11/1999 | Fitoussi et al. |
| 6,029,946 A | 2/2000 | Doyle |
| 6,036,171 A | 3/2000 | Weinheimer et al. |
| 6,039,302 A | 3/2000 | Cote, Sr. et al. |
| 6,041,805 A | 3/2000 | Gydesen et al. |
| 6,050,978 A | 4/2000 | Orr et al. |
| 6,063,062 A | 5/2000 | Paradis |
| 6,068,011 A | 5/2000 | Paradis |
| 6,068,617 A | 5/2000 | Richmond |
| 6,079,432 A | 6/2000 | Paradis |
| 6,106,502 A | 8/2000 | Richmond |
| 6,113,068 A | 9/2000 | Ryan |
| 6,142,446 A | 11/2000 | Leinsing |
| 6,152,913 A | 11/2000 | Feith et al. |
| 6,168,137 B1 | 1/2001 | Paradis |
| 6,170,522 B1 | 1/2001 | Tanida |
| 6,171,287 B1 | 1/2001 | Lynn et al. |
| 6,183,464 B1 | 2/2001 | Sharp et al. |
| 6,189,859 B1 | 2/2001 | Rohrbough et al. |
| 6,206,860 B1 | 3/2001 | Richmond |
| 6,221,029 B1 | 4/2001 | Mathis et al. |
| 6,224,578 B1 | 5/2001 | Davis et al. |
| 6,224,588 B1 | 5/2001 | Jentzen |
| 6,231,552 B1 | 5/2001 | Jentzen |
| 6,242,393 B1 | 6/2001 | Ishida et al. |
| 6,245,048 B1 | 6/2001 | Fangrow et al. |
| 6,290,206 B1 | 9/2001 | Doyle |
| 6,299,132 B1 | 10/2001 | Weinheimer et al. |
| 6,325,100 B1 | 12/2001 | Bunschoten et al. |
| 6,332,633 B1 | 12/2001 | Fitoussi et al. |
| 6,402,207 B1 | 6/2002 | Segal et al. |
| 6,428,520 B1 | 8/2002 | Lopez |
| 6,431,219 B1 | 8/2002 | Redler et al. |
| 6,485,472 B1 | 11/2002 | Richmond |
| 6,499,719 B1 | 12/2002 | Clancy et al. |
| 6,508,792 B2 | 1/2003 | Szames et al. |
| 6,508,807 B1 | 1/2003 | Peters |
| 6,541,802 B2 | 4/2003 | Doyle |
| 6,543,745 B1 | 4/2003 | Enerson |
| 6,581,906 B2 | 6/2003 | Pott et al. |
| 6,585,229 B2 | 7/2003 | Cote et al. |
| 6,595,964 B2 | 7/2003 | Finley et al. |
| 6,595,981 B2 | 7/2003 | Huet |
| 6,609,696 B2 | 8/2003 | Enerson |
| 6,612,624 B1 | 9/2003 | Segal et al. |
| 6,666,852 B2 | 12/2003 | Niedospial, Jr. |
| 6,673,059 B2 | 1/2004 | Guala |
| 6,681,803 B2 | 1/2004 | Taneya et al. |
| 6,695,817 B1 | 2/2004 | Fangrow |
| 6,745,998 B2 | 6/2004 | Doyle |
| 6,808,161 B1 | 10/2004 | Hishikawa |
| 6,840,501 B2 | 1/2005 | Doyle |
| 6,843,513 B2 | 1/2005 | Guala |

(56) References Cited

U.S. PATENT DOCUMENTS

| | | |
|---|---|---|
| 6,869,426 B2 | 3/2005 | Ganem |
| 6,875,205 B2 | 4/2005 | Leinsing |
| 6,893,056 B2 | 5/2005 | Guala |
| 6,899,315 B2 | 5/2005 | Mailville et al. |
| 6,911,025 B2 | 6/2005 | Miyahara |
| 6,955,669 B2 | 10/2005 | Curutcharry |
| 6,964,406 B2 | 11/2005 | Doyle |
| 6,991,608 B2 | 1/2006 | Young et al. |
| 6,997,917 B2 | 2/2006 | Niedospial, Jr. et al. |
| 7,004,934 B2 | 2/2006 | Vaillancourt |
| 7,037,302 B2 | 5/2006 | Vaillancourt |
| 7,040,598 B2 | 5/2006 | Raybuck |
| 7,044,441 B2 | 5/2006 | Doyle |
| 7,100,891 B2 | 9/2006 | Doyle |
| 7,125,396 B2 | 10/2006 | Leinsing et al. |
| 7,137,654 B2 | 11/2006 | Segal et al. |
| 7,140,592 B2 | 11/2006 | Phillips |
| 7,160,272 B1 | 1/2007 | Eyal et al. |
| 7,182,313 B2 | 2/2007 | Doyle |
| 7,195,228 B2 | 3/2007 | Tiberghien et al. |
| 7,244,249 B2 | 7/2007 | Leinsing et al. |
| 7,306,197 B2 | 12/2007 | Parrino et al. |
| 7,306,198 B2 | 12/2007 | Doyle |
| 7,306,566 B2 | 12/2007 | Raybuck |
| 7,309,326 B2 | 12/2007 | Fangrow, Jr. |
| 7,316,679 B2 | 1/2008 | Bierman |
| 7,347,458 B2 | 3/2008 | Rome et al. |
| 7,350,764 B2 | 4/2008 | Raybuck |
| 7,361,164 B2 | 4/2008 | Simpson et al. |
| 7,396,051 B2 | 7/2008 | Baldwin et al. |
| 7,448,653 B2 | 11/2008 | Jensen et al. |
| 7,497,484 B2 | 3/2009 | Ziman |
| 7,559,530 B2 | 7/2009 | Korogi et al. |
| 7,588,563 B2 | 9/2009 | Guala |
| 7,600,515 B2 | 10/2009 | Matlock |
| 7,628,781 B2 | 12/2009 | Roy et al. |
| 7,645,274 B2 | 1/2010 | Whitley |
| 7,651,481 B2 | 1/2010 | Raybuck |
| 7,666,170 B2 | 2/2010 | Guala |
| 7,670,326 B2 | 3/2010 | Shemesh |
| 7,717,874 B2 | 5/2010 | Landau et al. |
| 7,722,090 B2 | 5/2010 | Burton et al. |
| 7,758,566 B2 | 7/2010 | Simpson et al. |
| 7,762,524 B2 | 7/2010 | Cawthon et al. |
| 7,763,013 B2 | 7/2010 | Baldwin et al. |
| 7,766,304 B2 | 8/2010 | Phillips |
| 7,766,897 B2 | 8/2010 | Ramsey et al. |
| 7,770,939 B2 | 8/2010 | Jensen et al. |
| 7,803,139 B2 | 9/2010 | Fangrow, Jr. |
| 7,803,140 B2 | 9/2010 | Fangrow, Jr. |
| 7,806,139 B2 | 10/2010 | Packham et al. |
| 7,815,614 B2 | 10/2010 | Fangrow, Jr. |
| 7,837,658 B2 | 11/2010 | Cote et al. |
| 7,857,805 B2 | 12/2010 | Raines |
| 7,867,215 B2 | 1/2011 | Akerlund et al. |
| 7,875,019 B2 | 1/2011 | Barron et al. |
| 7,976,532 B2 | 7/2011 | Kitani et al. |
| 7,998,134 B2 | 8/2011 | Fangrow et al. |
| 8,066,692 B2 | 11/2011 | Simpson et al. |
| 8,113,546 B2 | 2/2012 | Jensen et al. |
| 8,123,738 B2 | 2/2012 | Vaillancourt |
| 8,162,914 B2 | 4/2012 | Kraushaar et al. |
| 8,177,760 B2 | 5/2012 | Rome et al. |
| 8,196,606 B2 | 6/2012 | Kitagawa |
| 8,196,614 B2 | 6/2012 | Kriheli |
| 8,197,452 B2 | 6/2012 | Harding et al. |
| 8,197,466 B2 | 6/2012 | Yokota et al. |
| 8,211,069 B2 | 7/2012 | Fangrow, Jr. |
| 8,225,826 B2 | 7/2012 | Horppu et al. |
| 8,231,567 B2 | 7/2012 | Tennican et al. |
| 8,235,426 B2 | 8/2012 | Pisula, Jr. et al. |
| 8,251,346 B2 | 8/2012 | Stroup |
| 8,262,628 B2 | 9/2012 | Fangrow, Jr. |
| 8,277,424 B2 | 10/2012 | Pan et al. |
| 8,281,824 B2 | 10/2012 | Molema et al. |
| 8,286,657 B2 | 10/2012 | Belley et al. |
| 8,286,936 B2 | 10/2012 | Kitani et al. |
| 8,287,513 B2 | 10/2012 | Ellstrom et al. |
| 8,287,518 B2 | 10/2012 | Kitani et al. |
| 8,298,195 B2 | 10/2012 | Peppel |
| 8,336,587 B2 | 12/2012 | Rosenquist et al. |
| 8,337,483 B2 | 12/2012 | Harding et al. |
| 8,361,408 B2 | 1/2013 | Lynn |
| 8,366,658 B2 | 2/2013 | Davis et al. |
| 8,366,676 B2 | 2/2013 | Harding et al. |
| 8,372,059 B2 | 2/2013 | Ziman |
| 8,377,010 B2 | 2/2013 | Harding et al. |
| 8,392,756 B2 | 3/2013 | Nakayama et al. |
| 8,397,756 B2 | 3/2013 | Packham et al. |
| 8,403,894 B2 | 3/2013 | Lynn et al. |
| 8,403,905 B2 | 3/2013 | Yow |
| 8,408,226 B2 | 4/2013 | Raines et al. |
| 8,409,165 B2 | 4/2013 | Niedospial, Jr. et al. |
| 8,414,554 B2 | 4/2013 | Garfield et al. |
| 8,414,555 B2 | 4/2013 | Garfield et al. |
| 8,448,994 B2 | 5/2013 | Pisula, Jr. et al. |
| 8,454,579 B2 | 6/2013 | Fangrow, Jr. |
| 8,511,352 B2 | 8/2013 | Kraus et al. |
| 8,529,524 B2 | 9/2013 | Newton et al. |
| 8,556,868 B2 | 10/2013 | Simpson et al. |
| 8,596,688 B2 | 12/2013 | Pisula, Jr. et al. |
| 8,603,047 B2 | 12/2013 | Stroup |
| 8,628,516 B2 | 1/2014 | Naftalovitz et al. |
| 8,636,720 B2 | 1/2014 | Truitt et al. |
| 8,640,725 B2 | 2/2014 | Truitt et al. |
| 8,641,685 B2 | 2/2014 | Mansour et al. |
| 8,647,310 B2 | 2/2014 | Fangrow, Jr. et al. |
| 8,667,997 B2 | 3/2014 | Costanzo |
| 8,671,964 B2 | 3/2014 | Py |
| 8,679,090 B2 | 3/2014 | Anderson et al. |
| 8,684,994 B2 | 4/2014 | Lev et al. |
| 8,702,675 B2 | 4/2014 | Imai |
| 8,715,222 B2 | 5/2014 | Truitt et al. |
| 8,715,247 B2 | 5/2014 | Mansour et al. |
| 8,721,614 B2 | 5/2014 | Takemoto et al. |
| 8,721,627 B2 | 5/2014 | Albert |
| 8,721,628 B2 | 5/2014 | Ziman |
| 8,746,278 B2 | 6/2014 | Py |
| 8,764,731 B2 | 7/2014 | Burgess et al. |
| 8,777,908 B2 | 7/2014 | Fangrow, Jr. |
| 8,777,909 B2 | 7/2014 | Fangrow, Jr. |
| 8,777,931 B2 | 7/2014 | Davis et al. |
| 8,801,678 B2 | 8/2014 | Panian et al. |
| 8,834,432 B2 | 9/2014 | Winsor et al. |
| 8,864,725 B2 | 10/2014 | Ranalletta et al. |
| 8,864,737 B2 | 10/2014 | Hasegawa et al. |
| 8,870,832 B2 | 10/2014 | Raday et al. |
| 8,870,846 B2 | 10/2014 | Davis et al. |
| 8,876,784 B2 | 11/2014 | Coete, Sr. et al. |
| 8,882,742 B2 | 11/2014 | Dikeman et al. |
| 8,888,758 B2 | 11/2014 | Mansour et al. |
| 8,899,267 B2 | 12/2014 | Diodati et al. |
| 8,910,919 B2 | 12/2014 | Bonnal et al. |
| 8,951,233 B2 | 2/2015 | Mansour |
| 8,968,261 B2 | 3/2015 | Kimball et al. |
| 8,968,271 B2 | 3/2015 | Guala |
| 8,974,425 B2 | 3/2015 | Tachizaki et al. |
| 8,979,804 B2 | 3/2015 | Ho et al. |
| 9,017,295 B2 | 4/2015 | Pan |
| 9,032,997 B2 | 5/2015 | Abura et al. |
| 9,039,047 B2 | 5/2015 | Imai |
| 9,044,554 B2 | 6/2015 | Wu et al. |
| 9,044,585 B2 | 6/2015 | Masuda et al. |
| 9,061,130 B2 | 6/2015 | Truitt et al. |
| 9,067,049 B2 | 6/2015 | Panian et al. |
| 9,089,680 B2 | 7/2015 | Ueda et al. |
| 9,089,681 B2 | 7/2015 | Ueda et al. |
| 9,114,242 B2 | 8/2015 | Fangrow et al. |
| 9,114,244 B2 | 8/2015 | Yeh et al. |
| 9,119,950 B2 | 9/2015 | Mansour et al. |
| 9,126,028 B2 | 9/2015 | Fangrow et al. |
| 9,126,029 B2 | 9/2015 | Fangrow et al. |
| 9,138,572 B2 | 9/2015 | Zeytoonian et al. |
| 9,149,622 B2 | 10/2015 | Bonnet et al. |

(56) References Cited

U.S. PATENT DOCUMENTS

| | | |
|---|---|---|
| 9,168,203 B2 | 10/2015 | Rosenquist et al. |
| 9,168,366 B2 | 10/2015 | Fangrow et al. |
| 9,198,831 B2 | 12/2015 | Rogers |
| 9,220,882 B2 | 12/2015 | Belley et al. |
| 9,234,616 B2 | 1/2016 | Carrez et al. |
| 9,238,128 B2 | 1/2016 | Yamaguchi et al. |
| 9,314,604 B2 | 4/2016 | Bonnal et al. |
| 9,345,641 B2 | 5/2016 | Kraus et al. |
| 9,351,906 B2 | 5/2016 | Garfield et al. |
| 9,358,182 B2 | 6/2016 | Garfield et al. |
| 9,358,379 B2 | 6/2016 | Fangrow |
| 9,393,398 B2 | 7/2016 | Truitt et al. |
| 9,409,007 B2 | 8/2016 | Yeh |
| 9,433,768 B2 | 9/2016 | Tekeste et al. |
| 9,592,344 B2 | 3/2017 | Simpson et al. |
| 9,636,492 B2 | 5/2017 | Fangrow, Jr. |
| 9,707,346 B2 | 7/2017 | Simpson et al. |
| 9,724,504 B2 | 8/2017 | Fangrow, Jr. et al. |
| 9,913,945 B2 | 3/2018 | Simpson et al. |
| 9,933,094 B2 | 4/2018 | Fangrow |
| 9,974,939 B2 | 5/2018 | Fangrow, Jr. |
| 9,974,940 B2 | 5/2018 | Fangrow, Jr. |
| 10,046,154 B2 | 8/2018 | Fangrow et al. |
| 10,105,492 B2 | 10/2018 | Simpson |
| 10,156,306 B2 | 12/2018 | Fangrow |
| 2002/0066715 A1 | 6/2002 | Niedospial, Jr. |
| 2002/0082586 A1 | 6/2002 | Finley et al. |
| 2002/0148514 A1 | 10/2002 | Taneya et al. |
| 2003/0060804 A1 | 3/2003 | Vaillancourt |
| 2003/0066978 A1 | 4/2003 | Enerson |
| 2003/0111623 A1 | 6/2003 | Enerson |
| 2003/0136932 A1 | 7/2003 | Doyle |
| 2003/0208165 A1 | 11/2003 | Christensen et al. |
| 2004/0074541 A1 | 4/2004 | Sharpe |
| 2004/0124388 A1 | 7/2004 | Kiehne |
| 2004/0124389 A1 | 7/2004 | Phillips |
| 2004/0238776 A1 | 12/2004 | Peters et al. |
| 2004/0244848 A1 | 12/2004 | Maldavs |
| 2005/0015075 A1 | 1/2005 | Wright et al. |
| 2005/0033268 A1 | 2/2005 | Decaria |
| 2005/0090805 A1 | 4/2005 | Shaw et al. |
| 2005/0124942 A1 | 6/2005 | Richmond |
| 2005/0212292 A1 | 9/2005 | Parrino et al. |
| 2005/0228362 A1 | 10/2005 | Vaillancourt |
| 2005/0245872 A1 | 11/2005 | Simpson et al. |
| 2006/0025751 A1 | 2/2006 | Roy et al. |
| 2006/0058734 A1 | 3/2006 | Phillips |
| 2006/0129109 A1 | 6/2006 | Shaw et al. |
| 2006/0142730 A1 | 6/2006 | Proulx et al. |
| 2006/0142735 A1 | 6/2006 | Whitley |
| 2006/0157984 A1 | 7/2006 | Rome et al. |
| 2006/0161115 A1 | 7/2006 | Fangrow |
| 2006/0192164 A1 | 9/2006 | Korogi et al. |
| 2006/0202146 A1 | 9/2006 | Doyle |
| 2006/0211996 A1 | 9/2006 | Trinchera et al. |
| 2006/0253084 A1 | 11/2006 | Nordgren |
| 2007/0073270 A1 | 3/2007 | Christensen et al. |
| 2007/0088292 A1 | 4/2007 | Fangrow |
| 2007/0088293 A1 | 4/2007 | Fangrow |
| 2007/0088294 A1 | 4/2007 | Fangrow |
| 2007/0088324 A1 | 4/2007 | Fangrow |
| 2007/0088327 A1 | 4/2007 | Guala |
| 2007/0102923 A1 | 5/2007 | Niemela |
| 2007/0179453 A1 | 8/2007 | Lim et al. |
| 2007/0179454 A1 | 8/2007 | Ziman et al. |
| 2008/0103485 A1 | 5/2008 | Kruger |
| 2008/0125756 A1 | 5/2008 | Dicarlo et al. |
| 2008/0287920 A1 | 5/2008 | Fangrow et al. |
| 2008/0140020 A1 | 6/2008 | Shirley |
| 2008/0190485 A1 | 8/2008 | Guala |
| 2008/0200900 A1 | 8/2008 | Aeschlimann et al. |
| 2008/0290657 A1 | 11/2008 | McKeon, III |
| 2009/0001720 A1 | 1/2009 | Cheon et al. |
| 2010/0063482 A1 | 3/2010 | Mansour et al. |
| 2010/0174242 A1 | 7/2010 | Anderson et al. |
| 2010/0211019 A1 | 8/2010 | Greco |
| 2010/0249723 A1 | 9/2010 | Fangrow, Jr. |
| 2010/0253070 A1 | 10/2010 | Cheon et al. |
| 2010/0264343 A1 | 10/2010 | Jeory |
| 2010/0292673 A1 | 11/2010 | Korogi et al. |
| 2011/0046572 A1 | 2/2011 | Fangrow |
| 2011/0062703 A1 | 3/2011 | Lopez |
| 2011/0074148 A1 | 3/2011 | Imai |
| 2011/0175347 A1 | 7/2011 | Okiyama |
| 2011/0276035 A1 | 11/2011 | Fangrow, Jr. |
| 2011/0306931 A1 | 12/2011 | Kamen et al. |
| 2011/0319859 A1 | 12/2011 | Zeytoonian et al. |
| 2012/0031515 A1 | 2/2012 | Whitaker |
| 2012/0041391 A1 | 2/2012 | Fangrow et al. |
| 2012/0046636 A1 | 2/2012 | Kriheli |
| 2012/0089101 A1 | 4/2012 | Carlyon et al. |
| 2012/0109077 A1 | 5/2012 | Ryan |
| 2012/0130305 A1 | 5/2012 | Bonnal et al. |
| 2012/0153201 A1 | 6/2012 | Larose et al. |
| 2012/0220955 A1 | 8/2012 | Maseda et al. |
| 2012/0220984 A1 | 8/2012 | Christensen et al. |
| 2012/0271246 A1 | 10/2012 | Guala |
| 2012/0277688 A1 | 11/2012 | Rogier |
| 2012/0316536 A1 | 12/2012 | Carrez et al. |
| 2012/0330247 A1 | 12/2012 | Fangrow, Jr. |
| 2013/0006211 A1 | 1/2013 | Takemoto |
| 2013/0030386 A1 | 1/2013 | Panian et al. |
| 2013/0035668 A1 | 2/2013 | Kitani et al. |
| 2013/0053815 A1 | 2/2013 | Mucientes et al. |
| 2013/0060205 A1 | 3/2013 | Mansour et al. |
| 2013/0066923 A1 | 3/2013 | Garfield et al. |
| 2013/0076019 A1 | 3/2013 | Takemoto |
| 2013/0079730 A1 | 3/2013 | Mosler et al. |
| 2013/0150806 A1 | 6/2013 | Fangrow, Jr. |
| 2013/0193359 A1 | 8/2013 | Yeh |
| 2013/0197453 A1 | 8/2013 | Yeh |
| 2013/0231616 A1 | 9/2013 | Fangrow, Jr. |
| 2013/0304037 A1 | 11/2013 | Fangrow |
| 2013/0317483 A1 | 11/2013 | Reichart et al. |
| 2014/0020792 A1 | 1/2014 | Kraus et al. |
| 2014/0174578 A1 | 6/2014 | Bonnal et al. |
| 2014/0209197 A1 | 7/2014 | Carrez et al. |
| 2014/0303601 A1 | 10/2014 | Fangrow |
| 2014/0316350 A1 | 10/2014 | Yamaguchi et al. |
| 2014/0358033 A1 | 12/2014 | Lynn |
| 2014/0358073 A1 | 12/2014 | Panian et al. |
| 2014/0371686 A1 | 12/2014 | Sano et al. |
| 2015/0008664 A1 | 1/2015 | Tachizaki |
| 2015/0045746 A1 | 2/2015 | Macy, Jr. et al. |
| 2015/0051555 A1 | 2/2015 | Fangrow, Jr. |
| 2015/0073380 A1 | 3/2015 | Mansour et al. |
| 2015/0148756 A1 | 5/2015 | Lynn |
| 2015/0157848 A1 | 6/2015 | Wu et al. |
| 2015/0196749 A1 | 7/2015 | Ziv et al. |
| 2015/0202424 A1 | 7/2015 | Harton |
| 2015/0209233 A1 | 7/2015 | Fukuoka |
| 2015/0209572 A1 | 7/2015 | Garfield et al. |
| 2015/0258324 A1 | 9/2015 | Chida et al. |
| 2015/0258325 A1 | 9/2015 | Panian et al. |
| 2015/0265829 A1 | 9/2015 | Truitt et al. |
| 2015/0320992 A1 | 11/2015 | Bonnet et al. |
| 2016/0114147 A1 | 4/2016 | Siopes et al. |
| 2016/0144109 A1 | 5/2016 | Stroup |
| 2016/0213910 A1 | 7/2016 | Fangrow, Jr. et al. |
| 2016/0250102 A1 | 9/2016 | Garfield et al. |
| 2016/0263367 A1 | 9/2016 | Fangrow et al. |
| 2016/0263369 A1 | 9/2016 | Naftalovitz et al. |
| 2016/0271327 A1 | 9/2016 | Simpson et al. |
| 2017/0296801 A1 | 10/2017 | Fangrow, Jr. |
| 2017/0304547 A1 | 10/2017 | Simpson |
| 2018/0015275 A1 | 1/2018 | Fangrow |
| 2018/0036524 A1 | 2/2018 | Fangrow, Jr. |
| 2018/0333568 A1 | 11/2018 | Fangrow, Jr. |

(56) References Cited

U.S. PATENT DOCUMENTS

2019/0038886 A1  2/2019  Fangrow
2019/0046731 A1  2/2019  Simpson

FOREIGN PATENT DOCUMENTS

| | | |
|---|---|---|
| CN | 1390286 A | 1/2003 |
| EP | 0 158 030 | 10/1985 |
| EP | 0 368 473 A2 | 5/1990 |
| EP | 0 791 371 | 8/1997 |
| EP | 0 795 342 | 9/1997 |
| EP | 1 946 792 | 7/2008 |
| EP | 2 123 322 | 11/2009 |
| GB | 2 116 277 | 9/1983 |
| GB | 2 118 440 | 11/1983 |
| GB | 2 353 078 | 2/2001 |
| JP | 56-72659 U1 | 6/1981 |
| JP | 58-13216 | 1/1983 |
| JP | 59-41429 | 3/1984 |
| JP | 60-89488 | 6/1985 |
| JP | 63-175383 | 11/1988 |
| JP | 11-311234 | 11/1999 |
| JP | 2001-187990 A | 7/2001 |
| JP | 2004-000483 A | 1/2004 |
| WO | WO 1988/08499 | 11/1988 |
| WO | WO 1995/32748 | 12/1995 |
| WO | WO 2001/03756 | 1/2001 |
| WO | WO 2001/23026 | 4/2001 |
| WO | WO 2002/096500 | 12/2002 |
| WO | WO 2003/013646 | 2/2003 |
| WO | WO 2004/060474 | 7/2004 |
| WO | WO 2004/082756 | 9/2004 |
| WO | WO 2006/076656 | 7/2006 |
| WO | WO 2006/088858 | 8/2006 |
| WO | WO 2006/124756 | 11/2006 |
| WO | WO 2008/144447 | 11/2008 |
| WO | WO 2009/095760 | 8/2009 |
| WO | WO 2013/036854 | 3/2013 |

OTHER PUBLICATIONS

Charney, "Baxter Healthcare InterlinkTM IV Access System" in 4 pages, from Handbook of Modern Hospital Safety. Published Mar. 1999.
European extended Search Report, re EP Application No. 12830016.7, dated May 19, 2015.
ICU Medical, Inc. U.S. Appl. No. 11/417,882, filed May 3, 2006.
ICU Medical, Inc. U.S. Appl. No. 11/417,923, filed May 3, 2006.
ICU Medical, Inc. U.S. Appl. No. 11/417,671, filed May 3, 2006.
ICU Medical, Inc. U.S. Appl. No. 11/417,648, filed May 3, 2006.
ICU Medical, Inc. U.S. Appl. No. 11/417,909, filed May 3, 2006.
Injection Site, Molded Products, Inc., Apr. 2, 2004, in 1 page, https://web.archive.org/web/20040402123354/https://www.moldedproducts.com/injectionsite.htm.
International Preliminary Report on Patentability and Written Opinion re PCT Application No. PCT/US2012/054289, dated Mar. 12, 2014.
International Search Report and Written Opinion re PCT Application No. PCT/US2012/054289, dated Jan. 24, 2013.

\* cited by examiner

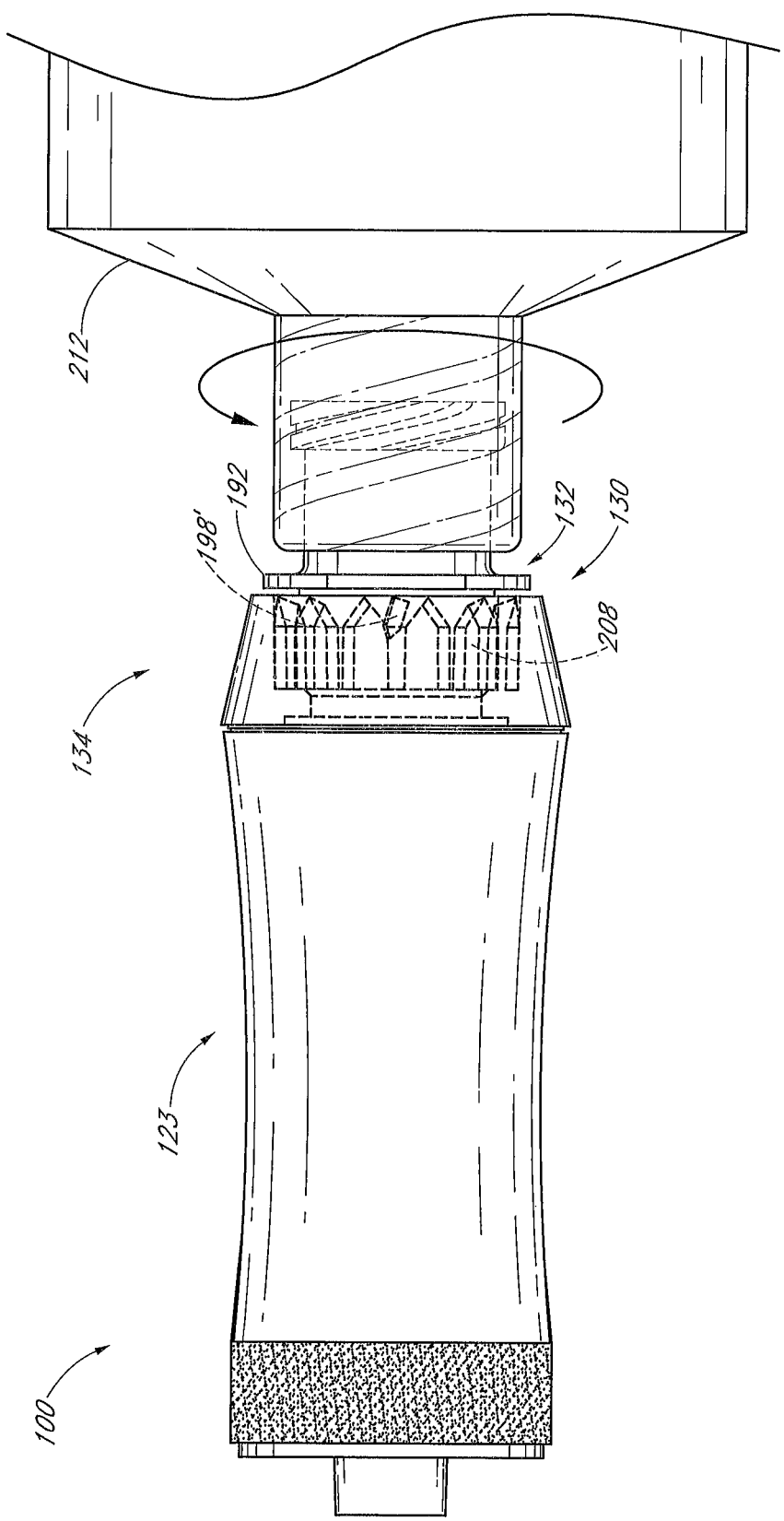

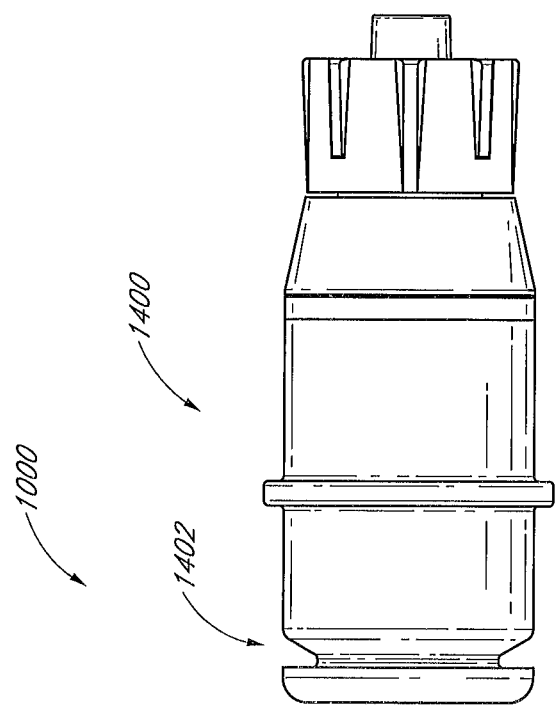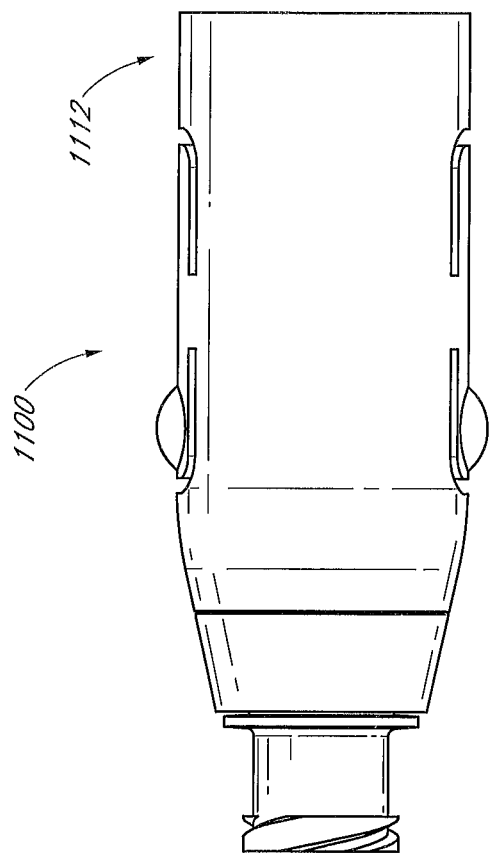
FIG. 49

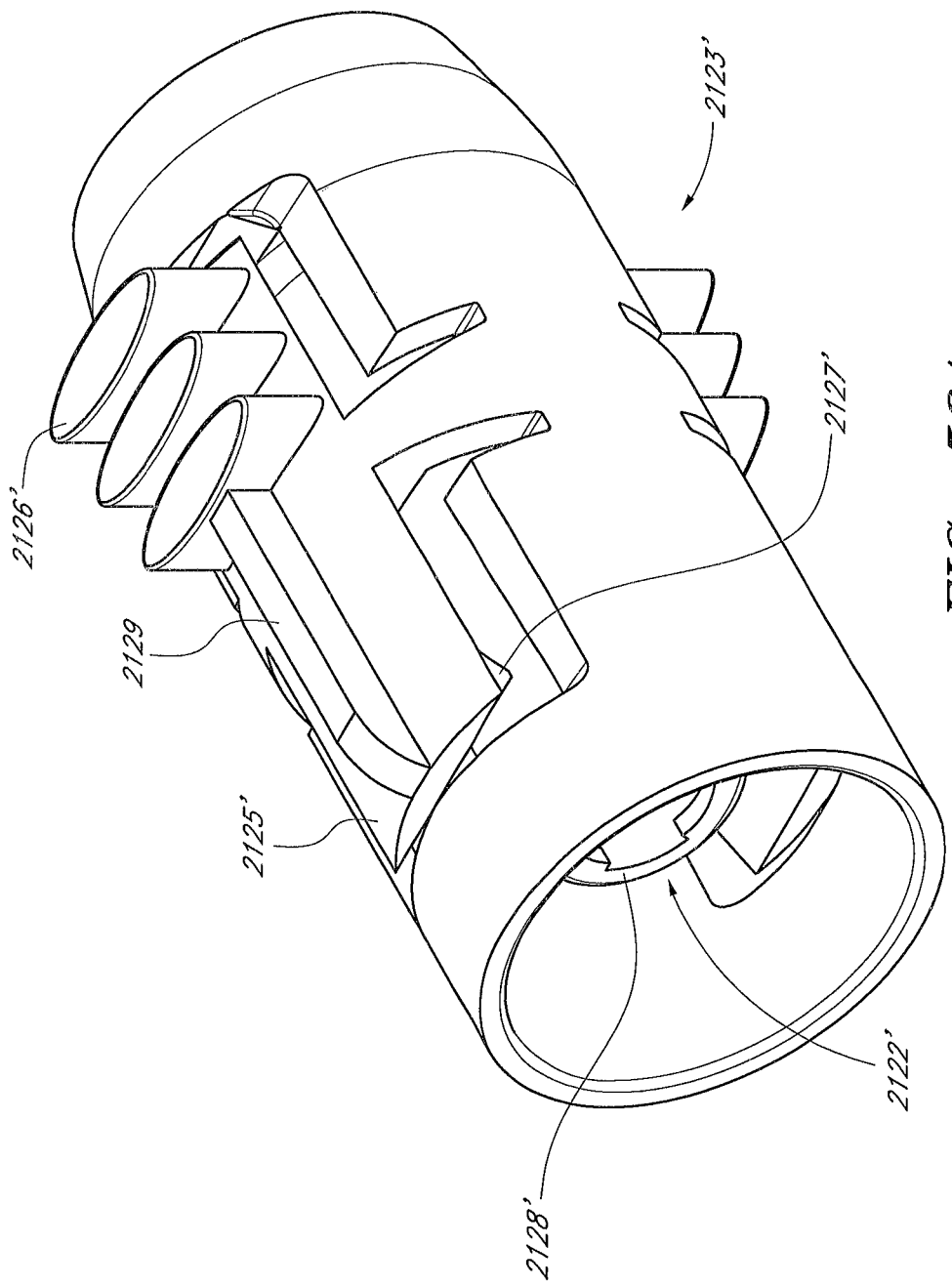

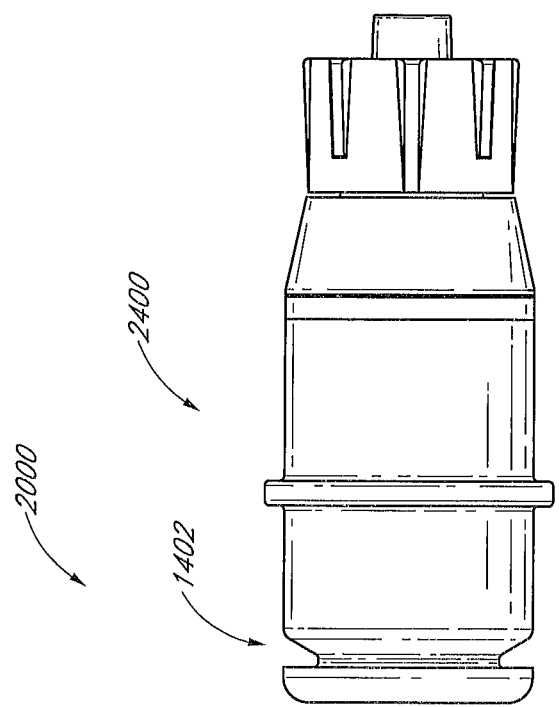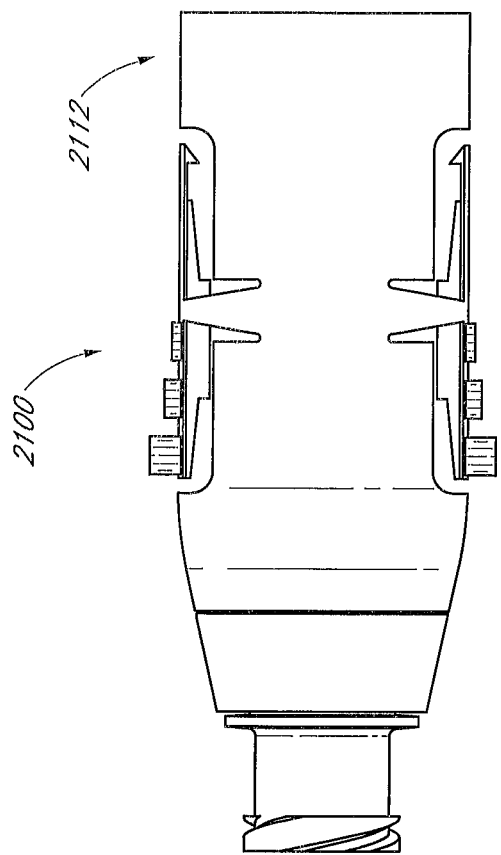
FIG. 62

AXIALLY ENGAGING MEDICAL CONNECTOR SYSTEM WITH DIMINISHED FLUID REMNANTS

RELATED APPLICATIONS

This application is a continuation of U.S. patent application Ser. No. 15/900,658, filed on Feb. 20, 2018, which is a continuation of U.S. patent application Ser. No. 14/199,836, filed on Mar. 6, 2014, now U.S. Pat. No. 9,933,094, which claims the benefit under 35 U.S.C. § 120 and 35 U.S.C. § 365(c) as a continuation of International Application No. PCT/US2012/054289, designating the United States, with an international filing date of Sep. 7, 2012, titled MEDICAL CONNECTORS WITH FLUID-RESISTANT MATING INTERFACES, which claims the benefit of U.S. Provisional Application No. 61/533,138, filed Sep. 9, 2011, titled MEDICAL CONNECTORS WITH INCREASED FLUID CONTAINMENT, U.S. Provisional Application No. 61/557,793, filed Nov. 9, 2011, titled MEDICAL CONNECTORS WITH FLUID-RESISTANT MATING SURFACES, U.S. Provisional Application No. 61/579,582, filed Dec. 22, 2011, titled MEDICAL CONNECTORS WITH FLUID-RESISTANT MATING SURFACES, U.S. Provisional Application No. 61/607,429, filed Mar. 6, 2012, titled MEDICAL CONNECTORS WITH FLUID-RESISTANT MATING SURFACES, and U.S. Provisional Application No. 61/692,516, filed Aug. 23, 2012, titled MEDICAL CONNECTORS WITH FLUID-RESISTANT MATING SURFACES. The entire contents of each of the above-identified patent applications are incorporated by reference herein and made a part of this specification for all that they disclose. Any and all priority claims identified in the Application Data Sheet, or any correction thereto, are hereby incorporated by reference under 37 CFR 1.57.

BACKGROUND

Technical Field

This invention relates generally to medical connectors through which fluids flow, and in particular, to medical connectors with increased fluid containment.

Description of the Related Art

Systems of connectors, valves, and tubing are routinely used in hospitals and other medical settings for facilitating the transfer of fluids to and from patients. It is often a challenge to keep such systems sterile and to avoid leakage or external residues of fluids (e.g., liquids and/or vapors) when the various components are engaged and disengaged.

In some medical applications, such as certain chemotherapy treatments, the fluids in the tubing and connectors can be harmful if released, even in relatively small amounts, especially after repeated exposures. In order to maintain a barrier against many types of fluid leakage, and to impede the ingress or egress of microbes or debris, connectors have been provided with closures, such as septa, flexible seals, or other impediments, at their mating ends. When a first connector is engaged with a second connector, the closure of one or both connectors is temporarily opened, pierced, or moved to allow fluid to flow between the two connectors. But these connectors may permit undesired fluid release, such as by transfer or vaporization of fluid remnants on the mating ends of the connectors after disconnection. These connectors have other drawbacks and disadvantages.

SUMMARY

Disclosed in some embodiments are medical connectors with increased fluid containment, isolation of fluid from, and/or lessening or elimination of fluid residue on, mating ends of the connectors, fluid-resistant mating interfaces, dry disconnections, and/or improved connection systems or mechanisms for securing the connectors together. In some embodiments, a dry disconnect medical connector has no fluid residue or leakage on the outside of the connector upon disconnection. In some embodiments, a dry disconnect medical connector has no appreciable fluid residue or leakage on the outside of the connector upon disconnection, such that any small amount of fluid residue or leakage does not present any significant functional disadvantages or significant health hazards to patients or healthcare providers. It is contemplated that any features, components, or steps of the various embodiments disclosed herein, and/or incorporated by reference herein, are combinable and/or replaceable to form additional embodiments. Such combinations and/or replacements are contemplated and are within the scope of this disclosure.

In some embodiments, a coupling system for transferring fluid comprises a first connector. The first connector can have a first central axis, a first end, a second end, and a male portion. In some embodiments, the first connector includes a valve member located at least partially in an interior space of the male portion and configured to transition between an opened position and a closed position. The valve member can have a first end and a second end. In some embodiments, the valve member can include a valve passageway extending within the valve member between the first end and the second end of the valve member. The valve member can include at least one port near the first end of the valve member. In some embodiments, the valve member can have a first mating surface on the first end of the valve member. The first end of the valve member can be configured to inhibit the passage of fluid from the valve passageway past the first end of the valve member when the valve member is in the closed position. In some embodiments, the first connector includes a biasing member configured to bias the valve member to the closed position. The coupling system can include a second connector configured to transition between an opened configuration and a closed configuration.

In some embodiments, the second connector includes a second housing having a second central axis, a first end configured to receive the male portion of the first housing, and a second end. The second connector can include a fluid conduit located at least partially within an interior space of the second housing and having a first end, a second end, a conduit passageway extending within the fluid conduit between the first end and the second end of the fluid conduit, at least one port near the first end of the fluid conduit extending through the fluid conduit and into the conduit passageway, and a second mating surface configured to releasably mate with the first mating surface of the valve member. In some embodiments, the second connector includes a sealing element located at least partially within an interior space of the second housing and having a first end, a second end, a biasing portion between the first end and the second end of the sealing element, and an aperture at the first end of the sealing element sized and shaped to correspond with the size and shape of the first end of the fluid conduit. The sealing element can be configured to inhibit fluid flow out from the conduit passageway through the at least one port of the fluid conduit when the second connector is in the closed configuration. The first connector and the second connector can be configured to connect with each other such that the valve member is transitioned to the opened position and the second connector is transitioned to the opened configuration when the first connector is connected with the second connector. In some embodiments, first mating surface and the second mating surface are configured to be coupled together in a manner that inhibits fluid penetration between the first mating surface and the second mating surface when fluid flows through the first and second connectors.

In some embodiments, as disclosed above, the biasing member is a spring or a flexible tube. The fluid conduit can be constructed from a rigid or semi-rigid material. In some embodiments, the male portion of the first connector is an ANSI-compliant male luer tip and/or the first end of the second connector is an ANSI-compliant female luer tip. The fluid conduit can be configured such that at least a portion of the fluid conduit is configured to enter the male portion of the first connector when the first connector is connected to the second connector. In some embodiments, at least one of the first mating surface and the second mating surface is constructed of a flexible material. The first connector can include a shroud portion having at least one engagement feature, the at least one engagement feature configured to engage with a coupling feature of the second connector.

In some embodiments, the shroud portion has an internal cross-sectional area that is greater than the outer cross-sectional area of a portion of the second connector near the first end of the second connector. The at least one engagement feature can be a tab with a hook, the hook configured to engage with the coupling feature of the second connector. In some embodiments, the tab can include a release structure configured to facilitate release of the at least one engagement feature from the coupling feature of the second connector. In some embodiments, the release structure is a domed protrusion and/or at least one ridge protruding from the at least one tab. The coupling feature can be an annular channel on an outer surface of the second connector. In some embodiments, the tab includes a longitudinal ridge. The second connector can include an abutment feature configured to limit passage of the shroud portion past the first end of the second connector. The abutment feature can have an outer cross-sectional area that is greater than the inner cross-sectional area of the shroud portion, the abutment feature comprising one or more flanges located on an outer surface of the second connector. In some embodiments, at least a portion of the fluid conduit is configured to enter into the male portion of the first connector when the first connector is connected to the second connector. The male portion can be configured such that at least a portion of the male portion of the first connector enters into the interior space of the second housing when the first connector is connected with the second connector. The various features, components, and characteristics described above can be combined with, or substituted for, one another in order to perform varying modes of the disclosed inventions.

A method of transferring a fluid from a fluid source to a fluid receiver can include connecting the fluid source to a first connector. The first connector can comprise a first housing having a first central axis, a first end, a second end, and a male portion, the second end configured to sealingly engage with the fluid source. In some embodiments, the first connector includes a valve member located at least partially in an interior space of the male portion and configured to transition between an opened position and a closed position, the valve member comprising a first end and a second end, a valve passageway extending within the valve member between the first end and the second end of the valve member, at least one port near the first end of the valve member, and a first mating surface on the first end of the valve member. The first end of the valve member can be configured to inhibit the passage of fluid from the valve passageway past the first end of the valve member when the valve member is in the closed position. In some embodiments, the first connector includes a biasing member configured to bias the valve member to the closed position. The method of transferring fluid from a fluid source to a fluid receiver can include connecting the fluid receiver to a second connector configured to transition between an opened configuration and a closed configuration. The second connector can comprise a second housing having a second central axis, a first end configured to receive the male portion of the first housing, and a second end configured to connect with the fluid receiver.

In some embodiments, the second connector includes a fluid conduit located at least partially within an interior space of the second housing and having a first end, a second end, a conduit passageway extending within the fluid conduit between the first end and the second end of the fluid conduit, at least one port near the first end of the fluid conduit extending through the fluid conduit and into the conduit passageway, and a second mating surface configured to releasably mate with the first mating surface of the valve member. In some embodiments, the second connector includes a sealing element located at least partially within an interior space of the second housing and having a first end, a second end, a biasing portion between the first end and the second end of the sealing element, and an aperture at the first end of the sealing element sized and shaped to correspond with the size and shape of the first end of the fluid conduit, the sealing element configured to inhibit fluid flow out from the conduit passageway through the at least one port of the fluid conduit when the second connector is in the closed configuration. The method of transferring fluid can include connecting the first connector to the second connector, wherein the valve member transitions from the closed position to the opened position and the second connector transitions to the opened configuration upon connection between the first connector and the second connector. In some embodiments, the method includes transferring the fluid from the fluid source, through the first connector, through the second connector, and into the fluid receiver and disconnecting the first connector from the second connector, wherein the first mating surface and second mating surface remain free of the fluid after disconnection from each other.

The method of transferring fluid can include connecting a male luer connection of the fluid source to the second end of the first connector. In some embodiments, connecting the fluid receiver to the second end of the second connector further includes connecting a female luer connection of the fluid receiver to the second end of the second connector. The method can further include connecting an engagement feature of the first connector with a coupling feature of the second connector. In some embodiments, the method includes inserting at least a portion of the fluid conduit into the male portion when the first connector is connected to the second connector. According to some variants, the method can include inserting at least a portion of the male portion into the first end of the second connector when the first connector is connected to the second connector. The various steps, features, components, and characteristics described above can be combined with, or substituted for, one another in order to perform varying modes of the disclosed inventions and methods.

A method of manufacturing a coupling system for fluid transfer can comprise providing a first connector including a first housing having a first central axis, a first end, a second end, and a male portion. The valve member can be located at least partially in an interior space of the male portion and can be configured to transition between an opened position and a closed position. In some embodiments, the valve member comprises a first end and a second end, a valve passageway extending within the valve member between the first end and the second end of the valve member, at least one port near the first end of the valve member, and a first mating surface on the first end of the valve member. The first end of the valve member can be configured to inhibit the passage of fluid from the valve passageway past the first end of the valve member when the valve member is in the closed position. In some embodiments, the first connector includes a biasing member configured to bias the valve member to the closed position. The method of manufacturing can include providing a second connector configured to transition between an opened configuration and a closed configuration including a second housing having a second central axis, a first end configured to receive the male portion of the first housing, and a second end. In some embodiments, the second connector includes a fluid conduit located at least partially within an interior space of the second housing and having a first end, a second end, a conduit passageway extending within the fluid conduit between the first end and the second end of the fluid conduit, at least one port near the first end of the fluid conduit extending through the fluid conduit and into the conduit passageway, and a second mating surface configured to releasably mate with the first mating surface of the valve member. A sealing element can be located at least partially within an interior space of the second housing and can have a first end, a second end, a biasing portion between the first end and the second end of the sealing element, and an aperture at the first end of the sealing element sized and shaped to correspond with the size and shape of the first end of the fluid conduit, the sealing element configured to inhibit fluid flow out from the conduit passageway through the at least one port of the fluid conduit when the second connector is in the closed configuration. The method of manufacturing can include connecting the first end of the first connector to the first end of the second connector such that the second connector is transitioned to the opened configuration and the valve member is transitioned to the opened position when the first connector is connected to the second connector. In some embodiments, the first mating surface and the second mating surface are configured to be coupled together in a manner that inhibits fluid penetration between them when fluid flows through the first and second connectors.

A closeable male connector configured to connect to a female connector can include a housing having a first central axis, a first end, a second end, and a male portion. In some embodiments, the male connector includes a valve member located at least partially in an interior space of the male portion and configured to transition between an opened position and a closed position, the valve member comprising a first end and a second end, a valve passageway extending within the valve member between the first end and the second end of the valve member, at least one port near the first end of the valve member, and a first mating surface on the first end of the valve member, wherein the first end of the valve member is configured to inhibit the passage of fluid from the valve passageway past the first end of the valve member when the valve member is in the closed position. According to some variants, the male connector includes a biasing member configured to bias the valve member to the closed position. The first mating surface can be sized and shaped to releasably mate with a second mating surface on a female connector such that the valve member is transitioned to the opened position the male connector is connected with the second connector. In some embodiments, the first mating surface is configured to be couple with the second mating surface in a manner that inhibits fluid penetration between the first mating surface and the second mating surface when fluid flows through the male and female connectors.

A closeable female connector configured to connect to a male connector can be configured to transition between an opened configuration and a closed configuration and can comprise a housing having a second central axis, a first end configured to receive the male portion of the first housing, and a second end. In some embodiments, the female connector comprises a fluid conduit located at least partially within an interior space of the housing and having a first end, a second end, a conduit passageway extending within the fluid conduit between the first end and the second end of the fluid conduit, at least one port near the first end of the fluid conduit extending through the fluid conduit and into the conduit passageway, and a mating surface. The female connector can include a sealing element located at least partially within an interior space of the housing and having a first end, a second end, a biasing portion between the first end and the second end of the sealing element, and an aperture at the first end of the sealing element sized and shaped to correspond with the size and shape of the first end of the fluid conduit, the sealing element configured to inhibit fluid flow out from the conduit passageway through the at least one port of the fluid conduit when the female connector is in the closed configuration. The female mating surface can be configured to releasably mate with a male mating surface of a male connector, and can be configured to be couple with the male mating surface in a manner that inhibits fluid penetration between the female mating surface and the male mating surface when fluid flows through the male and female connectors.

A coupling system for transferring medical fluid having an open stage and a closed stage can comprise a first connector. The first connector can comprise a first housing with a first central axis, the first housing comprising a first end with a male portion and a second end. A valve member can be disposed at least partially in an interior space of the male portion, the valve member comprising a closed end, a first passageway extending through the valve member, at least one port near the closed end of the valve member extending through the valve member and into the first passageway, and a first mating surface on the closed end. In some embodiments, the first connector includes a biasing member functionally coupled to the valve member. The coupling system can include a second connector having a second housing with a second central axis, the second housing comprising a first end configured to accept the male portion, and a second end. In some embodiments, the second connector includes a fluid conduit disposed at least partially in an interior space of the second housing, the fluid conduit comprising a closed end, a second passageway extending through the fluid conduit, at least one port near the closed end of the fluid conduit extending through the fluid conduit and into the second passageway, and a second mating surface on the closed end configured to couple with the first mating surface. The second connector can include a sealing member disposed within the second housing, the sealing member comprising a first end, a second end, and a biasing portion between the first end and the second end, the first end comprising an open aperture in both the open and closed stages, and the size and shape of the first end generally corresponding with the size and shape of the closed end of the fluid conduit, the sealing member configured to resist fluid flow through the at least one port of the fluid conduit. In some embodiments, the first mating surface and the second mating surface are configured to be coupled together in a manner that resists fluid penetration between them when fluid flows through the connectors.

According to some variants, a coupling system for transferring medical fluid can have an open stage and a closed stage and can comprise a first connector. In some embodiments, the first connector includes a first housing with a first central axis, the first housing comprising a first end with a male portion and a second end, the male portion having an inner cross-sectional area. The first connector can include a valve member disposed at least partially in an interior space of the male portion, the valve member comprising a closed end with a cross-sectional area, a first passageway extending between through the valve member, at least one port near the closed end of the valve member extending through the valve member and into the first passageway, and a first mating surface on the closed end. In some embodiments, the first connector includes a biasing member functionally coupled to the valve member. The coupling system can include a second connector having a second housing with a second central axis, the second housing comprising a first end configured to accept the male portion, and a second end. The second connector can include a fluid conduit disposed at least partially in an interior space of the second housing, the fluid conduit comprising an opened end, a closed end, a second passageway extending between the opened end and the closed end, at least one port near the closed end of the fluid conduit extending through the fluid conduit and into the second passageway, and a second mating surface on the closed end configured to couple with the first mating surface. According to some embodiments, the second connector includes a sealing member disposed within the second housing, the sealing member comprising a first end, a second end, a biasing portion between the first end and the second end, and an opening on the first end of the sealing member having a cross-sectional area in the open stage that is greater than or equal to the inner cross-sectional area of the male portion. The first mating surface and the second mating surface can be configured to be coupled together in a manner that resists fluid penetration between them when fluid flows through the connectors.

A coupling system for transferring medical fluid can have an open stage and a closed stage and can comprise a first connector having a first housing with a first central axis, the first housing comprising a first end with a male portion and a second end. In some embodiments, the first connector includes a valve member disposed at least partially in an interior space of the male portion, the valve member comprising a closed end with a cross-sectional area, a first passageway extending between the valve member and the second end of the first housing, at least one port near the closed end of the valve member extending through the valve member and into the first passageway, and a first mating surface on the closed end. The first connector can include a biasing member functionally coupled to the valve member. In some embodiments, the coupling system includes a second connector having a second housing with a second central axis, the second housing comprising a first end configured to accept the male portion, and a second end. In some embodiments, the second connector includes a fluid conduit disposed at least partially in an interior space of the second housing, the fluid conduit comprising an opened end, a closed end, a second passageway extending between the opened end and the closed end, at least one port near the closed end of the fluid conduit extending through the fluid conduit and into the second passageway, and a second mating surface on the closed end configured to couple with the first mating surface. A sealing member can be disposed within the second housing, the sealing member comprising a first end, a second end, a biasing portion between the first end and the second end, and an opening on the first end of the sealing member having a cross-sectional area in the open stage that is greater than or equal to the cross-sectional area of the valve member. In some embodiments, the first mating surface and the second mating surface are configured to be coupled together in a manner that resists fluid penetration between them when fluid flows through the connectors.

According to some variants, a medical system for transferring medical fluid can include a first connector having a first housing with a first central axis, the first housing comprising a first end with a male portion and a second end. In some embodiments, the first connector includes a valve member disposed at least partially in an interior space of the male portion, the valve member comprising a closed end, a first passageway extending through the valve member, at least one port near the closed end of the valve member extending through the valve member and into the first passageway, and a first mating surface on the closed end. The first connector can include a biasing member functionally coupled to the valve member. In some embodiments, the medical system includes a second connector having a second housing with a second central axis, the second housing comprising a first end configured to accept the male portion, and a second end. The second connector can include a fluid conduit disposed at least partially in an interior space of the second housing, the fluid conduit comprising a closed end, a second passageway extending through the fluid conduit, at least one port near the closed end of the fluid conduit extending through the fluid conduit and into the second passageway, and a second mating surface on the closed end configured to couple with the first mating surface. In some embodiments, the second connector has a sealing element disposed within the second housing and configured to resist fluid flow through the at least one port of the fluid conduit, the sealing element comprising a biasing portion. According to some configurations the first mating surface and the second mating surface are configured to be coupled together in a manner that resists fluid penetration between them when fluid flows through the connectors.

BRIEF DESCRIPTION OF THE DRAWINGS

Certain embodiments of this invention will now be discussed in detail with reference to the following figures. These figures are provided for illustrative purposes only, and the invention is not limited to the subject matter illustrated in the figures.

FIG. 20B is a side view of a coupled component substantially fully threadedly engaged with the embodiment of the male connector shown in FIG. 3.

FIG. 49 is a side view of the embodiment of the male connector shown in FIG. 33 adjacent the embodiment of the female connector shown in FIG. 41.

FIG. 58A is a perspective view of an embodiment of a male housing.

FIG. 62 is a side view of the embodiment of the male connector shown in FIG. 53 adjacent the embodiment of the female connector shown in FIG. 61.

DETAILED DESCRIPTION

In some embodiments, the present application describes a variety of means for increasing fluid containment such as by producing dry disconnections, isolating the mating ends of connectors from residual fluids, and/or resisting fluid ingress between mating ends of connectors. In some embodiments, closing mechanisms function to prevent and/or impede fluid from contacting, remaining upon, and/or contaminating the mating ends of a connector, while allowing fluid flow when the connectors are engaged with one another. As used herein, terms such as "closed" or "sealed" are intended to have their ordinary meaning in this field and should be understood to include obstructions or barriers to fluid flow. These terms should not be understood to require that a particular structure or configuration achieves a complete fluid closure in all circumstances; rather, the terms refer to a fluid closure to the degree required in the particular circumstances in which the devices are intended to be used.

Figure 1:
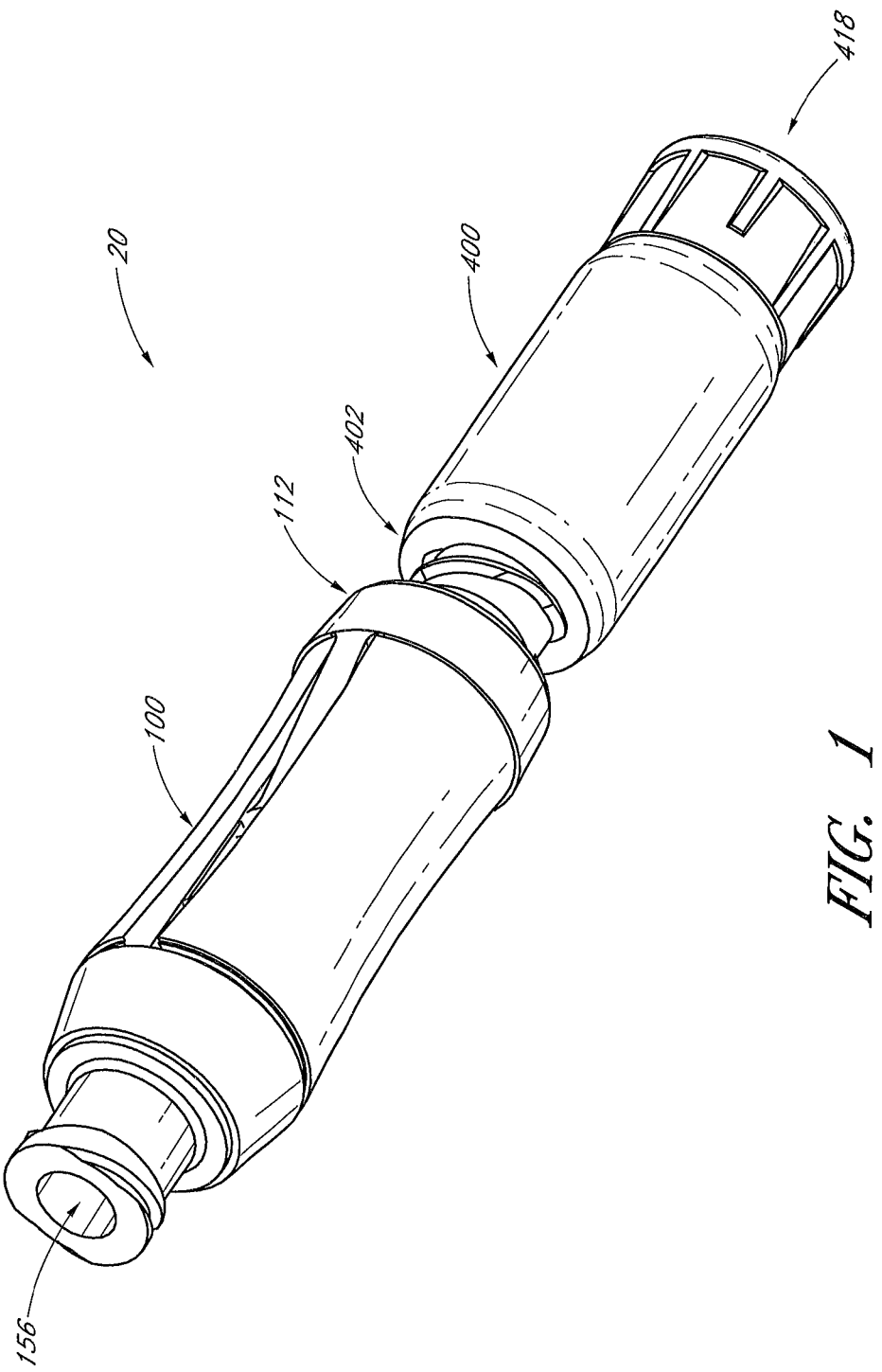
FIG. 1 is a perspective view of an embodiment of a male connector adjacent an embodiment of a female connector.

FIG. 1 illustrates a connector system 20 according to an embodiment of the present application, having a male connector 100 and a female connector 400. A first end 112 of the male connector 100 can releasably couple with a first end 402 of the female connector 400. The first ends 112, 402 are configured such that a fluid passageway 156 of the male connector 100 can be fluidly connected to the fluid passageway 418 of the female connector 400 when the first ends 112, 402 are coupled together. When the male connector 100 and female connector 400 are disconnected, the fluid pathways 156, 418 are closed to fluid transfer therethrough. The coupling between the male connector 100 and female connector 400 is configured so that either or both of the first ends 112, 402 are dry, leak-resistant, and/or substantially or entirely free of residual fluids after the connectors are disconnected. In this context, "substantially free" is used in accordance with its ordinary meaning in this field and applies when any negligible amount of residual fluid remaining on an external surface after disconnection or after closure is small enough as to present no significant functional disadvantages or health hazards in the particular application in which the connector system is employed. In this context, "dry" is used in accordance with its ordinary meaning in this field and applies when there is no fluid residue readily perceptible to the naked eye on an external surface after disconnection or after closure or when there is virtually no fluid residue readily perceptible using standard instruments or testing protocols (e.g., blotting tests, microscopy, or other tests) on an external surface after disconnection or after closure. In some embodiments, the mating interface of the connectors 100, 400 is fluid resistant when the connectors 100, 400 are connected, and both or at least one of the male 100 or female 400 connectors are substantially or entirely free of residual fluid after the connectors are disconnected.

Figure 2A:
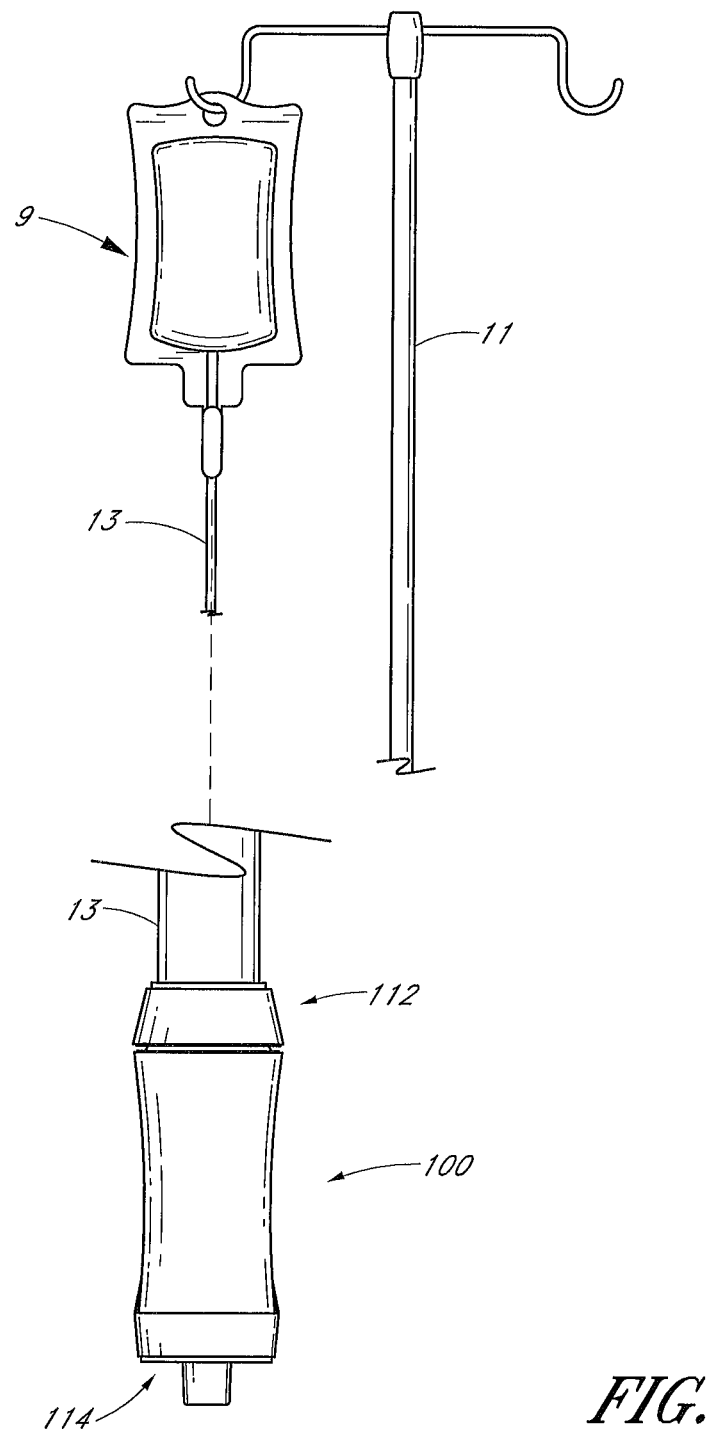
FIG. 2A shows a side view of an embodiment of a male connector attached to tubing configured to receive fluid from a hanging gravity-fed IV bag.

In FIG. 2A, an embodiment of a closable male connector 100 is shown in a closed position. In some embodiments, the male connector 100 can be attached to tubing connected to a gravity-fed IV bag 9 filled with fluid hanging from a pole stand 11. At the bottom of the bag 9, a section of tubing 13 is attached. The opposite end of the tubing 13 can be connected to the first end 112 of the male connector 100. A closing mechanism on the interior of the second end 114 of the male connector 100 can prevent the fluid contained within the bag 9 from flowing through the tubing 13 and leaking out of the male connector 100, as long as the male connector 100 remains in a closed configuration.

Figure 2B:
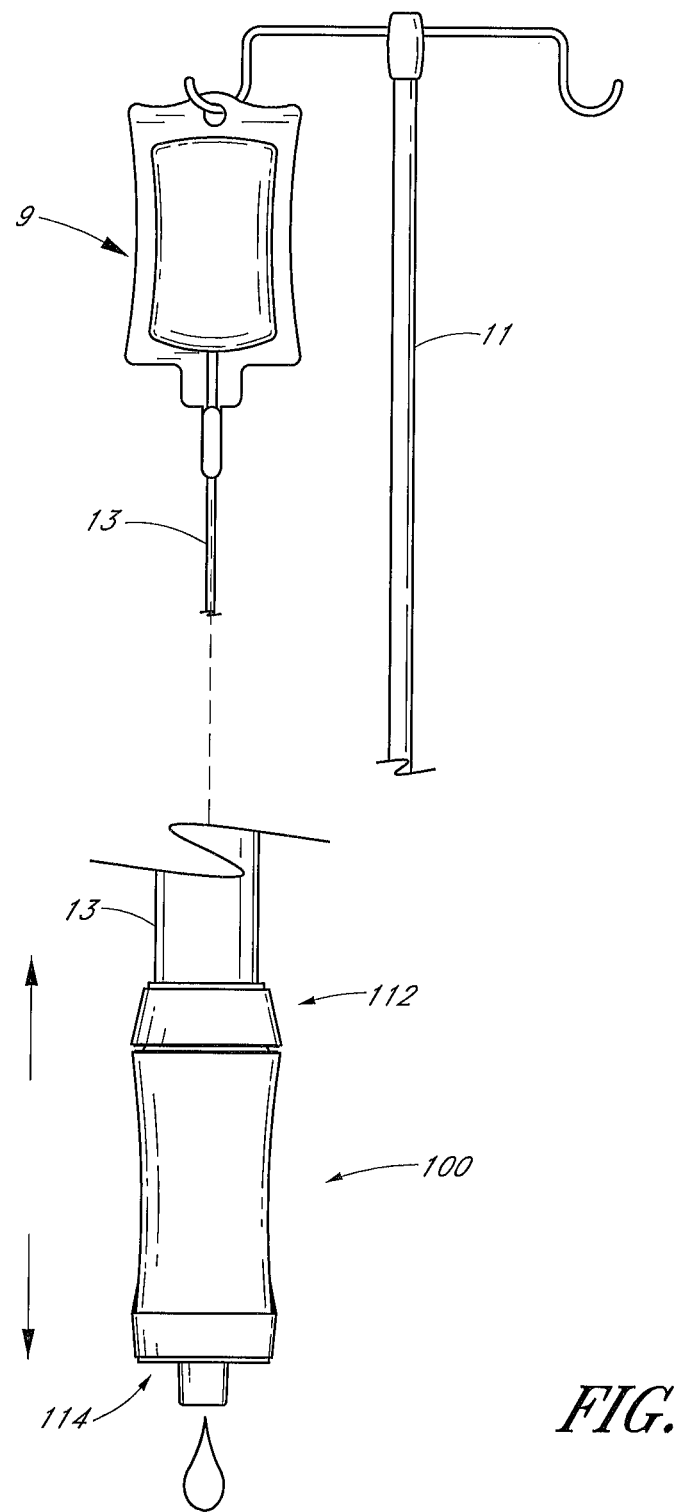
FIG. 2B shows a side view of the male connector of FIG. 1A in an open configuration.

In FIG. 2B, the male connector 100 is illustrated in an open position. Fluid can flow out into the first end 112 of the male connector 100 and out of the second end 114 of the male connector 100. In this example of a male connector 100, a health care provider can move the male connector 100 into this configuration by grasping the second end of the closable male connector 100 with two fingers, grasping the tubing 13 with two other fingers, and gently moving the fingers in opposite directions.

The IV delivery system illustrated in FIGS. 2A and 2B can be easily readied for fluid communication with a patient. In most circumstances, the tubing 13 is filled with air when it is initially connected to the IV bag 9. If the other end of the tubing 13 is connected to a closed connector, as illustrated in FIG. 2A, the air cannot escape and fluid cannot enter the tubing 13 from the IV bag 9. The male connector 100 is therefore manually moved into the opened position until all of the air has been purged through the male connector 100 and the fluid from the IV bag 9 fills the tubing 13 and male connector 100. This procedure is known as "priming." As soon as the fluid line and connector are properly primed, the health care provider can quickly release the opposing forces applied to the second end 114 of the male connector 100 and the tubing 13, and the closing mechanism of the male connector 100 can rapidly stop the flow of fluid through the male connector 100.

Figure 2C:
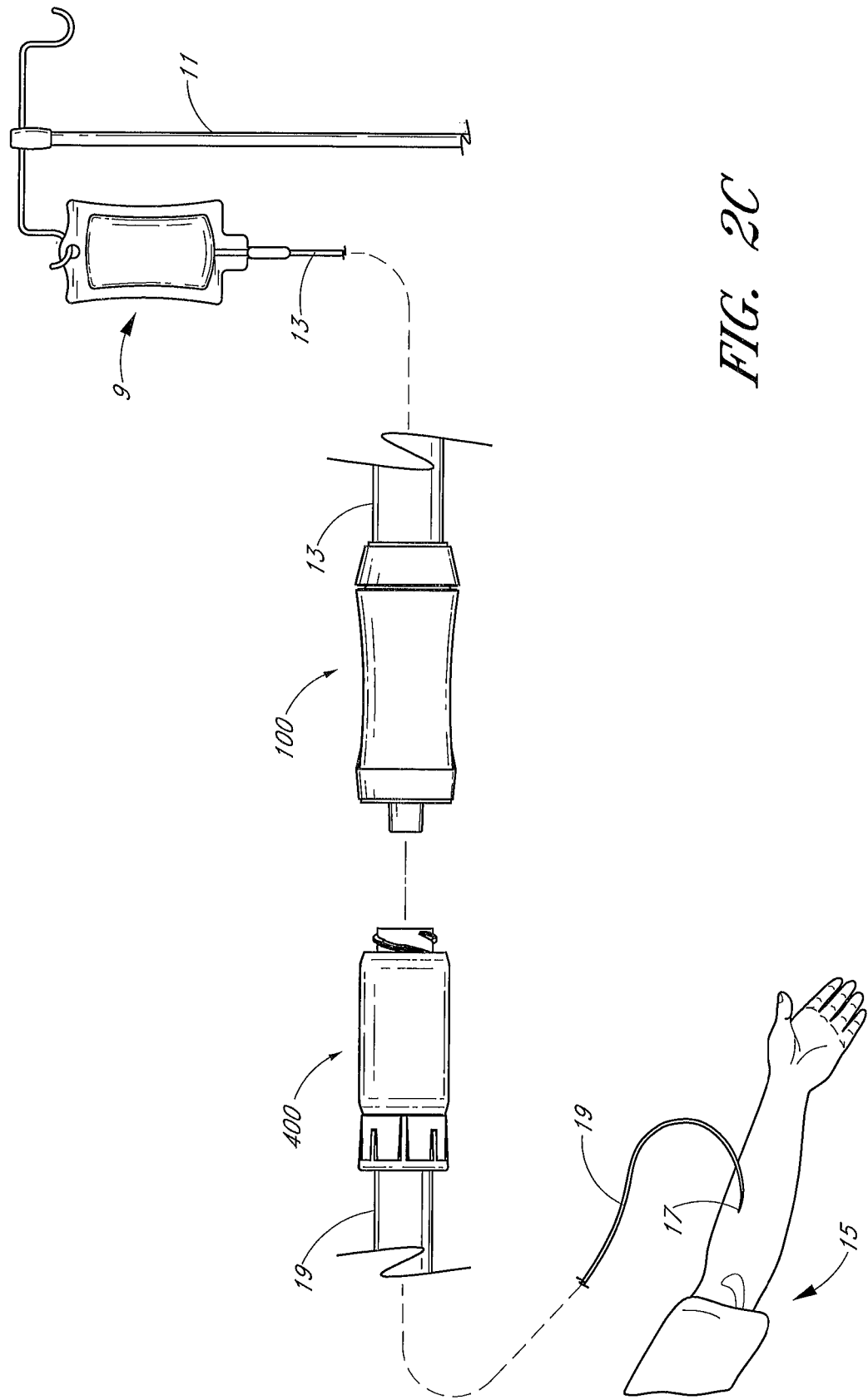
FIG. 2C shows a side view of an embodiment of the connector of FIG. 1A being connected to a female connector attached to tubing inserted into a patient.

Referring now to FIG. 2C, a catheter 17 has been inserted into a patient's arm 15. The catheter 17 penetrates the skin of the arm 15 and is preferably fluidly connected with the patient's bloodstream. The catheter 17 is also connected to a length of medical tubing 19 which can be attached to a female connector 400. The example of a female connector 400 illustrated in FIG. 2C is a version of the Clave® connector manufactured by ICU Medical, Inc., San Clemente, Calif. Various embodiments of a connector of this type are illustrated and described in U.S. Pat. No. 5,685,866, which is incorporated herein by reference in its entirety. It is contemplated that many of the male connector embodiments disclosed herein can be used with other types of female connectors. The tubing 19, catheter 17, and female connector 400 can be primed with fluid using standard procedures. The male connector 100 can be primed as described previously and brought into engagement with the female connector 400. As described in further detail below, when the male connector 100 and female connector 400 are engaged, fluid is permitted to flow from the IV bag 9 into the patient. When the male connector 100 and female connector 400 are disengaged, fluid is once again prevented from flowing out of the second end 114 of the male connector 100. In general, fluid is also prevented from flowing out of the opening in the female connector 400.

Additional embodiments of the connector system, some of which are disclosed herein, can be used in the illustrated fluid system, and in various modifications and alternatives thereof. Other embodiments of connector systems that can be used, in whole or in part, with the present inventions are disclosed in U.S. Pat. No. 7,815,614 and U.S. Patent Application Publication No. 2008/0287920, both of which are incorporated herein by reference in their entireties. Further, it is contemplated that the various embodiments of connectors in accordance with the inventions can be used in a wide variety of additional medical fluid systems. For example, the disclosed connectors can also be used to transfer bodily fluids such as blood, urine, or insulin, nourishing fluids, and/or therapeutic fluids such as fluids used in chemotherapy treatments. The disclosed connectors can also be used to interconnect various other components of fluid transfer systems.

Figure 3:
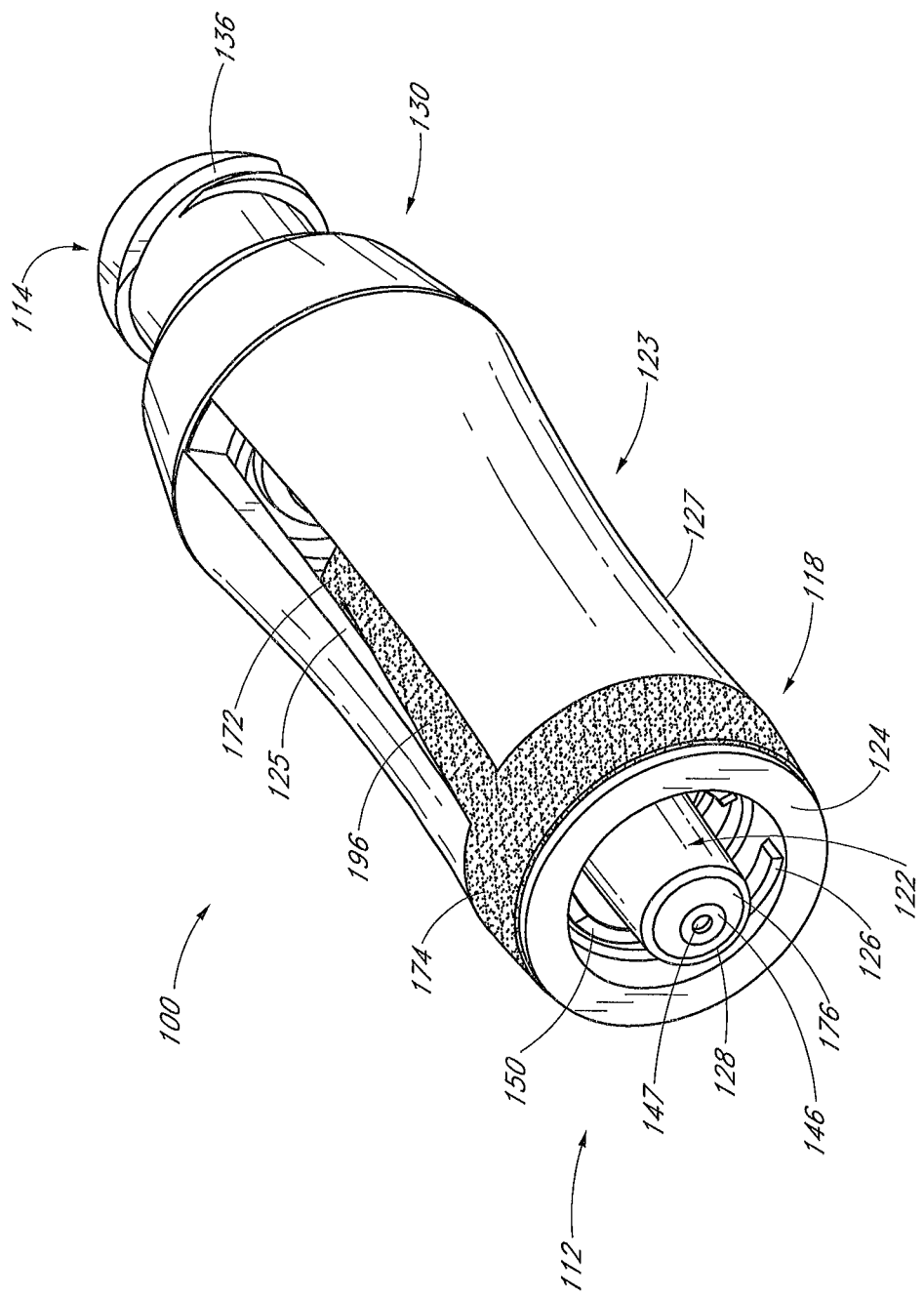
FIG. 3 is a perspective view of an embodiment of a male connector in a closed position.

FIG. 3 illustrates an embodiment of a closeable male connector 100. Any of the components comprising the male connector 100 can comprise any of the configurations, features, components, and/or materials of any of the other male connectors described herein and/or modifications thereof. Additionally, any of the other connectors described herein can comprise any of the configurations, features, and components of the male connector 100. For example, the features relating to preventing or inhibiting disconnection can be used with any suitable medical or other fluid connector.

Figure 4:
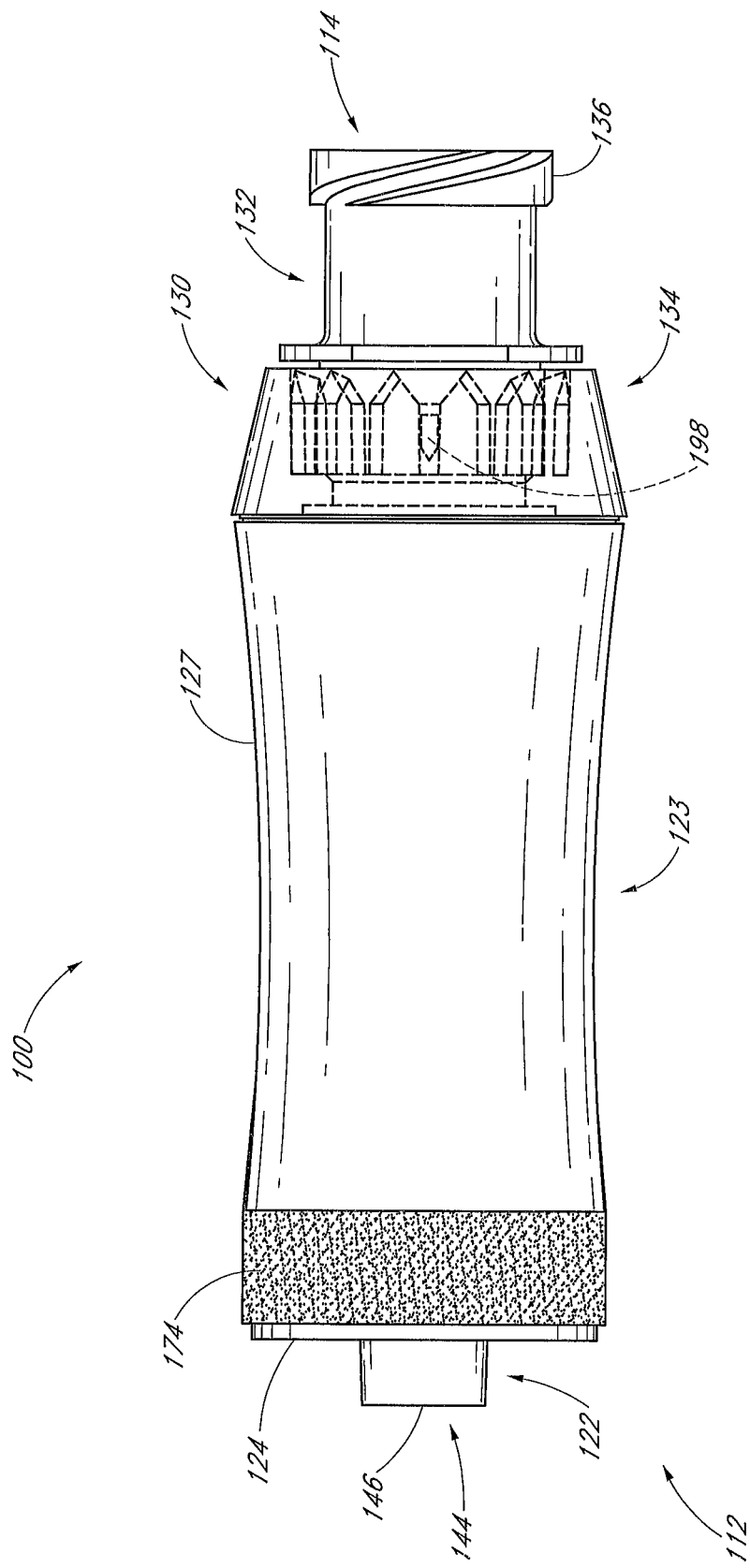
FIG. 4 is a side view of the embodiment of the male connector shown in FIG. 3 again in a closed position, showing certain internal features of the male connector in dashed lines.
Figure 5:
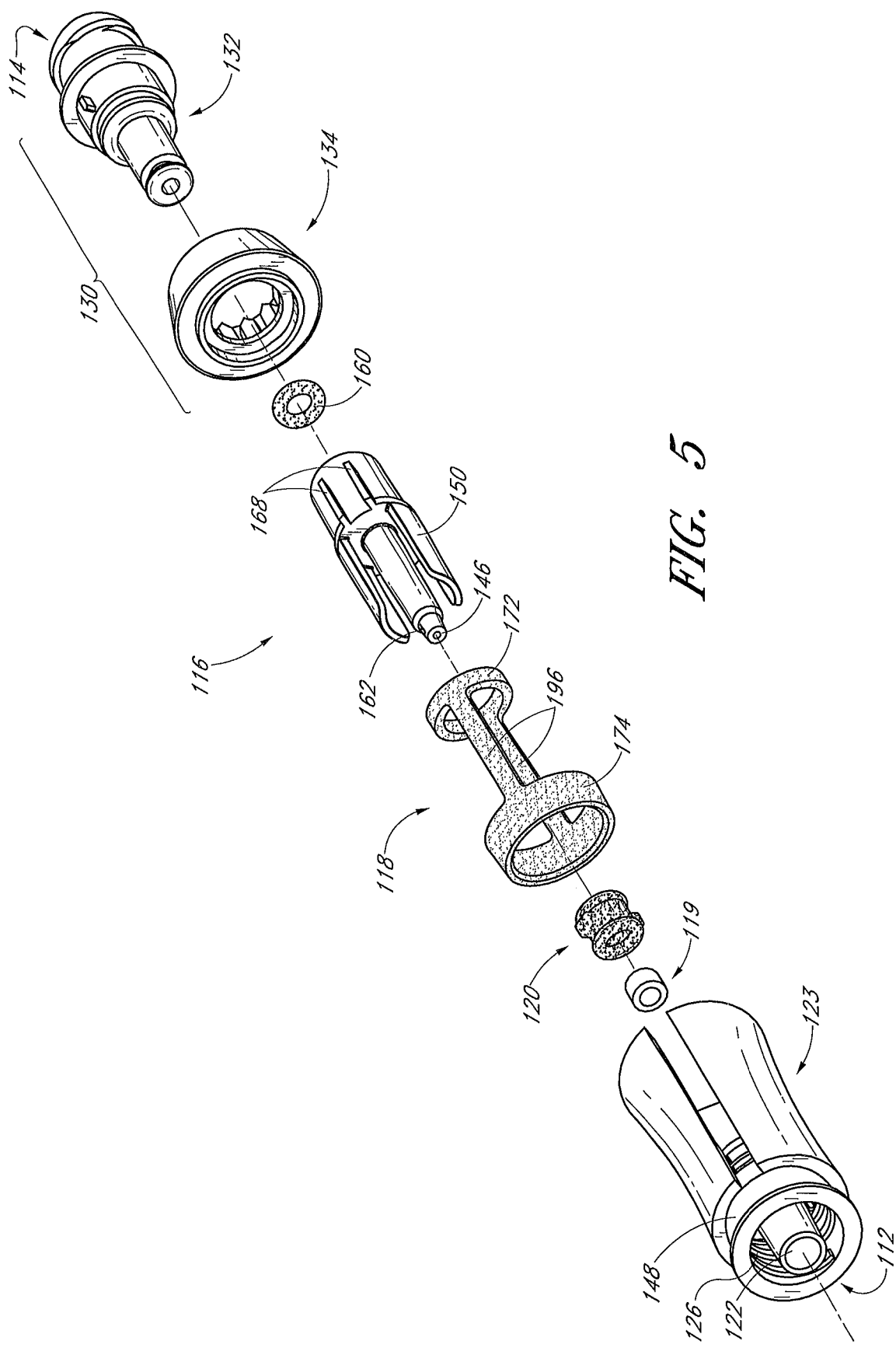
FIG. 5 is an exploded perspective view of the components of the embodiment of the male connector shown in FIG. 3.

FIGS. 3 and 4 are perspective view and side views, respectively, of the closeable male connector 100 in a first or closed position. In FIG. 4, some of the internal features of an embodiment of the closable male connector 100 are shown in phantom lines. FIG. 5 is an exploded perspective view of the components of the embodiment of the closeable male connector 100 shown in FIG. 3. With reference to FIGS. 3 and 4, the closeable male connector 100 can have a first end 112 and a second end 114. The first end 112 can be configured to mate with the female connector 400. In some embodiments, the first end 112 can include a protrusion 144 (see FIG. 7) that is configured to be inserted into the female connector 400. In some embodiments, the first end 112 can comprise a male luer tip 122 and a valve member 116 (see FIGS. 5 and 11). The luer tip 122 and valve member 116 can be supported by a male housing 123. The valve member 116 can be coupled to, and/or biased in a particular position against, the male housing 123 by a resilient member 118.

Figure 6:
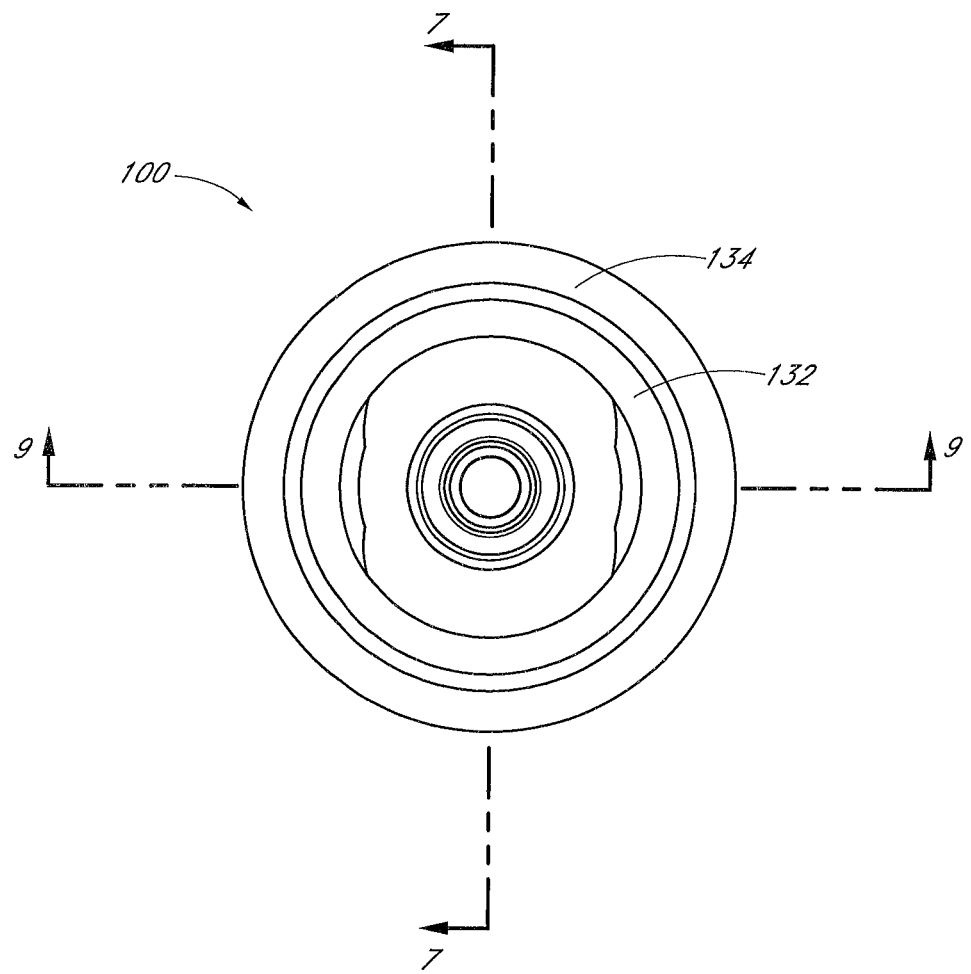
FIG. 6 is a rear view of the female end of the embodiment of the male connector shown in FIG. 3.
Figures 18, 19:
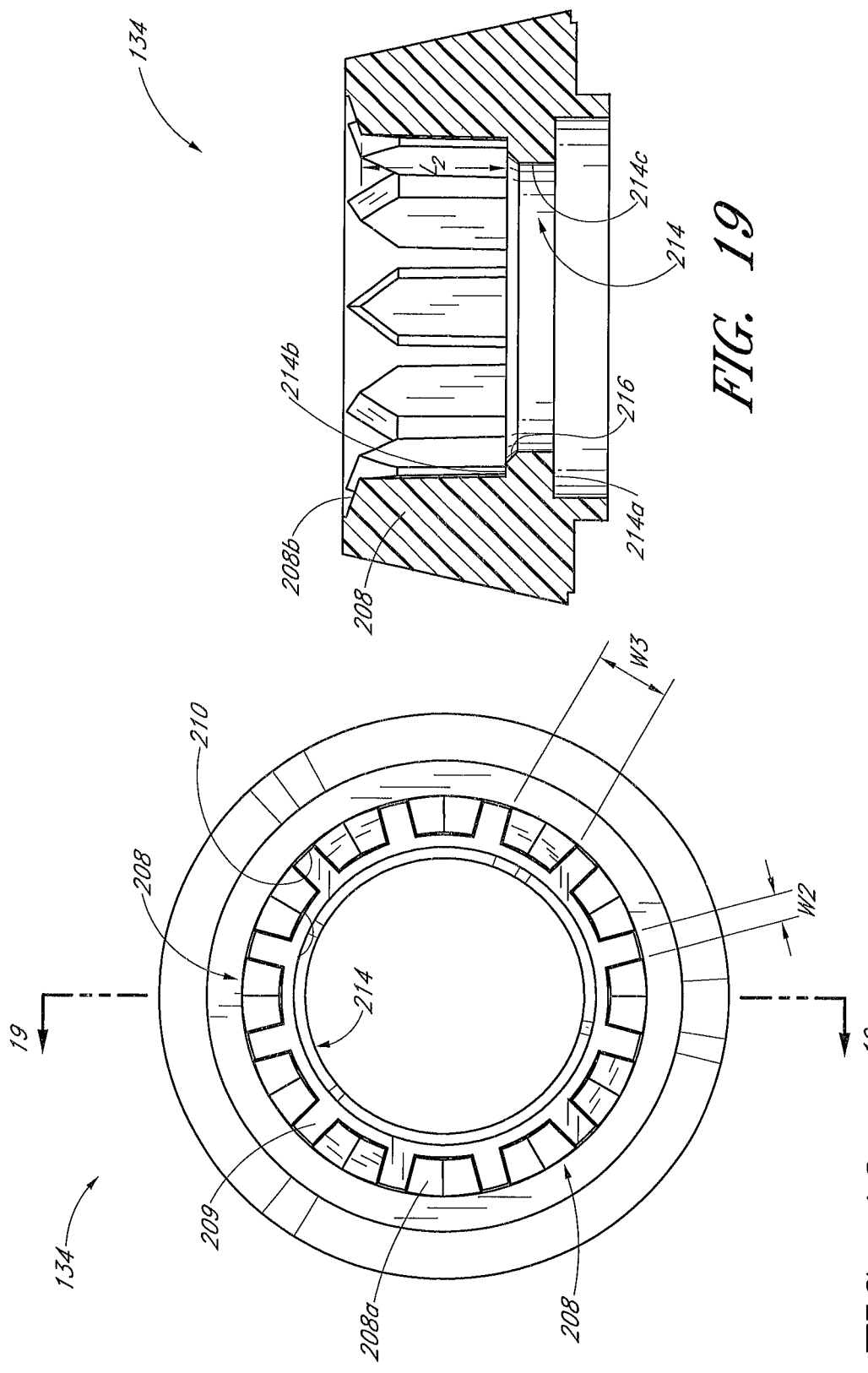
FIG. 18 is a front view of the second cap component shown in FIG. 17.
FIG. 19 is a cross-sectional side view of the second cap component shown in FIG. 17, taken along the line 19-19 in FIG. 18.

An end cap portion 130 (also referred to as an end cap or a female member) can be coupled to the male housing 123 near the second end 114 of the closeable male connector 100. One or more of the components of the end cap portion 130 can be integral or unitary with the housing. With reference to FIGS. 5 and 6, in some embodiments, the end cap 130 can comprise a first cap component 132 (also referred to as a first member) and a second cap component 134 (also referred to as a second member) that can be coupled together. With reference to FIG. 18, in some embodiments, the second cap component 134 can comprise an outer surface 134a that is generally tapered, generally conical, or substantially frusto-conical in shape. However, in some embodiments, the outside surface 134a can be substantially cylindrical or can have any other desired shape. The first cap component 132 can have external threads 136. As mentioned, the embodiment of a closeable male connector 100 shown in FIGS. 3 and 4 is in a closed position. In the closed position, valve member 116 can cooperate with male luer tip 122 to resist, substantially impede, or close the flow of fluid through the male connector 100.

As illustrated in FIG. 3, the male housing 123 can have a shroud 124 surrounding the luer tip 122. The shroud 124 can have a securing or attaching structure, such as internal threads 126. The internal threads 126 and luer tip 122 can form a male luer engagement that conforms to ANSI specifications for male connectors. In some embodiments, the securing or attaching structure 126, and/or the shape of the tip 122, form a male engagement that is non-standard (e.g., it does not conform to ANSI specifications for male luer connectors). The end cap 130 can have a receptacle shape that conforms to ANSI standards for female connectors and can receive a male connecting component of another connector, syringe, or other medical implement. In some embodiments, the end cap 130 is configured to be non-standard (e.g., non-compliant with ANSI standards). In some configurations, the end cap 130 or any other connecting components of any connectors described herein can be configured to engage only with specially-designated, non-standard components (e.g., the tip 122) of other connectors, syringes, or other medical implements, as a safety precaution, to ensure that high-sensitivity medical fluids, such as chemotherapy drugs, are not mistakenly infused through standard IV lines into the wrong patient or into the wrong tubing of the right patient. The external threads 136 can be disposed to threadedly engage corresponding internal threads of a male connecting portion of the coupling component. The luer tip 122 near the first end 112 of the male connector 100 can have a mating surface 128 at the end that is configured to form a substantially leak-free seal with at least a portion of the mating surface 466 of the compressible seal element 460, as explained further below. In the illustrated embodiment, the mating surface 128 is a thin annular ring at the end of the luer tip 122.

The valve member 116 can be at least partially enclosed by the male housing 123. As shown, the male housing 123 can have at least one side opening 125, exposing at least a portion of the valve member 116 and/or allowing at least a portion of the resilient member 118 to pass into the inside of the male housing 123. In some embodiments, male housing 123 can comprise two side openings 125 which can be disposed opposite each other on the sides of the male connector 100. In some embodiments, side opening 125 can extend part way along the male housing 123 (such as in a central region of the male housing 123 as shown) to provide increased strength in the housing near the second end 114. In the illustrated embodiment, the resilient member 118 can be coupled with the valve member 116 near the side openings of the male housing 123. The external outer surface 127 of the housing can be contoured. For example, the external surface of the housing can include a narrower portion near the central region of the male housing 123, or a generally hour-glass-shaped outer surface, or a larger cross-section portion(s) near the ends. These shapes can provide tactile confirmation of the proper placement of a user's fingers on the male connector 100 during use and/or provide a more comfortable gripping surface. In some embodiments, an outward projection or projections (not shown) can be incorporated on the resilient member 118 to provide additional or more effective gripping surfaces on the male connector 100.

Figure 7:
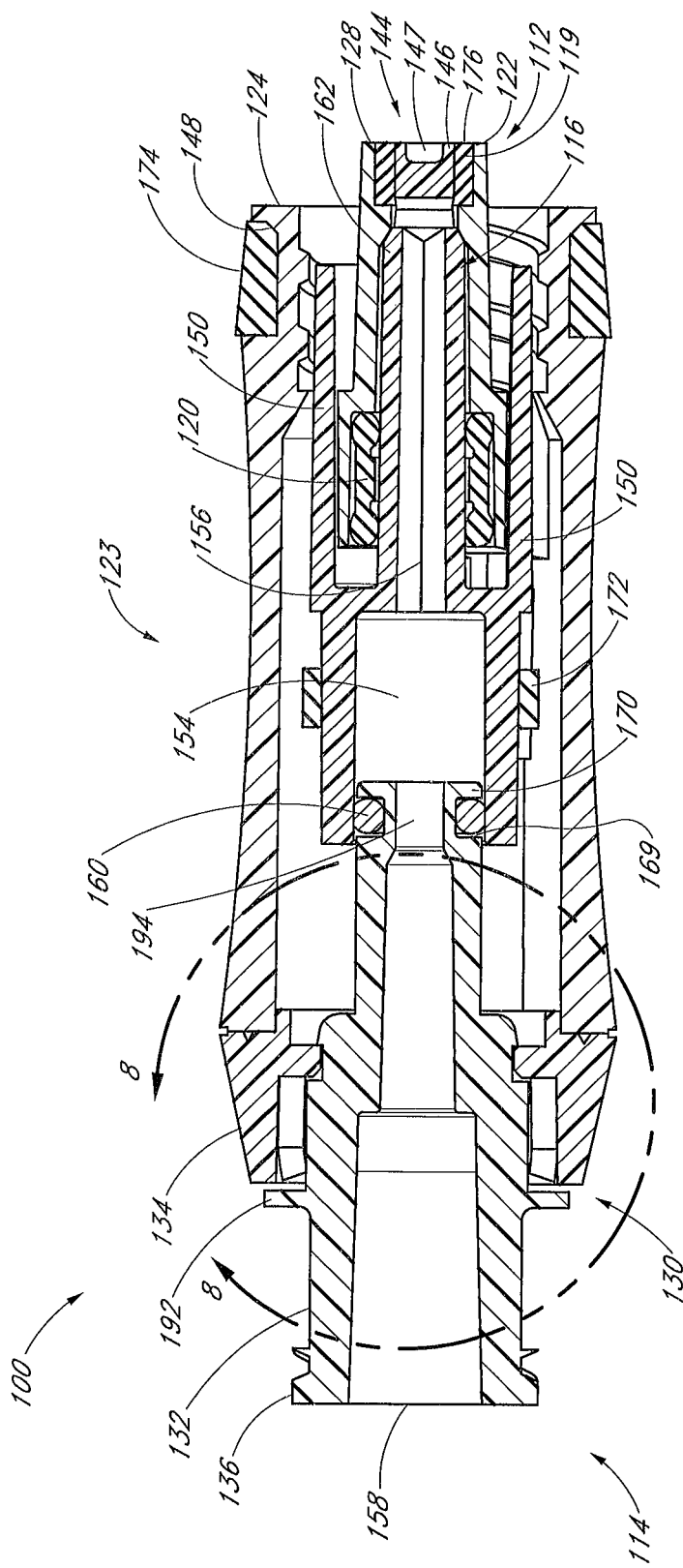
FIG. 7 is a cross-sectional view of the embodiment of the male connector shown in FIG. 3, taken along the line 7-7 in FIG. 6.
Figure 8:
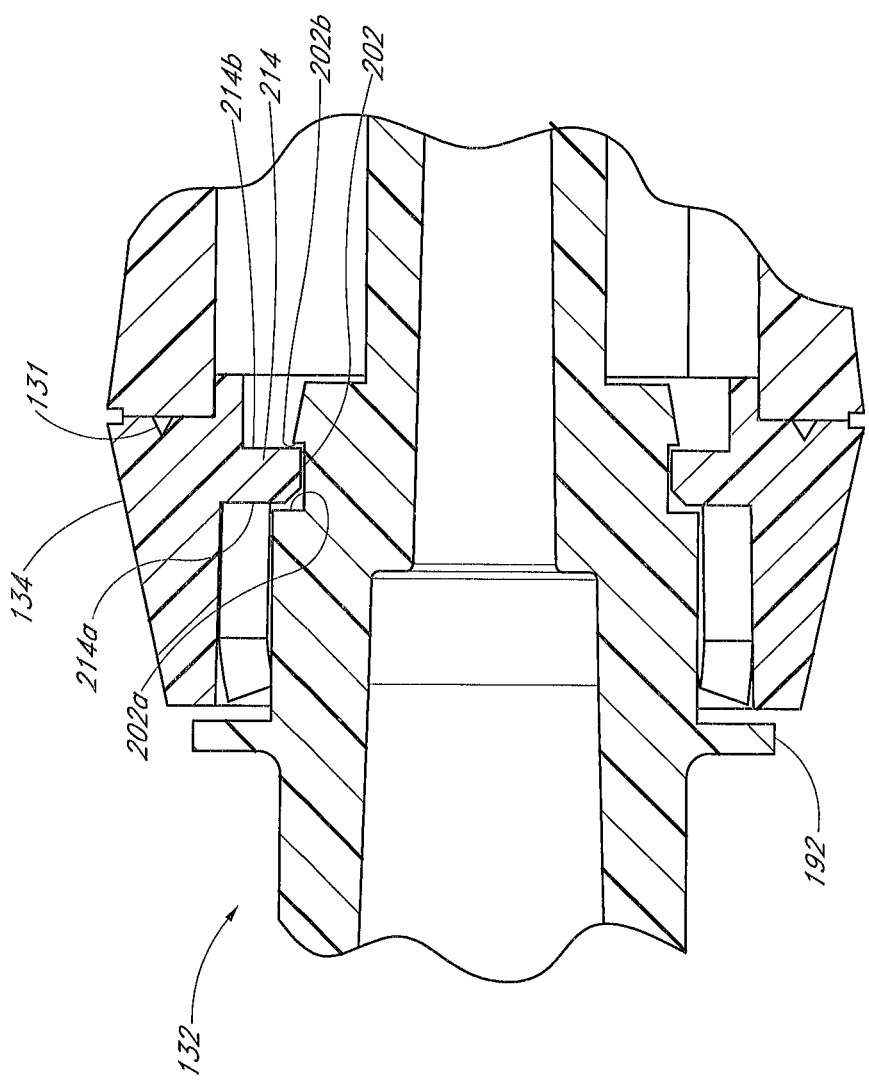
FIG. 8 is an enlarged cross-sectional view of the embodiment of the male connector shown in FIG. 3, taken along curve 8-8 in FIG. 7.
Figure 9:
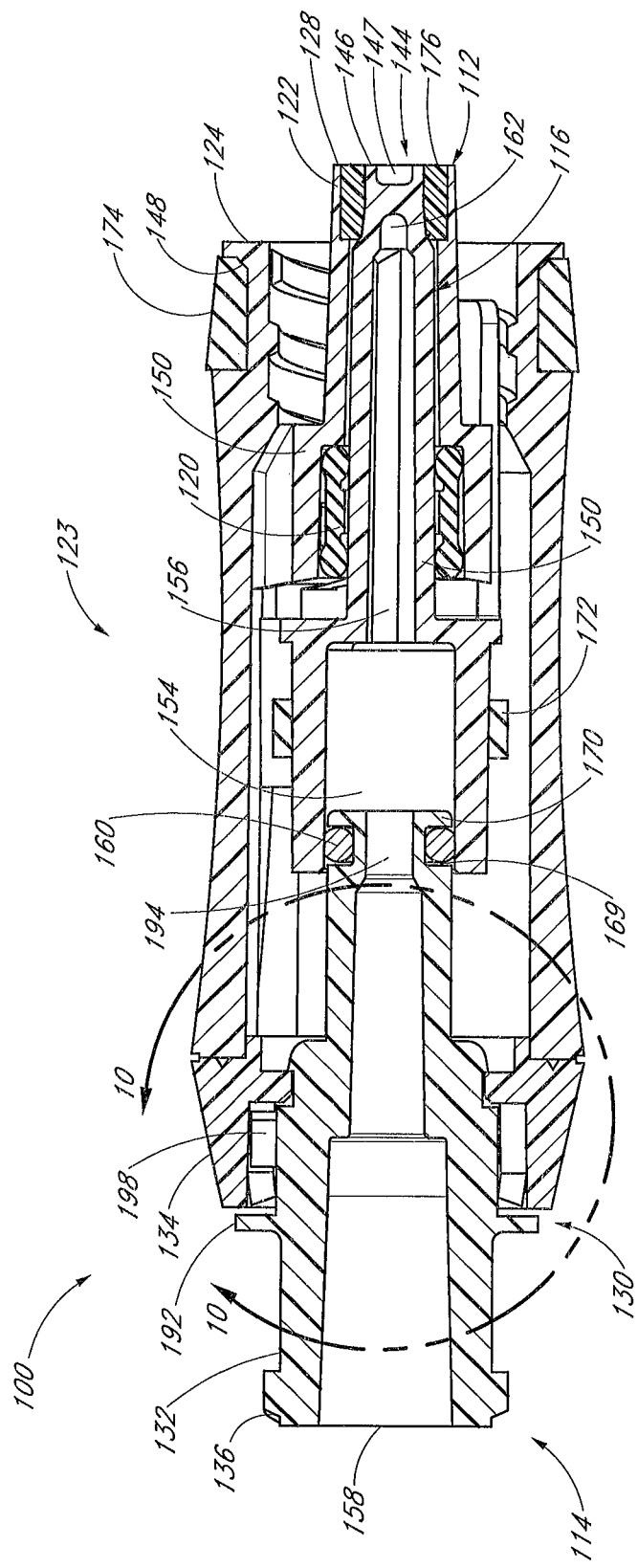
FIG. 9 is a cross-sectional view of the embodiment of the male connector shown in FIG. 3, taken along the line 9-9 in FIG. 6.
Figure 10:
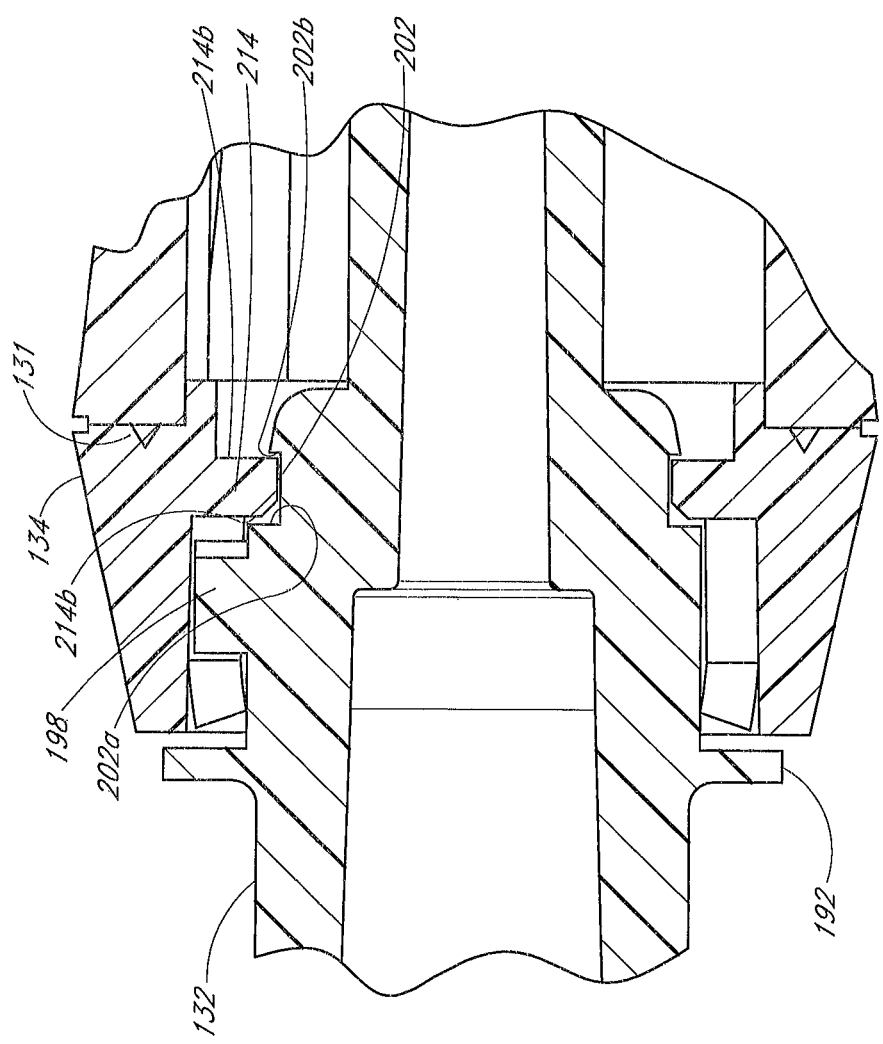
FIG. 10 is an enlarged cross-sectional view of the embodiment of the male connector shown in FIG. 3, taken along curve 10-10 in FIG. 9.
Figure 11:
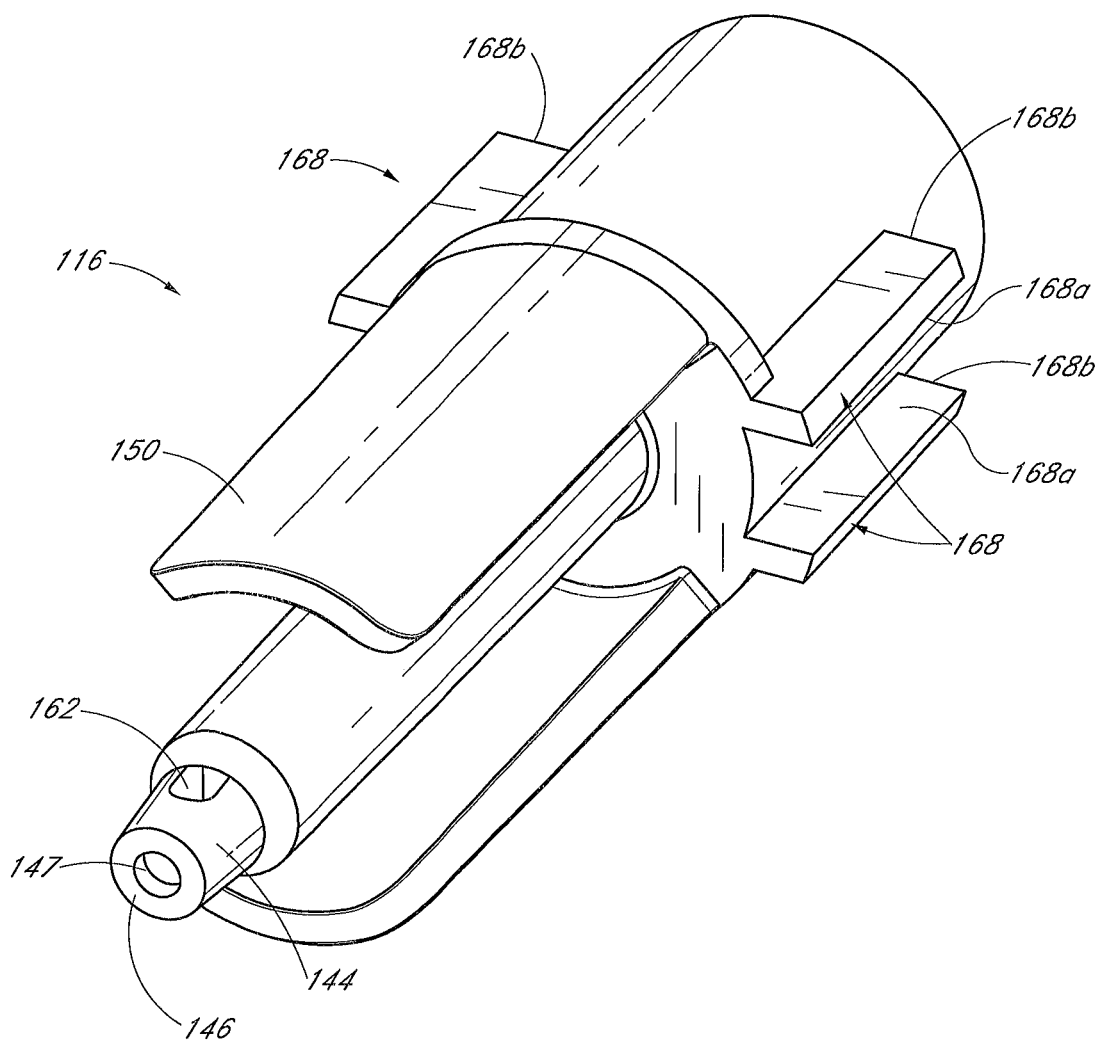
FIG. 11 is a perspective view of an embodiment of a valve member of the male connector shown in FIG. 3.
Figure 12:
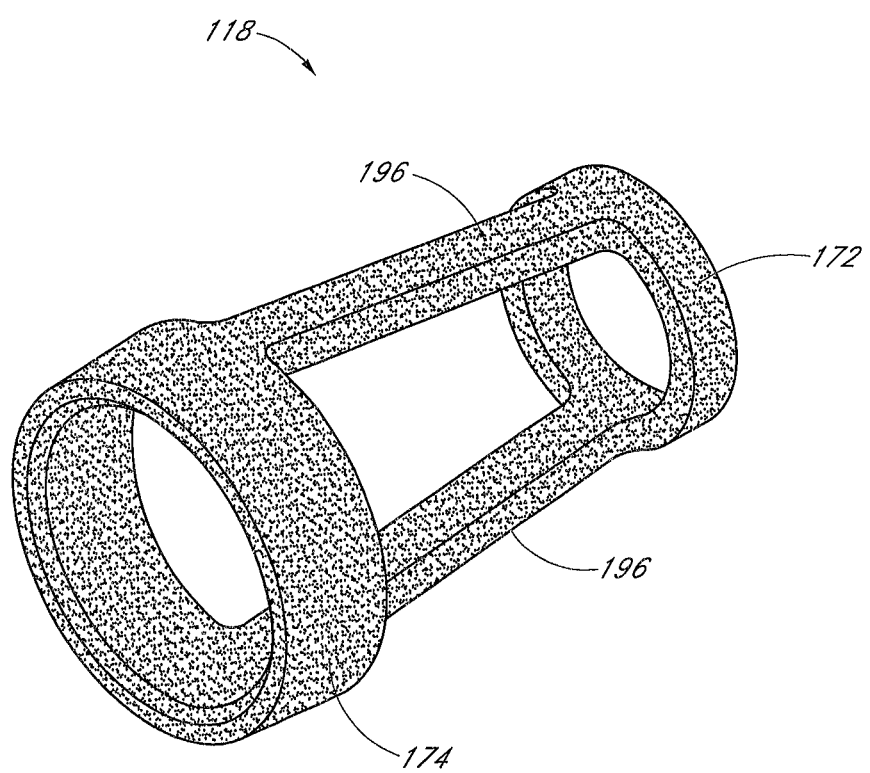
FIG. 12 is a perspective view of an embodiment of a resilient member of the male connector shown in FIG. 3.

As illustrated in FIGS. 7, 9 and 11, the valve member 116 can have a closure end 144 that blocks the flow of fluids through the male connector 100 in the closed configuration. The valve member 116 can have a mating surface 146 that can include a first alignment structure, such as a cavity 147, that can be coupled with a second alignment structure, such as a complementary or corresponding protrusion 490, on a first end 482 of the fluid conduit 480. In the illustrated embodiment, the cavity 147 is a generally circular indentation. In some embodiments, the cavity can have a plurality of different types of shapes, such as rectangular, square or polygonal in shape. In some embodiments, the cavity can be on the first end 482 of the fluid conduit 480 and the protrusion can be disposed on the mating surface 146 of the valve member 116. The cavity 147 and protrusion 490 can help to align and to closely connect the mating surfaces of the male connector 100 with the mating surfaces of the female connector 400. In some embodiments, as illustrated, the first and second alignment structures are each shaped to closely correspond in mating relationship with the other such that virtually no space exists between them when they are in contact with each other. In some embodiments, as illustrated, the first and second alignment structures contact each other in a fluid-resistant manner such that no appreciable amount of fluid can seep in between them during fluid transfer through the connectors.

In some embodiments, as illustrated in FIG. 7, the closure end 144 of the valve member 116 can comprise an outer region, such as a ring portion, that has a smaller surface area than an inner region, such as cavity 147. The outer region can be substantially flat, as shown, followed by a first abrupt or sharp change in shape, such as a first corner portion, and downward side portion, followed by another abrupt or sharp change in shape, such as second corner portion, and then a generally flat bottom portion. At least one of the corner portions can be generally curved or round, which can help with swabability in some embodiments. As illustrated, the multiple changes in shape can be formed by one or more intersections of generally perpendicular surfaces. In some embodiments, one or more changes in shape can further resist, diminish, or inhibit ingress of fluids between the contacting connector ends. Moreover, as illustrated, complementary non-planar mating surfaces, including those with multiple changes in shape, can resist or inhibit lateral movement (e.g., rocking or shifting) between the mating ends during connection, thereby resisting or inhibiting seepage of fluid between such ends.

In some embodiments, either or both of the respective contacting ends of the male luer connector and female connector can comprise a resilient material that is compressible. As the ends come together, either or both can be compressed, thereby further tightening the contact and diminishing any gap between the ends to further resist or inhibit fluid ingress between these mating structures. The resilient material can be applied or positioned at the ends in many ways, including by a coating or overmolding process, a resilient constriction or retraction force, adhesive, solving bonding, etc.

A luer tip seal 119 can be disposed in the interior of the luer tip 122, as illustrated in FIGS. 5, 7 and 9. In the illustrated embodiment, the luer tip seal 119 is disposed between the male housing 123 and the valve member 116 to form a seal between the valve member 116 and the luer tip seal 119 in the closed position. In some embodiments, an interference fit between the valve member 116 and the luer tip seal 119 inhibits fluid from flowing out of the luer tip 122. The luer tip seal 119 can be made of a resilient material that helps forms the seal, as discussed below. In some embodiments, the inner surface of the luer tip seal 119 can be tapered, decreasing in diameter toward the mating surface 176 of the luer tip seal 119. The end of the valve member 116 can also be tapered, decreasing in diameter toward the mating surface 146 of the valve member 116. The substantially matched tapering surfaces of the luer tip seal 119 and the valve member 116 can assist in providing a leak-resistant or leak-free closure of the male connector 100. In some embodiments, the natural outer diameter or cross-section of the mating surface 146 of the valve member 116 can be slightly larger than the natural inner diameter or cross section of the luer tip seal 119 to further diminish or eliminate any gap between them and to increase the sealing effect between them.

As shown in the embodiment of the male connector 100 illustrated in FIG. 3, the mating surface 146 of the valve member 116 is disposed generally flush across the luer tip 122 when the male connector 100 is in the closed position. In some embodiments, as illustrated, the mating surface 146 of the valve member 116 is swabable (e.g., cleansable with a sweeping, rotating, and/or wiping motion of an antiseptic-applying instrument) between or before connections. The mating surface, as illustrated, can be free from substantial gaps, indentations, openings, protrusions that would prevent or unduly interfere with effective motion contact with an antiseptic-applying instrument in order to effectively kill or remove microbes and debris to the degree that is clinically necessary. In some embodiments, the mating surface 146 of the valve member 116 can be configured to extend further beyond the mating surface 128 of the luer tip 122 when the male connector 100 is in the closed position. In some embodiments, the mating surface 146 of the valve member 116 can be recessed within the luer tip 122.

The male connector 100 can be manipulated to a second or open position. In the open position, the valve member 116 can be retracted from the luer tip 122, thereby allowing the fluid in the valve member 116 to exit from the ports 162 and around the closure end 144. As will be described in greater detail below, fluid can pass from the luer receptacle at the second end 114 through the interior of the male connector 100 and exit the valve member 116 when the male connector 100 is in the opened configuration. The fluid can then enter the fluid conduit 480 of the female connector 400, as discussed below. When closed, fluid is impeded or blocked from passing through the male connector 100 under normal operating conditions.

A biasing member can be provided in the form of a resilient member 118. The resilient member 118 can be constructed of a material that elastically deforms. Accordingly, in some embodiments, the male housing 123 can remain coupled to the valve member 116 by the resilient member 118 when the male connector 100 is moved to the open position. In the illustrated embodiment, the change in relative positions of the male housing 123 and valve member 116 can cause at least a portion of the resilient member 118 to extend. Consequently, the resilient member 118 exerts a closing force on the male housing 123 and valve member 116, biased toward returning the male connector 100 to a closed state. The amount of tension carried by the resilient member 118 can be adjusted by varying the distance by which the male housing 123 and valve member 116 are separated, by increasing the thickness of the resilient member 118, and/or by construction of the resilient member 118 from a variety of materials having different elastic properties. In some embodiments, the force required to open the male connector 100 is configured to be high enough to produce an adequate, reliable seal to prevent accidental or unintentional opening. In some embodiments, the difficulty of opening the connector is controlled at least in part by the tension carried by the resilient member 118. In some embodiments, the biasing member 118 can be configured as a spring or other elastic or resilient compressible or expanding member, positioned inside the male housing 123 for biasing the valve member 116 to the closed position. Movement of the male connector 100 to the open position can compress such a biasing member, and movement of the male connector 100 to the closed position can allow the biasing member to expand.

FIGS. 6-11 show the male connector 100 in the first or closed position. As can be seen in these figures, valve member 116 can comprise at least one actuating member, such as a strut 150. In the illustrated embodiment, the valve member 116 comprises two struts 150. In some embodiments, the valve member 116 can comprise more than two struts 150. In some embodiments, each strut 150 can extend from approximately the middle of the valve member 116 toward the first end 112 of the male connector 100. The struts 150 can be located around the luer tip 122, but within the male housing 123, as shown. The struts 150 can be located within the inner diameter of the inner threads 126. In some embodiments, the struts 150 can be positioned to contact with at least a portion of a female luer receptacle as it engages with the luer tip 122.

With reference to FIG. 3, the resilient member 118 can comprise at least a first ring 174 and at least one securing ring 172. In some embodiments, the resilient member 118 can comprise more than one ring 174 or more than one securing ring 172. The first ring 174 can be disposed in an indented groove 148 in the outer surface of the male housing 123 toward the first end 112. The resilient member 118 can be tight enough around the male housing 123 to keep the first ring 174 in place when a force is exerted on the resilient member 118 by a change in relative positions of the male housing 123 and the valve member 116. In some embodiments of the connector, the securing ring or rings 172 can be disposed around the valve member 116 in various patterns, as disclosed in U.S. Patent Application Publication No. 2008/0287920, which is incorporated by reference herein in its entirety.

As illustrated in FIG. 7, a passageway 156 can extend through a portion of the valve member 116 near the first end 112. The passageway 156 can be circular in cross-section, as shown in the illustrated embodiment, or the passageway 156 can have other cross-sectional geometric shapes. The passageway 156 can have at least one port 162 near the first end 112. In the illustrated embodiment, two ports 162 are located on opposite sides of the valve member 116 and are circular, though other locations and shapes can be used.

In the embodiment illustrated in FIG. 7, the male connector 100 is in a closed position, and the relative positions of the valve member 116 and male housing 123 can create a chamber disposed between the passageway 156 and the luer receiver 158. The chamber 154 can be in fluid communication with the passageway 156. The chamber 154 can be wider than the passageway 156, as illustrated. In some embodiments, chamber 154 can have generally the same diameter as the passageway 156. In some embodiments, chamber 154 can have a smaller diameter as compared to the passageway 156. The chamber 154 can also be configured with a non-circular cross-section in any other appropriate shape. The chamber 154 can be bounded on the end toward the second end 114 of the male housing 123 by the plunger 170.

The plunger 170 can be a portion of the end cap 130 extending towards valve member 116. The plunger 170 can have a conduit 194 through it. The conduit 194 can place the chamber 154 in fluid communication with the luer receiver 158. The plunger 170 can have an outer dimension sufficient to substantially close one end of the chamber 154, as shown. In the illustrated embodiment, the plunger 170 can be circular so as to match the geometry of the chamber 154, but other geometric shapes can be used, as appropriate.

The plunger 170 can have an outer dimension that is comparable to the inner dimension of the wall of the valve member 116 creating the chamber 154, but that does not contact such wall to permit relative movement between the components. To inhibit fluid from escaping past the plunger 170, a seal such as an O-ring 160 can be disposed in a groove 169 behind the plunger 170. The O-ring 160 can contact the wall of the valve member 116, as shown, inhibiting fluid from flowing out of the chamber 154. In some embodiments, the plunger 170 is a portion of the end cap 130. The end cap 130 can be fixed with the male housing 123 through sonic welding, an adhesive, or any other suitable method for coupling. In the illustrated embodiment, end cap 130 is coupled to male housing 123 with sonic welds 131. One such weld 131 has a substantially triangular shape as shown, though other shapes are also possible. Accordingly, the plunger 170 can be considered to be in a static position relative to the male housing 123. In some embodiments, the plunger 170 is formed unitarily or integrally with the male housing 123 and the end cap 130 is a separate piece appropriately attached to the male housing 123 such as by sonic welding. In some embodiments, the second cap component 134 can be integrally or unitarily formed with the male housing 123. However, as will be described in greater detail below, the first cap component 132 can also be formed separately as compared to the second cap component 134 or the male housing 123.

As shown in FIG. 7, fluid can flow into the luer receiver 158 and pass to the conduit 194. From the conduit 194, fluid can pass to the chamber 154 and from the chamber 154 into the passageway 156. As shown in the illustrated embodiment, when the male connector 100 is in the closed position, the valve closure end 144 of the valve member 116 can seal the hole in the luer tip 122, preventing fluid from passing out the end of the luer tip 122. Fluid generally can, however, exit the passageway 156 through the ports 162 in the valve member 116. The fluid can reside in the interior of the luer tip 122, but can be prevented from flowing out of the luer tip 122 by the luer tip seal 119 and prevented from flowing back towards the second end 114 on the outside of valve member 116 by a sealing member 120. Accordingly, when the male connector 100 is in the closed position, as illustrated, there generally can be fluid communication between the luer receiver 158 and the interior of the luer tip 122, without permitting fluid to exit the first end 112 of the male connector 100.

The male connector 100 can be changed to the open configuration when mated with a female connector 400. When the first end 402 of the female connector 400 is engaged with the first end 112 of the male connector 100, a coupling portion 446 of the female connector 400 can engage the shroud 124 of the male connector 100. The luer tip 122 at least partially advances into the female connector 400 and the fluid conduit 480 in the female connector 400 engages the valve member 116 to push the valve member 116 toward the second end 114 of the male connector 100. The connection of the male connector 100 and female connector 400 is described in further detail below.

In some embodiments, when the valve member 116 is displaced toward the second end 114, the valve closure end 144 (see FIGS. 7 and 9) separates from the luer tip 122, withdrawing the ports 162 from the luer tip seal 119. Accordingly, fluid can flow around the closure end 144 and into a coupled female connector 400. The sealing member 120 can inhibit fluid from exiting the interior of the luer tip 122 towards the second end 114 of the male connector 100. Accordingly, in the open position, fluid can pass from the luer receiver 158 through the conduit 194, chamber 154, passageway 156, port or ports 162 in the valve member 116, into the interior of the luer tip 122, and into a port in the female connector 400.

As can be seen in the illustrated embodiment, the valve member 116 can be displaced toward the second end 114 of the male connector 100, closer to the end cap 130. Accordingly, the wall portion of the valve member 116 containing the terminus of the passageway 156 is positioned closer to the plunger 170 portion of the end cap 130. The volume of the chamber 154 can be reduced when the male connector 100 is in the open position.

Correspondingly, when the male connector 100 is changing from an open position to a closed position, the volume of the chamber 154 can increase as the valve member 116 shifts toward the first end 112 of the male connector 100. As the volume of the chamber 154 increases, the valve closure end 144 of the valve member 116 advances towards the first end 112 to seal the hole in the luer tip 122. If no additional fluid is introduced into the male connector 100 through the luer receiver 158, the existing fluid in the luer tip 122 can be drawn back through the ports 162, through the passageway 156 towards the chamber 154 by the vacuum effect created when the volume of the chamber 154 increases. In some embodiments, fluid can be inhibited from exiting the hole in the luer tip 122 as the valve closure end 144 moves into place in the hole because the fluid can instead be drawn back to the chamber 154. In some embodiments, fluid near the mating surface 146 of the valve member 116 is encouraged to move into the interior of the male connector 100 rather than remain near the mating surface 146 as the valve member 116 moves toward the first end 112 of the male housing 123, thereby reducing the possibility of exposing the mating surface 146 to the fluid.

If, however, additional fluid is still being introduced into the male connector 100 through the luer receiver 158, the additional fluid can advance to the chamber 154 and collect there as the valve member 116 moves toward the first end 112 to close the luer tip 122. In this case, pressure from the newly-introduced fluid can be inhibited from forcing fluid to flow out the luer tip 122 as the luer tip seal 119 seals the luer tip 122. Accordingly, fluid flow can be permitted through the male connector 100 while a female connector 400 is coupled with the first end 112 of the male connector 100, but inhibited while the female connector 400 is being disengaged and after the female connector 400 has been decoupled.

In some embodiments, it is desirable to inhibit certain medicines from contacting the skin or being inhaled. Thus, the male connector 100 advantageously assists in retaining fluid within the male connector 100 while substantially eliminating remnant fluid on the luer tip 122 when it is being decoupled from a female connector 400 or other connection. Reducing the likelihood of remnant fluid remaining on the luer tip 122 after decoupling results in a corresponding reduction in the chance of exposure of toxic medicine to a user or a patient.

FIGS. 11-15 are perspective views of the valve member 116, the resilient member 118, the sealing member 120, the luer tip seal 119, and the first cap component 132, respectively, of the embodiment of the closeable male connector 100 shown in FIG. 3. As previously discussed, the resilient member 118 can have a first ring 174 that is disposed in the groove 148 of the male housing 123. The resilient member can extend towards the second end 114. The valve member 116 can have a plurality of outwardly-extending protrusions to support the resilient member 118. In particular, with reference to FIG. 10, the valve member 116 can comprise a plurality (e.g., four) notch flanges 168. The securing ring 172 (shown in FIG. 12) can be secured around the valve member 116 and held in place by the notch flanges 168. However, the valve member 116 can comprise any number of flanges in addition to or alternatively to the notch flanges 168 to secure the resilient member 118 or the securing ring 172 of the resilient member 118 to the valve member 116. In the illustrated embodiment, the inside surfaces 168a of the notch flanges 168 can provide lateral support to the bands 1296 of the resilient member 118 so as to prevent the bands 1296 from sliding laterally relative to the valve member 116. Additionally, the aft surfaces 168b of the notch flanges 168 can prevent the securing ring 172 of the resilient member 118 from sliding axially in the direction of the mating surface 146 of the valve member 116. In other embodiments, the resilient member 118 can comprise two or more, or, essentially, any number of rings or bands.

Additionally, with reference to FIG. 11, one or more of the ports 162 can be located near the mating surface 146, or as far back as is practical from the mating surface 146, before the sealing member 120. The ports 162 can be circular, as illustrated, or can have other shapes. The male connector 100 can be adapted to be opened when placed in mating engagement with a female connector 400. For example, the female connector 400 can include an engagement member such as, but not limited to, a complementary surface, a spike or other protrusion which could engage the valve closure face 144 to open the male connector 100. In some embodiments, a manually actuated slider or button can be appropriately configured to open the male connector 100. The struts 150 are shown extending toward the first end 112 of the valve member 116. There can be one, two, or more struts 150. In some embodiments, the male connector 100 does not include struts 150.

Figure 13:
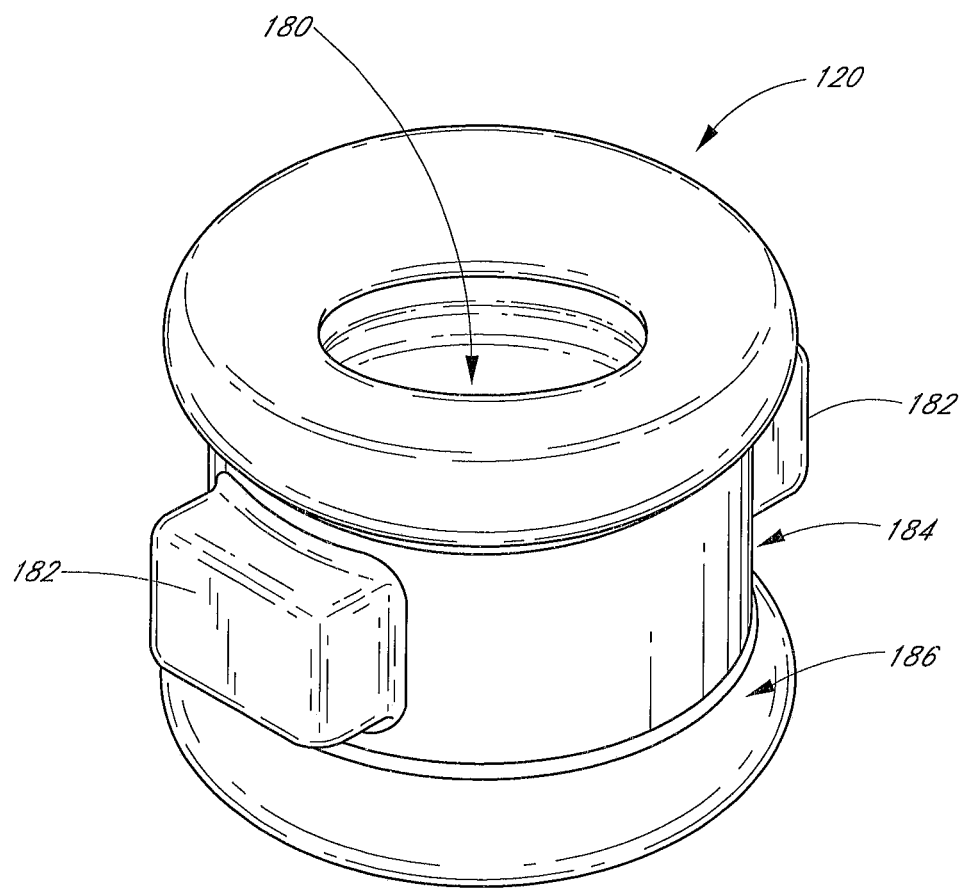
FIG. 13 is a perspective view of an embodiment of a sealing member of the male connector shown in FIG. 3.

Turing now to FIG. 13, the sealing member 120 is described in greater detail. In some embodiments, the sealing member 120 is substantially cylindrical and has a bore 180 extending therethrough. In some embodiments, the sealing member 120 further comprises a pair of generally rectangular protrusions 182 extending from the sidewalls of the cylindrical portion at diametrically opposed positions. The protrusions 182 can have different shapes and/or positions. The sealing member 120 can also have a generally smaller-diameter middle portion 184 surrounded by two rings 186 at either end with larger diameters.

The sealing member 120 can be constructed from a number of different materials. In some embodiments, the sealing member 120 is made from a silicon-based deformable material. Silicon-based deformable materials are among those that form generally fluid-tight closures with plastics and other rigid polymeric materials. In some embodiments, the sealing member 120 can be made from substantially the same material as the resilient member 118.

Figure 14:
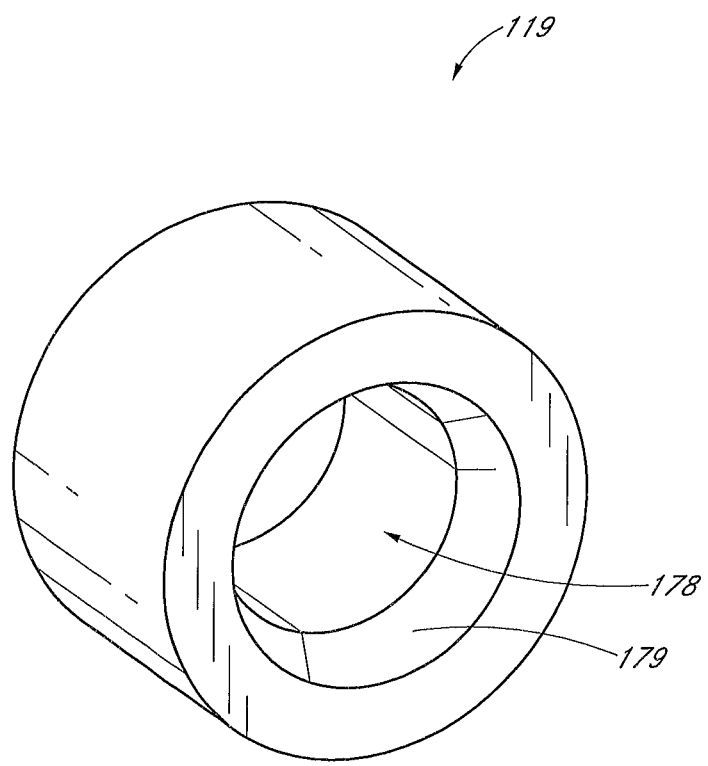
FIG. 14 is a perspective view of an embodiment of a luer tip seal of the male connector shown in FIG. 3.

With reference to FIG. 14, the luer tip seal 119 can be substantially cylindrical with an opening 178 extending along the longitudinal axis of the luer tip seal 119. In the illustrated embodiment, the inner edge opposite the mating surface 176 of the luer tip seal 119 has a chamfered or tapering edge 179. For example, as illustrated, the edge 179 can have a larger diameter or cross-section near the proximal end of the seal 119 than at a position that is spaced distally from the proximal end of the seal 119 such that the wall of the seal 199 is thicker in a distal region than in a proximal region. In some embodiments, as illustrated, the outer diameter or cross section of the seal 119 is generally similar in size to the length (e.g., the distance from the distal to the proximal face) of the seal 119. The luer tip seal 119 can be constructed from a number of different materials. In some embodiments, the luer tip seal 119 can be made from a silicon-based deformable material. Silicon-based deformable materials are among those that form substantially fluid-tight closures with plastics and other rigid polymeric materials. In some embodiments, the luer tip seal 119 can be made from substantially the same material as the resilient member 118.

Figure 15:
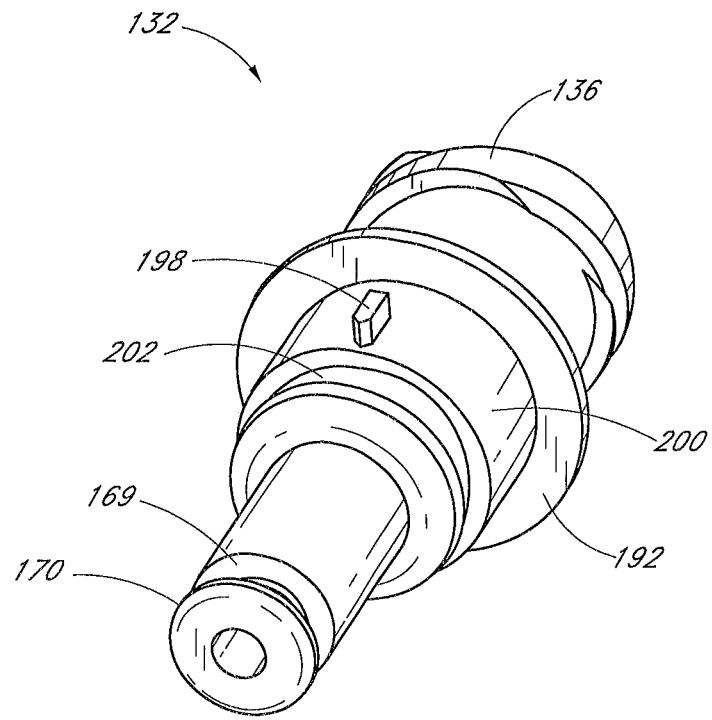
FIG. 15 a perspective view of an embodiment of a first cap component of the male connector shown in FIG. 3.
Figure 16:
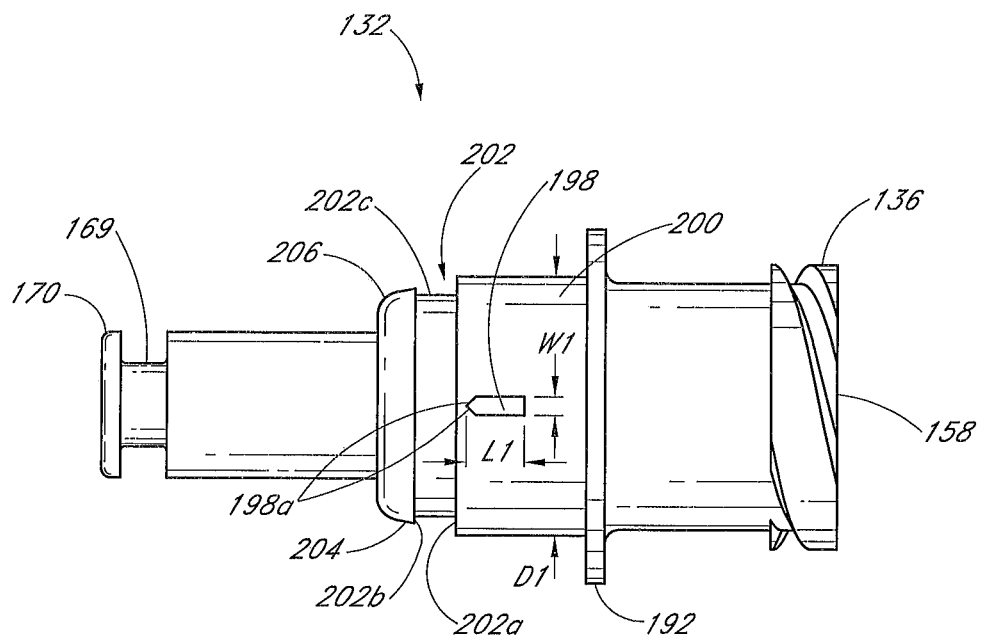
FIG. 16 is a side view of the first cap component shown in FIG. 15.

With reference to FIGS. 15 and 16, the first cap component 132 can have a covering portion 192 shaped and configured to substantially cover and, in some embodiments, seal a portion of the second end 114 of the male housing 123. The luer receiver 158 can extend away from the covering portion 192. The luer receiver 158 can be appropriately sized to couple with a male luer portion (see, e.g. FIG. 20A) conforming to ANSI standards for luer devices. The luer receiver 158 can have external threads 136 to engage the male luer portion, as shown. In some embodiments, raised tabs or other protrusions can be used to engage the male luer portion.

In some embodiments, the plunger 170 is at the generally opposite region of a portion of the first cap component 132 from the covering portion 192. The plunger 170 can be sized and configured to substantially seal the chamber 154 within the valve member 116. An indentation or slot 169 between the covering portion 192 and the plunger 170 can be sized and shaped to accommodate a seal such as an O-ring 160. Additionally, in some embodiments such as that illustrated in FIGS. 15 and 16, the first cap component 132 can comprise a pair of protrusions or tabs 198 (also referred to herein as locking elements or engaging surfaces) protruding radially outward from the outer surface 200. In some embodiments, the first cap component 132 can comprise a pair of tabs 198 arranged so as to be diametrically opposing one another. In some embodiments, the first cap component 132 can comprise only one tab 198 protruding from the surface 200. In some embodiments, the first cap component 132 can comprise more than two tabs 198 protruding from the surface 200. As will be described in greater detail below, the tabs 198 can engage or interlock with complementary tabs or protrusions on the second cap component 134 to prevent, at least temporarily, the first cap component 132 from rotating relative to the second cap component 134 when the two components are assembled together, as shown in FIG. 4 or 9.

Additionally the first cap component 132 can comprise an annular groove 202 which, as will be described in greater detail below, can interact with complementary features on the second cap component 134 to axially restrain the movement of the first cap component 132 with respect to the second cap component 134. Further, as illustrated in FIG. 16, the first cap component 132 can also comprise an angled or tapered surface 204 and a rounded surface 206 both positioned between the annular groove 202 and the plunger 170. As will be described in greater detailed below, the angled or tapered surface 204 and rounded surface 206 can facilitate the coupling or assembly of the first cap component 132 to the second cap component 134. In some embodiments, the first cap component 132 can comprise only an angled or tapered surface 204 or a rounded surface 206. In other embodiments, the first cap component 132 can be configured so as to not comprise either of those two features. In some embodiments, the first cap component 132 and/or the second cap component 134 can comprise any suitable features, lubricants, or materials to facilitate the coupling of the first cap component 132 and the second cap component 134, or, as will be discussed, to facilitate the rotation of the first cap component 132 relative to the second cap component 134.

In the illustrated embodiment, the tabs 198 are substantially rectangular in cross-section. However, the geometry of the tabs 198 is not so limited. The tabs 198 can comprise any suitable or desired cross-sectional geometry, such as, but not limited to, a square, circular, or ovular geometry. In some embodiments, for example, a plurality of tabs 198 each defining a circular cross-section can be arranged in a linear fashion along a side of the first cap component 132.

Figure 17:
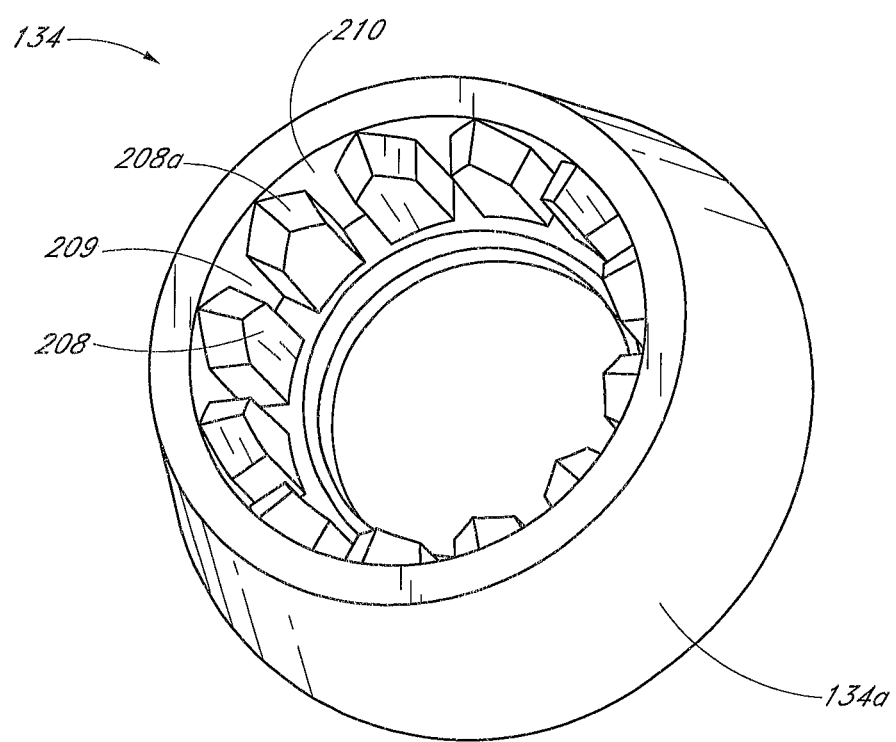
FIG. 17 is a perspective view of an embodiment of a second cap component of the male connector shown in FIG. 3.

With reference to FIGS. 16-17, the second cap component 134 can comprise an array of protrusions or tabs 208 (also referred to herein as locking elements or engaging surfaces) which protrude, in some embodiments, in a radially inward direction from the inside surface 210 of the second cap component 134, so as to create a radial array of depressions or channels 209. With reference to FIG. 16, the first cap component 132 can be assembled with the second cap component 134 such that each of the one or more tabs 198 formed on the first cap component 132 is positioned in one or more of the depressions or channels 209 between each of the plurality of tabs 208 formed on the second cap component 134. Accordingly, each of the one or more tabs 198 can be sized and configured such that the approximate width (represented by "W1" in FIG. 16) of each of the one or more tabs 198 formed on the surface 200 of the first cap component 132 is less than the approximate width (represented by "W2" in FIG. 18) of the depressions or channels 209 between each of the tabs 208 formed on the second cap component 134.

In the illustrated embodiment, the tabs 208 are substantially rectangular in cross-section. However, the geometry of the tabs 208 is not so limited. The tabs 208 can comprise any suitable or desired cross-sectional geometry, such as but not limited to a square, circular, or ovular geometry.

Additionally, each of the one or more tabs 198 on the first cap component 132 can be configured to shear or break off before any of the plurality of tabs 208 on the second cap component 134 shear or break off. Accordingly, in some embodiments, each of the one or more tabs 198 on the first cap component 132 can be configured so that the minimum approximate amount of force or torque required to shear or break each tab 198 away from the surface 200 on the first cap component 132 is less than the minimum approximate amount of force required to shear or break any of the tabs 208 away from the inside surface 210 of the second cap component 134. In some embodiments, the minimum amount of force required to shear or break each tab 198 away from the surface 200 on the first cap component 132 can be significantly less than the minimum amount of force required to shear or break any of the tabs 208 away from the inside surface 210 of the second cap component 134.

In some embodiments, the tabs or protrusions that are configured to shear or break off can be formed on the second cap component 134 instead of being formed on the first cap component 132, as described above. In other words, in some embodiments, one or more tabs formed on the second cap component 134 can be sized and/or configured the same as any of the tabs 198 described above, and one or more tabs formed on the first cap component 132 can be sized and/or configured the same as any of the tabs 208 described herein such that the tabs formed on the second cap component 134 shear or break off before any of the tabs formed on the first cap component 132. In some embodiments, the configurations of the tabs 198 in the tabs 208 described above can be generally reversed. In general, other complementary engaging surfaces may be employed. In the illustrated embodiments, each of the components includes radially projecting tabs. In some embodiments, one or the other of the components may include appropriately sized slots for accommodating a radially projecting tab.

In some embodiments, the approximate minimum amount of force required to shear or break each tab 198 away from the surface 200 on the first cap component 132 can be less than or equal to approximately one-third of the approximate minimum amount of force required to shear or break each of the tabs 208 away from the inside surface 210 of the second cap component 134. In some embodiments, the approximate minimum amount of force required to shear or break each tab 198 away from the surface 200 on the first cap component 132 can be between approximately one-third and one-half of the minimum approximate amount of force required to shear or break any of the tabs 208 away from the inside surface 210 of the second cap component 134.

In the illustrated embodiment, where two tabs 198 are formed on the surface 200, the amount of torque required to shear or break both of the two tabs 198 away from the surface 200 on the first cap component 132 can be approximately 4 in-lbs. or more.

In some embodiments, the amount of torque required to shear or break both of the two tabs 198 away from the surface 200 on the first cap component 132 can be approximately 3 in-lbs. or more. In some embodiments, the amount of torque required to shear or break both of the two tabs 198 away from the surface 200 on the first cap component 132 can be approximately 5 in-lbs. or more.

With reference to FIG. 16, the cross-sectional area of each of the tabs 198 can be based on the approximate length (represented by "L1" in FIG. 16) and approximate width (represented by "W1" in FIG. 16) of each of the one or more tabs 198 at the surface 200 of the first cap component 132. The tab 198 can be used to provide a band around the surface 200 calculated by multiplying the length L1 of the tab 198 by the circumference of the surface 200. In some embodiments, where each of the one or more tabs 198 is configured to shear away from the surface 200 of the first cap component 132 when the desired level of torque is reached, the aggregate cross-sectional area of the tab(s) 198 can be substantially smaller than the band around the surface 200.

In some embodiments, the ratio of the aggregate cross-sectional area of all of the one or more tabs 198 to the value of the outside diameter (represented by "D1" in FIG. 16) of the surface 200 of the first cap component 132 upon which each of the one or more tabs 198 can be formed or attached can be approximately 1 to 46 or higher. The cross-sectional area of each of the tabs 198 can be any suitable value that results in each of the one or more tabs 198 shearing away from the surface 200 when the desired level of torque is reached. For example, in some embodiments, the ratio can be between approximately 1 to 60 and approximately 1 to 30. In some embodiments, the ratio can be between approximately 1 to 50 and approximately 1 to 40.

In some embodiments, as in the illustrated embodiment, where each of the one or more tabs 198 is configured to shear away from the surface 200 of the first cap component 132 when the desired level of torque is reached, the width W1 of each of the one or more tabs 198 can be substantially smaller than the outside diameter D1 of the surface 200 of the first cap component 132 upon which each of the one or more tabs 198 can be formed or attached. The width W1 of each of the tabs 198 can be any suitable value that results in each of the one or more tabs 198 shearing away from the surface 200 when the desired level of torque is reached. For example, the one or more tabs 198 can be comparable in size or smaller than the diameter of the fluid opening in plunger 170 and/or the luer receiver 158. In some embodiments, the ratio of the aggregate width of the tabs 198 to the outside diameter D1 can be approximately 1 to 15 or higher. In some embodiments, the ratio can be between approximately 1 to 25 and approximately 1 to 10. In some embodiments, the ratio can be between approximately 1 to 16 and approximately 1 to 13. In some embodiments, multiple tabs 198 can be used wherein the widths W1 of each tab are different, but the aggregate widths are calculated to reach the desired level of torque to shear the tabs off.

Similarly, in some embodiments, as in the illustrated embodiment, where each of the one or more tabs 198 is configured to shear away from the surface 200 of the first cap component 132 when the desired level of torque is reached, the length L1 of each of the one or more tabs 198 can be substantially smaller than the outside diameter D1 of the surface 200 of the first cap component 132 upon which each of the one or more tabs 198 can be formed or attached. The length L1 of each of the tabs 198 can be any suitable value that results in each of the one or more tabs 198 shearing away from the surface 200 when the desired level of torque is reached. In some embodiments, the ratio of the aggregate length of the tabs 198 to the outside diameter D1 can be approximately 1 to 4 or higher. In some embodiments, the ratio can be between approximately 1 to 10 and approximately 1 to 2. In some embodiments, the ratio can be between approximately 1 to 5 and approximately 1 to 3. In some embodiments, multiple tabs 198 can be used wherein the widths W1 of each tab are different, but the aggregate widths are calculated to reach the desired level of torque to shear the tabs off.

In some embodiments, one or more tabs 198 can be configured such that the approximate width W1 of each of the one or more tabs 198 can be significantly less than the approximate width (represented by "W3" in FIG. 18) of one or more of the plurality of tabs 208 formed on the inside surface 210 of the second cap component 134 to ensure that the one or more tabs 198 shear or break before any of the tabs 208. Accordingly, in some embodiments, the approximate width W1 of each of the one or more tabs 198 can be between approximately one-third or less and approximately one-half or less of the approximate width W3 of each of the plurality of tabs 208. Moreover, in some embodiments, there are many more tabs 208 on the second cap component 134 than tabs 198 on the first cap component 132, thereby requiring greater torque to shear off the greater number of tabs 208 on the second cap component 134.

In some embodiments, the material selected to form each of the one or more tabs 198 can be the same as or different as compared to the material selected to form each of the one or more tabs 208. The strength of the material chosen to form the tabs 198, 208 can affect the amount of torque required to shear the tabs 198, 208. Accordingly, in some embodiments, the tab 198, 208 that is desired to be sheared can be formed from a weaker, softer, or lower durometer material as compared to the material used to form the tab 198, 208 that is desired to remain intact. For example, in the illustrated embodiment, it is desired that the tab 198 be sheared away from the surface 200 on the first cap component 132 when the desired level of torque between the first cap component 132 and the second cap component 134 is achieved. Thus, in the illustrated embodiment, the tab 198 can be formed from the weaker material as compared to the material used to form each of the tabs 208. However, because the cross-sectional area of the tabs 198, 208 can also affect the amount of torque required to shear the tabs 198, 208, the material selected to form each of the tabs 198, 208 can be the same.

In some embodiments, as in the illustrated embodiment, as mentioned, ensuring that the one or more tabs 198 shear or break before any of the tabs 208 can be achieved by also configuring each of the one or more tabs 198 such that the approximate cross-sectional area of each of the one or more tabs 198 is less than the cross-sectional area of each of the tabs 208 that is adjacent to and, hence, will contact each of the one or more tabs 198. With reference to FIG. 16, the cross-sectional area of each of the tabs 198 is based on the length (represented by "L1" in FIG. 16) and width (represented by "W1" in FIG. 16) of each of the one or more tabs 198. Similarly, width reference to FIGS. 18 and 19, the cross-sectional area of each of the tabs 208 is based on the length (represented by "L2" in FIG. 19) and width (represented by "W3" in FIG. 18) of each of the one or more tabs 208.

In some embodiments, without consideration of material differences, where the one or more tabs 198 are designed to shear before any of the tabs 208, cross-sectional area of each of the one or more tabs 198 can be substantially smaller than the cross-section of each of the one or more tabs 208. The ratio of the cross-sectional area of each of the one or more tabs 198 relative to the cross-sectional area of each of the one or more tabs 208 can be significantly less than one. For example, in some embodiments, as in the illustrated embodiment, the ratio can be approximately 1 to 14 or higher. In some embodiments, the ratio can be between approximately 1 to 25 and approximately 1 to 10. In some embodiments, the ratio can be between approximately 1 to 16 and 1 to 12.

Further, in some embodiments, as in the illustrated embodiment, the approximate length (represented by "L1" in FIG. 16) of each of the one or more tabs 198 is significantly less than the approximate length (represented by "L2" in FIG. 19) of each of the plurality of tabs 208 formed on the inside surface 210 of the second cap component 134. Accordingly, in some embodiments, the approximate length L1 of each of the one or more tabs 198 can be between approximately one-third or less and approximately two-thirds of the approximate length L2 of each of the plurality of tabs 208.

In some embodiments, the second cap component 134 can comprise depressions or channels into which each of the one or more tabs 198 formed on the first cap component 132 can be inserted when the first cap component 132 is coupled to the second cap component 134. In some embodiments, the number of depressions or channels formed on the second cap component 134 can be equal to the number of tabs 198 formed on the first cap component 132. In some embodiments, the number of depressions or channels formed on the second cap component 134 can be greater than the number of tabs 198 formed on the first cap component 132.

Figure 20A:
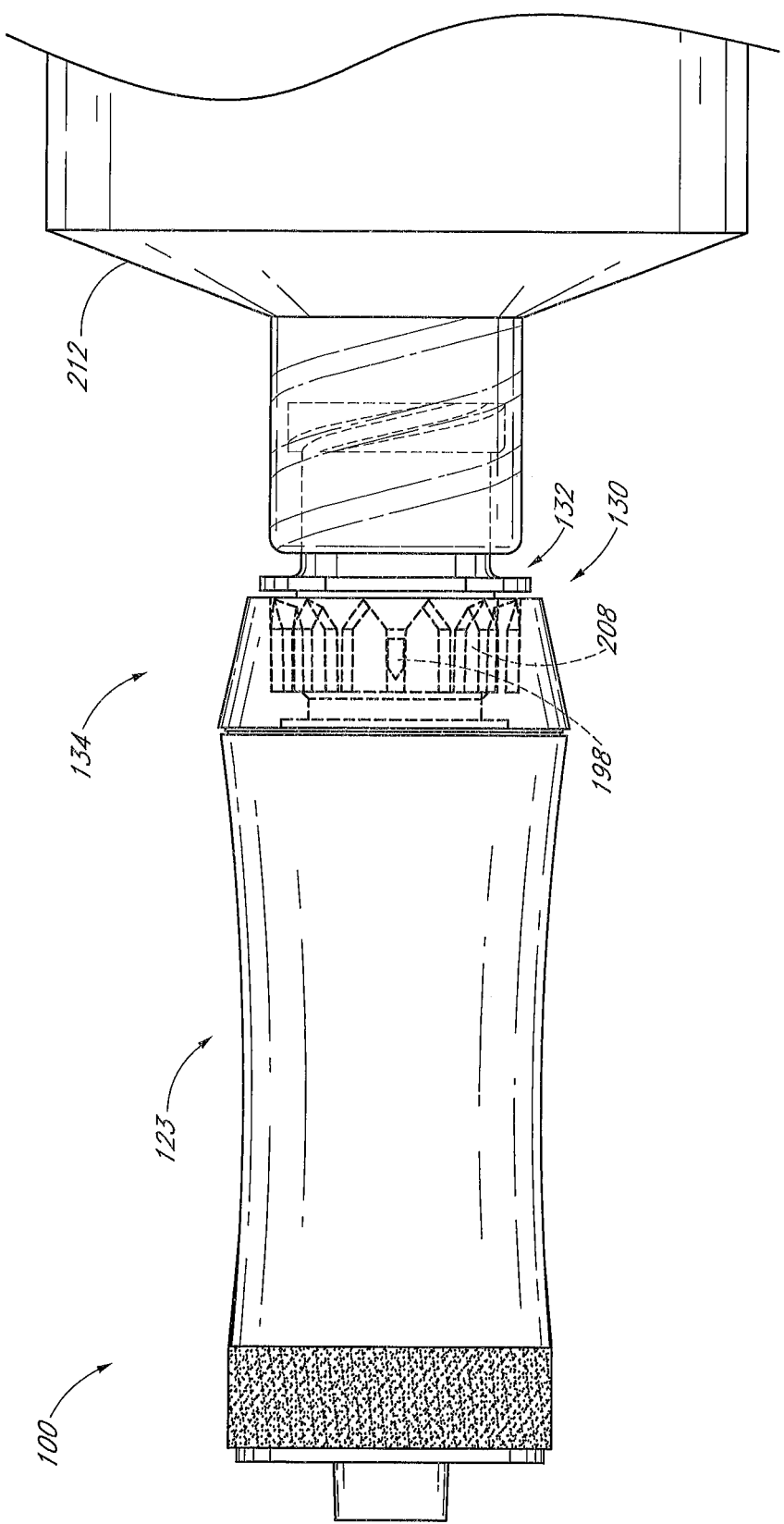
FIG. 20A is a side view of a coupled component threadedly engaged with the embodiment of the male connector shown in FIG. 3.

FIG. 20A is a side view of an example of a coupled component 212, showing the male connecting component of the coupled component 212 partially threadedly engaged with the first cap component 132 of the closeable male connector 100. FIG. 20A illustrates the end cap 130 before the one or more tabs 198 protruding radially outwardly from the surface 200 have been broken off. In FIG. 20A, the exemplifying coupled component 212 is a syringe. However, the coupled component 212 can be any suitable connector or medical instrument having a male connecting component. As illustrated therein, the coupled component 212 is only partially threadedly engaged with the first cap component 132 such that the torque that is exerted on the first cap component 132 from threading the coupled component 212 onto the first cap component 132 is less than the minimum threshold torque that is required to shear or break off each of the tabs 198 from the first cap component 132. Thus, until the minimum threshold torque required to shear or break off each of the tabs 198 is reached, the first cap component 132 can be rotationally fixed to the second cap component 134 by the abutment of each of the one or more tabs 198 formed on the first cap component 132 against one or more of the plurality of tabs 208 formed on the second cap component 134.

When the coupled component 212 is substantially fully threadedly engaged with the first cap component 132, further twisting of the coupled component 212 will ultimately exert a torque on the first cap component 132 that will exceed the minimum threshold torque required to break off the tabs 198 from the first cap component 132. In some embodiments, the minimum threshold torque required to break off the tabs 198 is at least approximately 4 in-lbs. of torque. Once the tabs 198 have broken away from the first cap component 132, the first cap component 132 is then able to rotate substantially freely within the second cap component 134. However, the first cap component 132 can still be retained in the housing by the abutment of the side surface 202b against the side surface 214b of the annular protrusion 214. Also, the O-ring 160 can prevent fluid exchange notwithstanding the ability of the first cap component 132 to rotate. In this way, the male connector 100 is prevented or inhibited from easily disconnecting from the coupled component 212 because the torque needed for such disconnection would merely spin the first cap component 132 relative to the male housing 123 and/or the second cap component 134 without unscrewing or other disconnecting these cap components 132, 134 from each other. Moreover, in some embodiments, there is little or virtually no exposed outside surface area on the first cap component 132 for contact by the fingers of a user after the coupled component 212 is attached, thereby making it difficult to apply opposing torque to the first cap component 132 and coupled component 212 to enable disconnection. This can effectively "fuse" these two components together.

The use of tabs configured to be sheared off is not required, nor is it required to use other structures and configurations to allow threadable connection between the end of the housing and the coupled component 212 in a first stage and then to allow rotation without unscrewing in a second stage to prevent or inhibit disconnection. The structures illustrated and described for inhibiting disconnection between the connectors 100, 400 are merely examples, and many other structures and methods can also be used to inhibit disconnection. Also, in some embodiments, there are no structures or steps to inhibit disconnection. In some embodiments, a first and/or a second end of the housing is permitted to rotate with respect to another portion of the housing without unscrewing or otherwise disconnecting during all stages of use.

FIG. 20B is a side view of the coupled component 212, showing the male connecting component of the coupled component 212 substantially fully threadedly engaged with the first cap component 132 of the male connector 100. FIG. 20B illustrates the first cap component 132 after the one or more tabs 198' have been broken off from the force exerted on each of the one or more tabs 198 by one or more of the plurality of tabs 208 formed on the inside surface 210 of the second cap component 134 in reaction to the twisting force transferred to the first cap component 132 from the substantially fully threadedly engaged coupled component 212. At this point, with each tab 198' broken away from the outside surface 200 of the first cap component 132, the first cap component 132 will be able to rotate substantially freely within the second cap component 134 without unscrewing. Any twisting motion applied to the coupled member 212 in either rotational direction relative to the male housing 123 in this arrangement will cause the first cap component 132 to rotate in unison with the coupled member 212. The coupled member 212 is thereby prevented from unthreading or otherwise becoming disengaged from the first cap component 132. Thus, in this manner, the male connector 100 is configured such that it cannot be removed or disengaged from the coupled member 212 after the male connector 100 and the coupled member 212 have been substantially fully coupled together.

After the one or more tabs 198' have been sheared or broken away from the first cap component 132, the covering portion 192 of the first cap component 132 can prevent each of the broken tabs 198' from falling out of the male connector 100, as shown in FIG. 20B. Additionally, as illustrated in FIG. 7, the second cap component 134 can be configured to prevent the broken tab 198' from moving into the interior space of the male housing 123. In particular, the second cap component 134 can be configured to comprise an annular protrusion 214 that can prevent the broken tab or tabs 198' from moving into the interior space of the male housing 123.

Figure 20C:
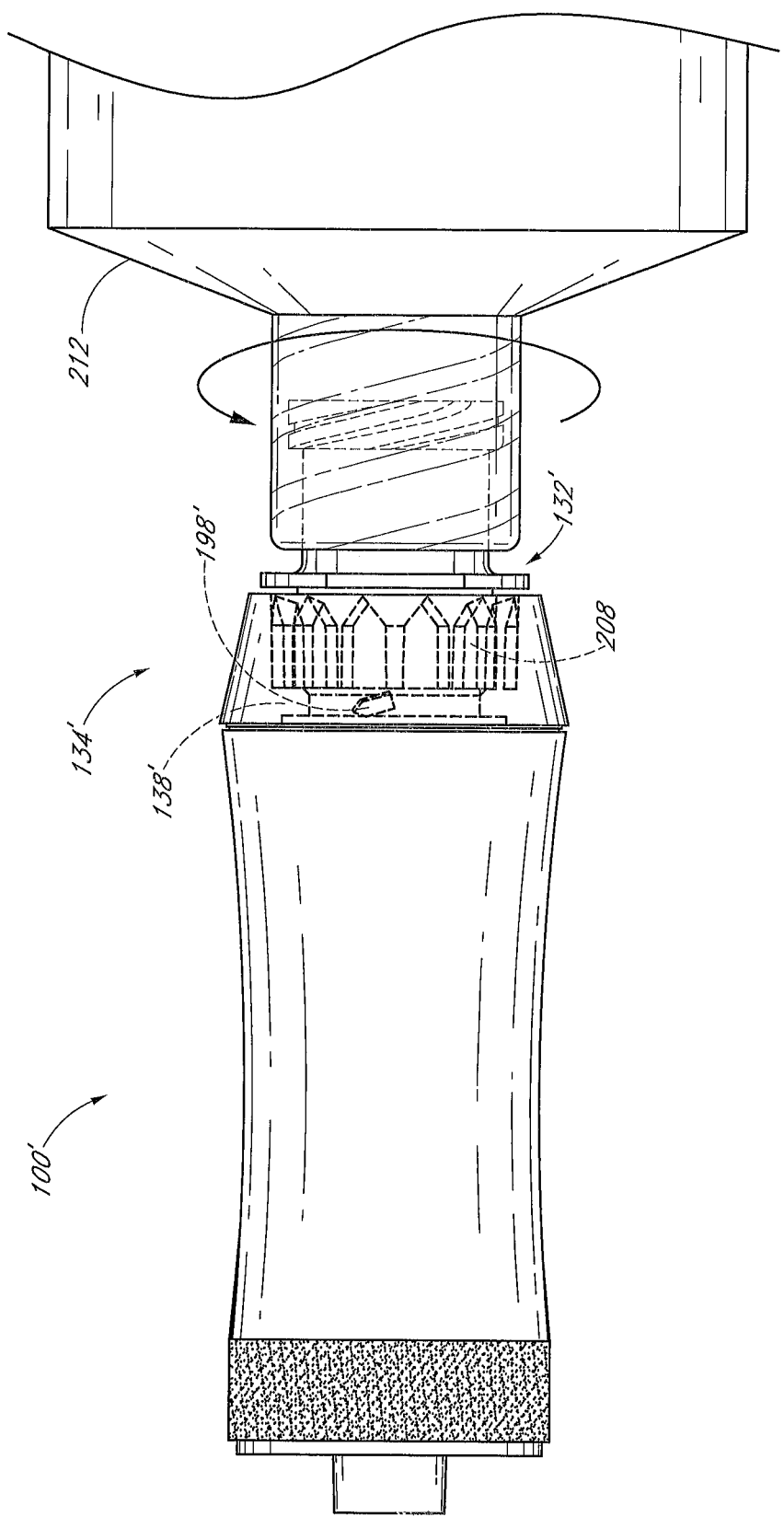
FIG. 20C is a side view of a coupled component substantially fully threadedly engaged with another embodiment of a male connector.

FIG. 20C is a side view of an example of a coupled component 212 substantially fully threadedly engaged with another embodiment of a closeable male connector 100'. In some embodiments, the closeable male connector 100' can be similar or identical to the closable male connector 100 described herein. In some embodiments, the second cap component 134' can be configured to comprise an annular space 138' adjacent to the tabs 208'. The annular space 138' can be sized and configured such that, when the one or more tabs 198' have broken away from the first cap component 132', the one or more tabs 198' can fall into and become contained within the annular space 138'.

In some embodiments, the first cap component 132 can be coupled to the second cap component 134 and, hence, coupled to the male connector 100, as described below. After the second cap component 134 has been attached to the male housing 123 following any of the methods described herein or any other suitable methods, the first cap component 132 can then be co-axially aligned with the second cap component 134 and also rotationally aligned so that the each of the one or more tabs 198 on the first cap component 132 is approximately aligned with the one or more spaces between the tabs 208 formed on the second cap component 134. Once the first cap component 132 is approximately axially and rotationally aligned, the first cap component 132 can be inserted into the second cap component 134 by pushing the first cap component 132 against the second cap component 134, while maintaining the approximate axial and rotational alignment described above. With reference to FIGS. 7, 13, and 16, the first cap component 132 can be pushed into the inner end until the first cap component 132 is positioned relative to the second cap component 134 such that the annular protrusion 214 formed on the second cap component 134 is radially adjacent to (i.e., axially aligned with) the annular groove 202 formed on the first cap component 132. In particular, in this position, the opposing sides surfaces 214a and 214b of the annular protrusion 214 formed in the second cap component 134 can be positioned between the optionally opposing side surfaces 202a and 202b of the annular groove 202 formed in the second cap component 134.

As shown in FIG. 7, in some embodiments, the first cap component 132 and the second cap component 134 can be formed such that there will be a small gap between the surfaces of the annular protrusion 214 and the surfaces of the annular groove 202. This configuration can facilitate rotation of the first cap component 132 within the second cap component 134, i.e., without friction between the surfaces 202 and 214, when the one or more tabs 198 have been sheared or broken off.

Additionally, with reference to FIG. 7, the first cap component 132 and the second cap component 134 can be sized and configured such that the side surface 202b of the annular groove 202 can overlap the side surface 214b of the annular protrusion 214 by an amount that is sufficient to prevent the first cap component 132 from inadvertently being pulled out of the second cap component 134. Additionally, the first cap component 132 and the second cap component 134 can be sized and configured such that, as described above, the first cap component 132 can be inserted into the second cap component 134 by axially aligning and pushing the first cap component 132 into the second cap component 134. Accordingly, if the side surface 202b of the annular groove 202 overlaps the side surface 214b of the annular protrusion 214 by too great of a distance, then it can be difficult in some configurations to couple the first cap component 132 with the second cap component 134 as described above.

To facilitate the insertion of the first cap component 132 into the second cap component 134, the first cap component 132 can be configured to have an angled or tapered annular surface 204 and/or a rounded annular surface 206 forward of the annular groove 202, as shown in FIG. 16. Similarly, the second cap component 134 can be configured to have an angled or tapered annular surface 216, to help align and essentially squeeze the first cap component 132 into the second cap component 134, as shown in FIG. 19.

Further, as shown in the illustrated embodiments, the one or more tabs 198 and the plurality of tabs 208 can comprise features and/or are configured to facilitate the insertion of the first cap component 132 into the second cap component 134. For example, in some embodiments, as illustrated in FIG. 16, each of the tabs 198 can comprise angled or tapered front surfaces 198a to help guide each of the tabs 198 into the space between the tabs 208 formed on the second cap component 134. Similarly, in some embodiments, as illustrated in FIGS. 17 and 19, the tabs 208 on the second cap component 134 can comprise angled or tapered surfaces 208a to help guide each of the tabs 198 into the space between each of the tabs 208. Additionally, in some embodiments, each of the tabs 208 can comprise an angled or tapered forward edge 208b to at least assist in axially aligning the first cap component 132 with the second cap component 134.

Any of the substantially rigid or semi-rigid components comprising the luer connector 100, including but not limited to the first cap component 132 and the second cap component 134, can comprise polycarbonate plastic, glass-filled polycarbonates, any other suitable water-impermeable materials, or any combinations thereof. The components comprising the luer connector 100 can also comprise a hydrophobic plastic. Other examples of materials suitable for construction of any of the substantially rigid or semi-rigid components comprising the luer connector 100 are glass-filled GE Valox 420 or polypropylene. Depending on the application, many other materials can also be used.

Figure 21:
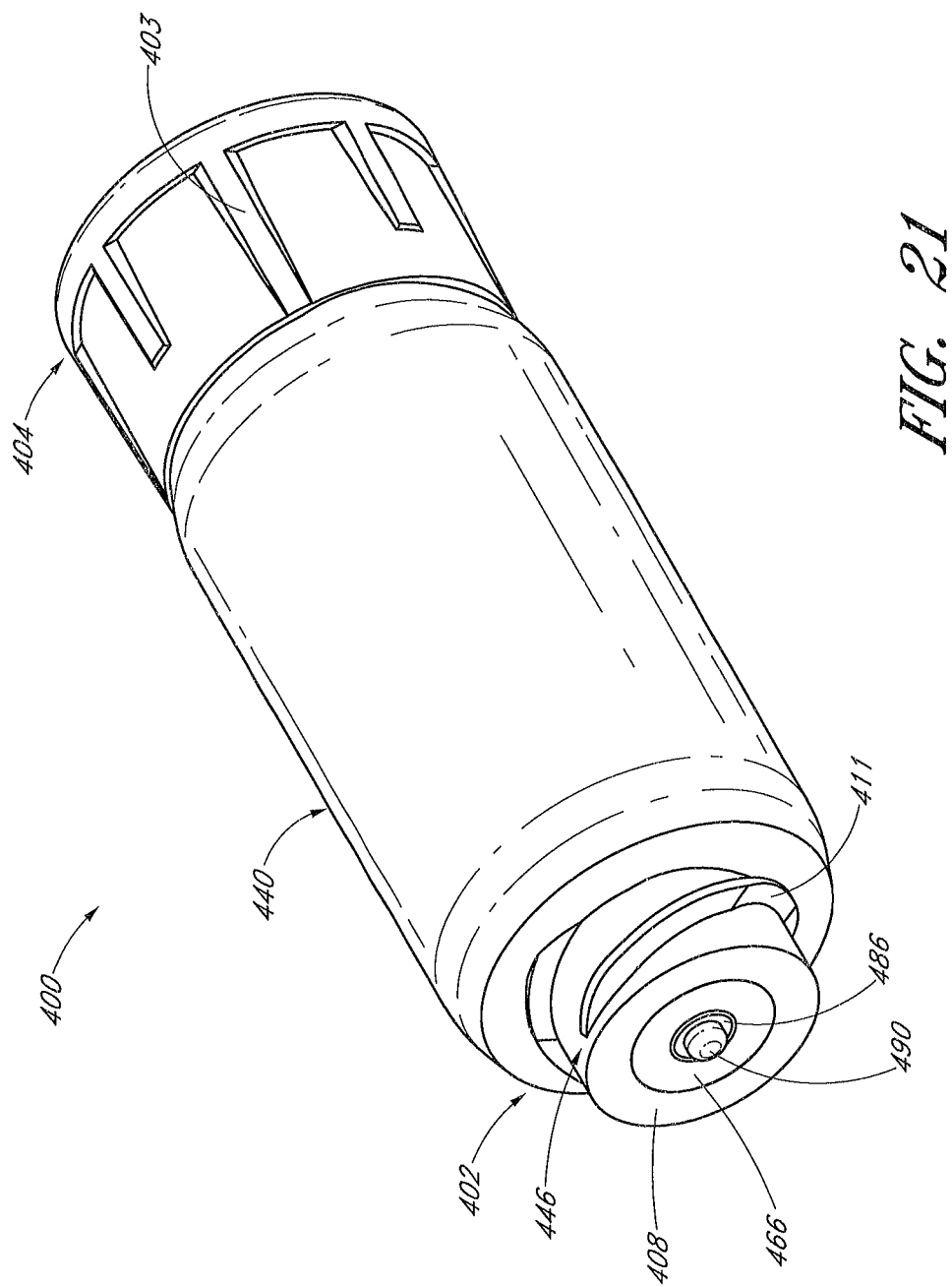
FIG. 21 is a perspective view of an embodiment of a female connector in a closed position.
Figure 22:
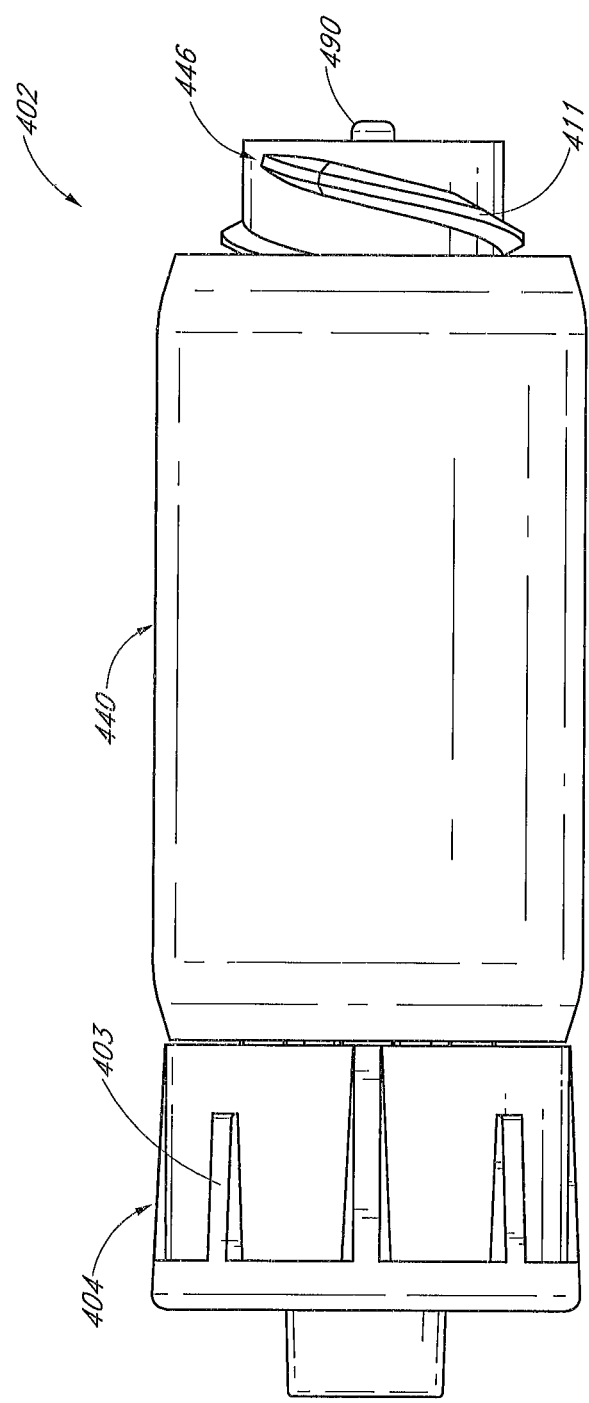
FIG. 22 is a side view of the embodiment of the female connector shown in FIG. 21 again in a closed position.

FIGS. 21 and 22 are a perspective view and a side view, respectively, of the female connector 400 in a first or closed position. In some embodiments, the female connector 400 can comprise any of the configurations, features, or components of other female connectors described herein, and any of the other connectors described herein can comprise any of the configurations, features, and components of the female connector 400. For example, the features relating to preventing or inhibiting disconnection can be used with any suitable medical or other fluid connector, on either or both of the female or male ends thereof.

Figure 23:
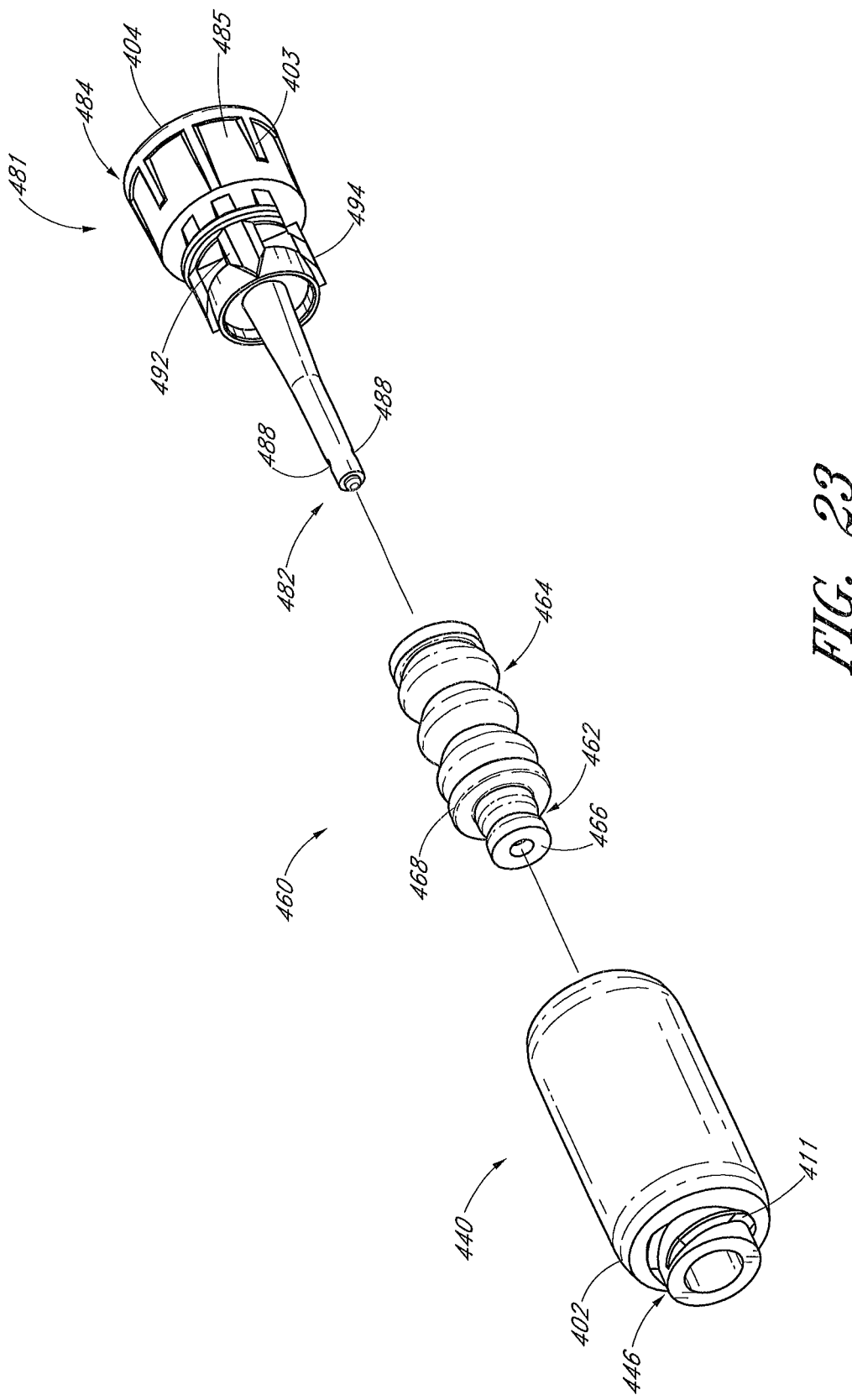
FIG. 23 is an exploded perspective view of the components of the embodiment of the female connector shown in FIG. 21.

FIG. 23 is an exploded perspective view of the components of the embodiment of the female connector 400 shown in FIG. 21. A fluid conduit 480 with one or more ports 488 can be coupled to the female housing 440 near the second end 404 of the female connector 400. One or more of the components of the fluid conduit 480 can be integral or unitary with the female housing 440. The fluid conduit 480 can have a second end 484 with a male luer engagement 485. A seal element 460 can surround at least a portion of the fluid conduit 480. The seal element 460 can obstruct the ports 488 on the fluid conduit 480 when the female connector 400 is in a closed configuration. The compressible seal element 460 and fluid conduit 480 can be contained at least partially within the female housing 440.

Figure 25:
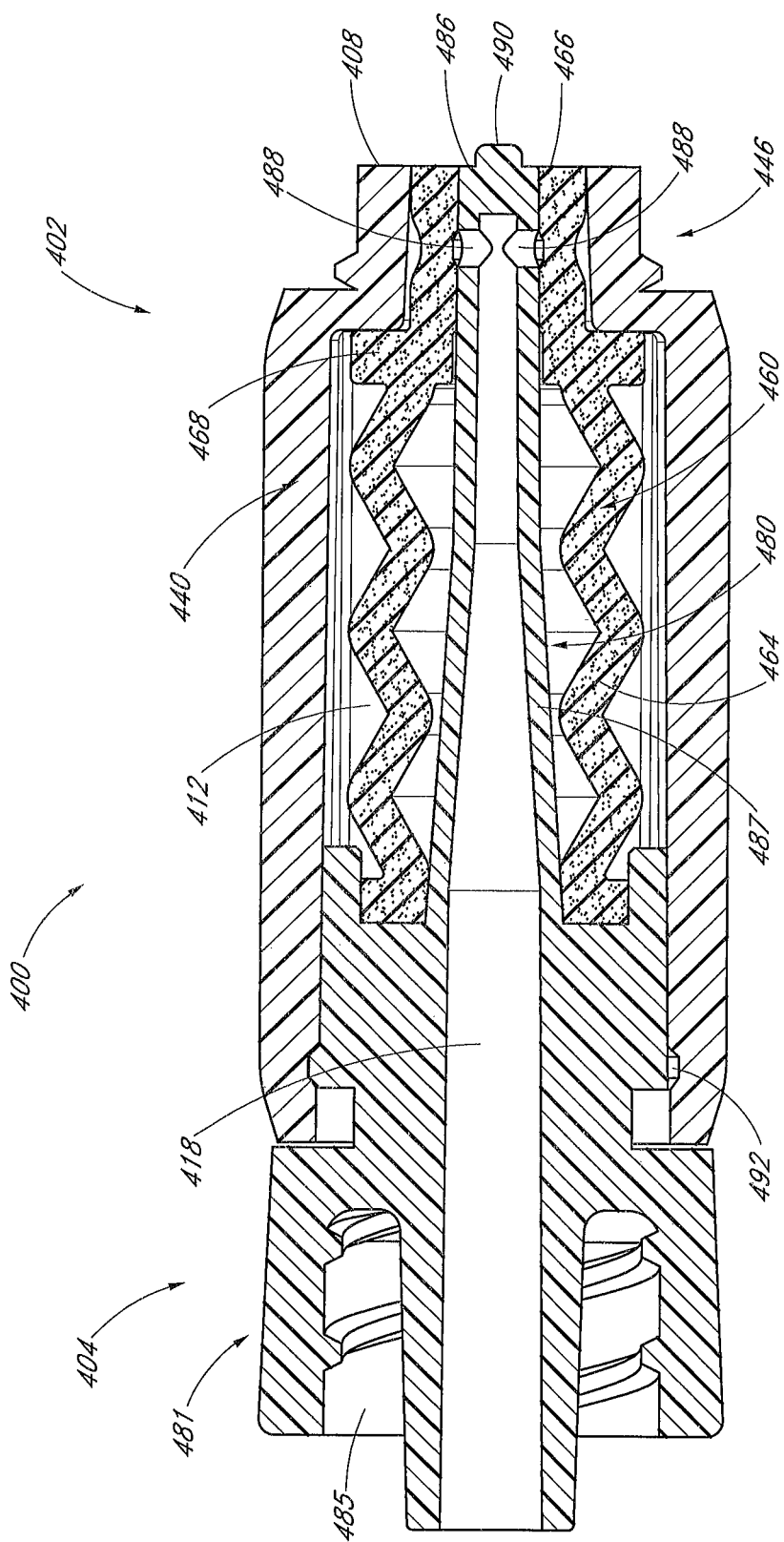
FIG. 25 is a cross-sectional view of the embodiment of the female connector shown in FIG. 21, taken along the line 25-25 in FIG. 24.

With reference to FIG. 25, the female connector 400 can include a female housing 440 containing a seal element 460 and a fluid conduit 480. A fluid passageway 418 extends through the center of the fluid conduit 480. A void space 412 is present between the seal element 460 and the female housing 440.

Figure 26:
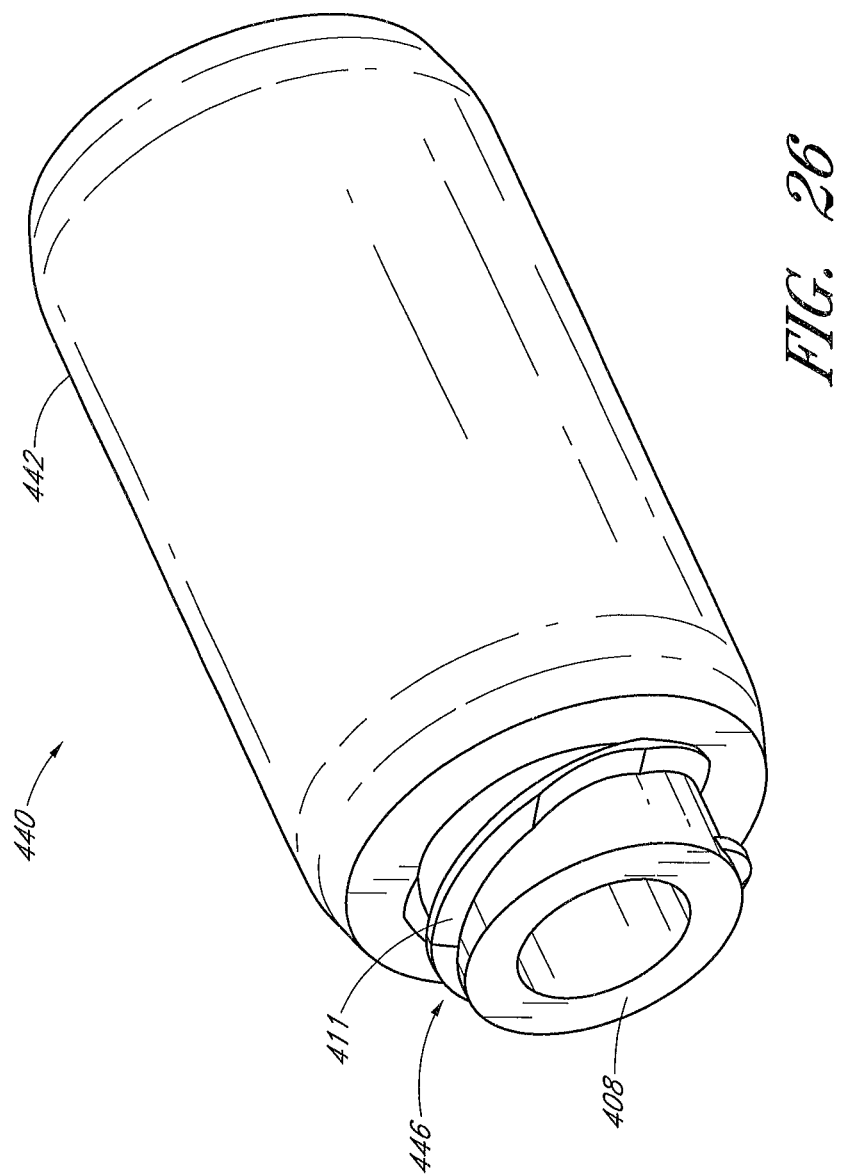
FIG. 26 is a perspective view of an embodiment of a housing of the female connector shown in FIG. 21.

As illustrated in FIGS. 21, 22 and 26, the female connector 400 can have a first end 402 and a second end 404. The first end 402 can be configured to mate with the male connector 100. In some embodiments, the female connector 400 can have a female housing 440 with a coupling portion 446 that is configured to be coupled to the male connector 100, as discussed further below. The coupling portion 446 can include a coupling structure that is complementary to the coupling structure on the shroud 124 of the male connector 100. In the illustrated embodiment, the coupling portion 446 comprises external threads 411 that can couple with the internal threads 126 on the shroud 124 of the male connector 100. The external threads 411 can form a female luer engagement that conforms to ANSI specifications for female connectors.

The female housing 440 of the female connector 400 can extend between the first end 402 and the second end 404. In the illustrated embodiment, the female housing 440 has a generally cylindrical body 442. In other embodiments, the body 442 can have a square cross-section, polygonal cross-section, or any other shape. In some embodiments, the coupling portion 446 can be integrally molded or otherwise formed with the female housing 440. In other embodiments, the coupling portion 446 can be a separate component that is connected to the female housing 440, such as by welding, adhesives, or fasteners. A compressible, resilient seal element 460 and a fluid conduit 480 are contained at least partially within the female housing 440. In some embodiments, at least a portion of the female connector and/or the male connector can be translucent, such as at least a portion of housings and/or the seal element 460, to permit external visual inspection of the flow of fluid therein. The housing can comprise an external gripping surface, such as ridges 403, to facilitate holding and/or twisting the female connector 400.

Figure 27:
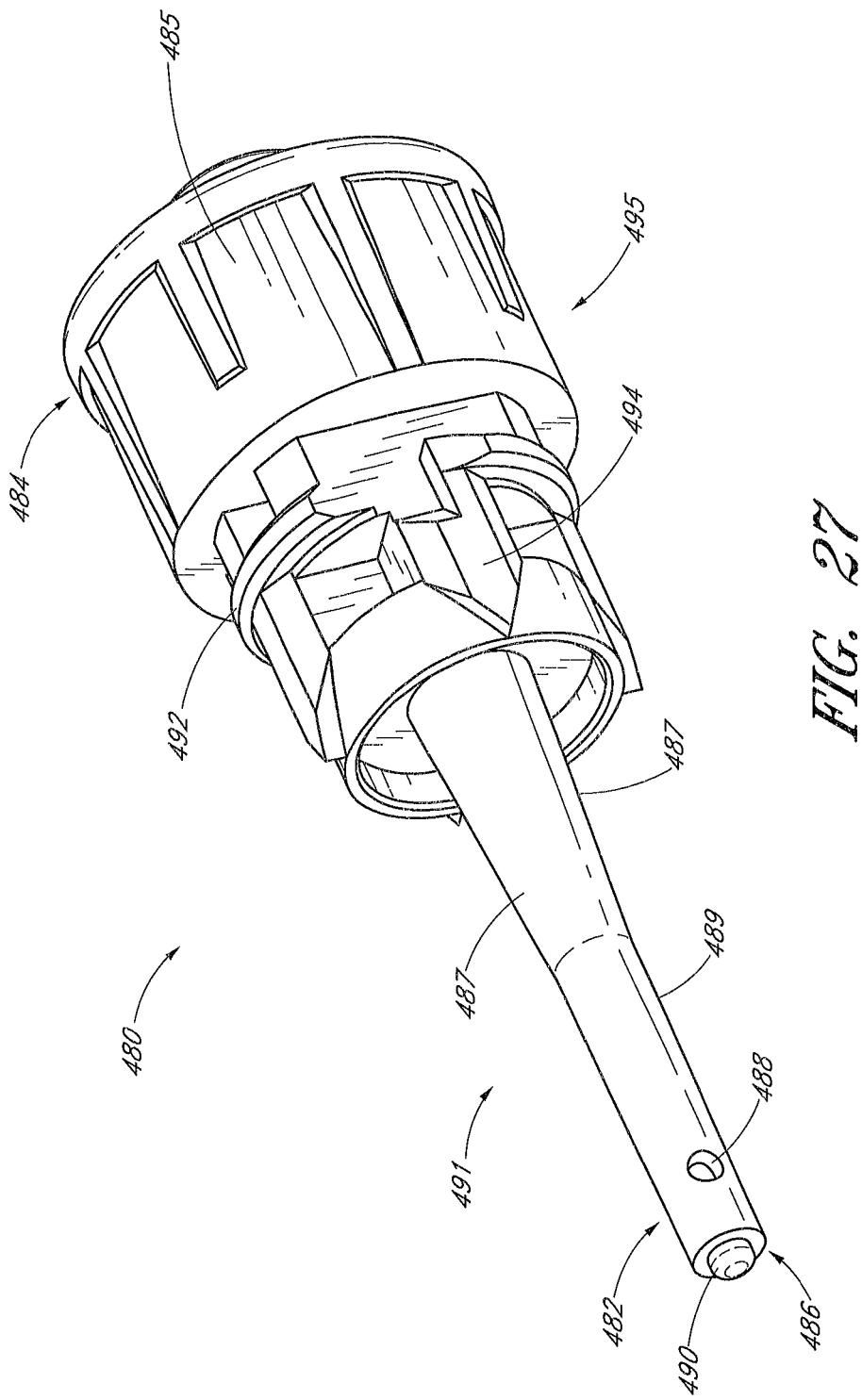
FIG. 27 is a perspective view of an embodiment of a fluid conduit of the female connector shown in FIG. 21.

With reference to FIG. 27, the fluid conduit 480 can have a first end 482 and a second end 484. The first end 482 can have a mating surface 486 that is configured to couple in close, non-planar correspondence with the mating surface 146 of the valve member 116 to facilitate contact between the mating surfaces 146, 486 that is slide-resistant (e.g., against lateral movement or rocking), and resistant to fluid ingress between the mating ends 146, 486, especially during the transition between the open and closed positions. In the region of the first end 482 can be at least one port 488 that is fluidly connected to a fluid passageway 418 (see FIG. 25) that extends through the interior of the fluid conduit 480. In the illustrated embodiment, the fluid conduit 480 has a plurality of ports (e.g., two ports). In some embodiments, the fluid conduit 480 can have more than two ports 488. The second end 484 of the fluid conduit 480 can be configured to couple to other medical devices such as connectors or devices. In the illustrated embodiment, the second end 484 has a male luer engagement 485 which includes a shroud with inner threads generally surrounding a male luer tip. In some embodiments, the male luer engagement 485 conforms to ANSI specifications for male medical connectors. The male luer engagement 485 can receive a female connecting component of another medical device such as a connector or syringe.

The second end 484 can also have features for coupling with the female housing 440. In the illustrated embodiment, the second end 484 has a coupler 492, such as a tapered cam surface 492, that protrudes radially outward and extends generally around the circumference of the fluid conduit 480. The coupler 492 can couple with a complementary coupler on the female housing 440, such as a channel on the inner surface of the female housing 440. The coupler 492 can facilitate connection of the fluid conduit 480 and the female housing 440, and can help to prevent the fluid conduit 480 from separating from the female housing 440 in the axial direction. The fluid conduit 480 can have rotation-resistant members, such as tabs 494, that can engage with corresponding rotation-resistant members, such as tabs, on the inner surface of the female housing 440. The rotation-resistant members, such as tabs 494, can help prevent the fluid conduit 480 from rotating relative to the housing. In some embodiments, the couplers and/or rotation-resistant members can facilitate the manufacturing process by eliminating a need in this step for more expensive processes and materials involved in other attachment means, such as welding, bonding, or adhering the components, which can also or alternatively be used. In some embodiments, the fluid conduit 480 can be attached to the female housing 440 in other ways, such as through welding, bonding, adhesives, or fasteners.

Extending generally from the first end 482 to the second end 484 can be a generally rigid tube 487 with a fluid passageway 418 extending through the middle of the tube 487. In the illustrated embodiment, the tube 487 can comprise a protruding portion 491 that extends proximally from a base 495 of the fluid conduit 480 that is generally cylindrical in a first portion 489 and generally frusto-conical in a second portion 487. In some embodiments, the tube can have other cross-sectional shapes, such as square, polygonal or oval. In some embodiments, the protruding portion 491 can provide support for and assist in the lateral positioning of the seal element 460, and the protruding portion 491 can cooperate with the seal element 460 to selectively open and close the fluid passageway 418. As illustrated, the first portion can comprise a generally constant outer diameter or cross-sectional width to facilitate opening (e.g., by facilitating sliding of the seal element) and the second portion can taper or flare outwardly in the direction of a wider distal region to facilitate an increasing sealing effect between the outer surface of the tube 487 and the inner surface of the bore 470 of the seal element 460 as the seal element 460 moves from the closed to the open position.

In some embodiments, the protruding portion 491 can be substantially shorter (e.g., similar in shape to a boss or grommet) that can help to position the seal element 460 without piercing or penetrating through the proximal portion of the seal element. In some embodiments, the protruding portion 491 can be omitted. In some embodiments, including some in which there is no piercing or penetrating protruding portion 491, the fluid transferred through the connector 402 in the open state can flow around the outside surface of the seal element and exit distally from the internal cavity 412 through one or more openings in the base 495 or in a distal portion of the seal element 460 and into the fluid pathway 418.

In some embodiments, the connector 400 can comprise a pressure-regulating member (e.g., a flexible variable-volume region) and/or a fluid-inhibiting member (e.g., a flexible second valve) positioned within the base or elsewhere within or in fluid communication with the connector 400. Some examples of pressure-regulating members and fluid inhibiting members are illustrated and/or described in U.S. Patent Application Publication No. 2010-0249723 A1, published on Sep. 30, 2010, which is incorporated herein by reference in its entirety.

As illustrated in FIG. 25, the fluid passageway 418 can extend through at least a portion of the fluid conduit 480. The fluid passageway 418 can be circular in cross-section, as shown in the illustrated embodiment, or the fluid passageway 418 can have other cross-sectional geometric shapes. The fluid passageway 418 can have at least one port 488 near the first end 482. In the illustrated embodiment, two ports 488 are located on opposite sides of the fluid conduit 480 and are circular in shape, though other locations and shapes can be used. The ports 488 can be located near and spaced distally from the mating surface 486 of the fluid conduit 480, or as far back as practical from the mating surface 486 while still allowing fluid to enter the ports 488 when the female connector 400 is mated with the male connector 100. In some embodiments, the size of the ports 488 can be approximately one millimeter in diameter, although irregular shapes and other sizes can be used. Ports of at least about 1 mm or approximately 1 mm-3 mm, or less than about 1 mm can also be used.

The fluid conduit 480 can be composed of a rigid material, such as polycarbonate plastic, which is capable of resisting deformation when a force sufficient to compress the seal element 460 is exerted upon the female connector 400. The ports 488 in the fluid conduit 480 can be in contact with and covered by the proximal end of the seal element 460 to resist or inhibit the fluid passageway 418 from being in fluid communication with the cavity 412 between the seal element 460 and the inner wall of the female housing 440.

Figure 28:
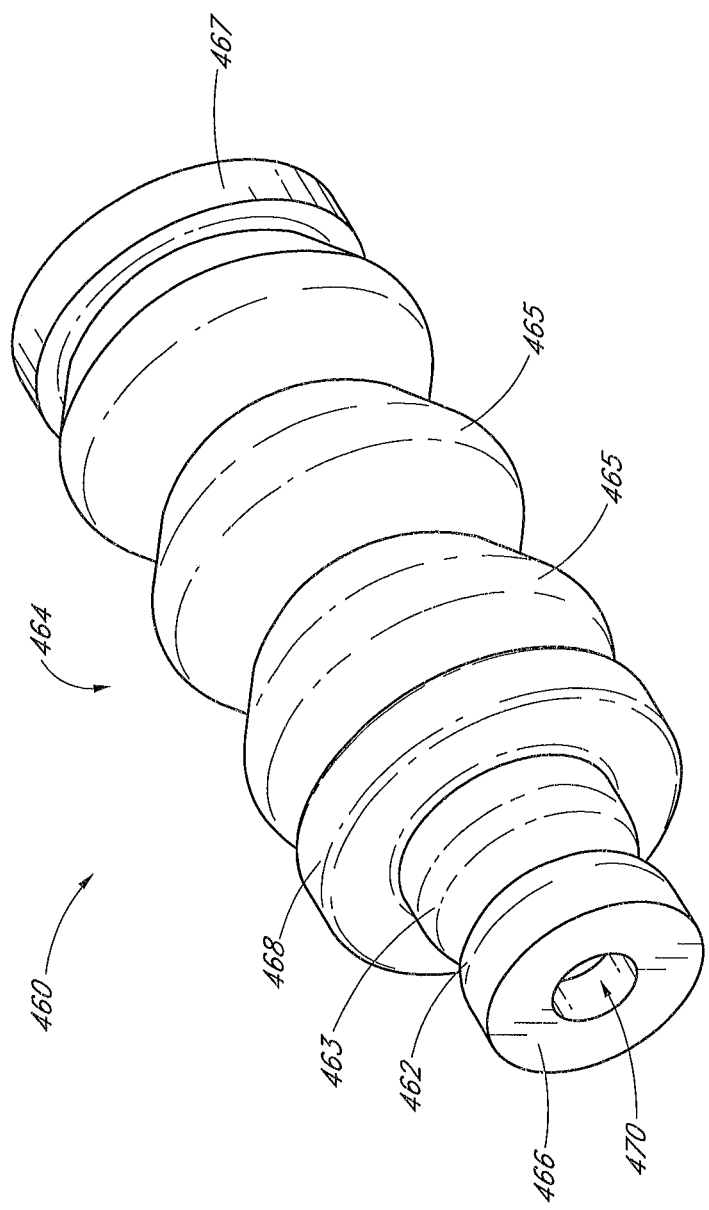
FIG. 28 is a perspective view of an embodiment of a compressible seal element of the female connector shown in FIG. 21.

With reference to FIG. 28, an embodiment of the seal element 460 is described in greater detail. In some embodiments, the seal element 460 is generally cylindrical and has a bore 470 extending therethrough. In some embodiments, the seal element 460 can have a sealing portion 462 and a collapsing portion 464. The sealing portion 462 can have an inner diameter that is configured to obstruct the first end 482 of the fluid conduit 480 to inhibit the flow of fluids out of the ports 488.

In the illustrated embodiment, collapsing portion 464 has portions of larger diameter separated by portions of smaller diameter, such that the collapsing portion 464 decrease in the longitudinal length (e.g., by folding, collapsing, compressing, or otherwise moving) when a force is applied in the longitudinal distal direction. In some embodiments, the collapsing portion 464 can be made of a resilient material such that a restoring force biases the collapsing portion 464 back to its starting length when the collapsing force is removed. In some embodiments, the collapsing portion 464 can have a plurality of different types of configurations for providing a seal. In some embodiments, the seal element can comprise a first end 466 with a generally round portion and a second portion 463 distal from the first end 466. The second portion 463 can comprise a smaller outer diameter than the diameter of the first end 466. One or more compressible elements 465 can be positioned distally from the second portion 463. In some embodiments, the outer diameter of the compressible elements 465 can be larger than the outer diameter of either the first end 466 or the second portion 463. A distal portion can comprise an outer diameter that is generally the same size as the outer diameter of the compressible element(s).

A shoulder 468 can be disposed between the sealing portion 462 and the collapsing portion 464. In the illustrated embodiment, the shoulder 468 is a portion having an enlarged diameter. As illustrated in FIG. 25, the shoulder 468 can engage with a surface of the female housing 440 to prevent the seal element 460 from overextending or exiting from the housing. The placement of the shoulder 468 on the seal element 460 is configured so that when the shoulder 468 engages with the female housing 440, the sealing portion 462 is positioned over the ports 488 on the fluid conduit 480.

The seal element 460 can be constructed of a material that elastically or resiliently deforms. The seal element 460 can be biased toward returning the female connector 400 to a closed configuration. The amount of compression resistance of the seal element 460 can be adjusted in many ways, such as by varying the length of the compressing portion 464 or the length of the chamber in the female housing 440 where the seal element 460 resides. The amount of compression resistance can also be adjusted by increasing the thickness of the seal element 460 and/or by construction of the seal element 460 from a variety of materials having different elastic properties. In some embodiments, the female connector 400 is configured to be sufficiently resistant to opening to generally prevent accidental or unintentional opening. The resistance to opening of the connector can be controlled at least in part by the compression resistance carried by the seal element 460. In some embodiments, the collapsing portion 464 can be configured as a spring positioned inside the female housing 440 for biasing the seal element 460 to the closed configuration. Movement of the female connector 400 to the open configuration can compress the spring and movement of the female connector 400 to the closed configuration can allow the spring to expand to release some or all of the compression.

Figure 24:
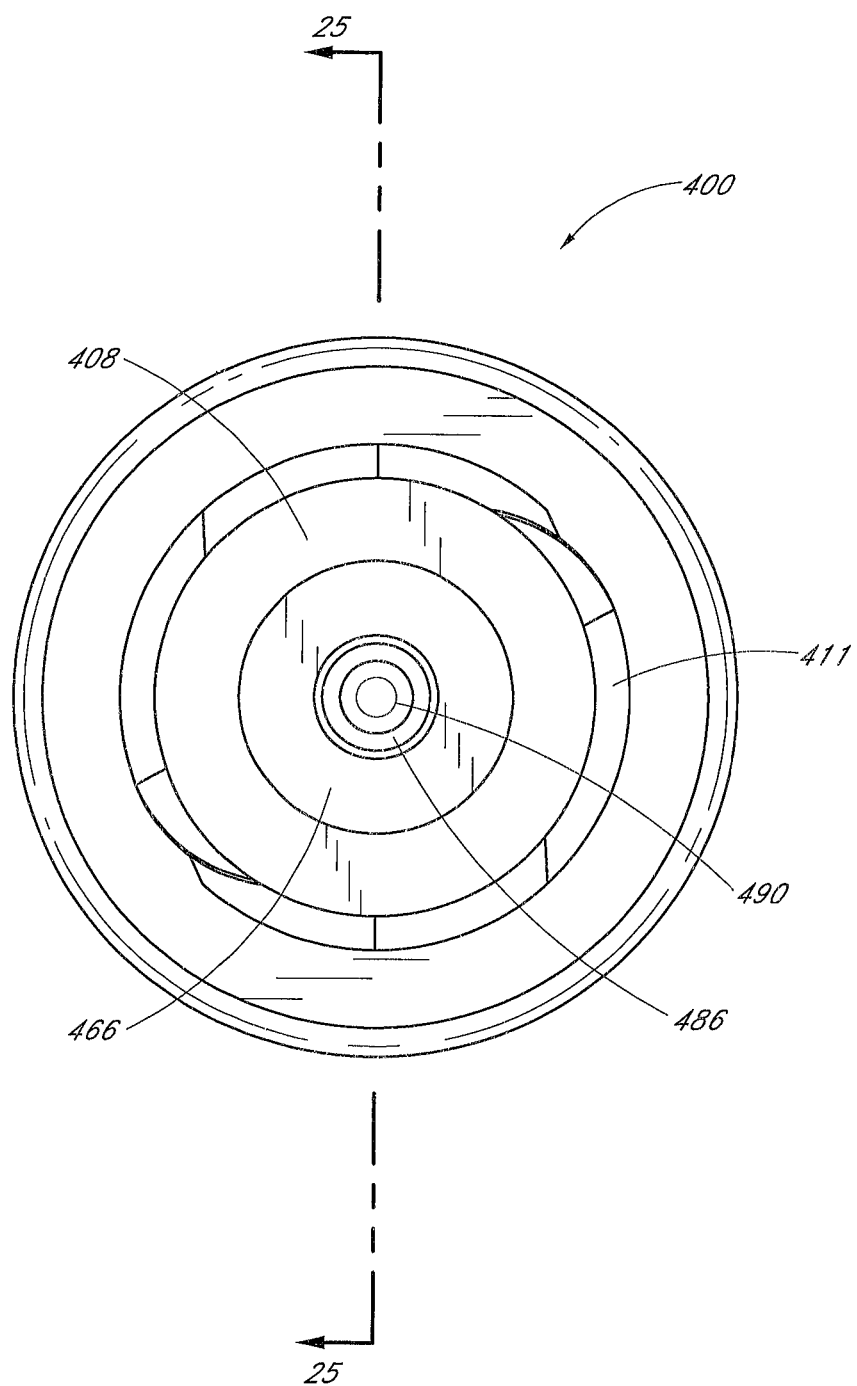
FIG. 24 is a front view of the embodiment of the female connector shown in FIG. 21.

As illustrated in FIGS. 21 and 24, the coupling portion 446 on the first end 402 of the female connector 400 can have a mating side 408 that is generally transverse to the longitudinal axis of the female connector 400. In the illustrated embodiment, the mating side 408 has a generally annular shape. The mating side 408 can have an opening in the middle for the seal element 460, wherein a mating surface 466 of the seal element 460 is exposed. The mating surface 466 of the seal element 460 is configured to form a leak-resistant and/or lateral-movement-resistant seal with the mating surface 128 of the male luer tip 122 and the mating surface 176 of the luer tip seal 119. Near the center of the seal element 460 can be an opening for the female connector fluid conduit 480. A first end 482 of the fluid conduit 480 can have a mating surface 486 configured to form a substantially leak-free seal with the mating surface 146 of the valve member 116.

Figure 32:
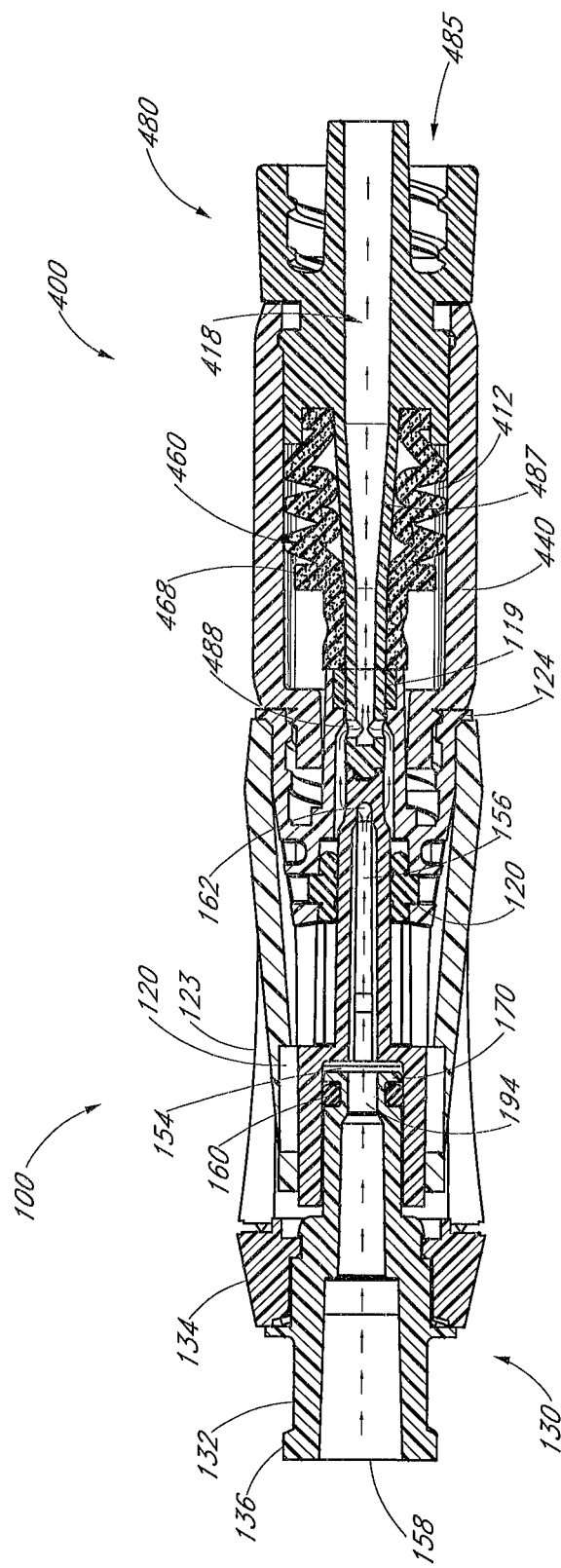
FIG. 32 shows a cross-sectional view of the connector system of FIG. 31 taken at line 32-32 in FIG. 31.

As shown in the embodiment of the female connector 400 illustrated in FIGS. 21 and 24, the mating surface 466 of the seal element 460 can be substantially flush with the mating side 408 of the female connector 400, and the end 466 of the seal element 410 can fill essentially completely the inner diameter or cross section of the end 114 of the female connector 100. In some embodiments, as illustrated in FIG. 32, the outer diameter of the proximal seal end 466 is generally the same size as the outer diameter of an ANSI-standard male medical luer connector. In some embodiments, the mating surface 486 of the fluid conduit 480 can be substantially flush with the mating side 408 of the female connector 400. In some embodiments, the mating surface 466 of the compressible seal element 460 and/or the mating surface 486 of the fluid conduit 480 can be configured to extend further beyond the mating side 408 of the female connector 400 in the closed position. In some embodiments, the mating surface 466 of the seal element 460 and/or the mating surface 486 of the fluid conduit 480 can be recessed within coupling portion 446. In some embodiments, a portion of the mating surface 466 of the compressible seal element and/or the mating side 408 of the female connector 400 is substantially flush, extends beyond, and/or is recessed within the coupling portion 446, depending on the purposes of the particular embodiment.

In some embodiments, the first end 482 of the fluid conduit 480 can have a protrusion 490 that couples with a complementary cavity 147 on the mating surface 146 of the valve member 116. In the illustrated embodiment, the protrusion 490 is a generally cylindrical protrusion with rounded edges. In some embodiments, the protrusion can have a plurality of different types of shapes, such as protrusions with a generally rectangular, generally square or generally polygonal cross-sectional shape, to generally match the shape of the cavity 147 in the mating surface 146 of the valve member 116. In some embodiments, the protrusion can be disposed on the mating surface 146 of the valve member 116 and the cavity can be on the first end 482 of the fluid conduit 480. The protrusion 490 and cavity 147 can help to align and to resist movement (e.g., lateral movement) between the mating surfaces of the male connector 100 and the mating surfaces of the female connector 400.

The seal element 460 can obstruct the first end 482 of the fluid conduit 480 to block the flow of fluids out of the ports 488 when the female connector 400 is in the closed configuration. A sealing portion 462 of the seal element 460 can be disposed in the interior of coupling portion 446 of the female housing 440, as illustrated in FIG. 25. In the illustrated embodiment, the sealing portion 462 of the seal element 460 is disposed between the female housing 440 and the fluid conduit 480. In some embodiments, an interference fit between the seal element 460 and the fluid conduit 480 can inhibit fluid from flowing out of the first end 402 of the female connector 400. The seal element 460 can be made of a resilient material that helps form the seal.

The female connector 400 can be manipulated to a second or open configuration. In the open configuration, the sealing portion 462 of the seal element 460 can be pushed back toward the second end 404 of the female connector 400, thereby allowing fluid to flow through the ports 488 in the fluid conduit 480. In the open configuration, fluid can enter the fluid conduit 480 through the ports 488 and travel through the fluid passageway 418, exiting through the male luer engagement 485 of the fluid conduit 480. In some embodiments, including some in which fluid flows around the outside of a seal element 460 rather than through it, the mating surface of the seal element 460 can include a surface shape with an alignment structure (e.g., any alignment structures of the type described and/or illustrated herein for the end of the protruding portion 491) on its forward end. In some embodiments, the seal element 460 does not have an opening and is closed on its mating end 466. In some embodiments, the housing includes an aperture to permit evacuation of air from the interior of a compressing seal element 460.

In some embodiments, it is desirable to inhibit certain human contact with some medicines (e.g., contact with the skin or inhalation of vapors), especially with drugs for treating oncology or auto-immune disorders. The female connector 400 can assist in retaining fluid within the female connector 400 while resisting remnant fluid on the first end 402 of the female connector 400 when it is being decoupled and after it is decoupled from a male connector 100 or other connector. Reducing the likelihood of remnant fluid remaining on the female connector 400 after decoupling can result in a corresponding reduction in the chance of exposure of toxic medicine to the skin of a user or a patient.

Figure 29:
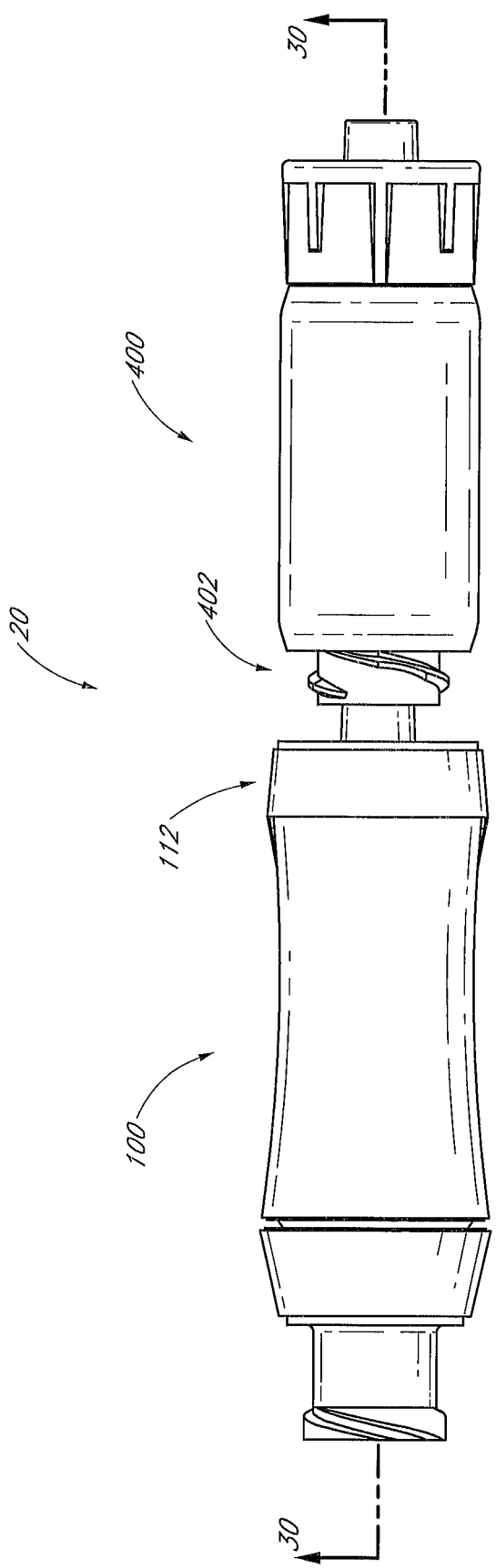
FIG. 29 is a side view of the embodiment of a male connector adjacent the embodiment of a female connector shown in FIG. 1.
Figure 30:
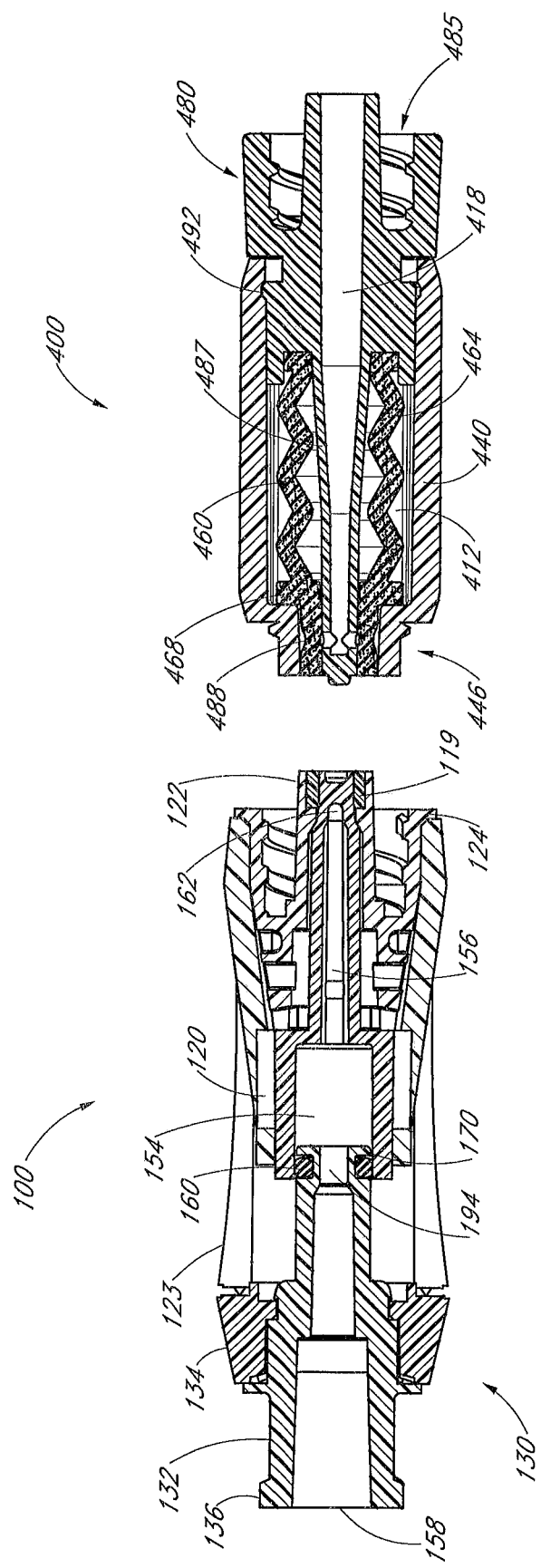
FIG. 30 shows a cross-sectional view of the connector system of FIG. 29, taken at line 30-30 in FIG. 29.
Figure 30A:
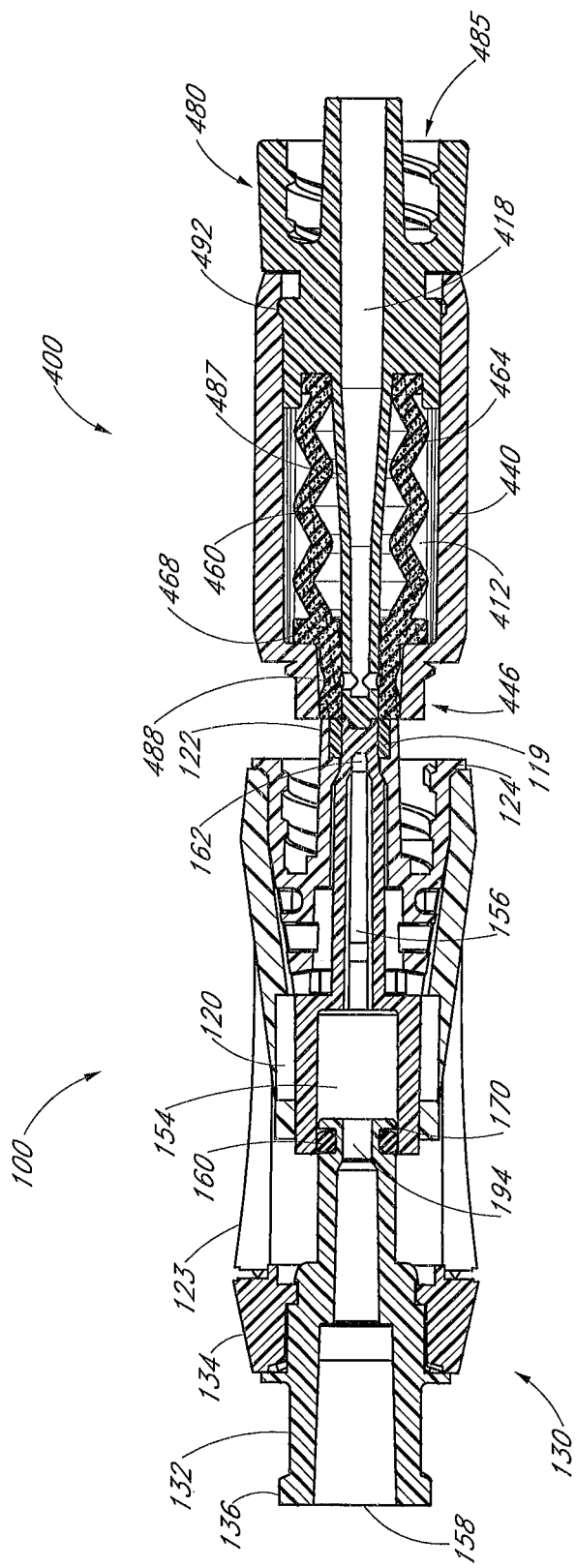
FIG. 30A shows a cross-sectional view of the connector system of FIG. 29.

With reference to FIGS. 29, 30 and 30A, the male connector 100 is displayed adjacent to a female connector 400. In the illustrated embodiment, both the male connector 100 and the female connector 400 are in a closed configuration. The female connector 400 is positioned with its first end 402 adjacent the first end 112 of the male connector 100. The male connector 100 can be threadedly engaged with the female connector 400.

Figure 31:
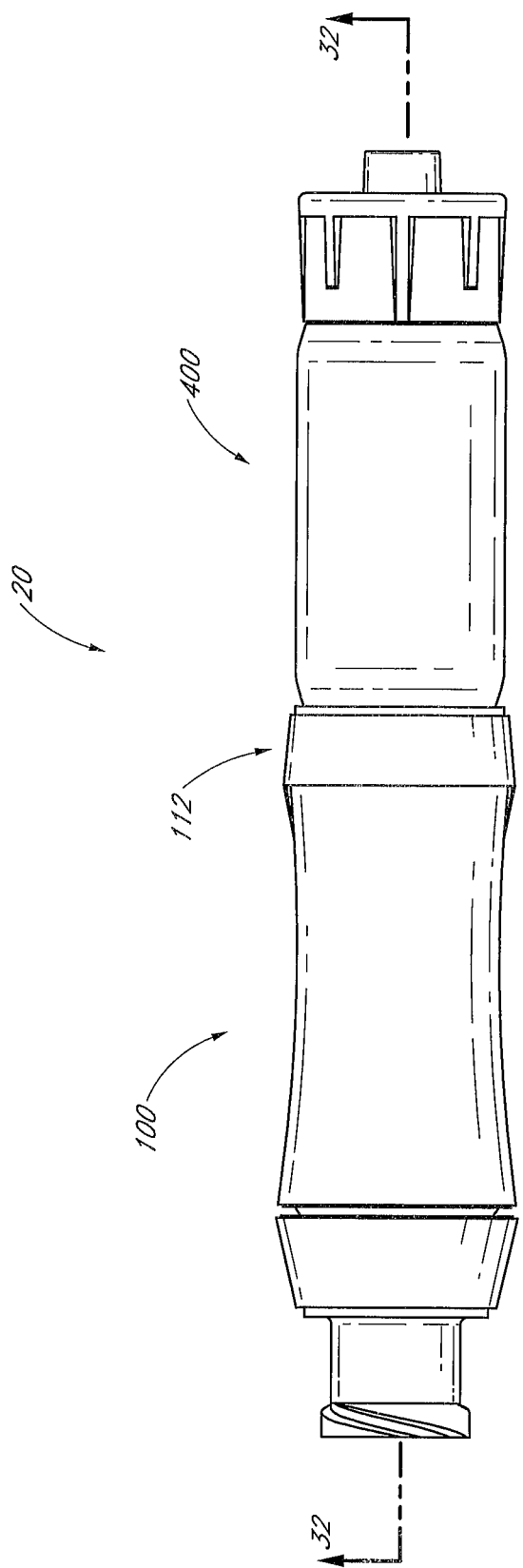
FIG. 31 is a side view of the embodiment of a male connector coupled to the embodiment of a female connector shown in FIG. 1.

As illustrated in FIGS. 31 and 32, the male connector 100 can be changed to the open configuration when a female connector 400 is coupled to the male connector 100. The first end 402 of the female connector 400 can engage with the first end 112 of the male connector 100. The coupling portion 446 of the female connector 400 can engage with the shroud 124 of the male connector 100 to engage the connectors 100, 400. The coupling portion 446 of the female connector 400 and the shroud 124 with luer tip 122 on the male connector 100 can conform to standard sizing for connectors, such as those that meet ANSI standards. In some embodiments, engagement between the coupling portion 446 of the female connector 400 and the shroud 124 can resist lateral movement between the mating surface 146 of the valve member 116 and the mating surface 486 of the fluid conduit 480. In some embodiments, engagement between the coupling portion 446 of the female connector 400 and the shroud 124 can resist tilting between the mating surface 146 of the valve member 116 and the mating surface 486 of the fluid conduit 480. Resistance of lateral movement and/or tilting between the mating surfaces 146, 486 can help reduce the likelihood that either mating surface 146, 486 will be exposed to fluid from within the connectors 100, 400.

As illustrated in FIG. 32, the mating surface 486 of the fluid conduit 480 can engage the mating surface 146 of the valve member 116. As the male connector 100 and the female connector 400 are brought together, the fluid conduit 480 can push the valve member 116 toward the second end 114 of the male connector 100. As the valve member 116 is pushed toward the second end 114 of the male connector 100, the ports 162 on the valve member 116 are displaced away from the luer tip seal 119, allowing fluid to flow out through the ports 162. Thus, the male connector 100 is in an open configuration when the valve member 116 is pushed towards the second end 114.

With continued reference to FIG. 32, the mating surface 176 of the luer tip seal 119 and the mating surface 128 of the male luer tip 122 can engage the mating surface 466 of the seal element 460. As the male connector 100 and the female connector 400 are brought together, the male luer tip 122 with the luer tip seal 119 can push the seal element 460 toward the second end 404 of the female connector 400, compressing the collapsing portion 464 of, or otherwise deforming or moving, the seal element 460. As the seal element 460 is pushed toward the second end 404 of the female connector 400, the ports 488 on the fluid conduit 480 are uncovered, allowing fluid to flow through the ports 480. In this configuration, the female connector 400 is in an open configuration. In some embodiments, as described herein, the fluid can flow around the outside of the seal rather than through it and into ports 482 on the protruding portion 491 (which can be omitted in some embodiments).

When the valve member 116 is pushed toward the second end 114 of the male connector 100, the resilient member 118 is stretched, producing tensile forces that exert a return force on the valve member 116 toward the first end 112 of the male connector 100. Thus, in the open configuration of the male connector 100, the valve member 116 can be biased toward the first end 112 toward a closed configuration. Similarly, when the seal element 460 is pushed toward the second end 404 of the female connector 400, the collapsing portion 464 is compressed and a return spring force is exerted to bias the seal element 460 to its original length and toward a closed configuration.

In some embodiments, the resilient member 118 can exert a closing force on the valve member 116 in a direction towards the first end 112 of the male connector 100. The mating surface 146 of the valve member 116 generally can maintain contact with the mating surface 486 of the fluid conduit 480 throughout the engagement between the male connector 100 and the female connector 400. In some embodiments, the mating surface 146 of the valve member 116 can have a cross-section that is substantially the same as a cross-section of the mating surface 486 of the fluid conduit 480. In some embodiments, the outer periphery of the mating surface 486 of the fluid conduit 480 can be in contact with, and/or generally complimentary in shape with the outer periphery of the mating surface 146 of the valve member 116 when the male connector 100 and/or female connector 400 is in an open configuration.

In some embodiments, the mating surfaces of the male connector 100 and/or the female connector 400 can be at least partially compressible to help form a substantially leak-free or leak-resistant seal between the mating surfaces. For example, the mating surface 146 of the valve member 116 can be made of an elastomeric material that can seal with the mating surface 486 of the fluid conduit 480 (which can itself be either flexible or rigid) so that fluid does not contact the mating surfaces of the male connector 100 and female connector 400. In some embodiments, the mating surface 486 of fluid conduit 480 can be made of an elastomeric material that can seal with the mating surface 146 of the valve member 116 (which can itself be either flexible or rigid). In some embodiments, the fluid can flow around the seal formed by the two mating surfaces 146, 486. In some embodiments, is impeded from passing within the periphery of the mating surfaces 146, 148 between the two mating surface 146, 148. In some embodiments, as described herein, the fluid can flow between the male connector 100 and the female connector 400 without requiring the piercing of or penetration of a normally closed septum. For example, the septum can comprise a constant opening through which a fluid conduit can pass, or the fluid can flow around the outside of a septum or other barrier. By sealing the mating surfaces from the fluid, the mating surface 146 of the valve member 116 and the mating surface 486 of the fluid conduit 480 can remain dry after disconnecting the two connectors 100, 400, and contamination to the health care provider or surrounding environment can be diminished or eliminated.

In some embodiments, the cross-section of the mating surface 146 of the valve member 116 can be about the same as or smaller than the cross-section of the bore 470 of the seal element 460. In some embodiments, inner cross-section of the luer tip seal 119 can be smaller than or about the same as the inner cross-section of the bore 470 of the seal element 460. In some embodiments, engagement between the periphery of the bore 470 and the first end 112 of the male connector 100 can help inhibit leakage of fluid to the mating surface 466 of the seal element 460. For example, in some embodiments, the periphery of the bore 470 can engage with the mating surface 176 of the luer tip seal 119 and form a substantially fluid tight seal between the fluid path within the two connectors and the mating surface 466 of the seal element 460. By sealing the mating surface 466 of the seal element 460 from the fluid, the mating surface 466 can remain dry during and after fluid transfer and lower the risk that a health care provider could be exposed to the fluid.

In some embodiments, the inner cross-section of the luer tip seal 119 can be smaller than or about the same as the outer cross-section of the rigid tube 487 near the first end 482 of the fluid conduit 480. In some embodiments, the luer tip seal 119 can "wipe" the outer surface of the rigid tube 487 as it passes through the luer tip seal 119 during opening and/or closing of the valve member 116. In some variants, wiping of the outer surface of the rigid tube 487 as it passes through the luer tip seal 119 can help inhibit the congregation of or leakage of fluid in the region of the first end 402 of the female connector 400. As explained above, in some embodiments, the natural outer cross-section of the mating surface 146 of the valve member 116 can be slightly larger than the natural inner cross section of the luer tip seal 119. In some embodiments, the luer tip seal 119 can wipe the outer surface of the valve member 116 as the valve member 116 moves toward a closed configuration from an open configuration. In some implementations, wiping of the outer surface of the valve member 116 can help reduce the likelihood of fluid congregation or leakage in the region of the first end 112 of the male connector 100 during and/or after disengagement between the mating surface 486 of fluid conduit 480 and the mating surface 146 of the valve member 116. By preventing congregation or leakage of fluid in the region of the first end 112 of the male connector 100 and/or in the region of the first end 402 of the female connector 400, the luer tip seal 119 can help to reduce the likelihood that health care providers would be exposed to the fluid.

As described above, the mating surface 146 of the valve member 116 can have a cavity 147 that can accept a complementary protrusion 490 on the mating surface 486 of the fluid conduit 480. In other embodiment the cavity can be on the fluid conduit 480 and the protrusion can be on the valve member 116. The cavity 147 and protrusion 490 can help to align the male connector 100 and female connector 400 during coupling so that the components align for proper displacement of parts. In some embodiments, the cavity and protrusion can have a circular cross-sectional shape. In some embodiments, the cavity and protrusion can be any of a plurality of different types of shapes, such as square or polygonal.

With reference to FIG. 32, in the open configuration, fluid can flow between (to or from) the tubing 13 at the second end 114 of the male connector 100, into the end cap portion 130, through the chamber 154, through the passageway 156, out the ports 162 on the valve member 116, into the luer tip 122, into the ports 488 on the fluid conduit 480, through the passageway 418, and out the male luer engagement 485 at the second end 404 of the female connector 400. In the open configuration, the second end of the male connector 100 is placed in fluid communication with the second end 404 of the female connector 400. Additionally, the sealing member 120 in the male connector 100 can maintain a fluid barrier between the inner surface of the luer tip 122 and the inner surface of the housing 123, confining the flow of fluid within the fluid pathway of the female connector 400. In the illustrated example, the central mating interface between the male and female connectors is positioned in the fully open configuration within a neck portion of the female connector, or within an outer region of the proximal opening of the female connector, and inside of the male luer tip 122 or outer sleeve.

In some embodiments, the connectors 100, 400 can be threadedly disengaged. During engagement, the force stored in the stretching of the resilient member 118 can return the male connector 100 to its pre-engaged state by biasing the valve member 116 to engage the inner surface of the luer tip 122. Likewise, the resilient material of the seal element 460 allows the seal element 460 to return to its shape in the closed configuration where the sealing portion 462 can seal the ports 488 on the fluid conduit 480.

Figure 33:
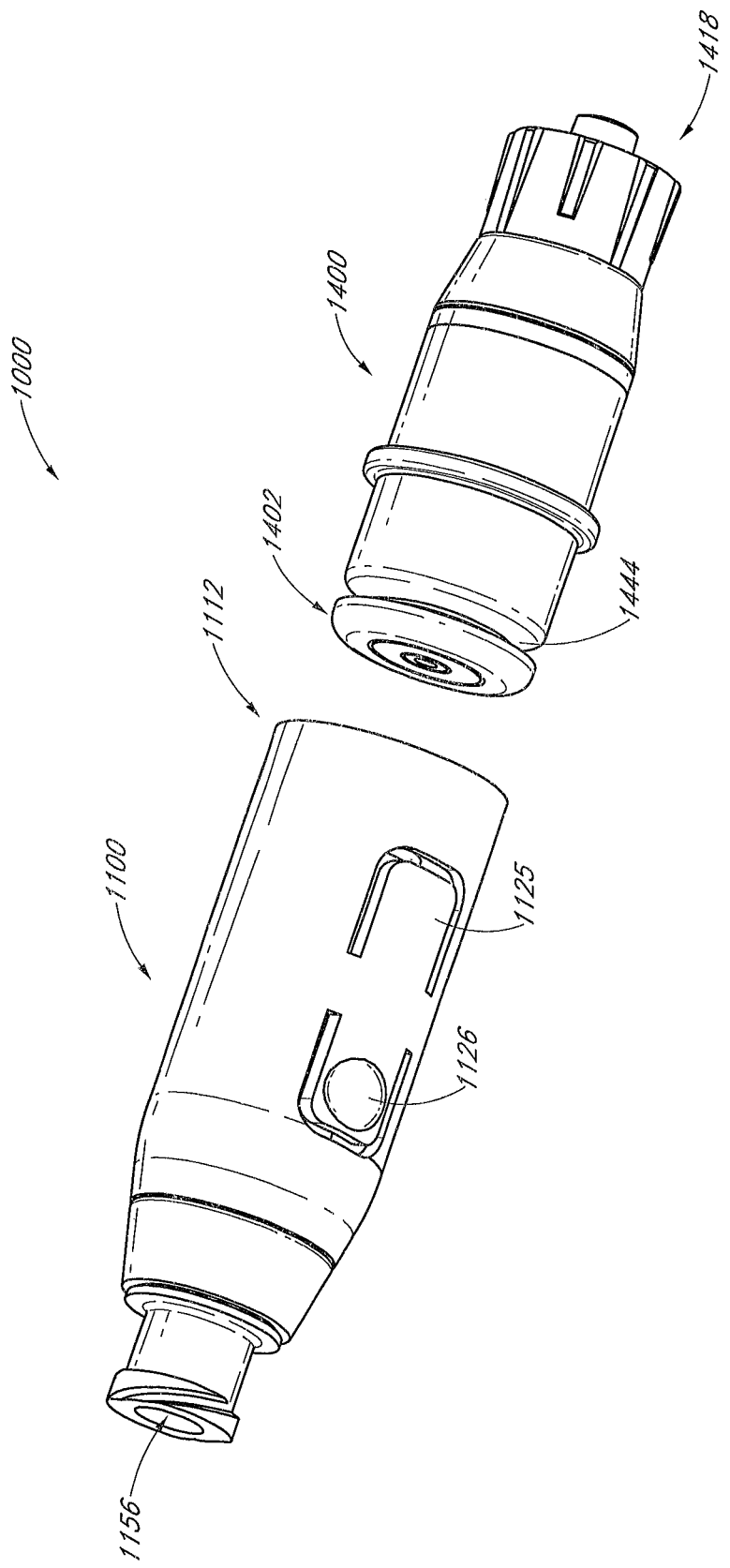
FIG. 33 is a perspective view of another embodiment of a male connector adjacent another embodiment of a female connector.

FIG. 33 illustrates another example of a connector system 1000 that comprises a male connector 1100 and a female connector 1400. In some embodiments, as illustrated, a first end 1112 of the male connector 1100 can releasably couple with a first end 1402 of the female connector 1400 while permitting but not requiring rotation of the male connector 1100 or female connector 1400. As illustrated, the first and second connectors 1100, 1400 can be selectively joined together in a substantially linear motion in which at least a portion (and in some cases a majority) of the outer surface area of one fits over at least a portion (and in some cases a majority) of the outer surface area of the other. In some embodiments, an audible sound can be produced when the connectors 1100, 1400 engage. In the illustrated embodiment, the male connector 1100 has a coupling element, such as tabs 1125 with hooks 1127 that engage with a channel 1444 on the female connector 1400 to secure the connectors together. Many other types of engagement arrangements can be employed to secure the connectors together. For example, the female connector 1400 can include a shroud or other attachment structure (e.g., a shroud 112 of the type illustrated on the male connector 1100) that fits over or outside of a portion of the male connector 1400. In some embodiments, as illustrated, the connection is reversible or detachable.

As explained further below, the first ends 1112, 1402 are configured such that a fluid passageway 1156 of the male connector 1100 can be fluidly connected to the fluid passageway 1418 of the female connector 1400 when the first ends 1112, 1402 are coupled together. When the male connector 1100 and female connector 1400 are disconnected, the fluid pathways 1156, 1418 are obstructed. The coupling between the male connector 1100 and female connector 1400 is configured such that the first ends 1112, 1402 are substantially absent of residual fluids after the connectors are disconnected.

Figure 34:
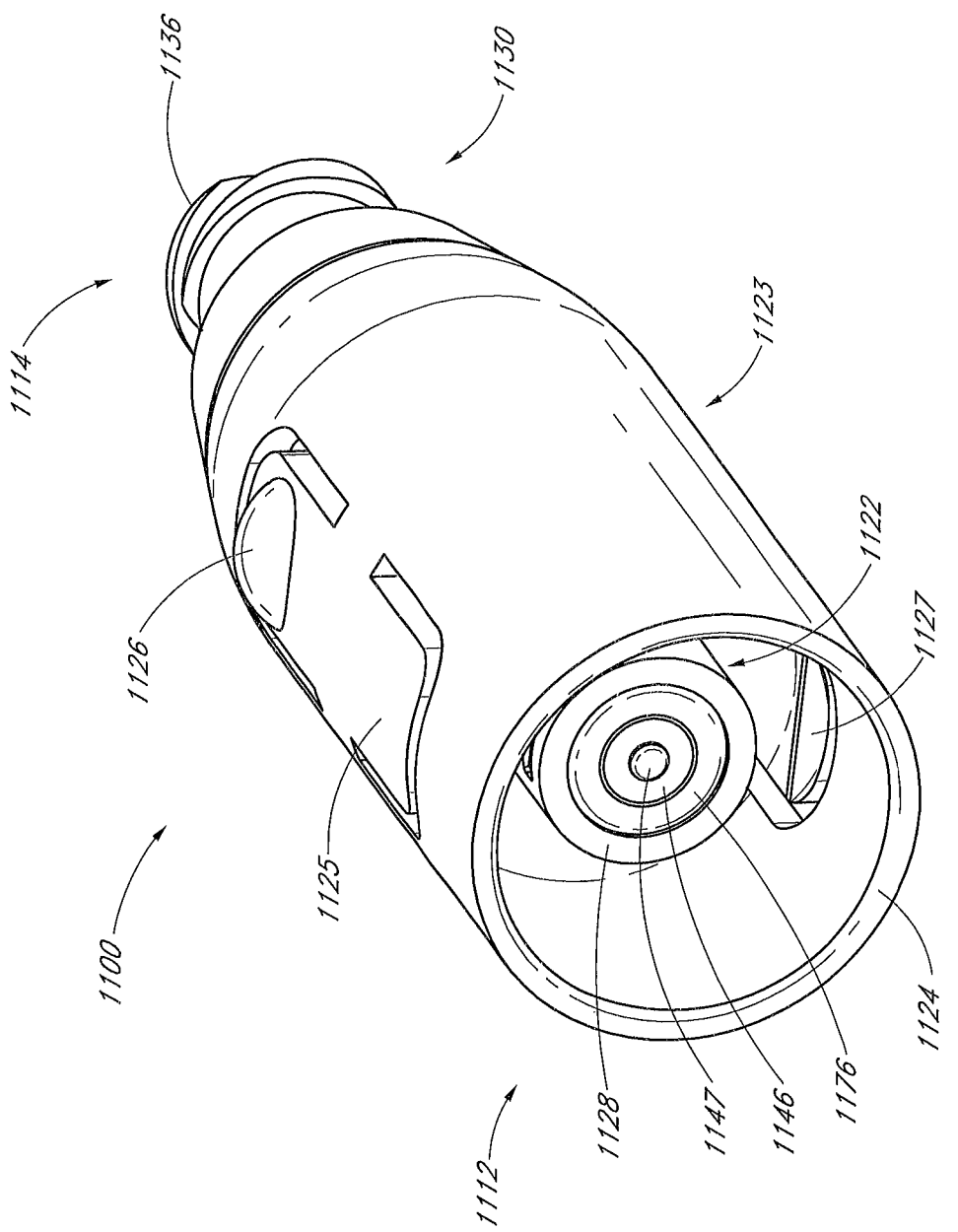
FIG. 34 is a perspective view of an embodiment of the male connector shown in FIG. 33 in a closed position.

FIG. 34 illustrates the embodiment of the closeable male connector 1100 in FIG. 33. Any of the configurations, features, components, and/or alternatives of the male connector 1100 can comprise, be interchangeable with, or be used with any of the configurations, features, components, materials, and/or alternatives of any other male connector. For example, the connection structure (e.g., hook and channel features) relating to preventing or inhibiting disconnection can be used with any suitable medical or other fluid connector.

Figure 35:
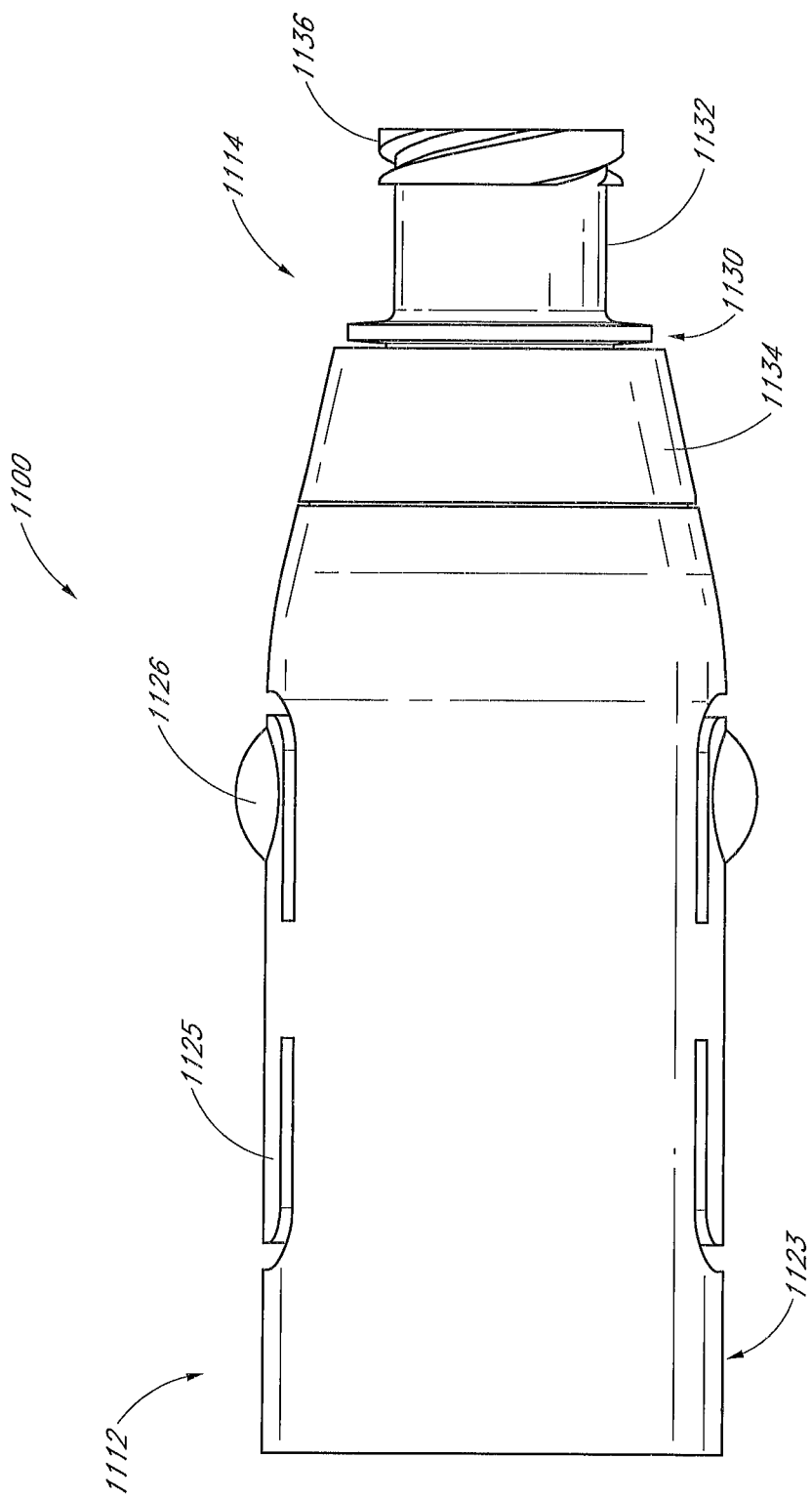
FIG. 35 is a side view of the embodiment of the male connector shown in FIG. 34 again in a closed position.

FIGS. 34 and 35 are a perspective view and a side view, respectively, of the closeable male connector 1100 in a first or closed position. The closeable male connector 1100 can have a first end 1112 and a second end 1114. The first end 1112 can be configured to mate with the female connector 1400. In some embodiments, the first end 1112 can include attachment and/or alignment structure (e.g., a protrusion) that is configured to be contacted with (e.g., inserted into) another attachment and/or alignment structure of the female connector 1400. In the illustrated embodiment, the first end 1112 has a male luer tip 1122 and a valve member 1116 (shown in more detail in FIGS. 36 and 39). In the closed position, valve member 1116 can cooperate with a luer tip seal 1119 on the male luer tip 1122 to impede or resist the flow of fluid through the male connector 1100.

Figure 36:
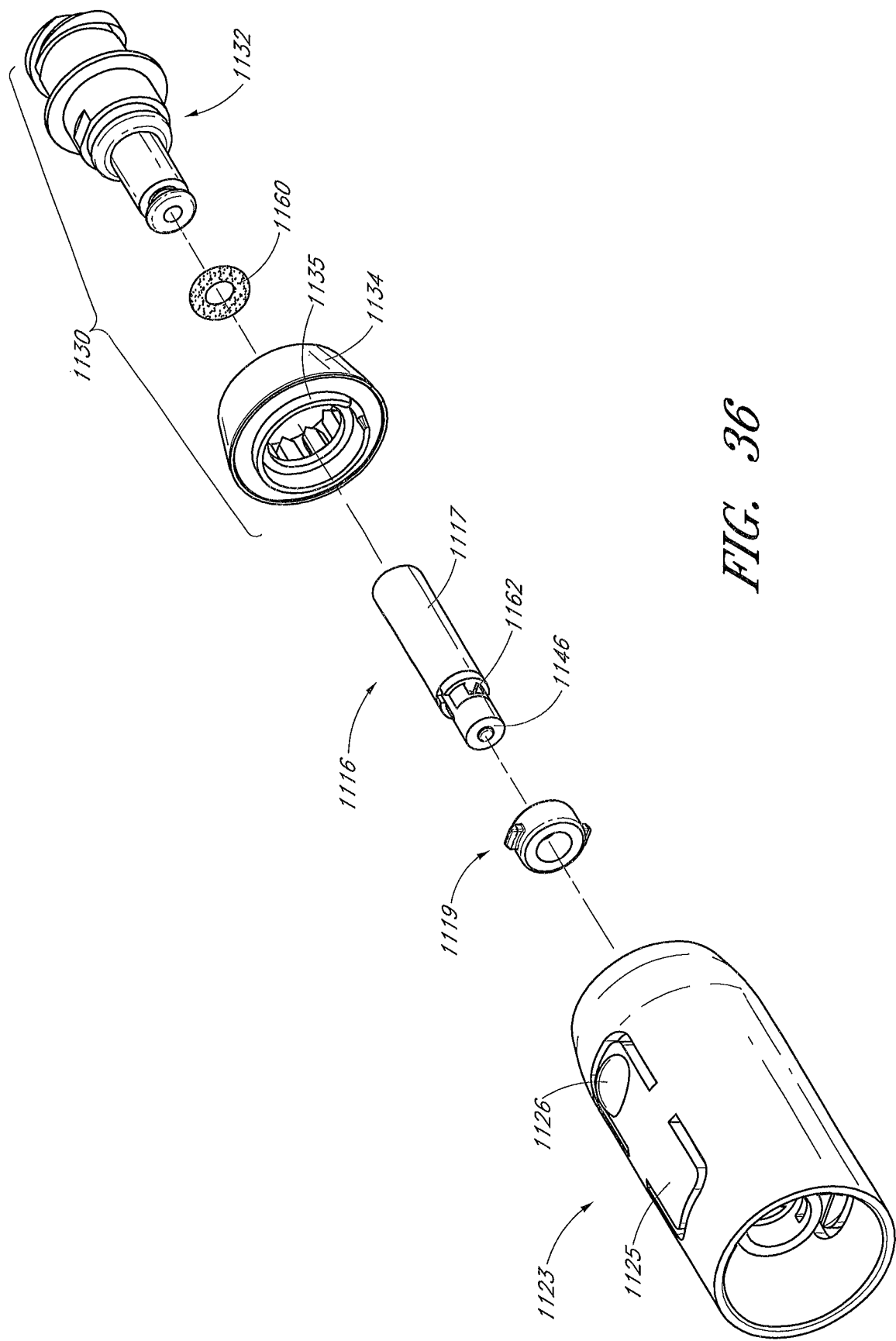
FIG. 36 is an exploded perspective view of the components of the embodiment of the male connector shown in FIG. 34.

FIG. 36 is an exploded perspective view of the components of the embodiment of the closeable male connector 1100 shown in FIG. 34. With reference to FIG. 36, an end cap portion 1130 can be coupled to the male housing 1123 near the second end 1114 of the closeable male connector 1100, as generally described herein in other embodiments.

As illustrated in FIG. 34, the male housing 1123 can have a shroud 1124 generally or completely surrounding the luer tip 1122. In some embodiments, the end of the shroud 1124 is spaced from the end 114 of the male connector to inhibit unintended external contact with the end 1114 of the male connector, thereby resisting contamination of the end 1114 from other surfaces and/or the contamination of other surfaces from contact with the end 1114. In some embodiments, the space between the end of the shroud 1124 and the end 1114 of the male connector is at least as large as the cross section of the fluid path within the valve member 1116. In some embodiments, the shroud 1124 can have an inner diameter or cross-section which can be greater than an outer diameter of cross-section of the male luer tip 1122. The shroud 1124 can have an engagement feature for securing the male connector 1100 to the female connector 1400. In the illustrated embodiment, the shroud 1124 has integrated tabs 1125 and release buttons 1126 for securing the male connector 1100 to the female connector 1400. The tabs 1125 can have hooks 1127 that engage with a channel 1444 on the female connector 1400. The hook and channel engagement allows the connectors 1100, 1400 to be coupled without requiring rotation of the connectors, which can be performed more quickly, can require less manual precision during coupling, and/or can reduce the risk of twisting the attached fluid lines. A release structure, such as a release button 1126, can be actuated (e.g., pressed) to lift the hooks 1127 from the channel 1444 to disconnect the connectors. In some embodiments, the engagement feature may not be integrated with the male housing 1123. For example, the tabs and release buttons can be a separate component that is attached to the male housing 1123. In some embodiments, other engagement features can be used to secure the connectors together, such as threads, pins, detents, channels, and/or protrusions (e.g., a bayonet-type connection).

The luer tip 1122 near the first end 1112 of the male connector 1100 can comprise a mating surface 1128 at the end that is configured to form a leak-resistant and/or leak-free seal with at least a portion of the mating surface 1466 of the seal element 1460, as explained herein in other embodiments. In the illustrated embodiment, the mating surface 1128 is a thin annular ring at the end of the luer tip 1122.

Figure 37:
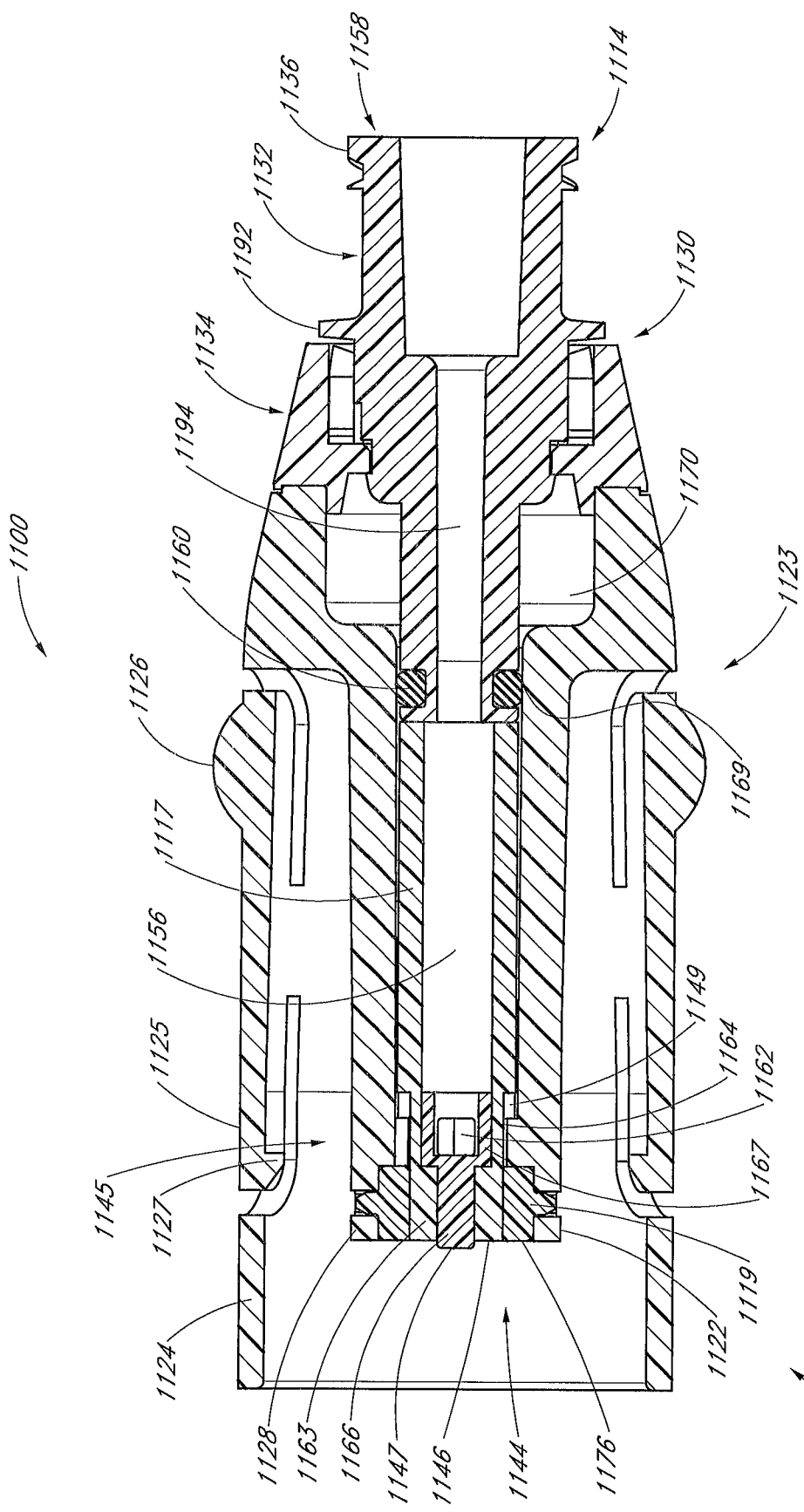
FIG. 37 is a cross-sectional side view of the embodiment of the male connector shown in FIG. 35.
Figure 38:
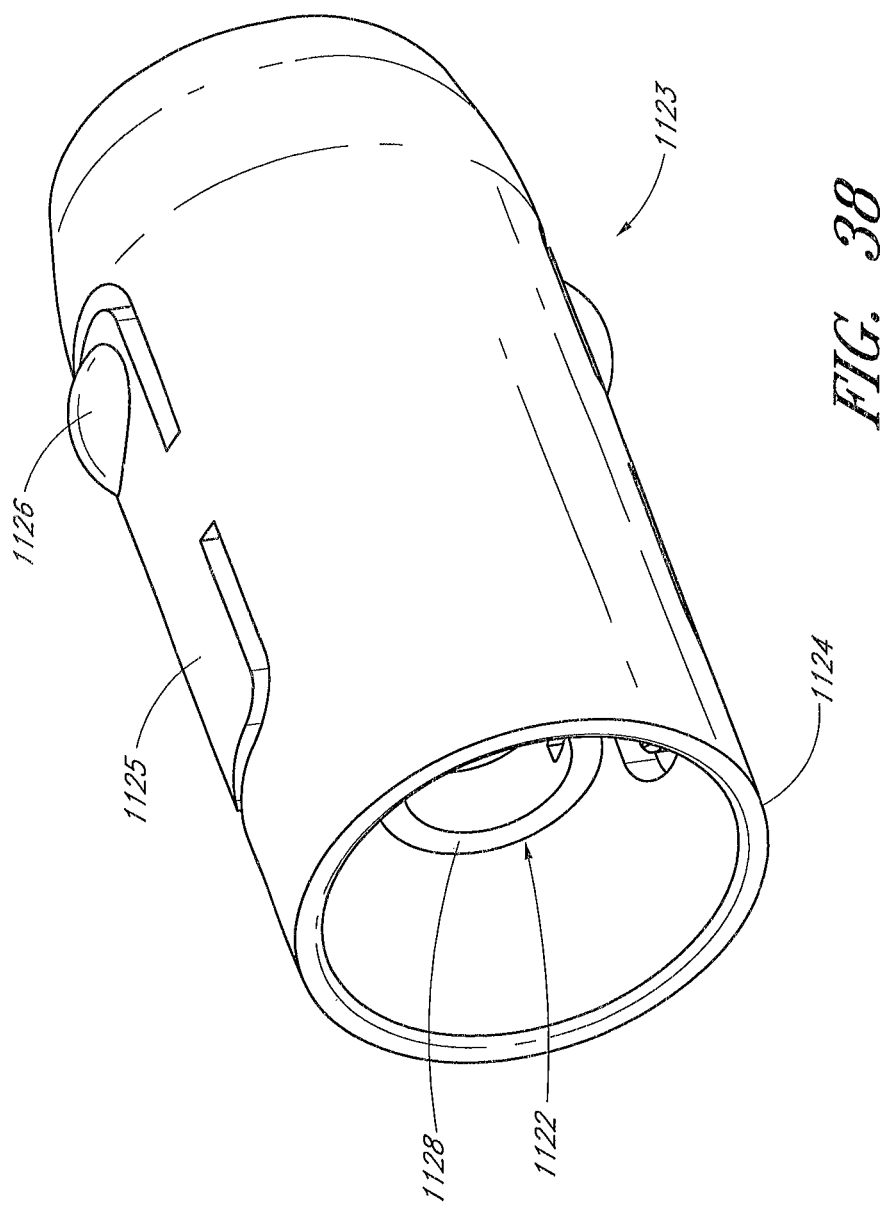
FIG. 38 is a perspective view of an embodiment of a male housing of the male connector shown in FIG. 34.
Figure 39:
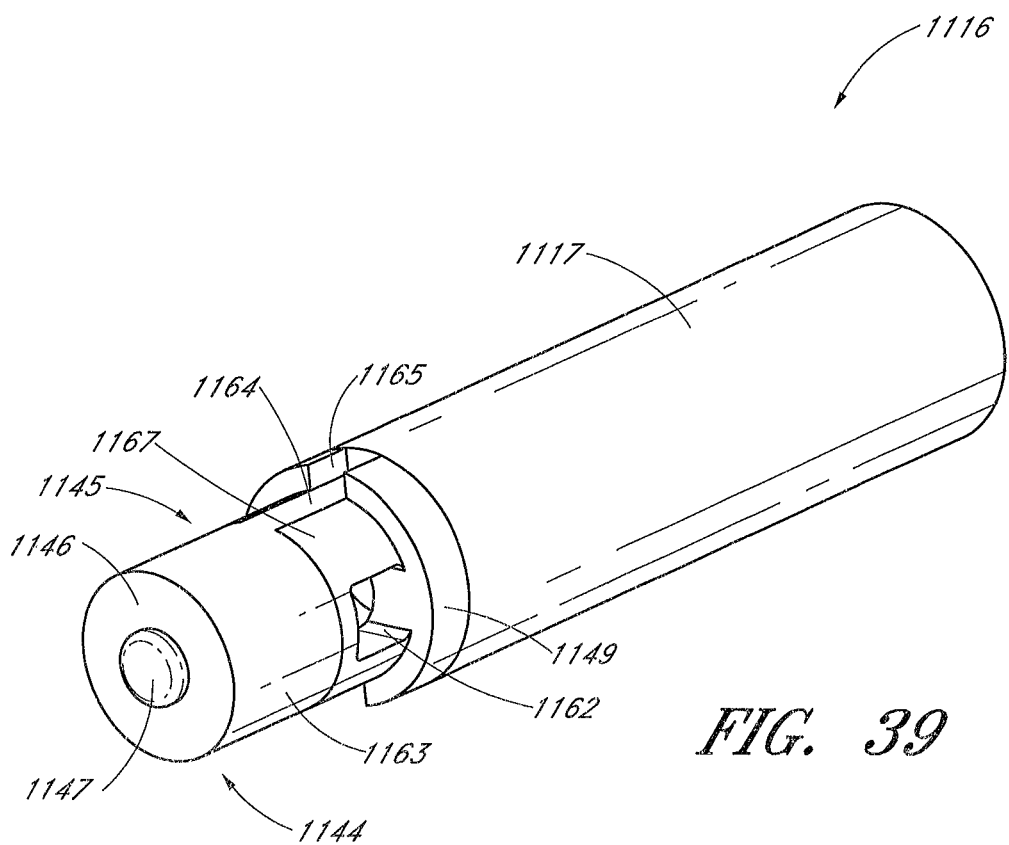
FIG. 39 is a perspective view of an embodiment of a valve member of the male connector shown in FIG. 34.

The valve member 1116 can be at least partially enclosed by the male housing 1123, such as in the illustrated embodiment of FIGS. 36 and 37. As illustrated in FIGS. 37 and 39, the valve member 1116 can have a closure end 1144 that blocks the flow of fluids through the male connector 1100 in the closed configuration. The valve member 1116 can have a mating surface 1146 that can include a protrusion 1147 that can be coupled with a generally complementary cavity 1490 on a first end 1482 of the fluid conduit 1480. In the illustrated embodiment, the protrusion 1147 is a generally cylindrical or generally discus protrusion with rounded edges. In some embodiments, the protrusion can have a plurality of different shapes, such as protrusions with a rectangular, square or polygonal cross-sectional shape, to generally match the shape of the cavity 1490 on the first end 1482 of the fluid conduit 1480. In some embodiments, the protrusion can be on the first end 1482 of the fluid conduit 1480 and the cavity can be disposed on the mating surface 1146 of the valve member 1116. The protrusion 1147 and cavity 1490 can help to align the mating surfaces of the male connector 1100 with the mating surfaces of the female connector 1400.

The valve member 1116 can have a tube section 1117 with a channel that extends within (e.g., through the middle of) the tube section 1117. Fluid can flow through the tube section 1117 of the valve member 1116 and out through ports 1162 on the valve member 1116. The tube section 1117 can be made of a resilient material that can elastically deform. When the male connector 1100 is in the open position, the valve member 1116 is pushed toward the second end 1114 of the male connector 1100, compressing the resilient tube section 1117. In some embodiments, the tube section 1117 deforms by a small amount so that the channel is not obstructed by the compressed tube section 1117. In some embodiments, the tube section 1117 can deform outwardly so that the channel is not obstructed. The tube section 1117 can exert a return spring force on the closure end 1144 toward the first end 1112 of the male connector 1100. This closing force on the valve member 1116 is biased toward returning the male connector 1100 to a closed configuration.

The amount of spring force exerted by the tube section 1117 can be modified by varying several parameters, such as the length of the tube section 1117, the thickness of the tube section 1117, and/or by construction of the tube section 1117 from a variety of materials having different elastic properties. In some embodiments, the male connector 1100 is configured to require enough opening force to prevent accidental or unintentional opening. In some embodiments, the force required to open the connector is controlled at least in part by the compression force of the tube section 1117. In some embodiments, the tube section can have a helical spring positioned inside the male housing 1123 for biasing the closure end 1144 of the valve member 1116 to the closed position. In some embodiments, the tube section can have other biasing members, such as elastic bands or actuators.

In some embodiments, the valve member 1116 can have an end piece 1145 near the closure end 1144 of the male luer tip 1122. In some embodiments, the end piece 1145 can have an end body portion 1167 with an outer diameter or cross-section. In some embodiments, the end piece 1145 can have a flange 1149 extending from the end body portion 1167. In some embodiments, the flange 1149 has at least one slot 1165. In some embodiments, the end piece 1145 can have at least one port 1162. The end piece 1145 can include an extension portion 1166 extending from the end body portion 1167 toward the closure end 1144 of the luer tip 1122. In some embodiments, the extension portion 1166 can have an outer diameter or cross-section which is smaller than the outer diameter or cross-section of the end body portion 1167. In some embodiments, the extension portion 1166 can form a unitary part with the protrusion 1147. In some embodiments, the end piece 1145 can be constructed of a rigid or semi-rigid material.

In some embodiments, valve member 1116 can have a sleeve portion 1163. In some embodiments, the sleeve portion 1163 has an inner diameter or cross-section and an outer diameter or cross-section. The sleeve portion 1163 can be constructed of a resilient material that can elastically deform. In some embodiments, the sleeve portion can have one or more indentations, protrusion, or grooves to facilitate compression and/or rebounding. In some embodiments, the sleeve portion 1163 can be configured to engage with the extension portion 1166. In some embodiments, the inner diameter or cross-section of the sleeve portion 1163 is less than the outer diameter or cross-section of the extension portion 1166, which can aid the valve member 1116 in resisting leakage between the sleeve portion 1163 and the extension portion 1166.

In some embodiments, the valve member 1116 can include a securement portion 1164. The securement portion 1164 can be constructed of a resilient material that can elastically deform. In some embodiments, the securement portion 1164, sleeve portion 1163, and/or tube section 1117 can be constructed of the same material and/or form a unitary part. In some embodiments, the securement portion 1164 can be configured to engage with the at least one slot 1165 in the flange 1149, as illustrated in FIG. 39. In some embodiments, the securement portion 1164 can be biased in a stretched configuration In some embodiments, the end piece 1145 can be attached to the tube section 1117 and/or sleeve portion 1163 via an adhesive. In some embodiments, the securement portion 1164 can be configured to exert a biasing force on the sleeve portion 1163 and the tube section 1117 and bias the sleeve portion 1163 toward the tube section 1117. A biasing force can secure the end piece 1145 between the sleeve portion 1163 and the tube section 1117. For example, in some embodiments the flange 1149 could engage with the tube section 1117 and the end body portion 1167 could engage with the sleeve portion 1163. Such an engagement can help the end piece 1145 resist disengagement from the sleeve portion 1167 and/or the tube section 1117.

A luer tip seal 1119 can be disposed in the interior of the luer tip 1122, as illustrated in FIGS. 36 and 37, as generally described in other embodiments. The luer tip seal 1119 can be disposed between the male housing 1123 and the valve member 1116 to form a seal over the ports 1162 of the valve member 1116 in the closed position. In the illustrated embodiment, the luer tip seal 1119 has a pair of protrusions 1177 that can couple with notches 1129 on the male luer tip 1122 to secure the luer tip seal 1119 in place as the valve member 1116 slides longitudinally in the male housing 1123. In some embodiments, the luer tip seal 1119 can be secured to the male luer tip 1122 by adhesives, welding, interference fit, friction fit, or any other suitable methods.

As shown in the embodiment of the male connector 1100 illustrated in FIG. 34, the mating surface 1146 of the valve member 1116 is disposed substantially flush across the luer tip 1122 when the male connector 1100 is in the closed position. In some embodiments, the mating surface 1146 of the valve member 116 can be configured to extend further beyond the mating surface 1128 of the luer tip 1122 when the male connector 100 is in the closed position. In some embodiments, the mating surface 1146 of the valve member 116 can be recessed within the luer tip 1122.

The male connector 1100 can be manipulated to a second or open position. In the open position, the valve member 1116 is retracted from the luer tip 1122, thereby allowing the fluid in the valve member 1116 to exit from the ports 1162 and around the closure end 1144. Fluid can pass from the luer receptacle at the second end 1114 through the interior of the male connector 1100 and exit the valve member 1116 when the male connector 1100 is in the opened configuration.

As illustrated in FIG. 37, a passageway 1156 can extend through at least a portion of the valve member 1116. The passageway 1156 can be circular in cross-section, as shown in the illustrated embodiment, or the passageway 1156 can have other cross-sectional geometric shapes. The passageway 1156 can have at least one port 1162 near the closure end 1144 of the valve member 1116. In the illustrated embodiment, two ports 162 are located on generally opposing sides of the valve member 1116 and are rectangular, though other locations and shapes can be used.

In the embodiment illustrated in FIG. 37, the male connector 1100 is in a closed position. An end of the valve member 1116 can abut a plunger 1170 of the first cap component 1132. In some embodiments, the end of the valve member 1116 can form a seal with the end of the plunger 1170 to substantially resist liquids from seeping into the junction between the valve member 1116 and the plunger 1170. In some embodiments, the end of the valve member 1116 can be attached to the plunger 1170 by any suitable methods, such as adhesives, sonic welding, solvent bonding, etc.

The passageway 1156 can be in fluid communication with a conduit 1194 of the first cap component 1132. The conduit 1194 can have a smaller cross-sectional area than the passageway 1156, as illustrated. In some embodiments, the conduit 1194 can have approximately the same size cross-sectional area as the passageway 1156. In some embodiments, the conduit 1194 can be wider than the passageway 1156. The conduit 1194 can be tubular, as illustrated, or configured with a non-circular cross-section in any other appropriate shape.

The plunger 1170 can have an outer dimension that is comparable to the inner dimension of the end of the male housing 1123, but that does not tightly contact such wall to permit relative movement (e.g., rotational movement) between the components. In the embodiment illustrated in FIG. 37, the plunger 1170 is circular so as to match the tubular geometry of the male housing 1123, but other geometric shapes can be used, as appropriate. To inhibit fluid from escaping past the plunger 1170, a seal (e.g., an O-ring seal 1160) can be disposed in a groove 1169 behind the plunger 1170. The O-ring 1160 can contact the wall of the male housing 1123, as shown, inhibiting fluid from flowing around the plunger 1170. In some embodiments, the plunger 1170 is a portion of the end cap 1130. The end cap 1130 can be coupled with the male housing 1123 through sonic welding, an adhesive, or any other suitable method for coupling, as described above. The plunger 1170 can be considered to be in a static position relative to the male housing 1123. In some embodiments, the plunger 1170 is formed integrally with the male housing 1123 and the end cap 1130 is a separate piece appropriately attached to the male housing 1123 such as by sonic welding. In some embodiments, the second cap component 1134 can comprise a ridge 1135.

Additionally, in some embodiments, the second cap component 1134 can be integrally or unitarily formed with the male housing 1123. The first cap component 1132 can be formed separately as compared to the second cap component 1134 or the male housing 1123.

As shown in FIG. 37, fluid can flow into the luer receiver 1158 and pass to the conduit 1194. From the conduit 1194, fluid can pass into the passageway 1156. As shown in the illustrated embodiment, when the male connector 1100 is in the closed position, the closure end 1144 of the valve member 1116 can seal the hole in the luer tip 1122, preventing fluid from passing out the end of the luer tip 1122. Fluid generally can, however, exit the passageway 1156 through the ports 1162 in the valve member 1116. The fluid can reside in the interior of the luer tip 1122, but can be prevented from flowing out of the luer tip 1122 by the luer tip seal 1119 and prevented from flowing back towards the second end 114 on the outside of valve member 116 by the tube section 1117. Accordingly, when the male connector 1100 is in the closed position, as illustrated, there can be fluid communication between the luer receiver 1158 and the interior of the luer tip 1122, without permitting fluid to exit the first end 1112 of the male connector 1100.

The male connector 1100 can be changed to the open configuration when mated with a female connector 1400. The luer tip 1122 at least partially advances into the female connector 1400 and the fluid conduit 1480 in the female connector 1400 engages the valve member 1116 to push the closure end 1144 of the valve member 1116 toward the second end 1114 of the male connector 1100. Also, the hooks 1127 on the shroud 1124 of the male connector 1100 can couple with the channel 1444 on the female connector 1400 to hold the connectors together. The connection of the male connector 1100 and female connector 1400 is described in further detail below.

When the valve member 1116 is displaced toward the second end 1114, the valve closure end 1144 can separate from the luer tip 1122, withdrawing the ports 1162 from the luer tip seal 1119. Accordingly, fluid can flow around the closure end 1144 and into a coupled female connector 1400. In some embodiments, the tube section 1117 can inhibit fluid from passing between the interior of the luer tip 1122 and valve member 1116 towards the second end 1114 of the male connector 1100. Accordingly, in the open position, fluid can pass from the luer receiver 1158 through the conduit 1194, passageway 1156, port or ports 1162 in the valve member 1116, into the interior of the luer tip 1122, and into a port in the female connector 1400.

Figure 52:
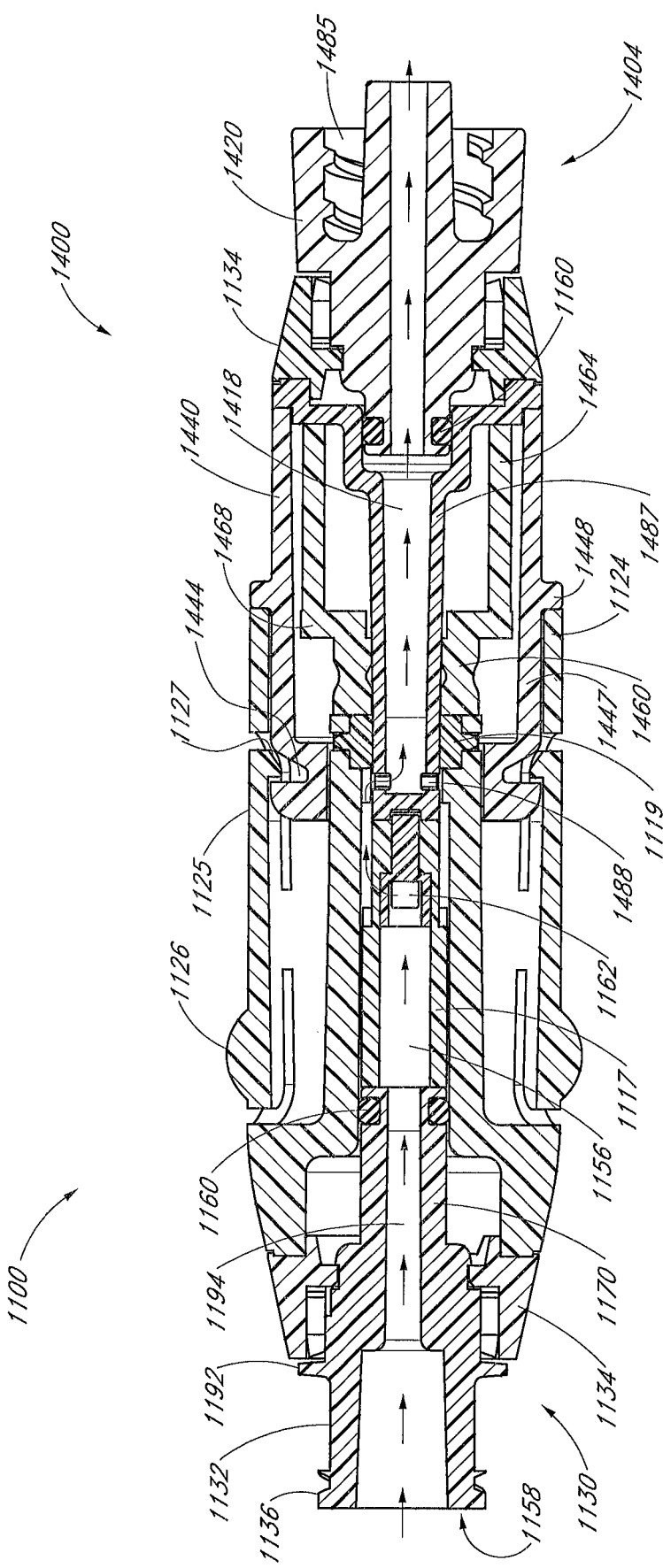
FIG. 52 shows a cross-sectional side view of the connector system of FIG. 51.
Figure 53:
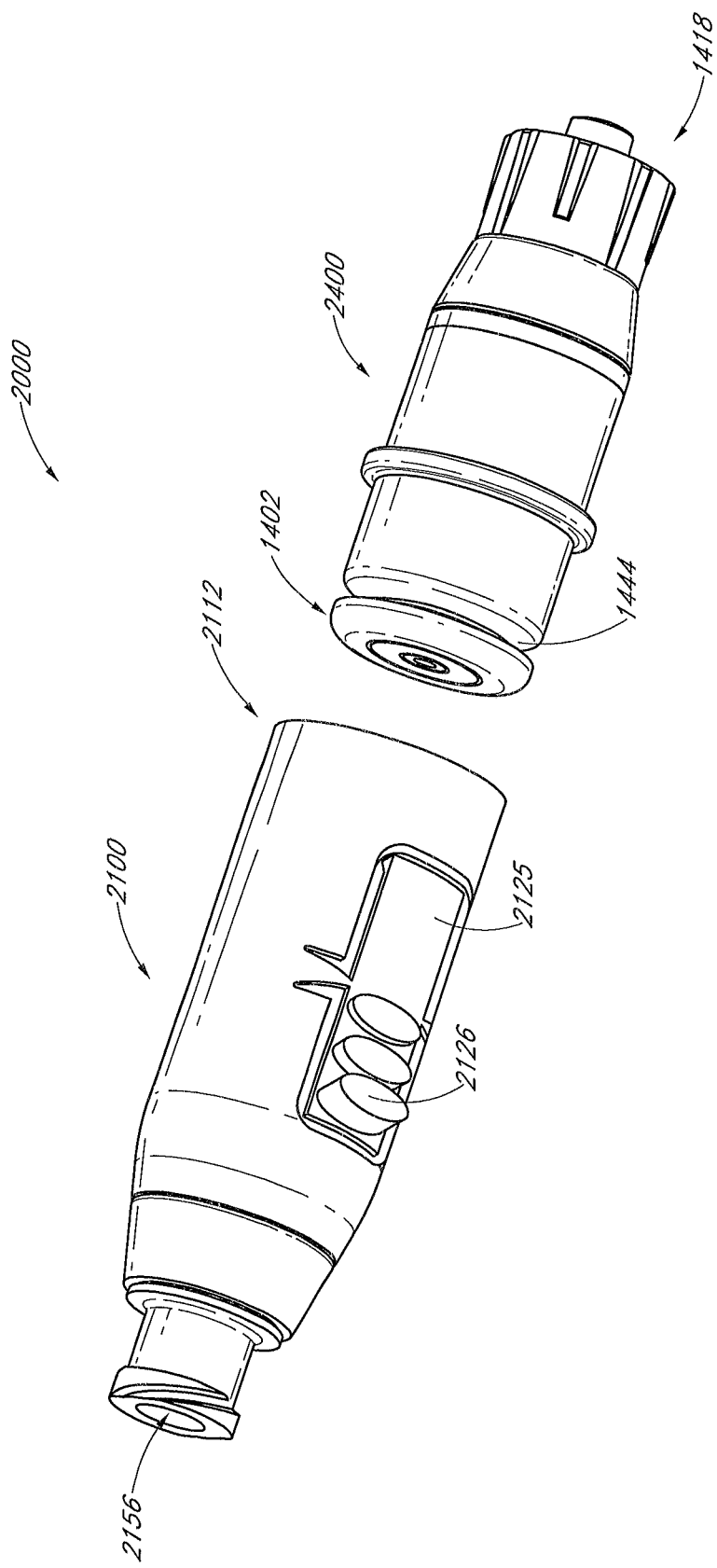
FIG. 53 is a perspective view of another embodiment of a male connector adjacent another embodiment of a female connector.
Figure 54:
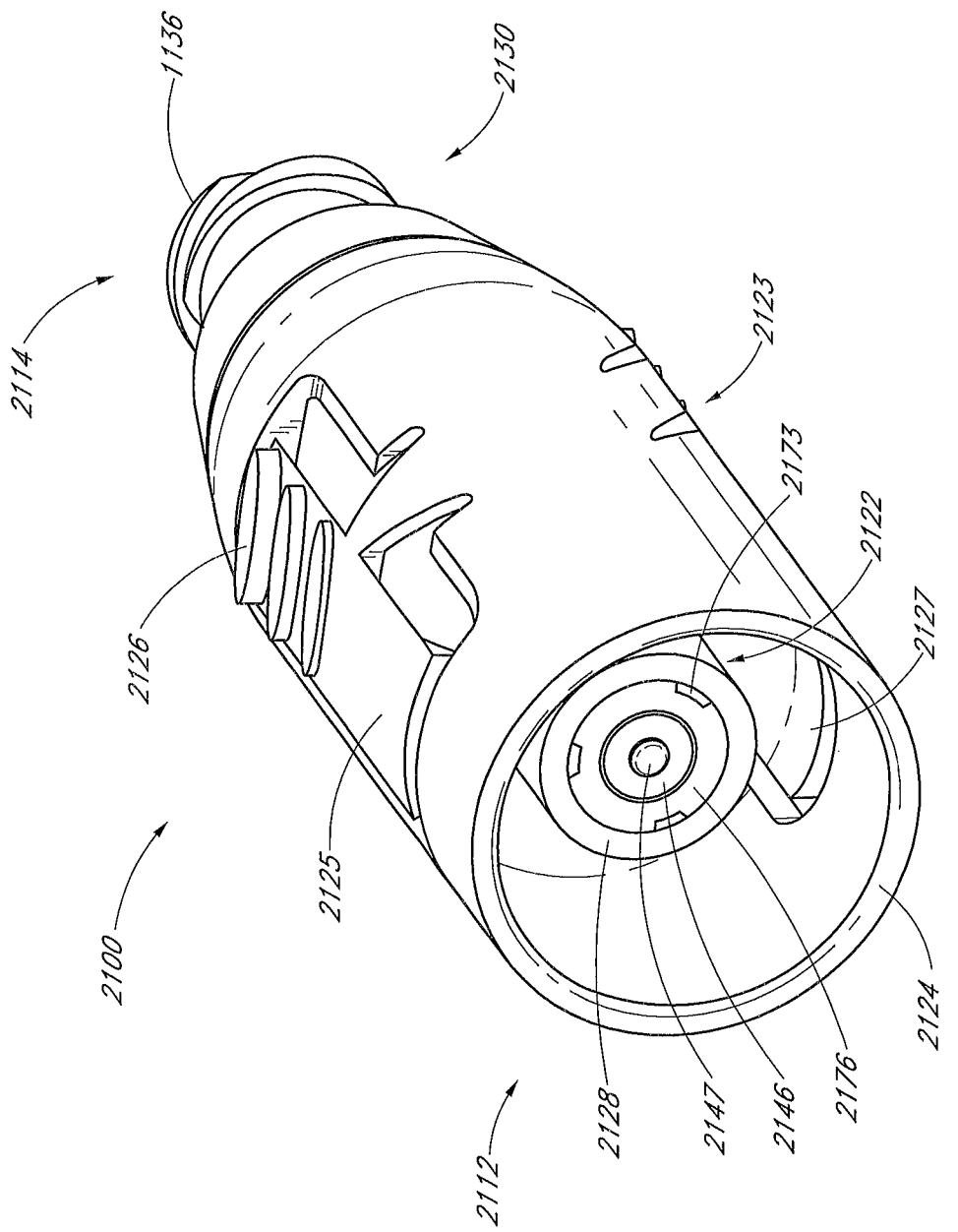
FIG. 54 is a perspective view of an embodiment of the male connector shown in FIG. 53 in a closed position.
Figure 55:
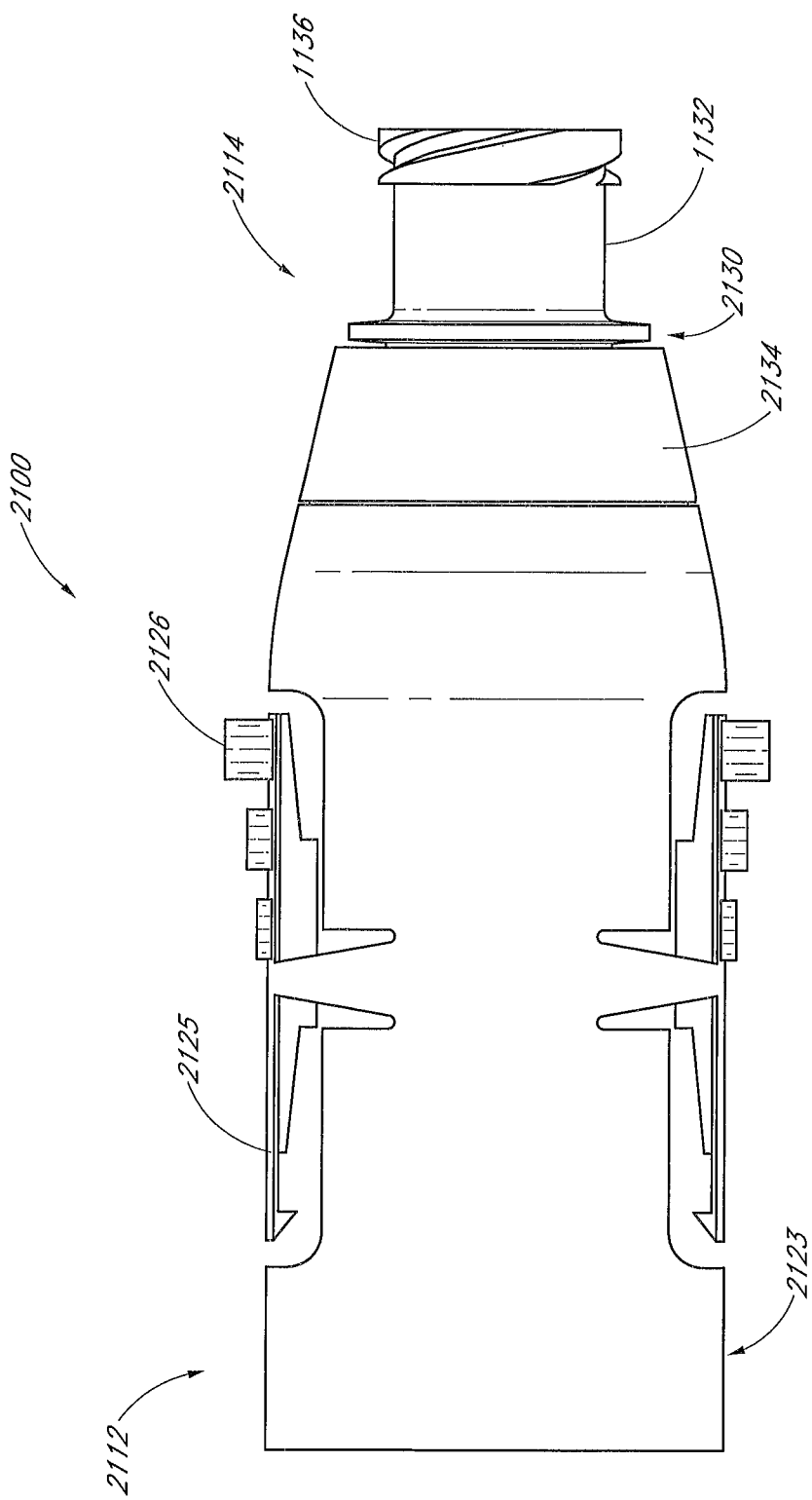
FIG. 55 is a side view of the embodiment of the male connector shown in FIG. 54 again in a closed position.

As can be seen in the embodiment illustrated in FIG. 52, when the male connector 1100 is in the open position, the closure end 1144 of the valve member 1116 can be displaced toward the second end 1114 of the male connector 1100, closer to the plunger 1170 portion of the end cap 1130. Accordingly, tube section 1117 is compressed and the volume of the passageway 1156 can be reduced in the open position.

Correspondingly, when the male connector 1100 is changing from an open position to a closed position, the volume of the passageway 1156 increases as the closure end 1144 of the valve member 1116 shifts toward the first end 1112 of the male connector 1100. As the valve closure end 1144 of the valve member 1116 advances towards the first end 1112, the closure end 1144 can seal the hole in the luer tip 1122. If no additional fluid is introduced into the male connector 1100 through the luer receiver 1158, the existing fluid in the luer tip 1122 can be drawn back through the ports 1162, toward the passageway 1156 by the vacuum effect created when the volume of the passageway 1156 increases. In this case, fluid can be inhibited from exiting the hole in the luer tip 1122 as the valve closure end 1144 moves into place in the hole because the fluid can instead be drawn back to the passageway 1156. In some embodiments, fluid near the mating surface 1146 of the valve member 1116 is encouraged to move into the interior of the male connector 100 rather than remain near the mating surface 1146 as the closure end 1144 moves toward the first end 1112 of the male housing 1123, thereby resisting exposure of the mating surface 1146 to the fluid.

If, however, additional fluid is still being introduced into the male connector 1100 through the luer receiver 1158, the additional fluid can advance to the passageway 1156 and collect there as the closure end 1144 moves toward the first end 1112 to close the luer tip 1122. Pressure from the newly-introduced fluid can be inhibited from forcing fluid to flow out the luer tip 1122 as the luer tip seal 1119 seals the luer tip 1122. Accordingly, fluid flow is permitted through the male connector 1100 while a female connector 1400 is coupled with the first end 1112 of the male connector 1100, but inhibited while the female connector 1400 is being disengaged and after the female connector 1400 has been decoupled.

As described above, in some embodiments, it can be desirable to inhibit certain medicines from contacting the skin or being inhaled. The male connector 1100 can assist in retaining fluid within the male connector 1100 while substantially eliminating remnant fluid on the luer tip 1122 when it is being decoupled from a female connector 1400 or other connection. Accordingly, reducing the likelihood of remnant fluid remaining on the luer tip 1122 after decoupling, results in a corresponding reduction in the chance of exposure of toxic medicine to the skin of a user or a patient.

Figure 40:
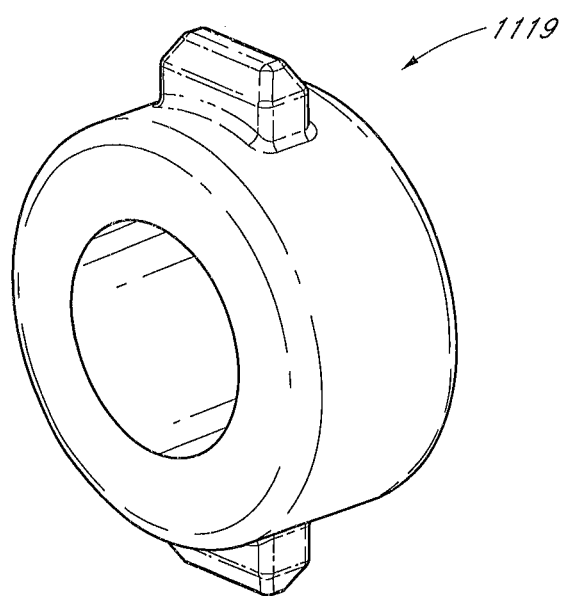
FIG. 40 is a perspective view of an embodiment of a luer tip seal of the male connector shown in FIG. 34.

FIGS. 39-40 are perspective views of an example of a valve member 1116 and the luer tip seal 119, respectively, of the embodiment of the closeable male connector 1100 shown in FIG. 34. With specific reference to FIG. 39, one or more of the ports 1162 can be located near the mating surface 1146. The ports 1162 can be rectangular, as illustrated, or can have other shapes. The male connector 1100 can be adapted to be opened when placed in mating engagement with a female connector 1400. For example, the female connector 1400 can include an engagement member such as, but not limited to, a surface generally complementary to the protrusion 1147 with a cavity which can engage the valve closure face 1144 to open the male connector 1100. In some embodiments, a manually actuated slider, button, or other actuator can be appropriately configured to open the male connector 1100.

With reference to FIG. 40, the luer tip seal 1119 can be substantially cylindrical with an opening 1178 extending along the longitudinal axis of the luer tip seal 1119. The side facing the first end 1112 of the male connector 1100 can have a mating surface 1176 that is configured to mate with a corresponding surface of the female connector 1400. The luer tip seal 1119 can be constructed from a number of different materials. In some embodiments, the luer tip seal 1119 can be made from a silicon-based deformable material. Silicon-based deformable materials are among those that can form fluid-tight closures with plastics and other rigid polymeric materials.

The end cap portion 1130 (see FIG. 37) can be similar to the end cap portion 130 described above in other embodiments. The end cap portion 1130 and the corresponding components are referenced in the current embodiment with similar reference numbers, except increased by an order of 1000.

Figure 41:
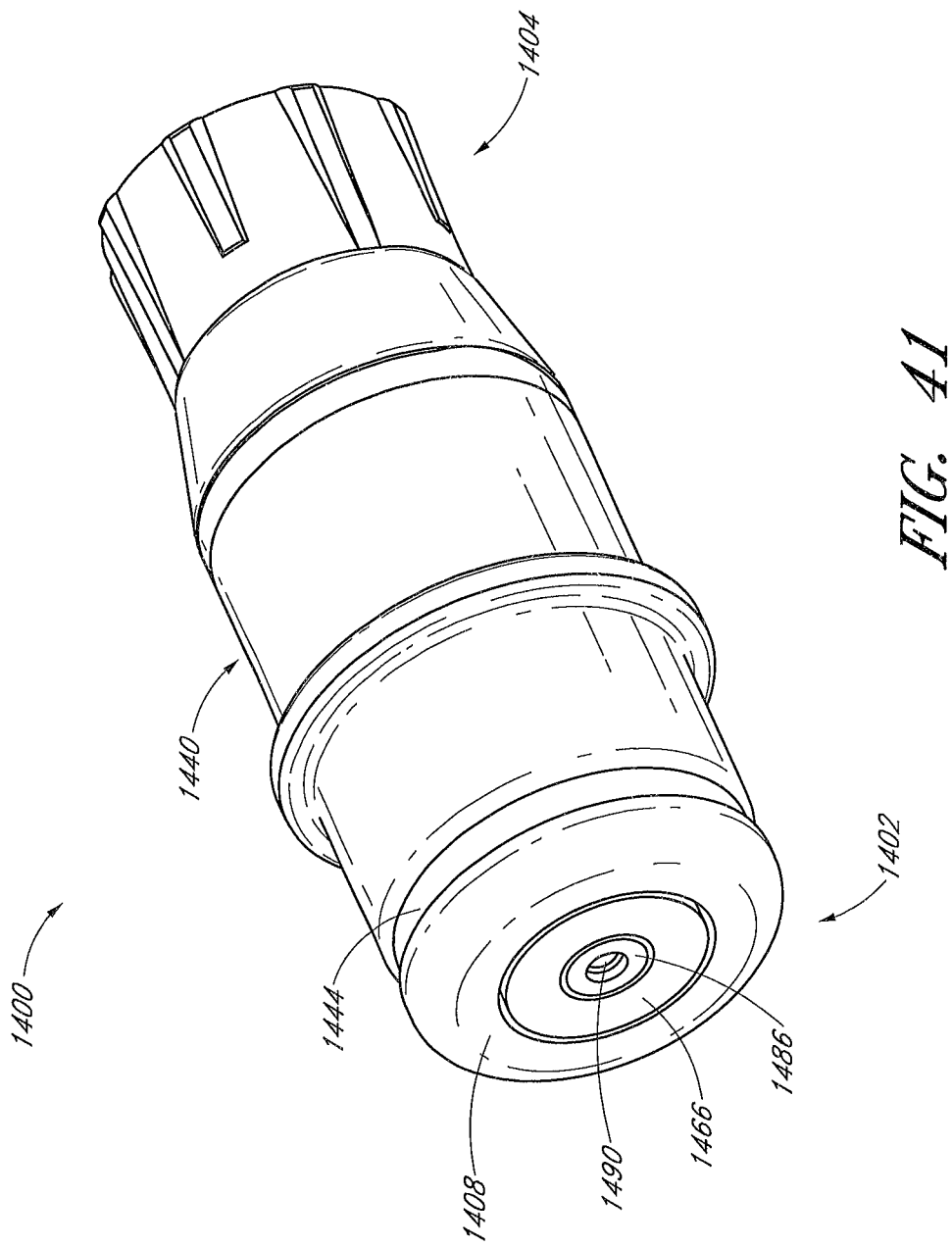
FIG. 41 is a perspective view of an embodiment of the female connector shown in FIG. 33 in a closed position.
Figure 42:
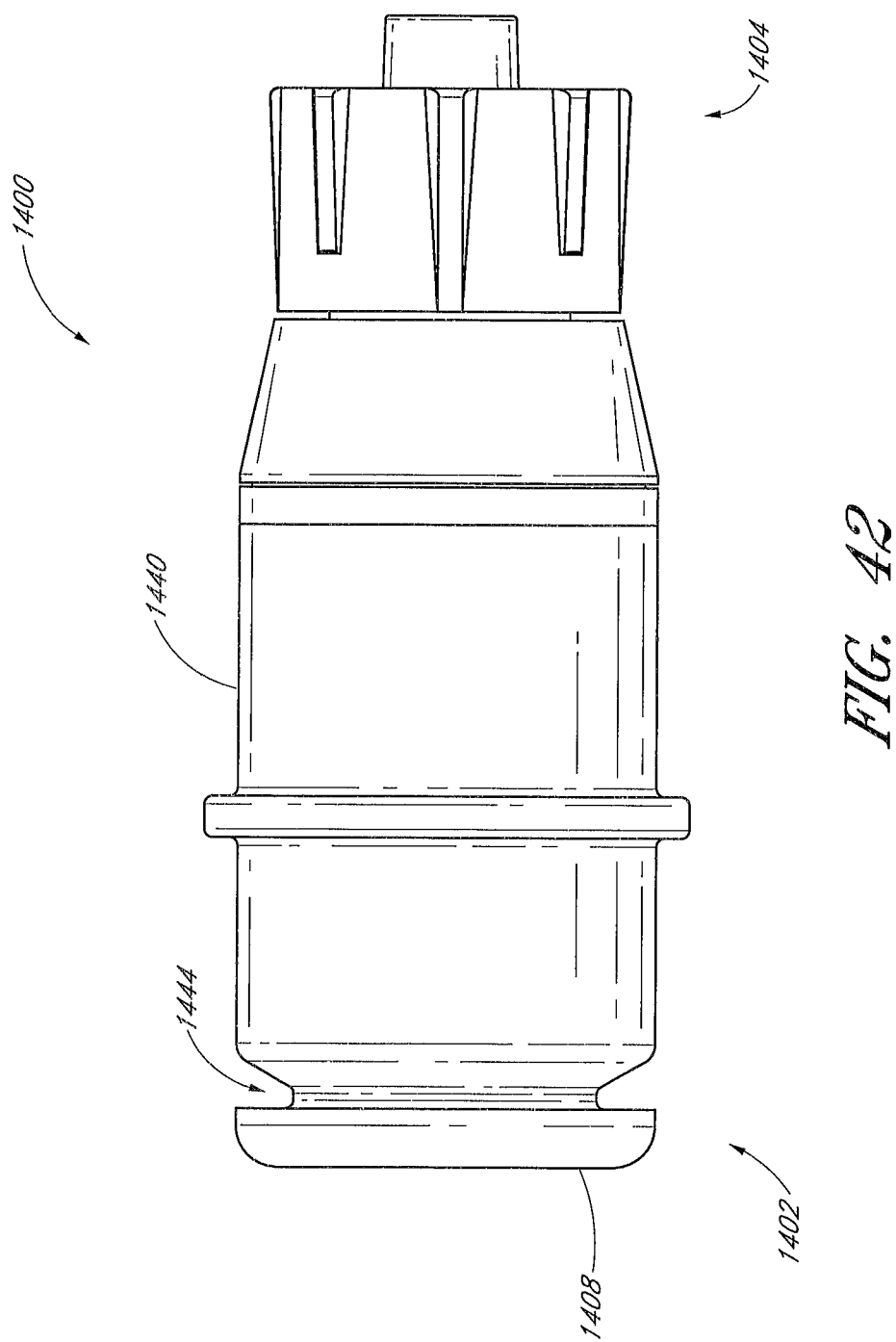
FIG. 42 is a side view of the embodiment of the female connector shown in FIG. 41 again in a closed position.

FIGS. 41 and 42 are a perspective view and a side view, respectively, of the female connector 1400 in a first or closed position. Any of the configurations, features, components, and/or alternatives of the female connector 1400 can comprise, be interchangeable with, or be used with any of the configurations, features, components, materials, and/or alternatives of any other female connector. Additionally, any of the other connectors described herein can comprise any of the configurations, features, and components of the female connector 1400. For example, the features relating to preventing or inhibiting disconnection of the male and female connectors can be used with any suitable medical or other fluid connectors.

Figure 43:
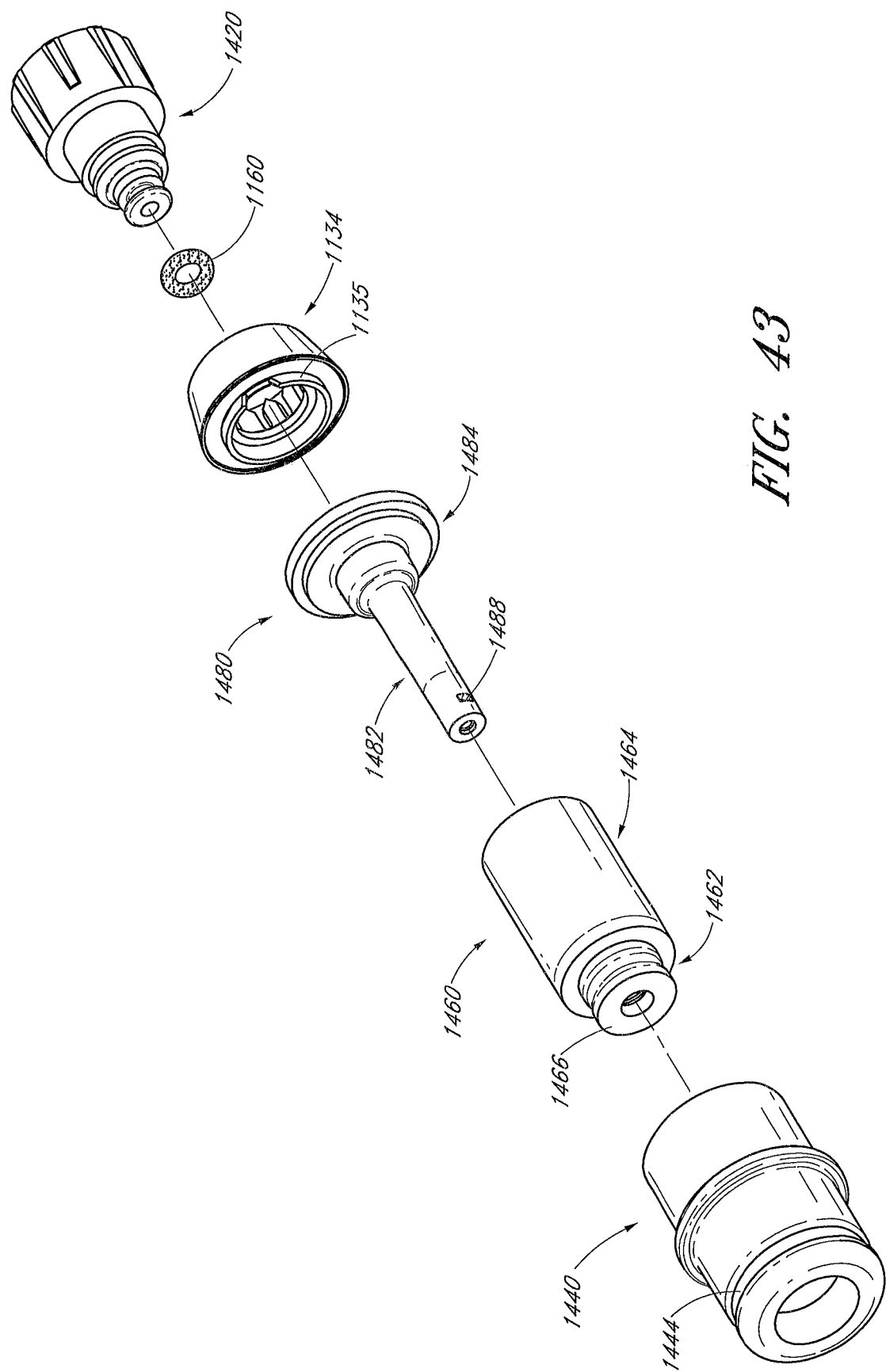
FIG. 43 is an exploded perspective view of the components of the embodiment of the female connector shown in FIG. 41.

FIG. 43 is an exploded perspective view of the components of the embodiment of the female connector 1400 shown in FIG. 41. A fluid conduit 1480 with one or more side ports 1488 can be coupled to the female housing 1440 near the second end 1404 of the female connector 1400. One or more of the components of the fluid conduit 1480 can be integral or unitary with the female housing 1440. In some embodiments, the fluid conduit 1480 can have a second end 1484 that is configured to couple with a second cap component 1134. The fluid conduit 1480 and the second cap component 1134 can be coupled by various methods, such as adhesives, sonic welding, solvent bonding, snap-fitting, etc. A first cap component 1420 can also be coupled to the second cap component 1134 and the fluid conduit 1480. The first cap component 1420 can be rotatable relative to the second cap component 1134 and the fluid conduit 1480. A generally compressible or deformable seal element 1460 can surround at least a portion of the fluid conduit 1480. The seal element 1460 can obstruct the ports 1488 on the fluid conduit 1480 when the female connector 1400 is in a closed configuration. The seal element 1460 and fluid conduit 1480 can be contained at least partially within the female housing 1440.

As illustrated in FIGS. 41 and 42 the female connector 1400 can have a first end 1402 and a second end 1404. The first end 1402 can be configured to mate with the male connector 1100. In some embodiments, the female connector 1400 can have a female housing 1440 with a mating side 1408 that is configured to be coupled to the male connector 1100. The first end 1402 can include a coupling structure that is complementary to the coupling structure on the shroud 1124 of the male connector 1100. In the illustrated embodiment, the female connector 1400 has a selectively attachable connection surface, such as a groove, indentation, or channel 1444, that engages with a corresponding selectively attachable connection surface, such as snaps, catches, grasping members, or hooks 1127, on the male connector 1100 to removably secure the connectors together. Many other types of engagement elements can be employed to secure the connectors together.

Figure 45:
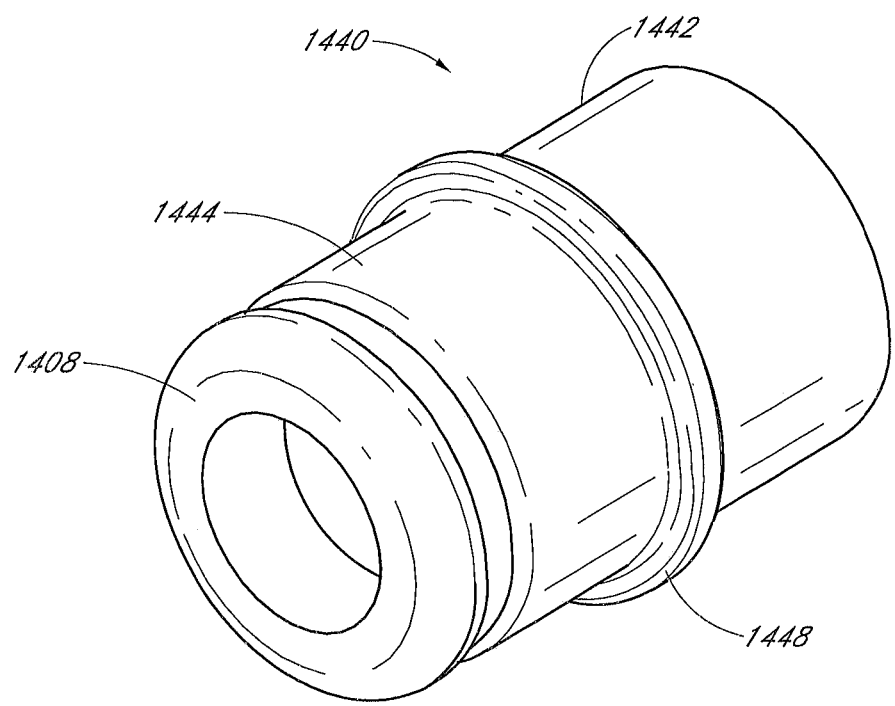
FIG. 45 is a perspective view of an embodiment of a housing of the female connector shown in FIG. 41.

The female housing 1440 of the female connector 1400 can extend between the first end 1402 and the second end 1404. In the embodiment illustrated in FIG. 45, the female housing 1440 has a generally cylindrical body 1442. In some embodiments, the body 1442 can have a generally circular, generally square, generally polygonal cross-section, or any other suitable shape. A compressible or resilient seal element 1460 and a fluid conduit 1480 are contained at least partially within the female housing 1440.

Near the first end 1402 can be a channel 1444 that extends around the outer circumference of the female housing 1440. The channel 1444 can accept hooks 1127 on the tabs 1125 of the male housing 1123. In some embodiments, the mating side 1408 of the female housing 1440 can be chamfered or rounded to allow the hooks 1127 to slide around the first end 1402 of the female connector 1400 as the two connectors are joined together.

The female housing 1440 can have a coupling limiter, such as a coupling flange 1448 that protrudes from the circumference of the female housing 1440, to provide a shoulder or stop to prevent the male connector 1100 from being inserted too far into the female connector 1400. In some embodiments, the coupling flange 1448 extends continuously around the entire circumference of the female housing 1440. In some embodiments, the coupling flange 1448 can be broken or segmented and extend around less than the entire circumference of the female housing 1440, e.g. as one or more protrusions or in a series of broken segments. In some embodiments, the coupling portion 446 can be integrally molded or otherwise formed with the female housing 440. In some embodiments, the coupling portion 1446 can be a separate component that is connected to the female housing 1440, such as by welding, adhesives, or fasteners. In some embodiments, the position of the coupling limiter can be closer to the first or proximal end than to the second or distal end. The outermost radial extent of the coupling limiter can be larger than or approximately equal to the inner diameter of the shroud 1124 of the closeable male luer connector 1123. In some embodiments, the female housing can have an extended portion 1447 between the coupling limiter and the channel 1444.

Figure 46:
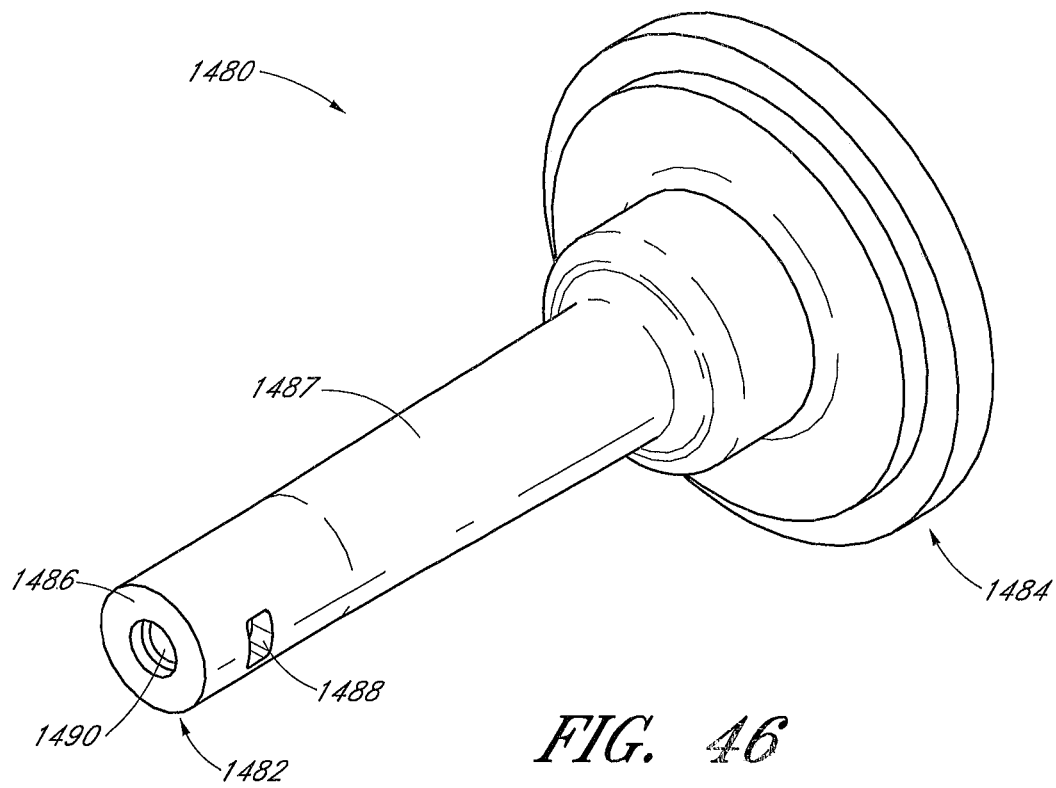
FIG. 46 is a perspective view of an embodiment of a fluid conduit of the female connector shown in FIG. 21.

With reference to FIG. 46, the fluid conduit 1480 can be similar to the fluid conduit 480 (see, e.g., FIG. 27), and the description of each fluid conduit 480, 1480, and the uses and alternatives thereof, applies to the other. The fluid conduit 1480 can have a first end 1482 and a second end 1484. The first end 1482 can have a mating surface 1486 that is configured to couple with the mating surface 1146 of the valve member 1116. Near the first end 1482 can be at least one port 1488 that is fluidly connected to a fluid passageway 1418 that extends through the middle of the fluid conduit 1480. In the illustrated embodiment, the fluid conduit 1480 has two ports on approximately opposite sides. In some embodiments, the fluid conduit 1480 can have more than two ports 1488. The second end 1484 of the fluid conduit 480 can be configured to couple to a first cap component 1420 and a second cap component 1134.

Extending from the first end 1482 to the second end 1484 can be a tube 1487 with a fluid passageway 1418 (see FIG. 50) extending through the interior (e.g., middle) of the tube 1487. In the embodiment illustrated in FIG. 44, the tube 1487 is generally cylindrical near the first end 1482 and generally frusto-conical near the second end 1484. In some embodiments, the tube can have other cross-sectional shapes, such as generally square, generally polygonal or generally oval.

Figure 44:
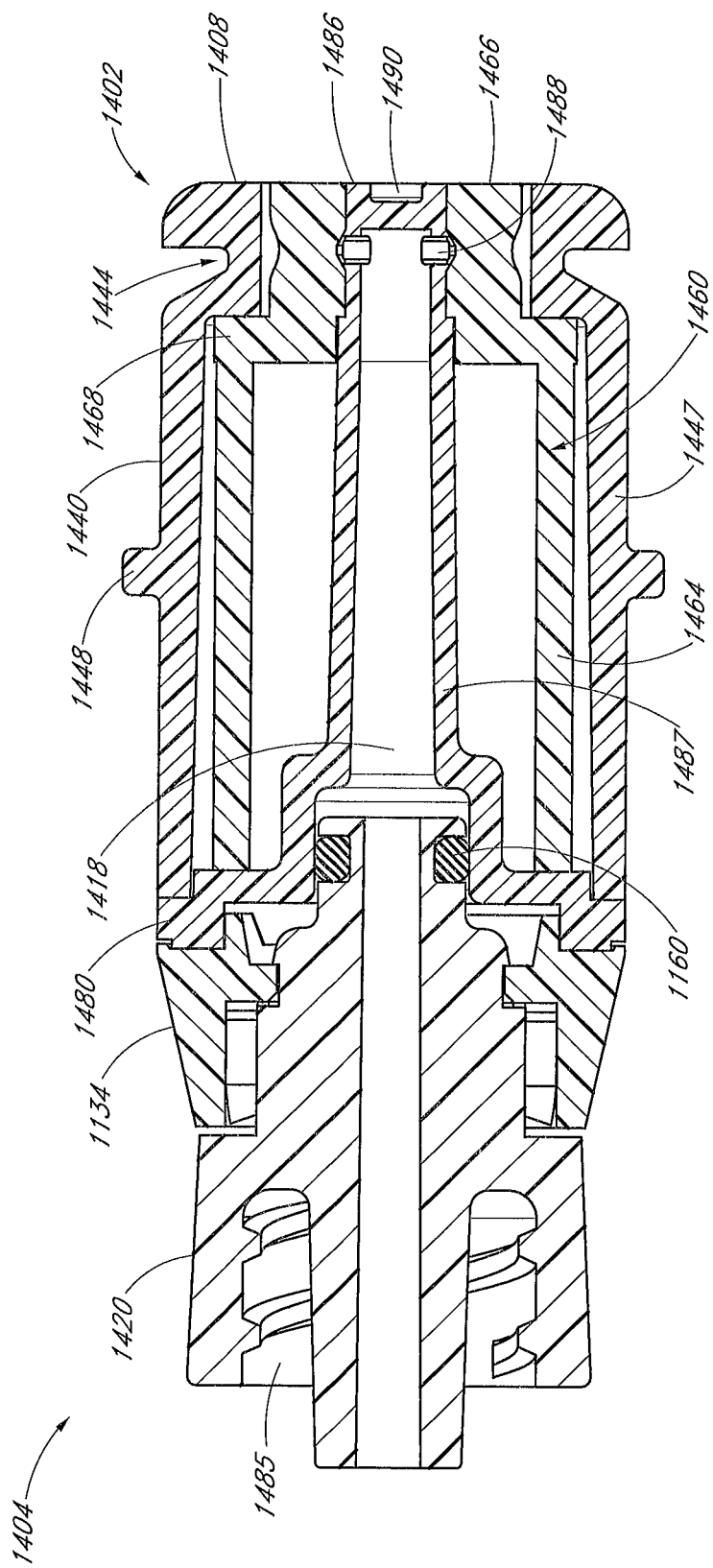
FIG. 44 is a cross-sectional side view of the embodiment of the female connector shown in FIG. 42.

As illustrated in FIG. 44, the fluid passageway 1418 can be circular in cross-section, or the fluid passageway 1418 can have other cross-sectional geometric shapes. In the illustrated embodiment, two ports 1488 are located on generally opposite sides of the fluid conduit 1480 and are rectangular in shape, though other locations and shapes can be used. The side ports 1488 can be located near the mating surface 1486 of the fluid conduit 1480, or positioned on the side of the fluid conduit 1480 as far back as practical from the mating surface 1486 while still allowing fluid to enter the ports 1488 when the female connector 1400 is mated with the male connector 1100. As illustrated, the proximal end or proximal region of the fluid conduit 1480 can be blunt, non-tapered, generally planar, and closed to fluid flow. In some embodiments, the size of the ports 1488 can be approximately one millimeter in length and/or width, although irregular shapes and other sizes can be used. Ports of at least about 1 mm or approximately 1 mm to approximately 3 mm, or less than or equal to about 1 mm can also be used. The cross-sectional width (or outer diameter) of the proximal end of the fluid conduit 1480 can be very large, as illustrated. For example, as shown, the cross-sectional width (or outer diameter) of the proximal end of the fluid conduit 1480 can be about the same size as the outer diameter of the fluid conduit 1480, or larger than or about the same size as the inner diameter of the male tip on the distal end of the female connector, or about the same size as or larger than an inner diameter of the fluid conduit 1480 near the base of the fluid conduit, or generally about the same size as the thickness of the wall of the sealing element at the proximal end or in the neck region of the housing, or substantially larger than the thickness of the housing wall.

The fluid conduit 1480 can be composed of a rigid material, such as polycarbonate plastic, which is capable of resisting compression or deformation when a force sufficient to compress or deform the seal element 1460 is exerted upon the female connector 1400. The ports 1488 in the fluid conduit 480 can be sealed by the seal element 1460 to prevent the fluid from escaping the fluid passageway 1418 when the female connector 1400 is in the closed configuration.

Figure 47:
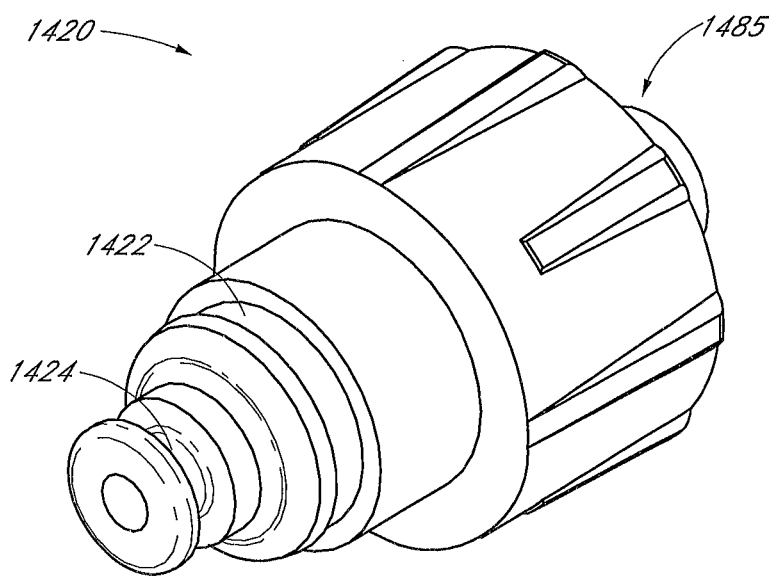
FIG. 47 is a perspective view of an embodiment of a first cap component of the female connector shown in FIG. 41.

The female connector 1400 can include a first cap component 1420 and a second cap component 1134 near the second end 1404, similar to the male connector 1100. In some embodiments, the second cap component 1134 can be the same as, or similar to, the second cap component described in the male connector 1100. As illustrated in FIGS. 44 and 47, the first cap component 1420 can be configured to have a protrusion to couple with the fluid conduit 1480 at one end and to have a male luer engagement 1485 at the other end. A fluid pathway can extend longitudinally through the first cap component 1420 so that the fluid conduit 1480 can be in fluid communication with the male luer engagement 1485. The male luer engagement 1485 includes a shroud with inner threads surrounding a male luer tip. The male luer engagement 1485 can conform to ANSI specifications for male connectors. The male luer engagement 1485 can receive a female connecting component of another connector or syringe.

As illustrated in FIG. 44, the second cap component 1134 can be coupled to the second end 1484 of the fluid conduit 1480 and/or the female housing 1440. In some embodiments, the second cap component 1134 can be fixedly attached to the fluid conduit 1480 or female housing 1440 through sonic welding, adhesives, or any other suitable method. In the illustrated embodiment, the first cap component 1420 is rotatably coupled to the second cap component 1134 as well as the fluid conduit 1480. In some embodiments, the first cap component 1420 and/or the second cap component 1134 can be integral or unitary with the female housing 1440.

In some embodiments, the portion of the first cap component 1420 that couples with the fluid conduit 1480 can have an outer dimension that is comparable to the inner dimension of the wall of the fluid conduit 1480, but does not contact such wall to permit relative movement between the components. To inhibit fluid from escaping between the fluid conduit 1480 and the first cap component 1420, a flexible or resilient seal, such as an O-ring 1160, can be disposed in a groove 1424 on the first cap component 1420. The groove 1424 can extend around the outer circumference of the first cap component 1420 where it couples with the fluid conduit 1480. The O-ring 1160 can contact the wall of the fluid conduit 1480, as shown, inhibiting fluid from escaping out of the fluid passageway 1418. The first cap component 1420 is able to rotate relative to the fluid conduit 1480 so that the male luer engagement 1485 can be connected to another connector without twisting the entire female connector 1400.

Additionally, the first cap component 1420 can comprise an annular groove 1422 which, can interact with complementary features on the second cap component 1134 to axially restrain the movement of the first cap component 1420 with respect to the second cap component 1134. With reference to FIG. 44, the first cap component 1420 and the second cap component 1134 can be sized and configured to prevent the first cap component 1420 from inadvertently being pulled out of the second cap component 1134.

Further, as illustrated in FIG. 47, the first cap component 1420 can comprise an angled or rounded surface positioned between the annular groove 1422 and the O-ring channel

1424. The angled or rounded surface can facilitate the coupling or assembly of the first cap component 1420 to the second cap component 1134. In some embodiments, the first cap component 1420 and/or the second cap component 1134 can comprise any suitable features, lubricants, or materials to facilitate the coupling of the first cap component 1420 and the second cap component 1134, or, to facilitate the rotation of the first cap component 1420 relative to the second cap component 134.

In some embodiments, the cap components can comprise structures to resist disconnection of the male end 1485 of the female connector 1400 and/or that can facilitate rotation of the male end 1485 of the female connector 1400. For example, the first cap component 1420 can have break off tabs that prevent the first cap component 1420 from rotating relative to the second cap component 1134 during an initial stage, as described herein. Once the tabs have broken away from the first cap component 1420, the first cap component 1420 is then able to rotate substantially freely within the second cap component 1134. However, the first cap component 1420 can still be retained in the female connector 1400 by the coupling of the annular groove 1422 and the annular protrusion on the second cap component 1134. Also, the O-ring 1160 can resist or prevent fluid leakage notwithstanding the ability of the first cap component 1420 to rotate. The female connector 1400 can resist disconnection from the coupled components because the torque needed for such disconnection would merely spin the first cap component 1420 relative to the female housing 1400 and/or the second cap component 1134.

Figure 48:
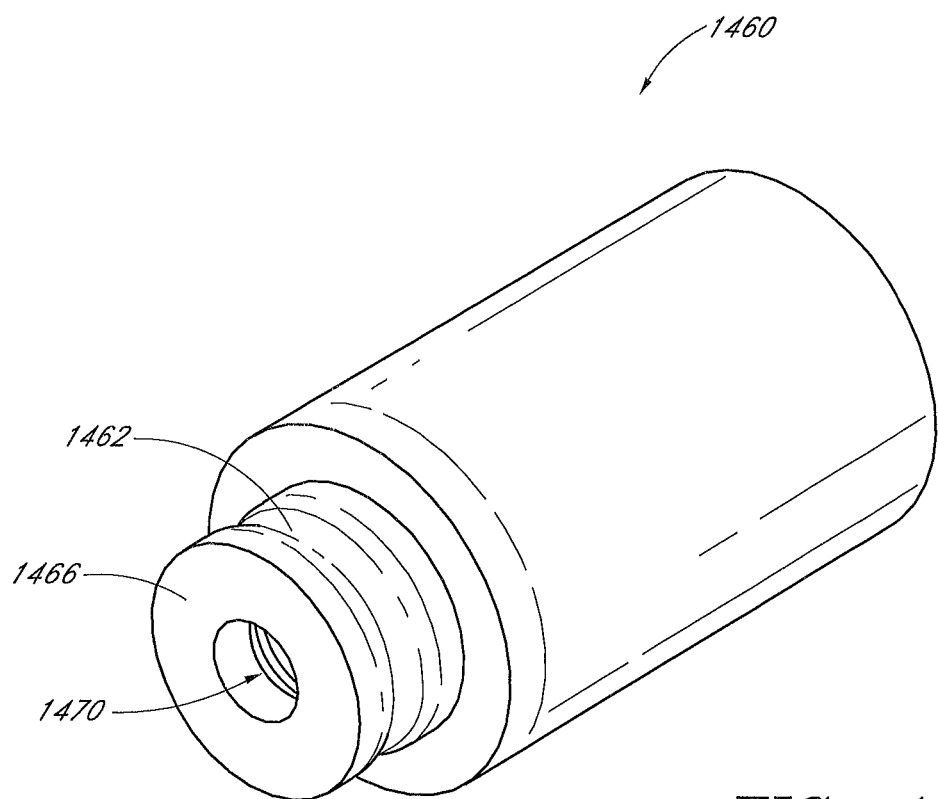
FIG. 48 is a perspective view of an embodiment of a compressible seal element of the female connector shown in FIG. 41.

With reference to FIG. 48, the seal element 1460 is described in greater detail. In some embodiments, the seal element 1460 is generally cylindrical and has a bore 1470 extending therethrough. The seal element 1460 can have a sealing portion 1462 and a collapsing portion 1464. The sealing portion 1462 can have an inner diameter that is configured to obstruct the first end 1482 of the fluid conduit 1480 to block the flow of fluids out of the ports 1488.

In the illustrated embodiment, at least the distal portion 1464 is generally cylindrical and can deform, compress, or otherwise decrease in length. The collapsing portion 1464 is made of a resilient or deformable material such that a restoring force biases the distal portion 1464 back to its starting length when the distally directed force is removed. In some embodiments, the collapsing portion 1464 can have a plurality of different types of configurations for providing a compressible seal, such as in other embodiments described herein.

A shoulder or stop 1468 can be disposed between the sealing portion 1462 and the collapsing portion 1464. In the illustrated embodiment, the stop 1468 is a portion with an enlarged outer diameter. As illustrated in FIG. 44, the stop 1468 can engage with a surface of the female housing 1440 to prevent the compressible seal element 1460 from overextending or exiting the female housing. The placement of the stop 1468 on the seal element 1460 is configured so that when the stop 1468 engages with the female housing 1440, the sealing portion 1462 is positioned over the ports 1488 on the fluid conduit 1480.

The seal element 1460 can be constructed of a material that elastically compresses or deforms. The seal element 1460 is biased toward returning the female connector 1400 to a closed configuration. The amount of compression resistance carried by the seal element 1460 can be adjusted by varying the length of the compressing portion 1464 or the length of the chamber in the female housing 1440 where the seal element 1460 resides. The amount of compression resistance can also be adjusted by increasing the thickness of the seal element 1460 and/or use of a variety of materials having different elastic properties. In some embodiments, the collapsing portion 1464 can be configured as a spring positioned inside the female housing 1440 for biasing the seal element 1460 to the closed configuration, as described in other embodiments.

As illustrated in FIGS. 41 and 44, the first end 1402 of the female connector 1400 can have a mating side 1408 that is generally transverse to the longitudinal axis of the female connector 1400. In the illustrated embodiment, the mating side 1408 has a generally annular shape. The mating side 1408 can have an opening in the middle region for the seal element 1460, wherein a mating surface 1466 of the seal element 1460 is exposed. The mating surface 1466 of the seal element 1460 is configured to form a leak-resistant seal with the mating surface 1128 of the male luer tip 1122 and the mating surface 1176 of the luer tip seal 1119. Near the center of the seal element 1460 can be an opening for the female connector fluid conduit 1480. A first end 1482 of the fluid conduit 1480 can have a mating surface 1486 configured to form a leak-resistant seal with the mating surface 1146 of the valve member 1116.

As shown in the embodiment of the female connector 1400 illustrated in FIGS. 41 and 44, the mating surface 1466 of the seal element 1460 can be substantially flush with the mating side 1408 of the female connector 1400. In some embodiments, the mating surface 1486 of the fluid conduit 1480 can be substantially flush with the mating side 1408 of the female connector 1400. In some embodiments, the mating surface 1466 of the seal element 1460 and/or the mating surface 1486 of the fluid conduit 1480 can be configured to extend further beyond the mating side 1408 of the female connector 1400 in the closed position. In some embodiments, the mating surface 1466 of the seal element 1460 and/or the mating surface 1486 of the fluid conduit 1480 can be recessed within coupling portion 1446.

In some embodiments, the first end 1482 of the fluid conduit 1480 can have a cavity 1490 that couples with a complementary protrusion 1147 on the mating surface 1146 of the valve member 1116. In the illustrated embodiment, the cavity 1490 is a rounded hole. In some embodiments, the cavity can have a plurality of different types of shapes, such as rectangular, square or polygonal in shape. In some embodiments, the cavity can be disposed on the mating surface 1146 of the valve member 1116 and the protrusion can be on the first end 1482 of the fluid conduit 1480. The cavity 1490 and protrusion 1147 can help to align the corresponding mating surfaces of, and to resist lateral movement and fluid leakage between, the male connector 1100 and the female connector 1400.

The seal element 1460 can obstruct the first end 1482 of the fluid conduit 1480 to block the flow of fluids out of the ports 1488 when the female connector 1400 is in the closed configuration. A sealing portion 1462 of the seal element 1460 can be disposed in the interior of coupling portion 1446 of the female housing 1440, as illustrated in FIG. 44. In the illustrated embodiment, the sealing portion 1462 of the seal element 1460 is disposed between the female housing 1440 and the fluid conduit 1480. In some embodiments, an interference fit between the seal element 1460 and the fluid conduit 1480 can inhibit fluid from flowing out of the first end 1402 of the female connector 1400. The seal element 1460 can be made of a resilient material that helps forms the seal.

The female connector 1400 can be manipulated to a second or open configuration. In the open configuration, the sealing portion 1462 of the seal element 1460 can be pushed back toward the second end 1404 of the female connector 1400, thereby allowing fluid to flow through the ports 1488 in the fluid conduit 1480. In the open configuration, fluid can enter the fluid conduit 1480 through the ports 1488 and travel through the fluid passageway 1418, exiting through the male luer engagement 1485.

The female connector 1400 can assist in retaining fluid within the female connector 1400 while substantially or entirely eliminating remnant fluid on the first end 1402 of the female connector 1400 when it is being decoupled from a male connector 1100 or other connection. Resisting remnant fluid remaining on the female connector 1400 after decoupling can result in a corresponding reduction in of exposure of toxic medicine to a user or a patient.

Figure 50:
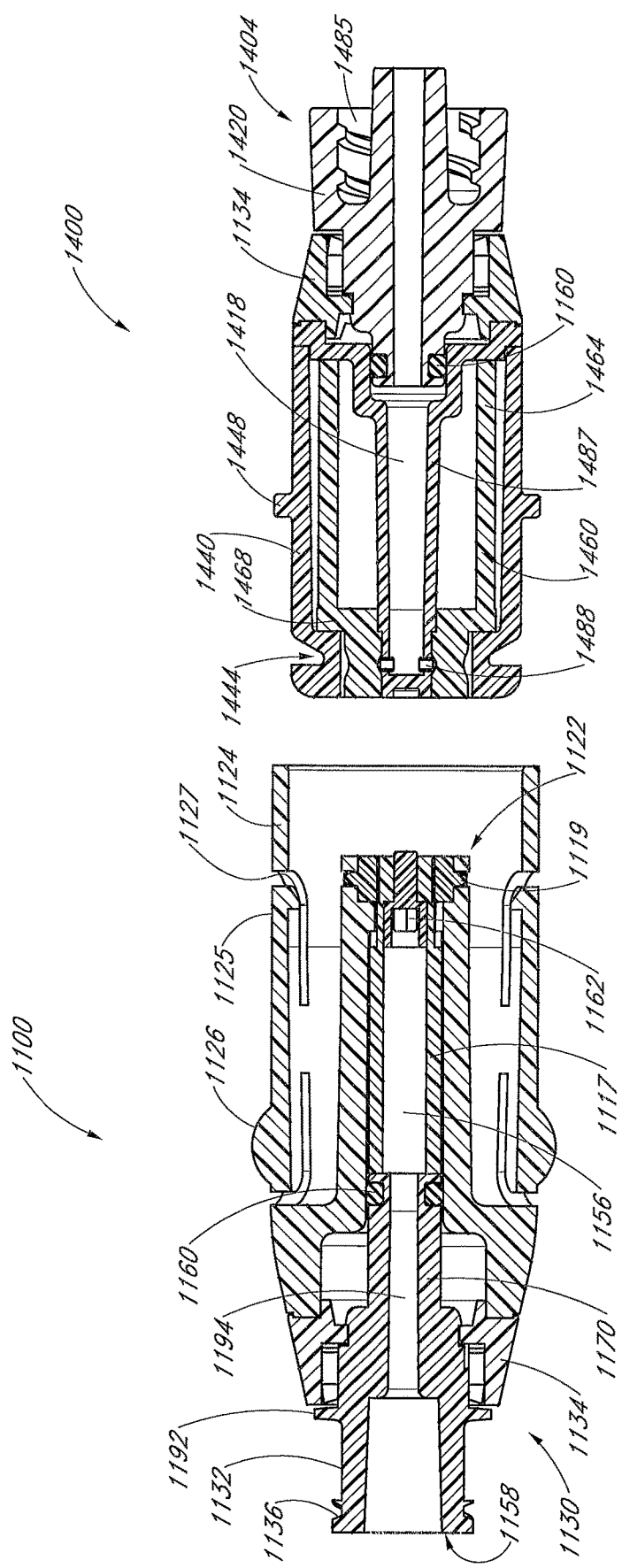
FIG. 50 shows a cross-sectional side view of the connector system of FIG. 49.
Figure 50A:
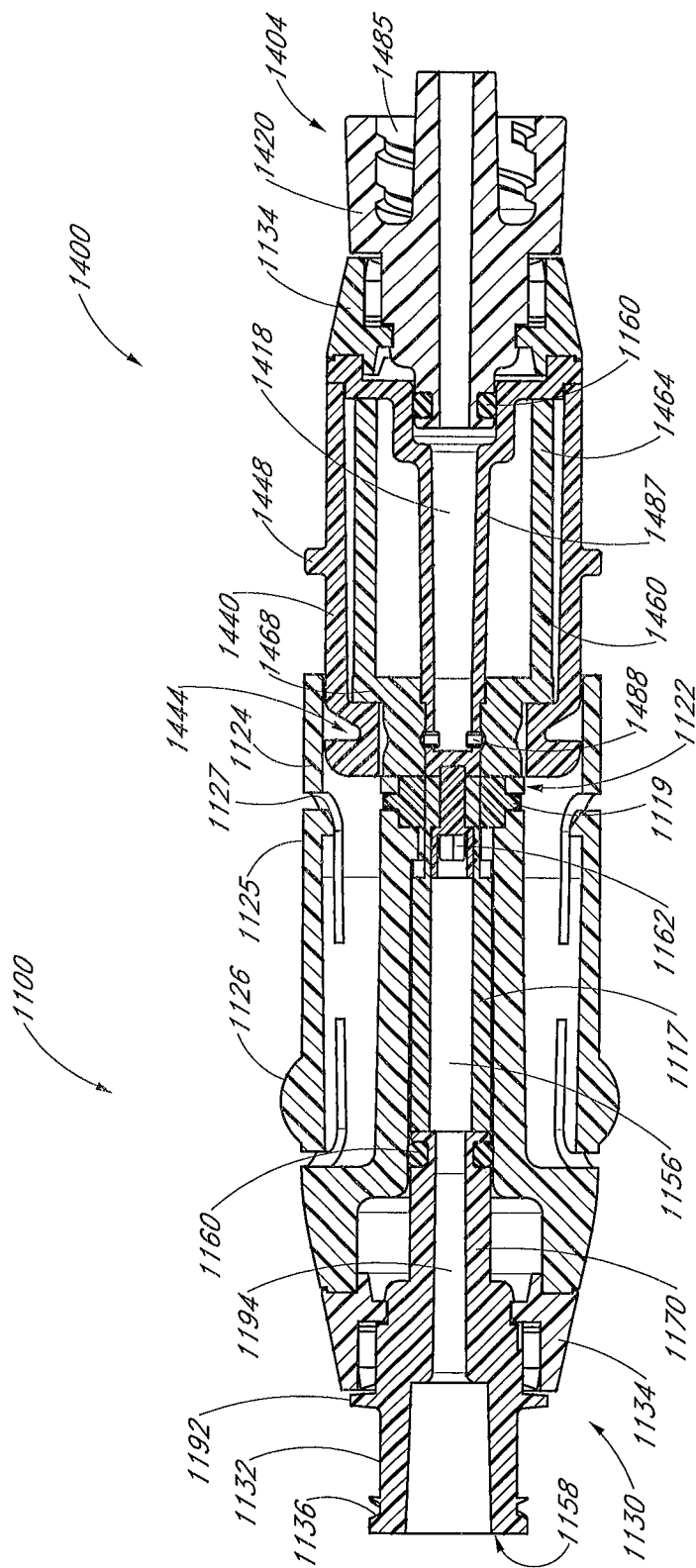
FIG. 50A shows a cross-sectional side view of the connector system of FIG. 49.

With reference to FIGS. 49 and 50, the male connector 1100 is displayed adjacent to a female connector 1400. In the illustrated embodiment, both the male connector 1100 and the female connector 1400 are in a closed configuration. The female connector 1400 is positioned with its first end 1402 adjacent the first end 1112 of the male connector 1100. The male connector 1100 can be engaged with the female connector 1400 by pushing the connectors together without requiring twisting or rotating of either connector.

Figure 51:
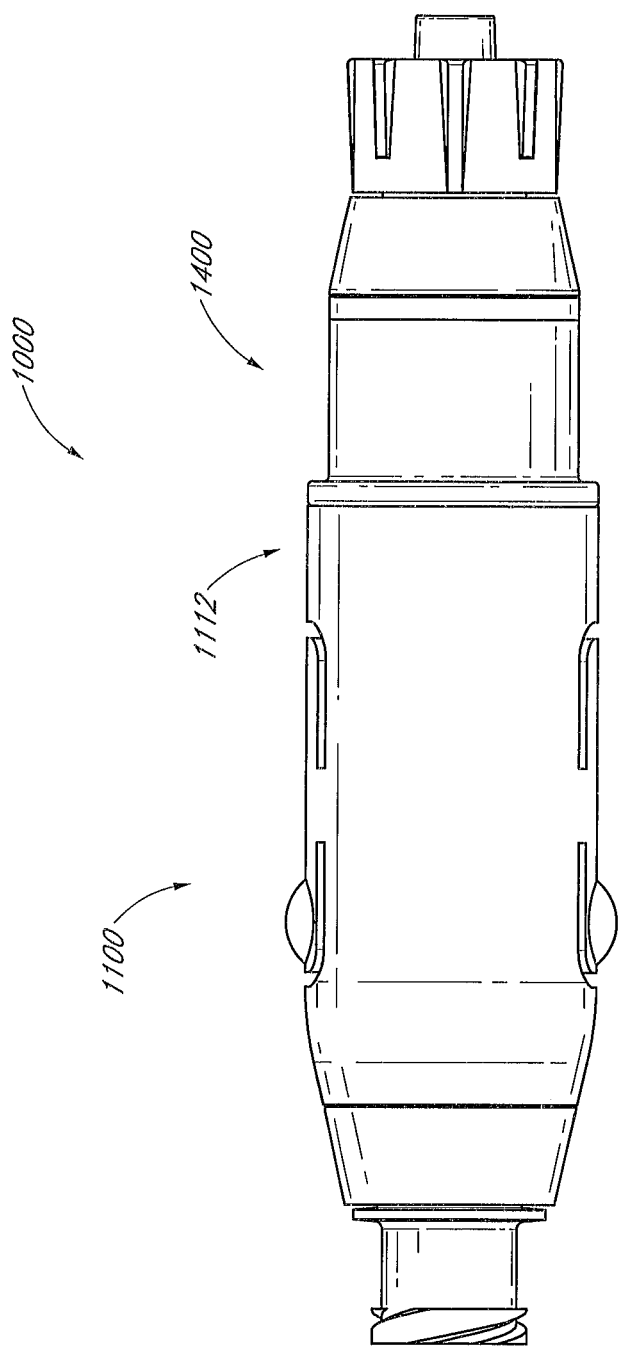
FIG. 51 is a side view of the embodiment of the male connector shown in FIG. 33 coupled to the embodiment of the female connector shown in FIG. 41.

As illustrated in FIGS. 51 and 52, the male connector 1100 can be changed to the open configuration when a female connector 1400 is coupled to the male connector 1100. The first end 1402 of the female connector 1400 can engage with the first end 1112 of the male connector 1100. A first biased engagement portion, such as the hooks 1127 on the tabs 1125, of the male connector 1100 can engage with a second engagement portion, such as the channel 1444, on the female connector 1400 to removably secure the connectors together. The hook and channel engagement allows the connectors 1100, 1400 to be coupled without requiring rotation of the connectors, which reduces the risk of twisting the attached fluid lines and requires less precise manual manipulation by the health care professional. The locations of the first and second engagement portions on the respective connectors can be reversed. In some embodiments, the hooks 1127 can slide over the mating side 1408 of the female connector 1400 and fall into the channel 1444. In some embodiments, an audible sound can be produced when the hooks 1127 positively engage with the channel 1444 on the female connector 1400. The release button 1126 can be pressed to lift the hooks 1127 from the channel 1444 to disconnect the connectors.

In some embodiments, engagement between the hooks 1127 of the male connector 1100 and the channel 1444 of the female connector 1400 can reduce the likelihood of lateral movement between the mating surface 1146 of the valve member 1116 and the mating surface 1486 of the fluid conduit 1480. In some embodiments, engagement between the hooks 1127 of the male connector 1100 and the channel 1444 of the female connector 1400 resist tilting between the mating surface 1146 of the valve member 1116 and the mating surface 1486 of the fluid conduit 1480 during and/or after coupling. Reduction of lateral movement and/or tilting between the mating surfaces 1146, 1486 can help reduce the likelihood that either mating surface 1146, 1486 will be exposed to fluid from within the connectors 1100, 1400.

The mating surface 1486 of the fluid conduit 1480 can engage the mating surface 1146 of the valve member 1116. These tightly fitting, non-planar mating surfaces 1186, 1146 and/or the interaction between the tightly fitting exterior shroud 1124 and an outer surface of the adjoining connector (e.g. the outer surface of the extended portion 1447 of the female connector), can resist lateral motion between the mating surfaces 1186, 1146 to resist fluid penetration or ingress between them. As the male connector 1100 and the female connector 1400 are coupled together, the fluid conduit 1480 can push the closure end 1144 of the valve member 1116 toward the second end 1114 of the male connector 1100. As the closure end 1144 is pushed toward the second end 1114 of the male connector 1100, the ports 1162 on the valve member 1116 are displaced away from the luer tip seal 1119, allowing fluid to flow out through the ports 1162. Thus, the male connector 1100 is moved to an open configuration when the closure end 1144 of the valve member 1116 is pushed towards the second end 1114.

As illustrated in FIG. 52, the mating surface 1176 of the luer tip seal 1119 and the mating surface 1128 of the male luer tip 1122 can engage the mating surface 1466 of the seal element 1460. As the male connector 1100 and the female connector 1400 are coupled together, the male luer tip 1122 with the luer tip seal 1119 can push the seal element 1460 toward the second end 1404 of the female connector 1400, applying force to the compressing portion 1464 of the seal element 1460. As the seal element 1460 is pushed toward the second end 1404 of the female connector 1400, the ports 1488 on the fluid conduit 1480 are uncovered, allowing fluid to flow through the ports 1480. In this example, the female connector 1400 is in an open configuration. Since the seal element 1460 includes an opening or bore 1470 on its proximal end, the tube 1487 in the female connector, the male luer tip 1122 in the male connector, and/or the valve member 116 of the male connector are not required to puncture, pierce, cut, penetrate, pass through, spread apart, force open, or otherwise substantially modify the size, shape or dimensions of the proximal end of the seal element 1460. Rather, in some embodiments, as illustrated, the proximal end of the seal element 1460 is moved by the entry of the male connector, but the shape of the proximal end of the seal element 1460 remains integral and unchanged during both opening and closing. The size and shape of the bore 1470, and the size and shape of the proximal end of the seal element 1460, and/or an aperture, bore, or opening in the proximal end of the seal element 1460, can be generally the same in the closed and open stages, and during the transitions between these stages.

When the closure end 1144 of the valve member 1116 is pushed toward the second end 1114 of the male connector 1100, the tube section 1117 of the valve member 1116 is compressed, producing a return force on the closure end 1144 toward the first end 1112 of the male connector 1100. Thus, in the open configuration of the male connector 1100, the closure end 1144 of the valve member 1116 can be biased toward the first end 1112 toward a closed configuration. Similarly, when the seal element 1460 is pushed toward the second end 1404 of the female connector 1400, the compressing portion 1464 exerts a return spring force to bias the seal element 1460 to its original length and toward a closed configuration. As illustrated, the valve member 1116, in some embodiments, remains inside of the male connector housing, or inside of the luer tip 1122, in both the open and closed positions, and during the transition between these two stages, thereby diminishing the risk of exposing the valve member 1117, and consequently the fluid path, to undesirable foreign objects (such as pathogens, toxins, or debris) in the environment, and diminishing the risk that fluid within the fluid path will escape into the environment.

In some embodiments, the valve member 1116 and the seal element 1460 can exert closing forces to help the mating surfaces 1146, 1486 maintain contact throughout the engagement. In some embodiments, the mating surface 1146 of the valve member 1116 can have a cross-section that is substantially the same as a cross-section of the mating surface 1486 of the fluid conduit 1480. In some embodiments, the outer periphery of the mating surface 1486 of the fluid conduit 1480 can be in contact with, and/or generally complimentary in shape with, the outer periphery of the mating surface 1146 of the valve member 1116 when the male connector 1100 and/or female connector 1400 is in an open configuration.

In some embodiments, the mating surfaces of the male connector 1100 and/or the female connector 1400 can be at least partially compressible to help form a substantially leak-free or leak-resistant seal between the mating surfaces, as described above in other embodiments. For example, the mating surface 1146 of the valve member 1116 can be made of an elastomeric material that can seal with the mating surface 1486 of the fluid conduit 1480 (which can itself be either flexible or rigid) so that fluid does not contact the mating surfaces of the male connector 1100 and female connector 1400. In some embodiments, the mating surface 1486 of fluid conduit 1480 can be made of an elastomeric material that can seal with the mating surface 1146 of the valve member 1116 (which can itself be either flexible or rigid). In some embodiments, the fluid can flow around the seal formed by the two mating surfaces 1146, 1486. In some embodiments, fluid is impeded from passing within the periphery of the mating surfaces 1146, 1148 between the two mating surface 1146, 1148. In some embodiments, as described herein, the fluid can flow between the male connector 1100 and the female connector 1400 without requiring the piercing of or penetration of a normally closed septum. For example, the septum can comprise a constant opening through which a fluid conduit can pass, or the fluid can flow around the outside of a septum or other barrier. By isolating the mating surfaces from the fluid, the mating surface 1146 of the valve member 1116 and the mating surface 1486 of the fluid conduit 1480 can remain dry after disconnecting the two connectors, and undesired contamination to the health care provider or surrounding environment can be resisted.

In some embodiments, the cross-section of the mating surface 1146 of the valve member 1116 can be about the same as or smaller than the cross-section of the bore 1470 of the seal element 1460. In some embodiments, the inner cross-section of the luer tip seal 1119 can be smaller than or about the same as the inner cross-section of the bore 1470 of the seal element 1460. In some embodiments, engagement between the periphery of the bore 1470 and the first end 1112 of the male connector 1100 can help inhibit leakage of fluid to the mating surface 1466 of the seal element 1460. For example, in some embodiments, the periphery of the bore 1470 can engage with the mating surface 1176 of the luer tip seal 1119 and form a substantially fluid tight seal between the fluid path within the two connectors and the mating surface 1466 of the seal element 1460. By sealing the mating surface 1466 of the seal element 1460 from the fluid, the mating surface 1466 can remain dry during and after fluid transfer and lower the risk that a health care provider could be exposed to the fluid.

In some embodiments, the inner cross-section of the luer tip seal 1119 can be smaller than or about the same as the outer cross-section of the tube 1487 near the first end 1482 of the fluid conduit 1480. In some embodiments, the luer tip seal 1119 can "wipe" the outer surface of the tube 1487 as it passes through the luer tip seal 1119 during opening and/or closing of the valve member 1116. In some variants, wiping of the outer surface of the tube 1487 as it passes through the luer tip seal 1119 can help inhibit the congregation of or leakage of fluid in the region of the first end 1402 of the female connector 1400. As explained above, in some embodiments, the natural outer cross-section of the mating surface 1146 of the valve member 1116 can be slightly larger than the natural inner cross section of the luer tip seal 1119. In some embodiments, the luer tip seal 1119 can wipe the outer surface of the valve member 1116 as the valve member 116 moves toward a closed configuration from an open configuration. In some implementations, wiping of the outer surface of the valve member 1116 can help reduce the likelihood of fluid congregation or leakage in the region of the first end 1112 of the male connector 1100 during and/or after disengagement between the mating surface 1486 of fluid conduit 1480 and the mating surface 1146 of the valve member 1116. By preventing congregation or leakage of fluid in the region of the first end 1112 of the male connector 1100 and/or in the region of the first end 1402 of the female connector 1400, the luer tip seal 1119 can help to reduce the likelihood that health care providers would be exposed to the fluid.

The mating surface 1146 of the valve member 1116 can have a protrusion 1147 that can accept a complementary cavity 1490 on the mating surface 1486 of the fluid conduit 1480. In some embodiments, as described herein, the protrusion can be on the fluid conduit 1480 and the cavity can be on the valve member 1116. The protrusion 1147 and cavity 490 can help to align the male connector 1100 and female connector 1400 during coupling so that the components align for proper displacement of parts. In some embodiments, the cavity and protrusion can have a circular cross-sectional shape. In other embodiments, the cavity and protrusion can be any of a plurality of different types of shapes, such as square or polygonal.

In some embodiments, the extended portion 1447 of the female housing 1440 can have an outer diameter or cross-section that is substantially similar to the inner diameter or cross-section of the shroud 1124 of the male connector 1100. In some embodiments, engagement between the outer diameter or cross-section of the extended portion 1447 and the inner diameter or cross-section of the shroud 1124 can help the male connector 1100 and the female connector 1400 resist tilting off-axis with respect to each other, especially during the initial coupling stage (e.g. to help to keep the longitudinal axis of the male connector 1100 aligned with the longitudinal axis of the female connector 1400). In some embodiments, engagement between the outer cross-section of the extended portion 1447 and the inner cross-section of the shroud 1124 can help prevent lateral movement between the connectors 1100, 1400 and between the mating surfaces 1486, 1146. Maintaining general or substantial alignment between the longitudinal axes of and/or preventing lateral movement of the female connector 1400 and the male connector 1100 can help maintain sealed contact between the mating surface 1486 of the fluid conduit 1480 and the mating surface 1146 of the valve member 1116. Maintaining sealed contact between the two mating surfaces 1146, 1486 can help reduce the likelihood that fluid will come into contact with either mating surface 1146, 1486.

With reference to FIG. 52, in the open configuration, fluid can flow from the second end 1114 of the male connector 1100, into the end cap portion 1130, through the passageway 1156, out the ports 1162 on the valve member 1116, into the luer tip 1122, into the ports 1488 on the fluid conduit 1480, through the passageway 1418, through the first cap component 1420 on the female connector 1400, and out the male luer engagement 1485 at the second end 1404 of the female connector 1400. Thus, in the open configuration, the second end of the male connector 1100 can be in fluid communication with the second end 1404 of the female connector 1400.

The connectors 1100, 1400 can be disengaged by actuating the release button 1126 on the tabs 1125 of the male connector 1100. In the illustrated embodiment, the release button 1126 can be pressed to lift the hooks 1127 out of the channel 1444 of the female connector 1400. The force stored in the compressing of the tube section 1117 of the valve member 1116 during engagement can return the male connector 1100 to its pre-engaged state by biasing the closure end 1144 of the valve member 1116 to engage the inner surface of the luer tip 1122. Likewise, the resilient material of the seal element 1460 allows the seal element 1460 to return to its shape in the closed configuration where the sealing portion 1462 can seal the ports 1488 on the fluid conduit 1480. In some embodiments, during the closing process, the valve member of the male connector 1100 and the tube 1487 of the female connector 1400, and the respective fluid-flow openings 1162, 1488 in these structures, are positioned within the respective housings of the male and female connectors 1100, 1400, in contact with, behind, and/or sealed off by, resilient or flexible sealing components, before the mating ends of the devices are separated from each other upon disconnection, as illustrated.

FIGS. 53-65 illustrate another embodiment of a connector system 2000 that comprises a male connector 2100 and a female connector 2400. Some numerical references to components in FIGS. 53-65 are the same as or similar to those previously described for the connector system 1000 and corresponding male connector 1100 and female connector 1400, (e.g. male connector 2100 v. male connector 1100). It is to be understood that the components can be the same in function or are similar in function to previously-described components. The connector system 2000 of FIGS. 53-65 shows certain variations to the connector system 1000 of FIGS. 33-52.

Figure 56:
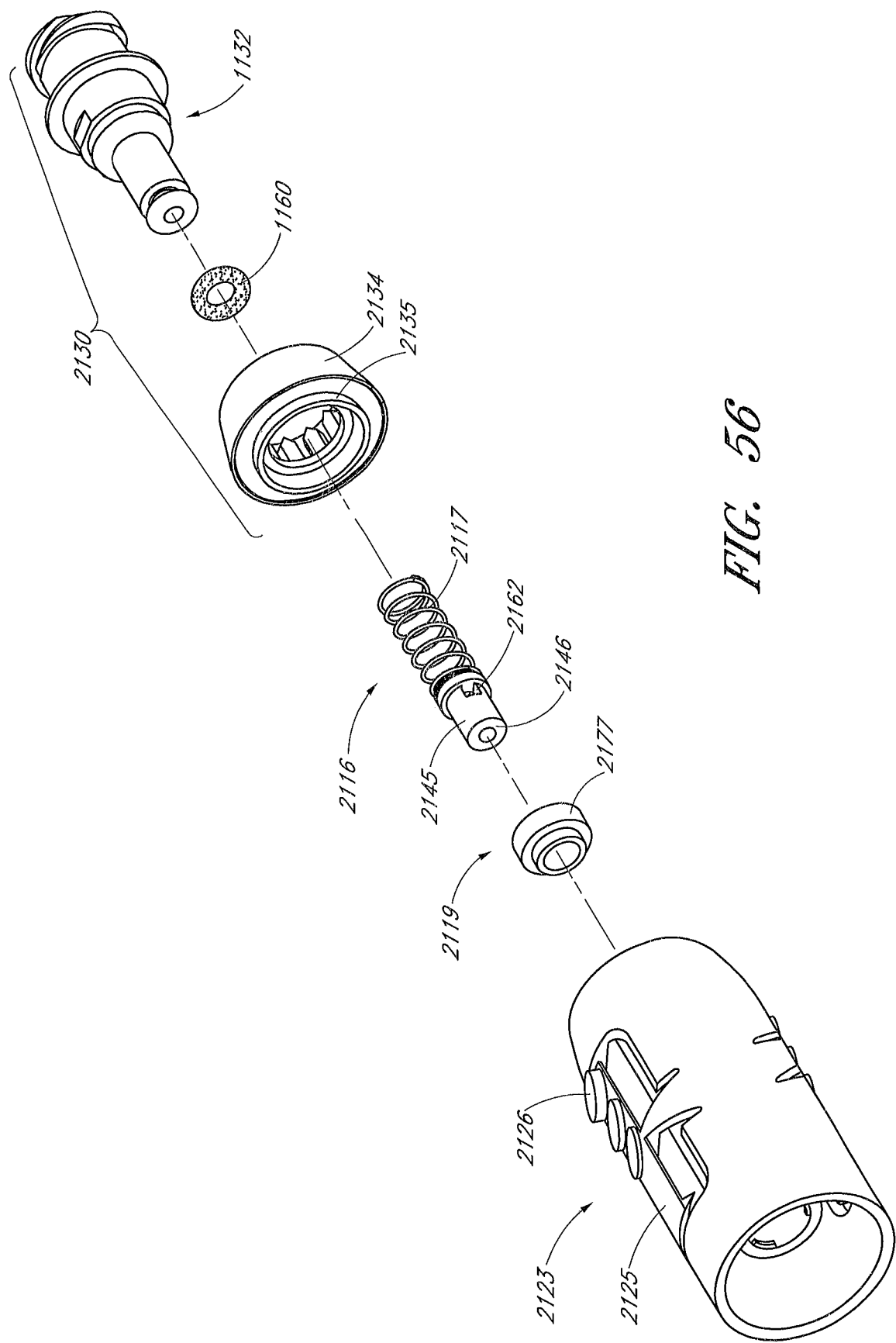
FIG. 56 is an exploded perspective view of the components of the embodiment of the male connector shown in FIG. 54.

In some embodiments, the male connector 2100 comprises tactile release ridges 2126. In some embodiments, the male connector 2100 and female connector 2400 each comprise a second cap portion 2134 (see FIG. 55) which has an annular ridge 2135 (see FIG. 56). The annular ridge 2135 can comprise one or more notches (e.g., as shown in FIG. 43) or no notches (e.g., as shown in FIG. 56). In some embodiments, the male connector 2100 can comprise a valve member 2116 with a spring member 2117 and an end piece 2145. The end piece 2145 can comprise a mating surface 2146, a protrusion 2147, an annular flange 2149 and/or one or more ports 2162. In some embodiments, the end piece 2145 can be formed of a generally rigid material such as a hard plastic, or it can be formed of a resilient or flexible material.

Figure 57:
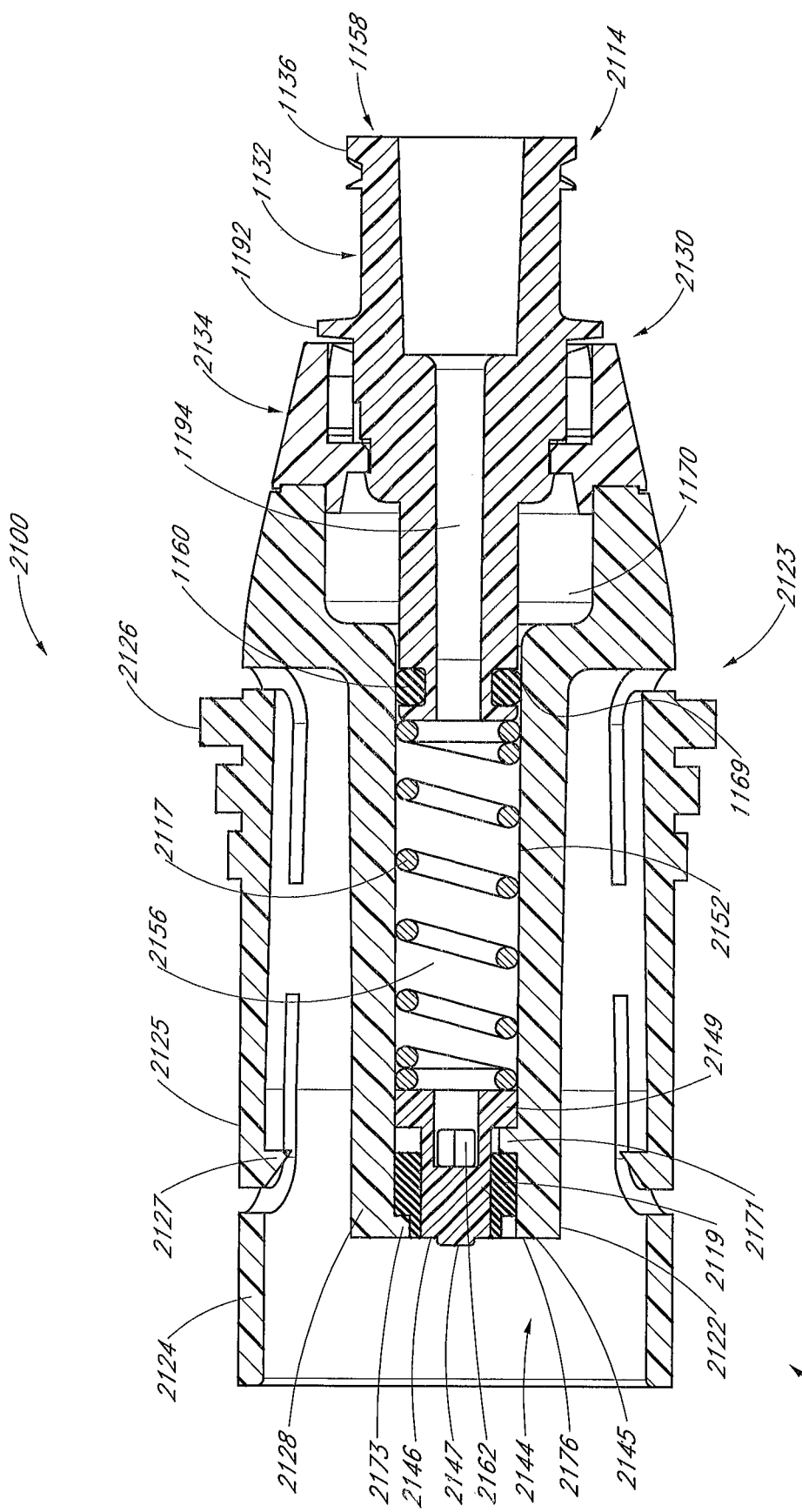
FIG. 57 is a cross-sectional side view of the embodiment of the male connector shown in FIG. 55.
Figure 58:
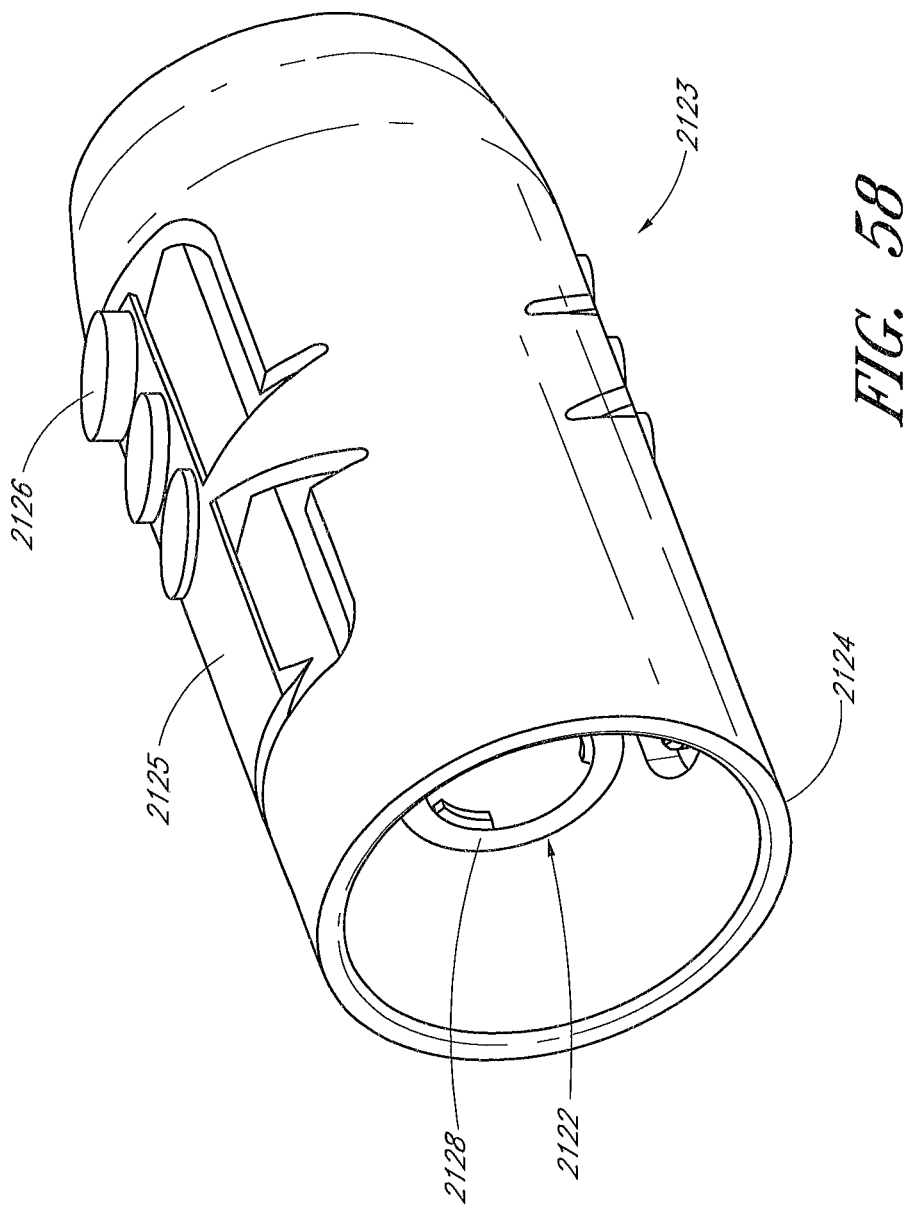
FIG. 58 is a perspective view of an embodiment of a male housing of the male connector shown in FIG. 54.
Figure 59:
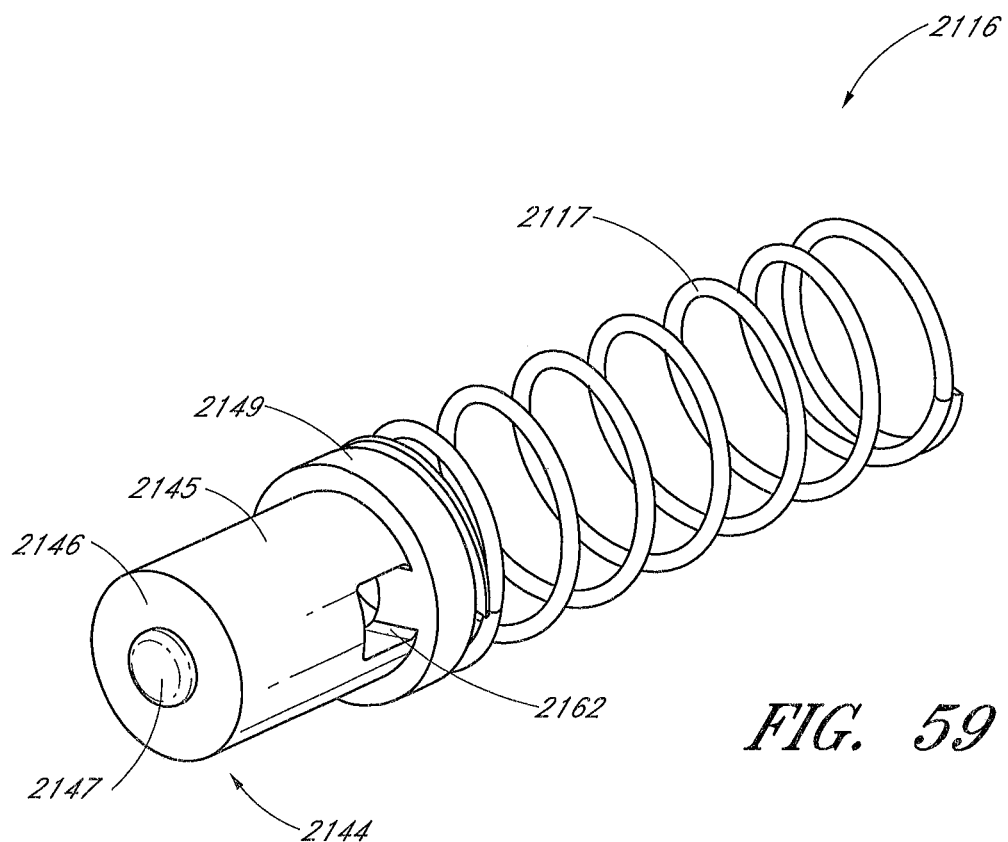
FIG. 59 is a perspective view of an embodiment of a valve member of the male connector shown in FIG. 54.
Figure 60:
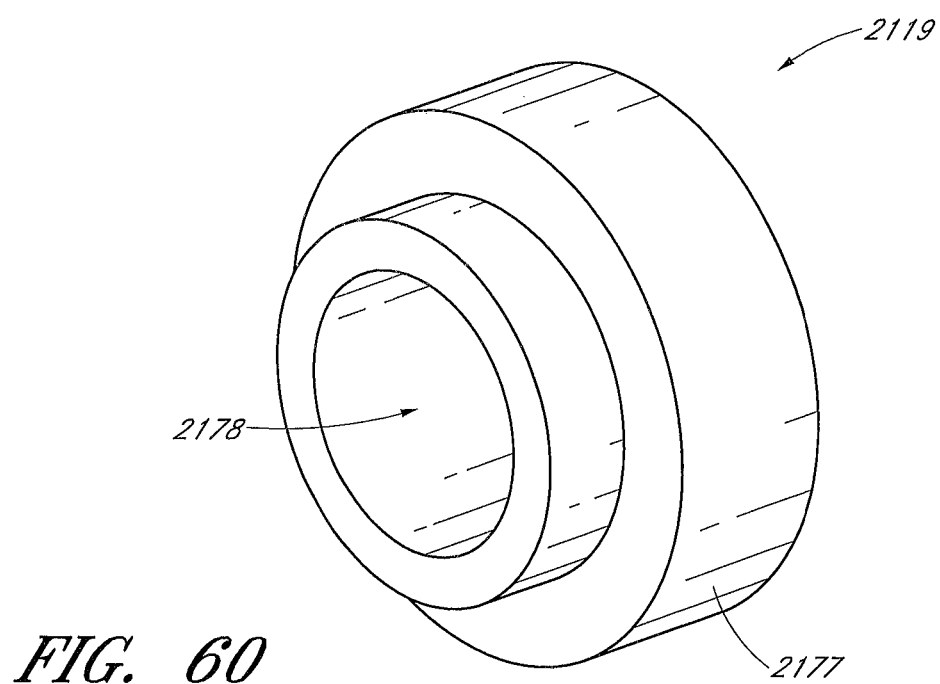
FIG. 60 is a perspective view of an embodiment of a luer tip seal of the male connector shown in FIG. 54.
Figure 61:
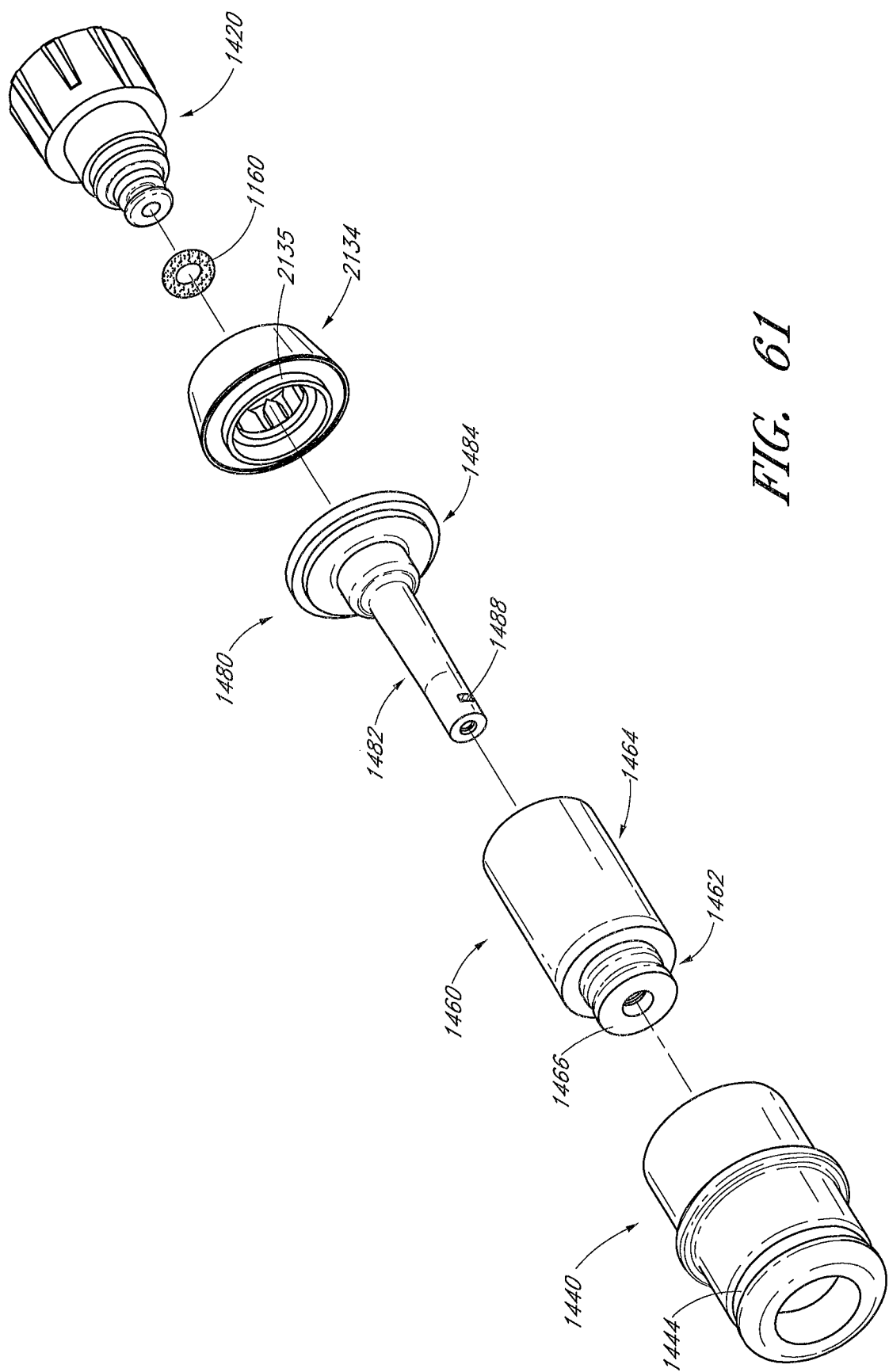
FIG. 61 is an exploded perspective view of the components of the embodiment of the female connector shown in FIG. 53.

In some configurations, the male connector 2100 can comprise a luer tip seal 2119 which can be disposed between the male housing 2123 and the valve member 2116. In some configurations, the luer tip seal 2119 can inhibit or seal fluid flow from the ports 2162 of the end piece 2145 when the male connector 2100 is in a closed configuration, as illustrated in FIG. 57. In some embodiments, the luer tip seal 2119 can be substantially cylindrical and can comprise an annular flange 2177 and a central opening. The annular flange 2177 can be retained in the axial direction by one or more retaining structures, such as by being positioned between a plurality of interior retainer tabs 2171 and a plurality of exterior retainer tabs 2173 on the male luer tip 2122, as illustrated in FIG. 57. In some embodiments, the luer tip seal 2119 can be secured to the male luer tip 2122 by adhesives, welding, interference fit, friction fit, or any other suitable means.

Figure 65:
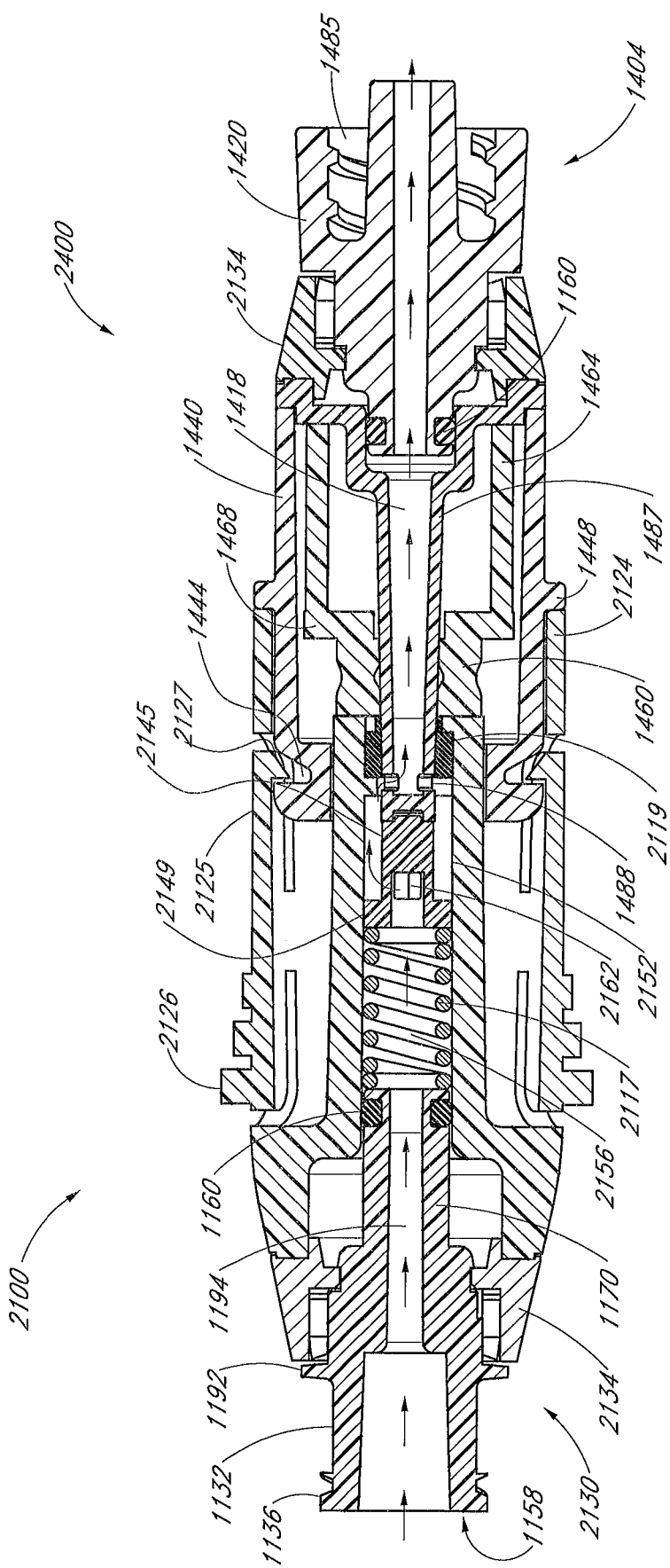
FIG. 65 shows a cross-sectional side view of the connector system of FIG. 64.

FIGS. 57 and 65 illustrate an embodiment of the male connector 2100 in a closed and open configuration, respectively. The spring member 2117 can bias the end piece 2145 of the valve member 2116 toward the first end 2112 of the male connector 2100. When the male connector 2100 is in a closed position, the interior retainer tabs 2171 can contact the annular flange 2149 of the end piece 2145 and inhibit movement of the end piece 2145 in the direction of the first end 2112 of the male connector 2100. When the male connector 2100 is in the open position, the end piece 2145 of the valve member 2116 can be displaced toward the second end 2114 of the male connector 2100. The annular flange 2149 of the end piece 2145 can be configured to have a shape that generally corresponds to the shape of an interior wall 2152 of the male connector 2100. In some configurations, contact between the outer surface of the annular flange 2149 and the interior wall 2152 can maintain substantially consistent alignment between the central axis of the passageway 2156 and the central axis of the end piece 2145 when the end piece 2145 moves between an open configuration and a closed configuration.

Figure 63:
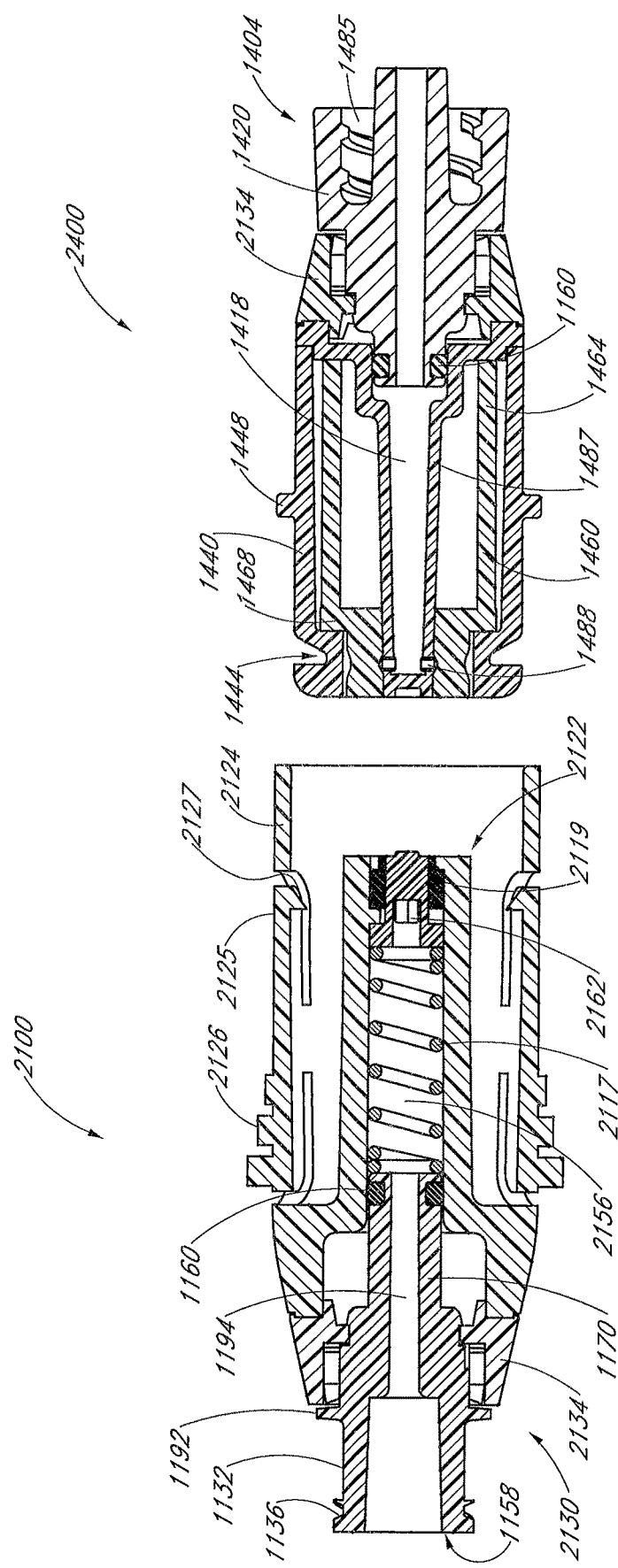
FIG. 63 shows a cross-sectional side view of the connector system of FIG. 62.
Figure 63A:
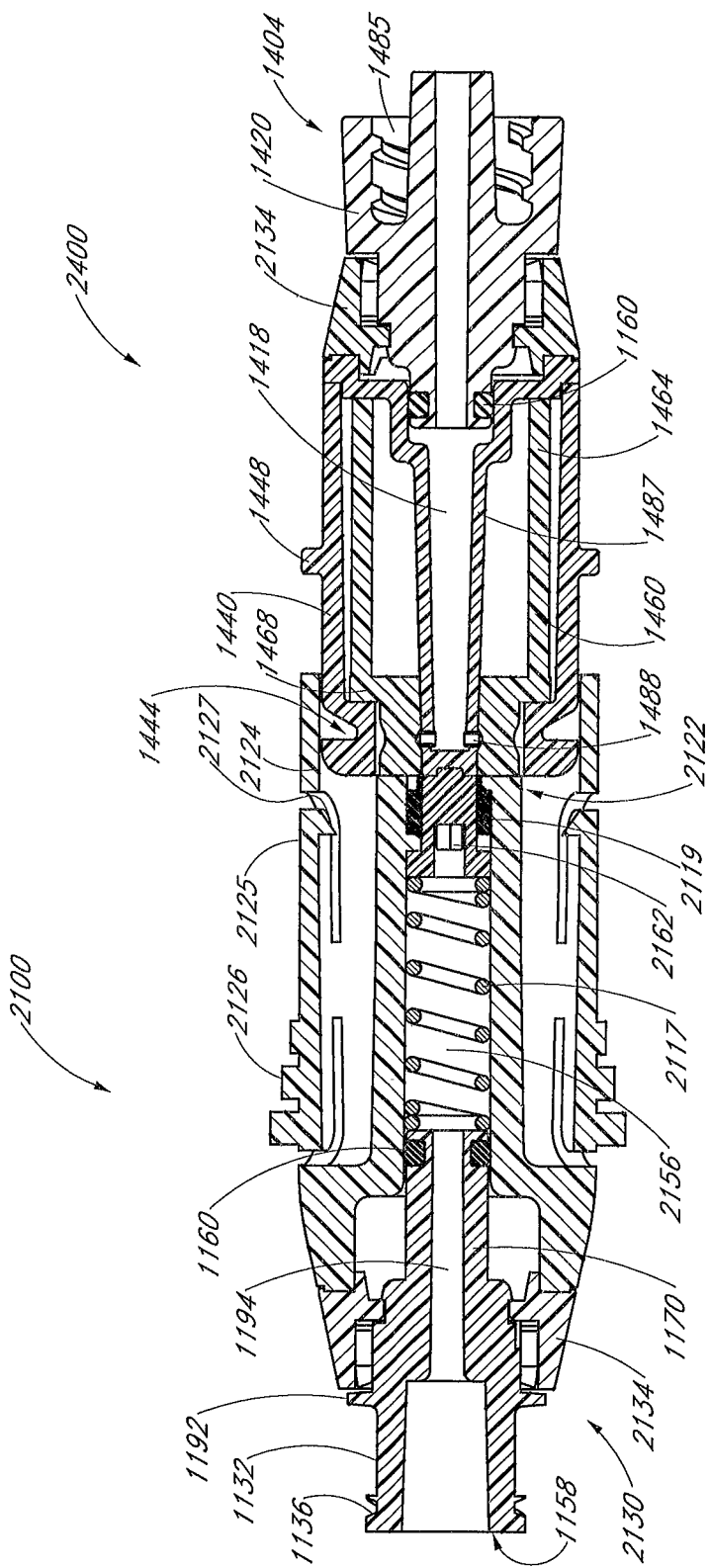
FIG. 63A shows a cross-sectional side view of the connector system of FIG. 62.
Figure 63B:
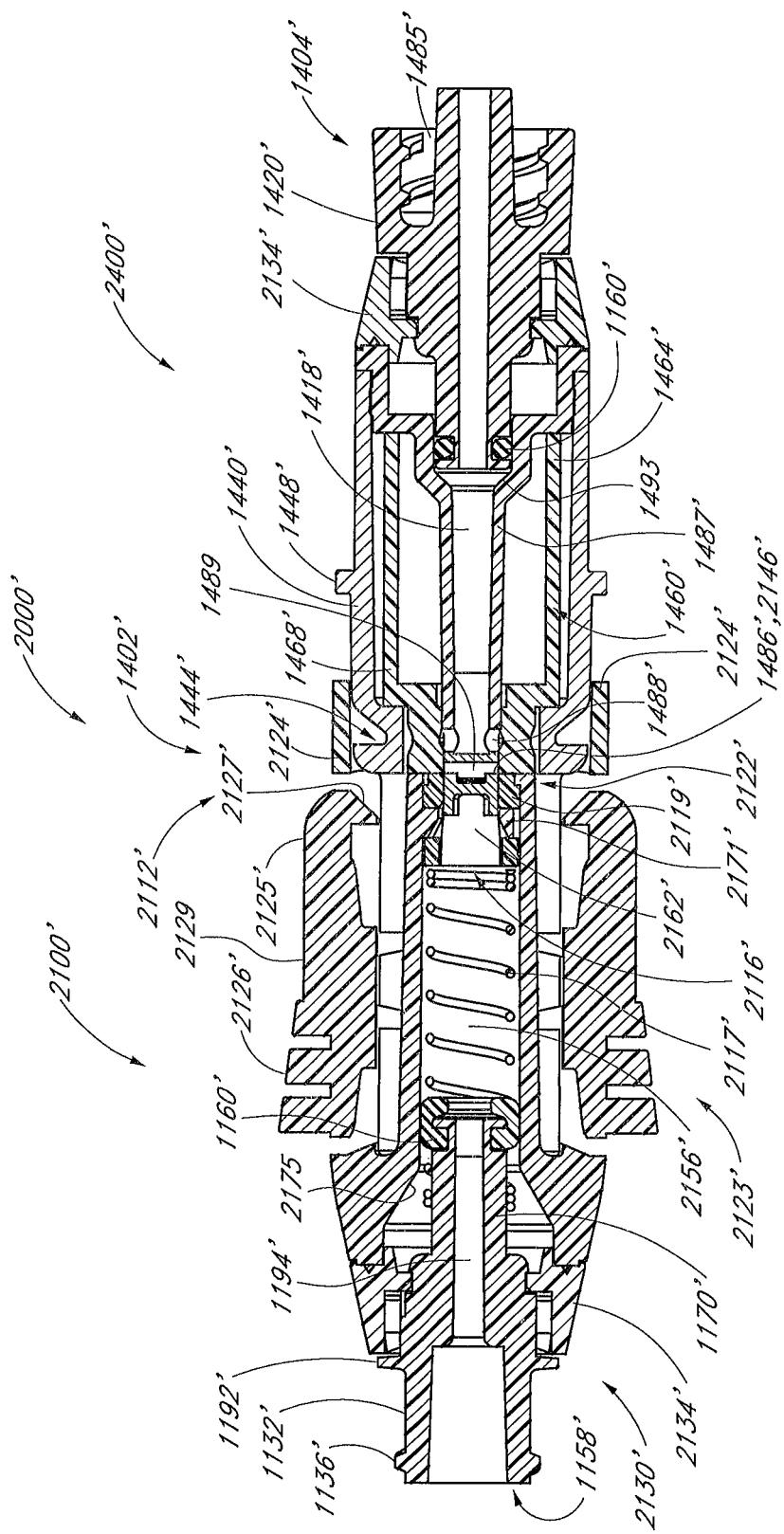
FIG. 63B shows a cross-sectional side view of an embodiment of a connector system including the male housing of FIG. 58A.
Figure 64:
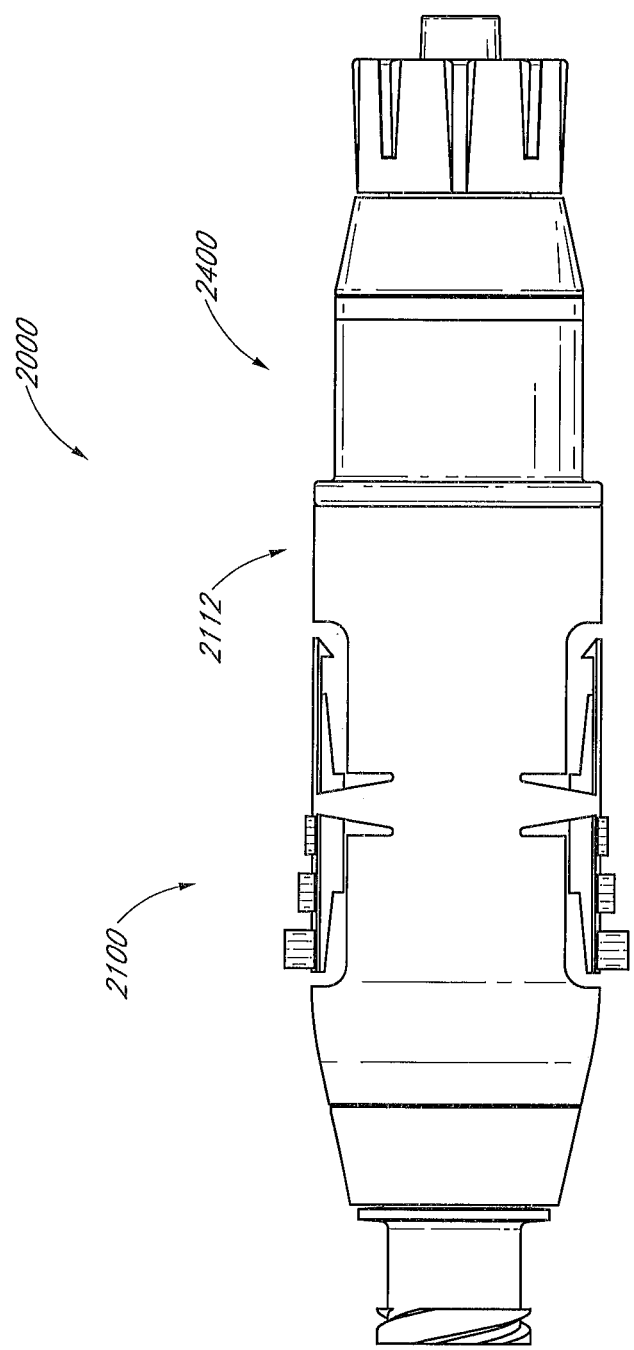
FIG. 64 is a side view of the embodiment of the male connector shown in FIG. 53 coupled to the embodiment of the female connector shown in FIG. 61.

FIG. 63B illustrates an embodiment of a connector system 2000' including a male connector 2100' and a female connector 2400' configured to connect with each other. Numerical references to components are the same as or similar to those previously described in connection with FIG. 63, except that a prime symbol (') has been added to the references. Where such references occur, it is to be understood that the components are the same or substantially similar to previously-described components. As illustrated, the male connector 2100' can include a valve member 2116' housed at least partially inside a male portion 2122'. The valve member 2116' can be biased toward the first end 2112' of the male connector 2100' by a spring member 2117' or other bias-providing member (e.g., a flexible tube). The valve member 2116' can be retained within the male portion 2122' via retainer tabs 2171'. The retainer tabs 2171' can include a sloped portion that can help facilitate high flow rates, and/or generally laminar, generally non-turbulent fluid flow, through the valve member 2116' when the male connector 2100' is in an opened configuration. In some embodiment, the retainer tabs 2171' can help resist or avoid turbulent flow through the valve member 2116' when fluid is passed through the valve member 2116' from the male connector 2100' to the female connector 2400'.

In some embodiments, a seal 1160' can be configured to engage with an end of a plunger 1170' and to sealingly contact the walls of the male housing 2123' to inhibit fluid from flowing around the plunger 1170'. In some embodiments, a portion of the seal 1160' can be configured to engage with an annular channel on an outer surface of the plunger 1170'. The seal 1160' can extend around an end of the plunger 1170' such that the spring member 2117' can be retained within the male portion 2122' between the valve member 2116' and a seal 1160'. In some embodiments, the seal 1160' is configured to contact the walls of the male housing 2123' along an axial extent (e.g., axial distance parallel to the axial centerline of the male housing 2123') greater than the axial extent of the covering portion 1192' of the first cap component 1132'.

As illustrated in FIG. 58A, a male connector 2100' can include tabs 2125' with tactile release ridges 2126' and hooks 2127' configured to engage with a portion of the female connector 2400'. The tabs 2125' can include one or more support structures, such as longitudinal ribs 2129, extending between tactile release ridges 2126' and the hooks 2127'. The tabs 2125' with ribs 2129 can be generally rigid and can resist bending between the ridges 2126' and the hooks 2127'. In some embodiments, the tabs 2125' with ribs 2129 can resist accidental disconnection of the hooks 2127' from the female connector 2400'.

The tactile release ridges 2126' of the tabs 2125' can extend radially outward from the axial centerline of the male connector 2100'. The male connector 2100' can include a plurality of release ridges 2126' or a single release ridge 2126'. In some embodiments, one or more of the release ridges 2126' has a different height (e.g., radial extend from the axial centerline of the male portion 2122') from one or more of the other release ridges 2126'. For example, and without limitation, the release ridges 2126' on the tabs 2125' can be arranged in a stepped pattern, wherein the heights of the ridges 2126' sequentially increase from a shortest release ridge 2126' closest to the first end of the male connector 2100' to a tallest release ridge 2126' closest to the second end of the male connector 2100'. In some such configurations, slippage of a user's fingers along the axial extent of the release ridges 2126' can be resisted while the user disconnects the male connector 2100' from the female connector 2400'.

In some embodiments, the radial distance between the tallest tactile release ridge 2126' and the axial centerline of the male portion 2122' (e.g., the height of the tallest tactile release ridge 2126') is greater than or equal to about 120% and/or less than or equal to about 180% of the radial distance between the radially outward-most point of the shroud 2124' and the axial centerline of the male portion 2122'. In some embodiments, the aforementioned ratio is about 165%. Many variations are possible. The radial thickness of each of or at least one of the release ridges 2126', as measured from the radially outermost surface of the shroud 2124, can, in some embodiment, be greater than the radial thickness of the rib 2129, as measured from the radially outermost surface of the shroud 2124. In some embodiments, tall tactile release ridges 2126' (e.g., ridges 2126' with great radial heights) can reduce the likelihood that the fingers of a user of the male connector 2100' would touch the portions of the male housing 2123' near and around the release tabs 2125' when releasing the tabs 2125' from engagement with the female housing 2400'.

The male housing 2123' can include a sloped portion 2175 at an end of the male housing 2123' opposite the mating surface 2128' of the male portion 2122'. The sloped portion 2175 can help facilitate insertion of the plunger 1170' into the male housing 2123' during manufacture of the male connector 2100'. For example, the sloped surface 2175 can help guide (e.g., function as a funnel) an end of the plunger 1170' into the end of the male portion 2122' opposite the end of the male portion 2122' having the mating surface 2128'.

In some embodiments, the conduit 1480' includes a conduit tip at or near the first end 1402' of the female connector 2400'. The conduit tip can have a mating surface 1486'. The conduit tip can include an engagement portion 1489. The engagement portion 1489 can be a separate component adhered to or otherwise attached to the end of the conduit 1480' closest to the first end 1402' of the female connector 2400'. In some embodiments, the engagement portion 1489 and conduit 1402' form a monolithic part. The engagement portion 1489 can be constructed from a flexible or semi flexible material.

In some embodiments, the engagement portion 1489 has a first surface (e.g., the mating surface 1486') and a second surface. The mating surface 1486' can include an alignment structure 1490' (e.g., a protrusion, recess, or other surface geometry). The second surface can be located opposite the mating surface 1486' and can be interfaced with (e.g., adhered to, welded to) the tip of the conduit 1480'. In some embodiments, the mating surface 1486' and the second surface of the engagement portion 1489 can move toward each other upon connection between the female connector 2400' and the male connector 2100'. In some such configurations, movement of the mating surface 1486' toward the second surface can compress the material of the engagement portion 1489. Compression can bias the mating surface 1486' and alignment structure 1490' toward the mating surface 2146' of the valve member 2116'. In some configurations, passage of fluid between the mating surface 2146' and the mating surface 1486' is inhibited and the exposure of the mating surface 2146' and the mating surface 1486' to fluid is resisted.

The conduit 1480' of the female connector 2400' can include a sloped portion 1493 located near the end of the conduit 1480' opposite the mating surface 1486'. In some embodiments, the sloped portion 1493 resists or avoids turbulence in the flow of fluid through the female connector 2400'. In some embodiments, the sloped portion 1493 of the conduit 1480' helps to inhibit the conduit 1480' from buckling under compressive loading.

Figure 66:
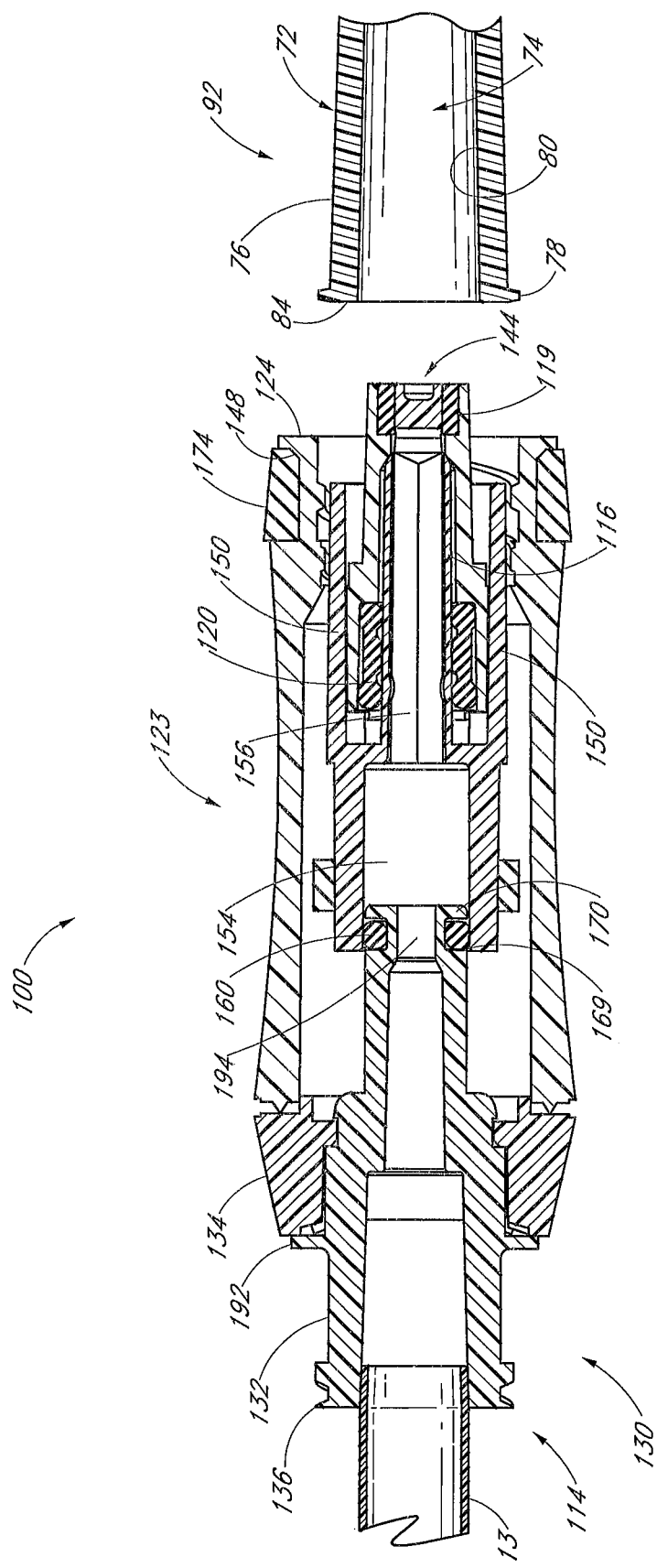
FIG. 66 shows a cross-sectional view of the male connector of FIG. 3 adjacent a female portion of another medical implement.

In some embodiments, the male connector 100 can be used with other connectors. FIG. 66 illustrates a cross-section of the male connector 100 of an embodiment adjacent an example of an open-ended female luer 92. The female luer 92 can comprise an elongate body 72 having a fluid passageway 74 therethrough, and the female luer 92 can have a first end 76. In some embodiments, the first end 76 of the female luer 92 can have a radially extending surface 78 disposed on its external surface. The female luer 92 can have a fluid conduit positioned within the female luer 92. The fluid conduit is not included or required in all female connectors compatible with the male connectors 100 disclosed herein. Along an inner surface 80 of the female luer 92, the fluid passageway 74 can be flared outwardly or tapered such that the diameter of the fluid passageway 74 increases towards the first end 76.

FIG. 66 illustrates the male connector 100 in a closed configuration. The struts 150 of the valve member 116 extend through slots in the male housing 123 such that their ends extend to positions near the end of the shroud 124 toward the first end 112 of the male connector 100. These struts 150 are configured to engage the mating ends 84 of the female luer 92 as the female luer 92 advances into engagement with the male connector 100.

In FIG. 66, the male connector 100 and female luer 92 are shown in an uncoupled configuration. To couple the male connector 100 and female luer 92, the radially extending surface 78 of the female luer 92 are screwed into the inner threads 126 of the male connector 100.

Figure 67:
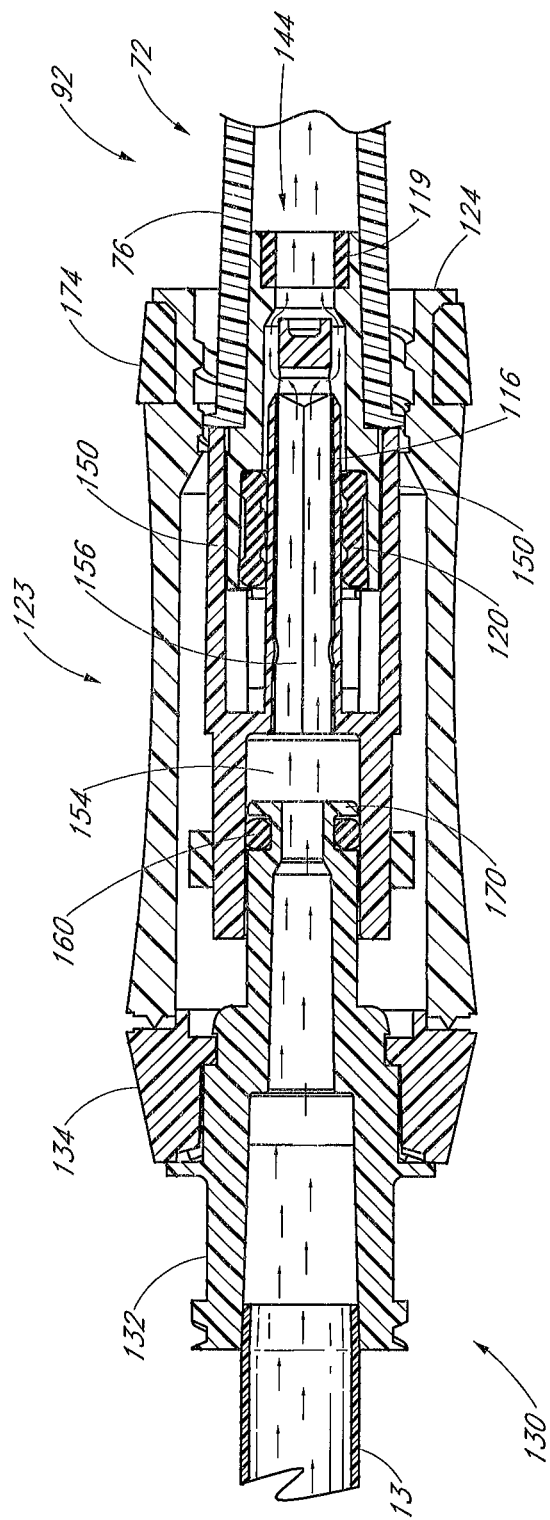
FIG. 67 shows a cross-sectional view of the male connector of FIG. 3 in engagement with the medical implement of FIG. 66.

As shown in FIG. 67, the male connector 100 and female luer 92 can be threadedly engaged towards one another until the taper of the inner surface 80 of the female luer 92 lies adjacent the correspondingly tapered external surface of the male luer tip 122 of the male connector 100.

As the male connector 100 and female luer 92 move towards each other into threaded engagement, the mating end 84 of the tip of the female luer 92 contacts the struts 150 of the valve member 116. As the male connector 100 and female luer 92 move further into threaded engagement, the struts 150, and thereby the valve member 116, are moved in the direction of the second end 114 of the male connector 100 by the female luer 92, displacing the valve member 116 relative to the male housing 123. Thus, the closure end 144 moves from the end of the male luer tip 122 of the male housing 123 towards the second end 114 of the male connector 100. As the closure end 144 separates from the male luer tip 122, a space forms between the valve member 116 and the male housing 123 and fluid is allowed to pass through the ports 162 and into the fluid passageway 74 of the female luer 92, or vice versa. In some embodiments, the closure remains intact until the inner surface 80 of the female luer 92 has formed a closing engagement with the outer surface of the male luer tip 122 of the male luer 10. Thus, the passageway 156 of the male connector 100 does not come into fluid communication with the external environment.

Figure 68:
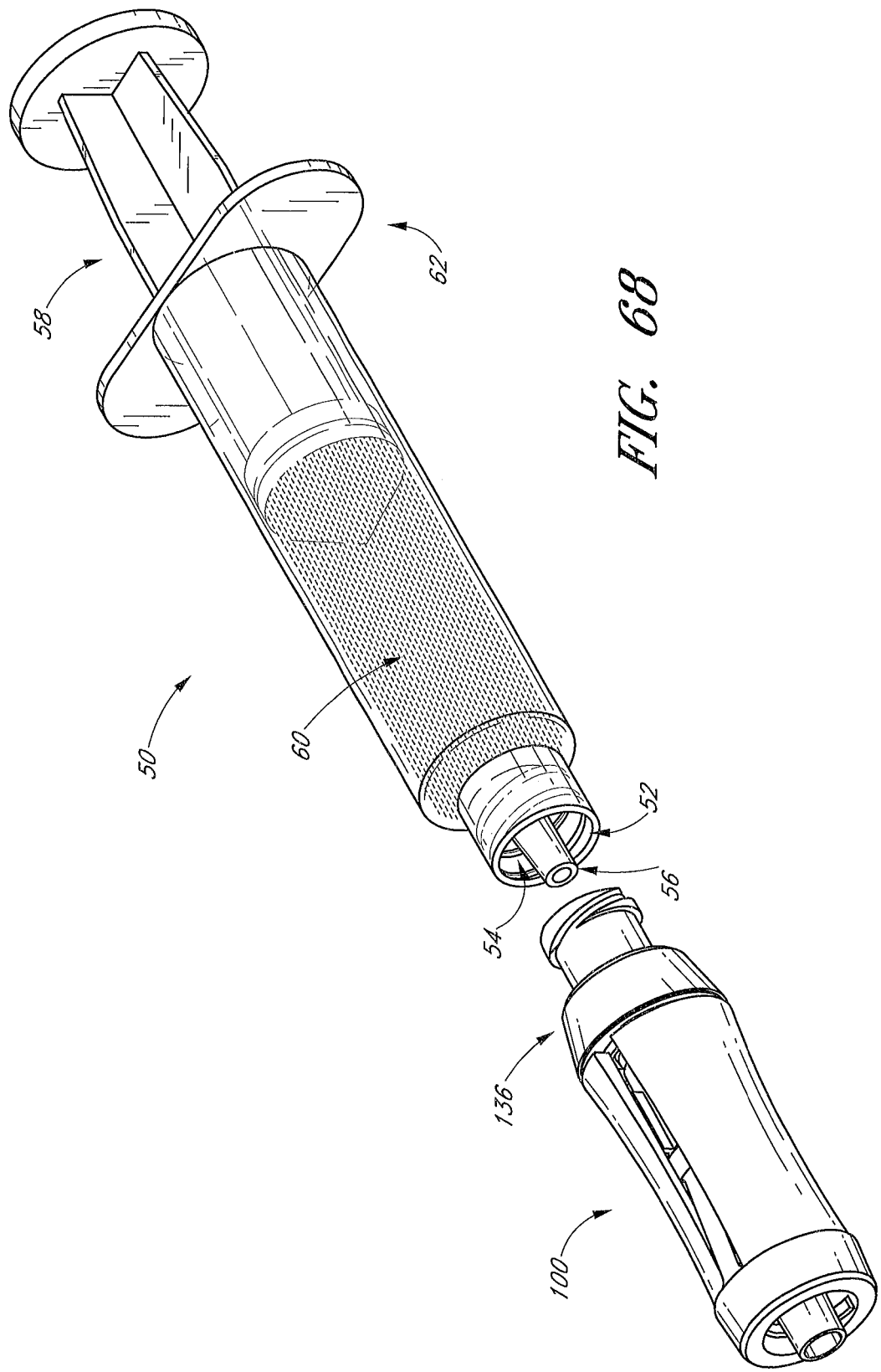
FIG. 68 shows a perspective view of the male connector of FIG. 3 adjacent a syringe with a male luer tip.

In some embodiments, the male connector 100 can be engaged with a syringe 50, as illustrated in FIG. 68. The syringe 50 and male connector 100 are displayed adjacent to each other. The syringe can include a male connector 52, a plunger 58, a reservoir 60, and convenient finger anchors 62. The connector 52 can have an internally threaded shroud 54 and a syringe luer tip 56. In the illustrated embodiment of the male connector 100, external threads 136 are disposed on the outside surface of the second end 114 of the male connector 100.

Figure 69:
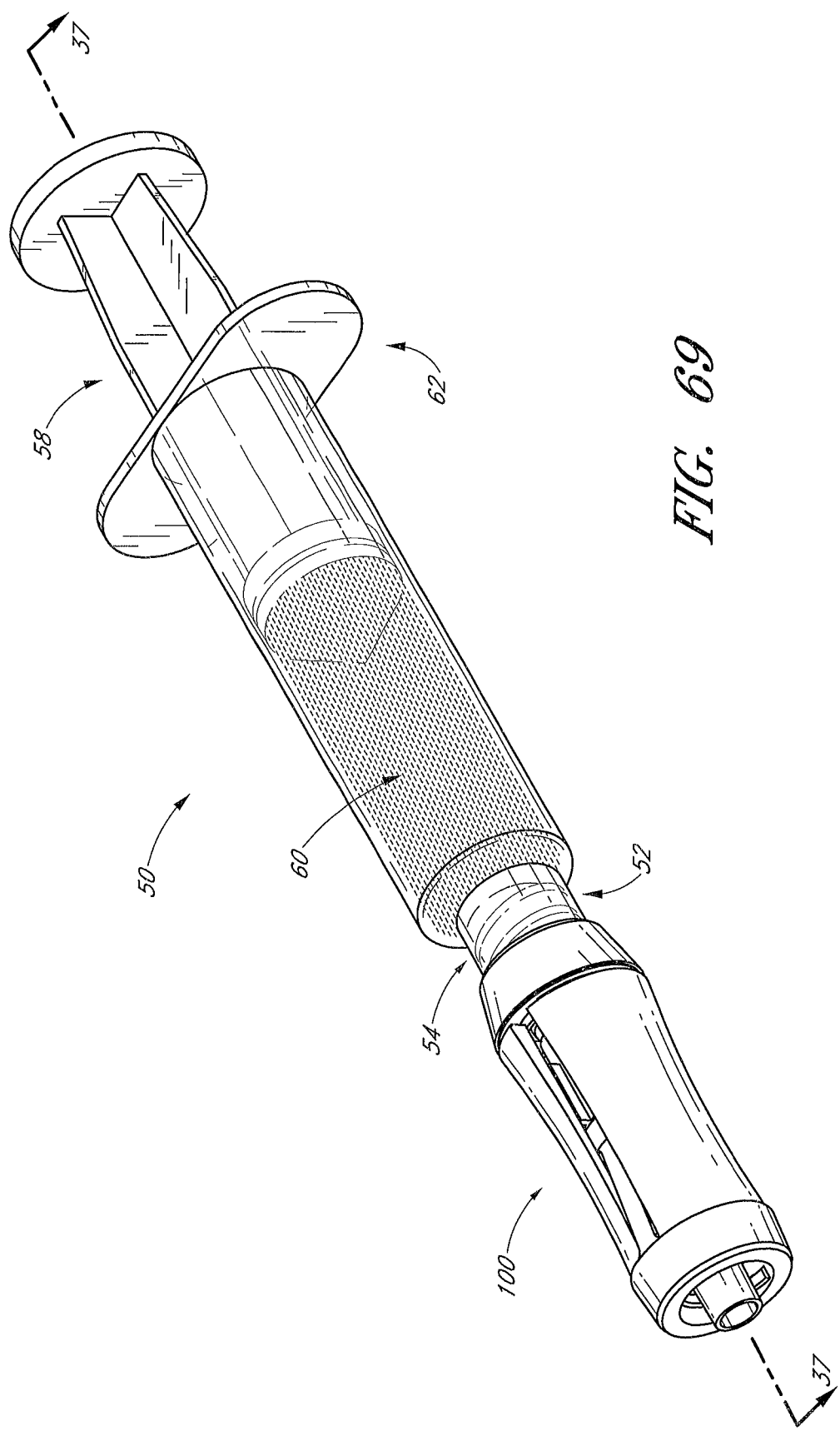
FIG. 69 shows a perspective view of the components of FIG. 68 after engagement.

With reference now to FIG. 69, the male connector 100 can be threadedly engaged with the syringe 50. The shroud 54 can engage with the second end 114 of the male connector 100 to connect the male connector 100 to the syringe 50. The reservoir 60 of the syringe 50 can be placed in fluid communication with the passageway 156 of the male connector 100.

Figure 70:
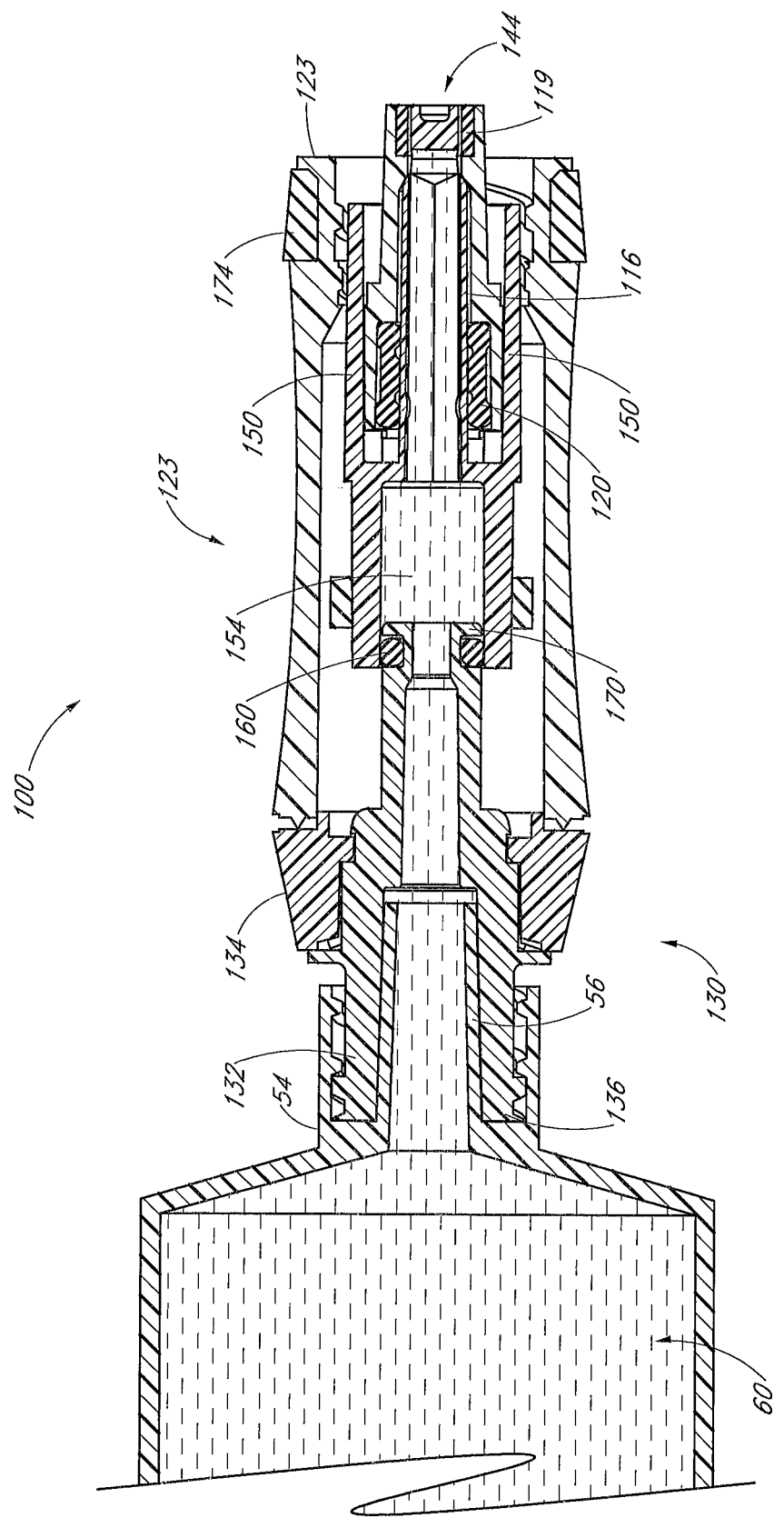
FIG. 70 shows a cross-sectional view of the male connector and the male luer tip of the syringe of FIG. 69.

Turning to FIG. 70, the engagement illustrated in FIG. 69 is shown in a cross-sectional view. The syringe 50 is threadedly engaged with the male connector 100 by the engagement between the shroud 54 and the external threads 136 of the first cap component 132. The luer tip 56 of the syringe 50 is inserted into first cap component 132. The reservoir 60 of the syringe can be in fluid communication with the passageway 156 of the male connector 100. The fluid can pass through the valve member 116 and towards the luer tip 122 of the male connector 100. In the illustrated embodiment, the fluid cannot exit the male connector 100 because the male connector 100 is in a closed configuration.

Figure 71:
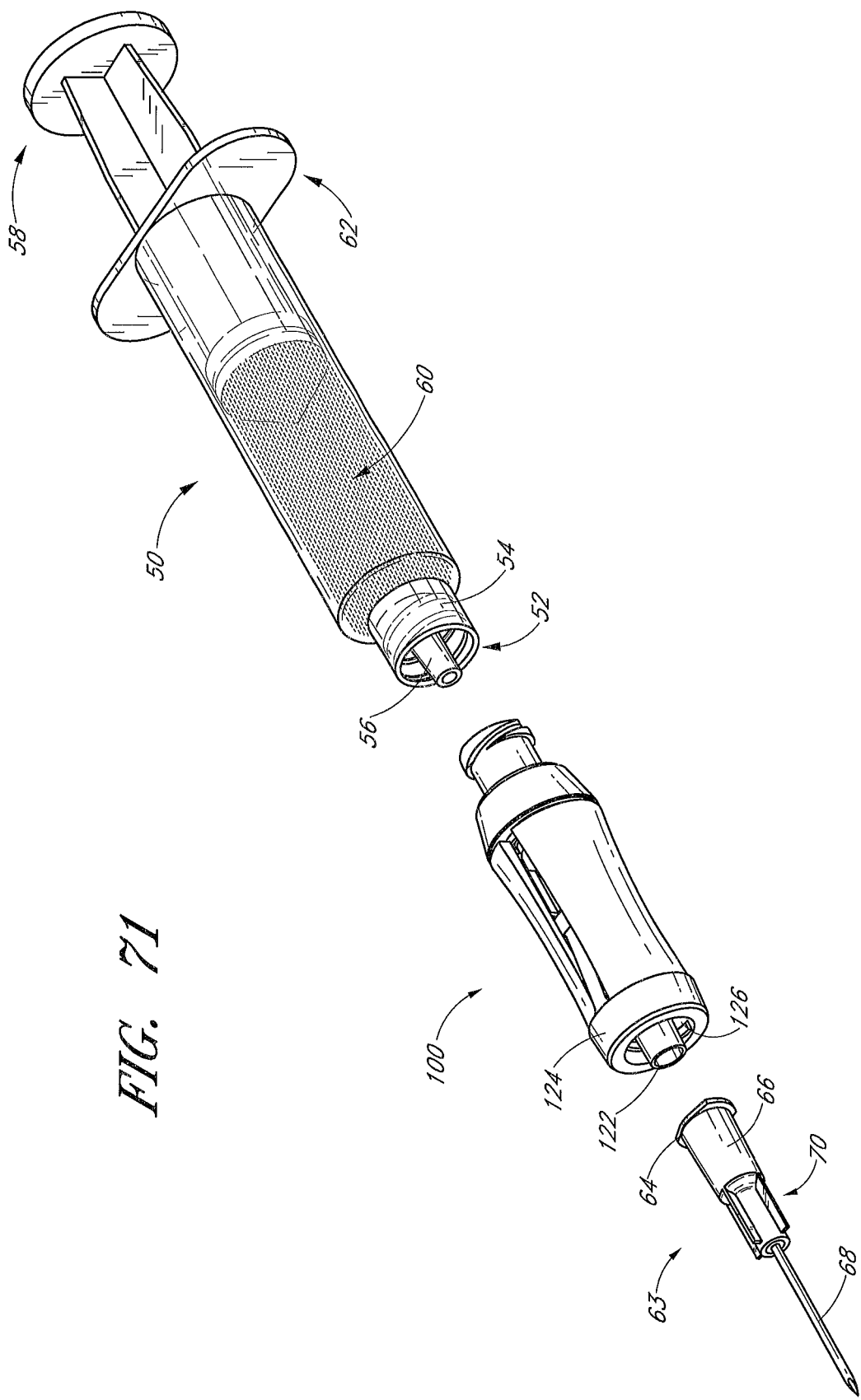
FIG. 71 shows a perspective view of the male connector of FIG. 3 located with its first end adjacent a needle assembly with a female luer attachment portion and with its second end adjacent a syringe with a male luer tip.

Referring to FIG. 71, the male connector 100 is shown between a syringe 50 and a needle assembly 63 with sheath 70. The syringe 50, like that of FIG. 68, can comprise a male connector 52, a plunger 58, a reservoir 60, and convenient finger anchors 62. The connector 52 can further comprise an internally threaded shroud 54 and a syringe luer tip 56. The needle assembly 63 can comprise a housing 66 with raised tabs 64 on the engagement end and a needle 68.

Figure 72:
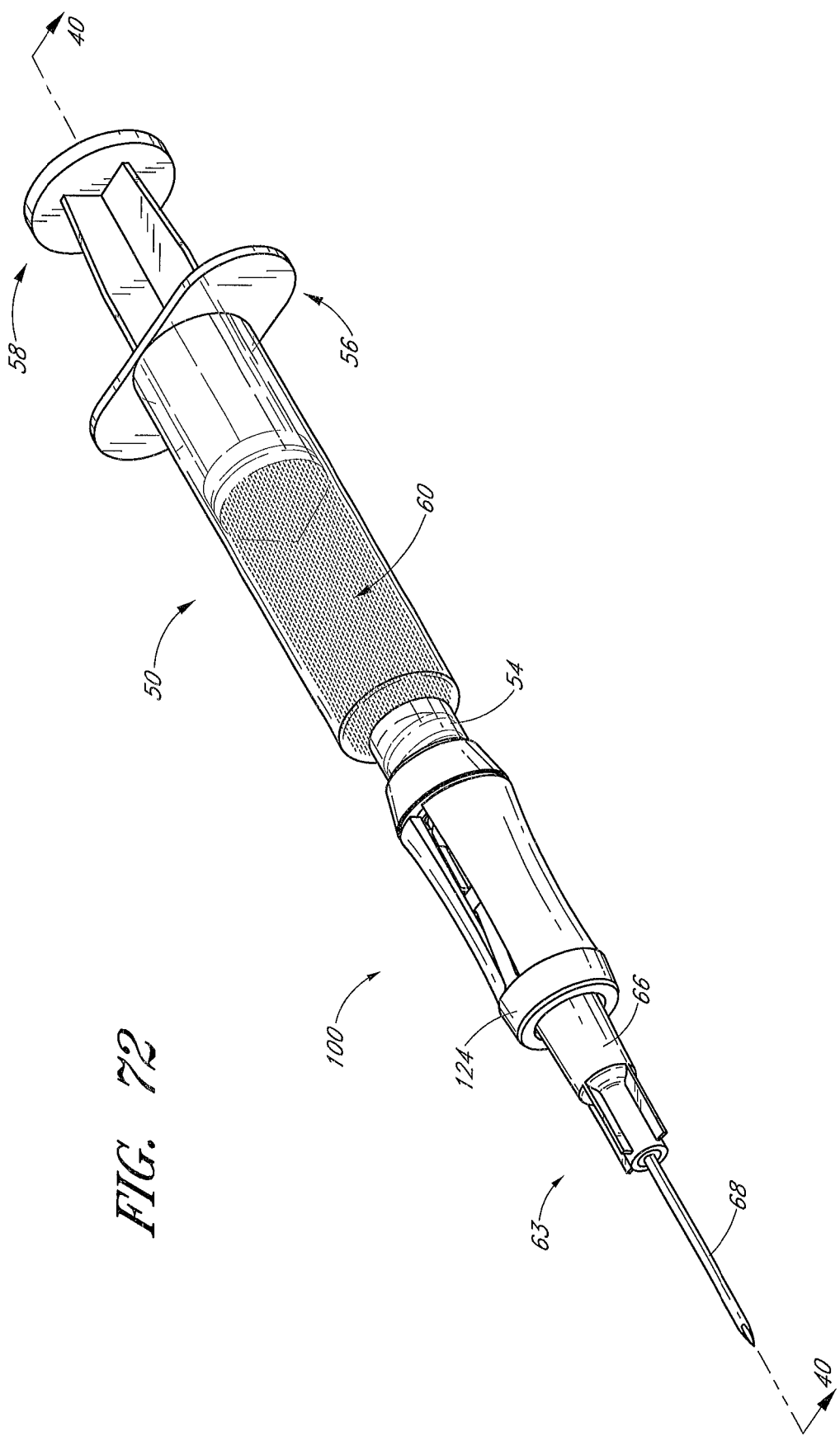
FIG. 72 shows a perspective view of the components of FIG. 71 in engagement.

With reference to FIG. 72, the male connector 100 is shown threadedly engaged with both the syringe 50 and needle assembly 63. The external threads 136 of the first cap component 132 of the male connector 100 can engage with the threaded shroud 54 of the syringe 50. Accordingly, the luer tip 56 on the syringe 50 can insert into the luer receiver 158 of the male connector 100. Similarly, the raised tabs 64 on the needle assembly 63 can engage with the internal threads 126 of the shroud 124 of the male connector 100. The luer tip 122 of the male connector 100 can insert into the housing 66 of the needle sheath.

Figure 73:
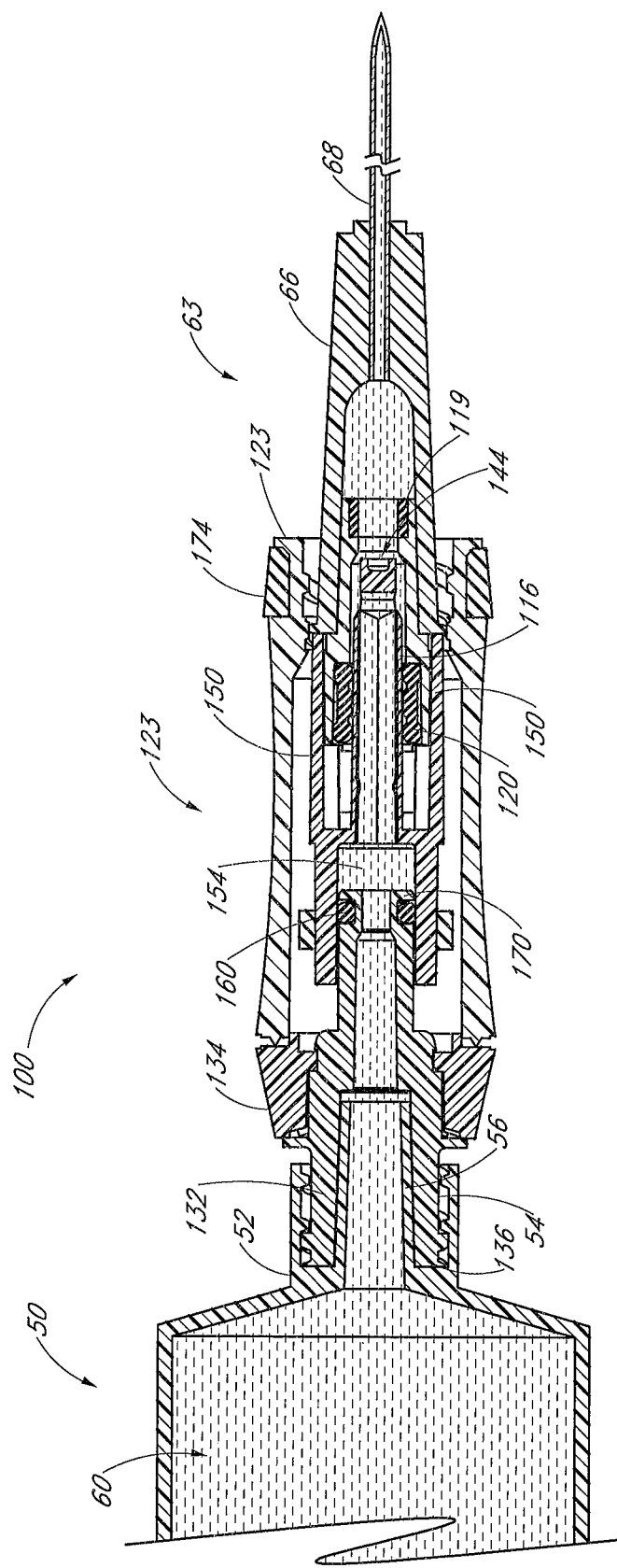
FIG. 73 is a cross-sectional view of the male connector, male luer tip of the syringe, and needle assembly of FIG. 72.

In FIG. 73, the engagement shown in FIG. 72 is illustrated in a cross-sectional view. The male connector 100 is engaged by a syringe 50 and a needle with a sheath 70. The syringe 50 is threadedly engaged with the external thread 136 of the first cap component 132 of the male connector 100. The needle assembly 63 is threadedly engaged with the internal threads 126 of the shroud 124 of the male connector 100.

The male connector 100 is engaged with the needle assembly 63. The housing 66 of the needle assembly 63 has raised tabs 64 near one end. The raised tabs 64 can threadedly engage the internal threads 126 of the shroud 124 of the male connector 100. As the luer tip 122 advances into the housing 66 of the needle assembly 63, the tabs 64 of the housing 66 can contact the struts 150 of the valve member 116. When the needle assembly 63 is fully engaged with the male connector 100, the valve member 116 is displaced a distance which separates the closure end 144 from the luer tip 122 sufficiently to permit fluid to flow out the ports 162 of the valve member 116. The fluid can then flow out the first end 112 of the male connector 100 and into the housing 66 of the needle assembly 63. The hollow needle 68 can allow the fluid to flow from within the housing 66 out the tip of the needle 68. At this stage, the syringe 50 can be in fluid communication with the distal tip of the needle 68. As was previously illustrated in FIGS. 69 and 70, in some embodiments, the male connector 100 can be in a closed configuration without a component engaged with the first end 112 of the male connector 100. The component illustrated in FIGS. 71-73 is a needle assembly 63; however, other components, such as those which permit fluid flow and possess a female luer engagement portion, can also be used.

At present, some potentially harmful medications are distributed in sealed vials. The medication is removed from the vial by inserting a needle, and drawing the medication into a syringe. The needle is then withdrawn from the vial and the medication can be dispensed. However, by inserting the needle into the medication for drawing into the syringe, medication is disposed on the outside of the needle, which can inadvertently come in contact with the skin and cause harm. In some embodiments, a vial adaptor which penetrates the vial with a penetrating system can be used. In such a vial adaptor, the medication is drawn through the mechanism and passed directly to a syringe or other medical device for injection without the additional step of withdrawing the mechanism from the vial. Even if such a vial adaptor is used, there is still the possibility of latent medication remaining on the male end used to withdraw and then later to inject the medication, or on the vial adaptor after it may be decoupled from the male end.

With closeable medical connectors of the type disclosed herein, flow of the medication out of a syringe with a needle is resisted, except during desired application. For example, in some embodiments, a syringe with a male connector will not leak medication when packaged for shipment, even if the package is vacuum-sealed. Once the package is opened, the male connector can be engaged with a female connector of an IV tube, for example, and the medication dispensed only when the connection is engaged. Following flow of the medication from the syringe through the engaged connectors and into the IV tube, the male connector can be disengaged from the female connector. In some embodiments, the connectors can close on disengagement, preventing excess flow through the connectors. The mating ends of the connectors can be isolated from the medication, such that after the connectors are disengaged, residual medication does not migrate onto the mating ends.

FIGS. 74-77 illustrate another embodiment of a connector system 3000 that comprises a male connector 3100 and a female connector 3400. Some numerical references to components in FIGS. 74-77 are the same as or similar to those previously described for the connector system 1000 and corresponding male connector 1100 and female connector 1400, (e.g. male connector 3100 v. male connector 1100). It is to be understood that the components can be the same in function or are similar in function to previously-described components. The connector system 3000 of FIGS. 74-77 shows certain variations to the connector system 1000 of FIGS. 33-52. As with all embodiments disclosed herein, it is contemplated that any function, step, or structure illustrated or described in one or more embodiments can be used with, substituted for, or replaced with, any function, step, or structure of one or more other embodiments, with adaptations as necessary.

In some embodiments, the male connector 3100 has a first end 3112 and a second end 3114. The male connector 3100 can have a tube member 3187. The tube member 3187 can have a closed end 3144 and an opened end 3149. In some embodiments, both ends of the tube member 3187 are closed. In some embodiments, such as those with other means for selectively closing the fluid path on the first end, both ends of the tube member 3187 can be open. The tube member 3187 can have a generally cylindrical shape, an internal cross-section, an external cross-section, and an axial centerline. In some embodiments, there are one or more tapered and/or flared portions along the axial length of the tube member 3187. In some embodiments, the tube member 3187 has a generally rectangular prism shape, a generally triangular prism shape, a generally oval shape, a generally hexagonal prism shape, or any other shape suitable for a channel. The tube member 3187 can include an internal passageway 3156 extending between the closed end 3144 and the opened end 3149 of the tube member 3187. In some embodiments, the internal passageway 3156 can terminate near the closed end 3144 at one or more ports 3162. The one or more ports 3162 can extend from the internal passageway 3156 through the wall of the tube member 3187. In some embodiments, the internal passageway 3156 is in fluid communication with the conduit 1194.

In some embodiments, the male connector 3100 has a sleeve member 3163. The sleeve member 3163 can have a generally cylindrical shape, an internal cross-section, an external cross-section, and an axial centerline. In some embodiments, the sleeve member 3163 can be substantially coaxial with the tube member 3187. In some embodiments, the sleeve member 3163 can include one or more flared and/or tapered sections along its axial length. The internal cross-section of the sleeve member 3163 can be substantially the same shape as or a shape similar to the external cross-section of the tube member 3187.

Figure 74:
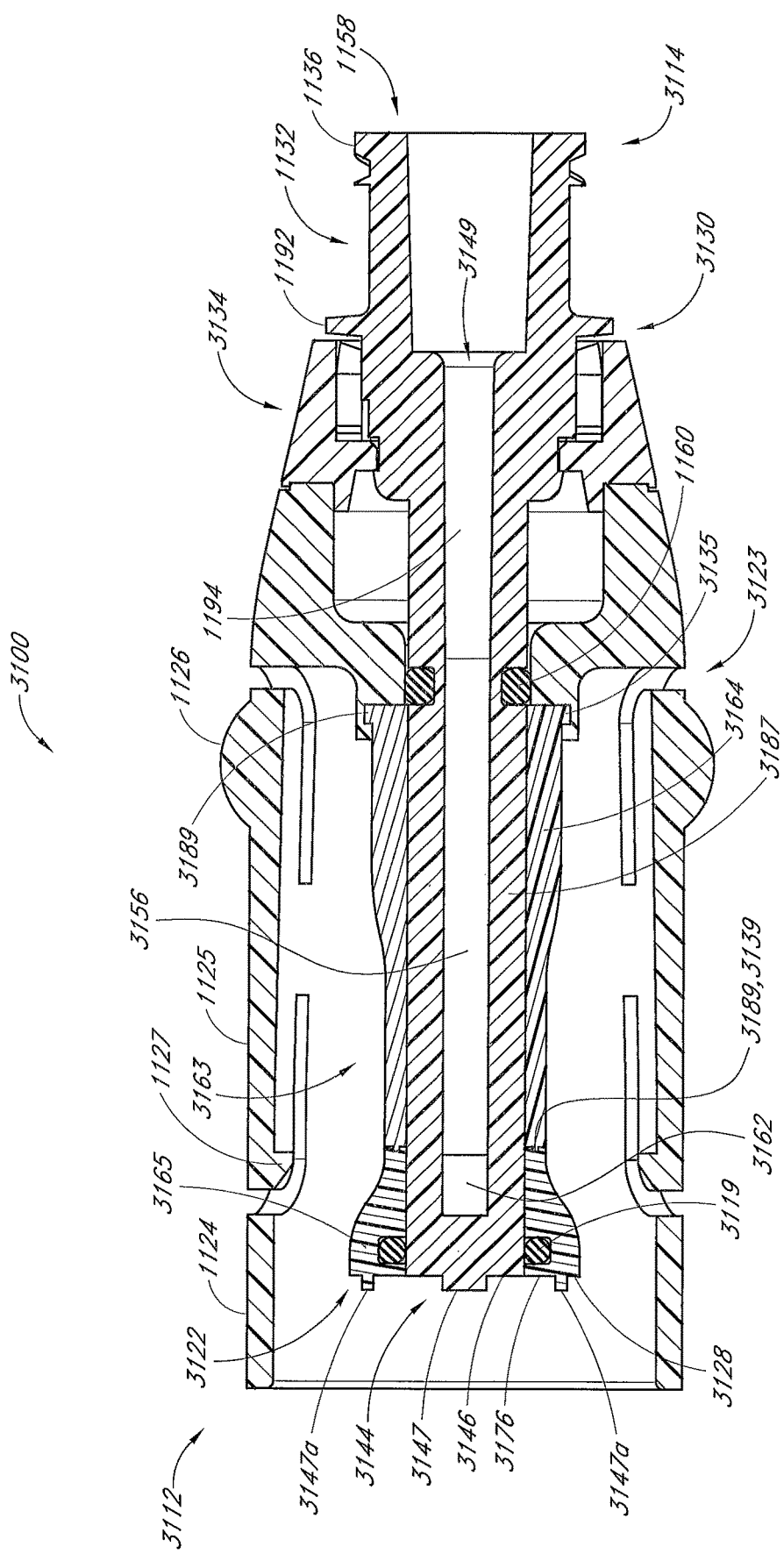
FIG. 74 shows a cross-sectional side view of another embodiment of a male connector.

As illustrated in FIG. 74, the sleeve member 3163 can include a first sleeve portion 3165 generally adjacent to the closed end of the tube member 3187 and a second sleeve portion 3164 spaced from the closed end of the tube member and/or generally adjacent to the end of the tube member 3187 opposite the ports 3162. In some embodiments, the first sleeve portion 3165 connects to the second sleeve portion 3164 via an adhesive, sonic welding, solvent bonding, or some other suitable means of adhering. The first sleeve portion 3165 can be constructed of a plastic or some other rigid or semi-rigid polymeric material. In some embodiments, the second sleeve portion 3164 can be constructed of a material that is less hard or less rigid than the first sleeve portion 3165, such as a rubber, silicone, or some other resilient, flexible or semi-flexible material. In some embodiments, the first sleeve portion 3165 is constructed of a flexible or semi-flexible material. In some embodiments, the second sleeve portion 3164 is constructed of a rigid or semi-rigid material. In some embodiments, both the first sleeve portion 3165 and the second sleeve portion 3164 are constructed of either a flexible material or a rigid material. The first sleeve portion 3165 can have a mating surface 3176 near the first end 3112 of the male connector 3100. In some embodiments, the tube member 3187 has a mating surface 3146 generally adjacent the mating surface 3176 of the first sleeve portion 3165.

The first sleeve portion 3165 can include one or more grooves on its inner wall (e.g., toward the axial centerline of the sleeve portion 3163). In some embodiments, at least one groove can be located near the closed end 3144 of the tube member 3187 when the sleeve portion 3163 is in a closed position, as illustrated in FIG. 74. A sealing member 3119 can be housed at least partially within the groove. In some embodiments, the sealing member 3119 can contact the outer (e.g., away from the axial centerline of the tube member 3187) surface of the tube member 3187. In some embodiments, contact between the sealing member 3119 and the tube member 3187 can create an annular seal around the tube member 3187. A seal can inhibit fluid from contacting the mating surfaces 3146, 3176 of the male connector 3100 when the sleeve portion 3163 is in the closed position. In some embodiments, the sealing member 3119 can be located at least partially within a groove in the outside surface of the tube member 3187 near the closed end 3144 of the tube member 3187.

In some embodiments, the second sleeve portion 3164 includes a flange 3189. The flange 3189 can be configured to engage with a slot 3135 in the male housing 3123. In some embodiments, engagement between the flange 3189 and the slot 3135 can inhibit the sleeve member 3163 from separating from the male housing 3123 in the axial direction. In some embodiments, the portion of the sleeve member 3163 that is spaced apart from the first end 3112 of the male connector 3100 is attached to the male housing 3123 via adhesive(s), snap-fit, solvent bonding, sonic welding, or some other suitable means of attachment.

Figure 75:
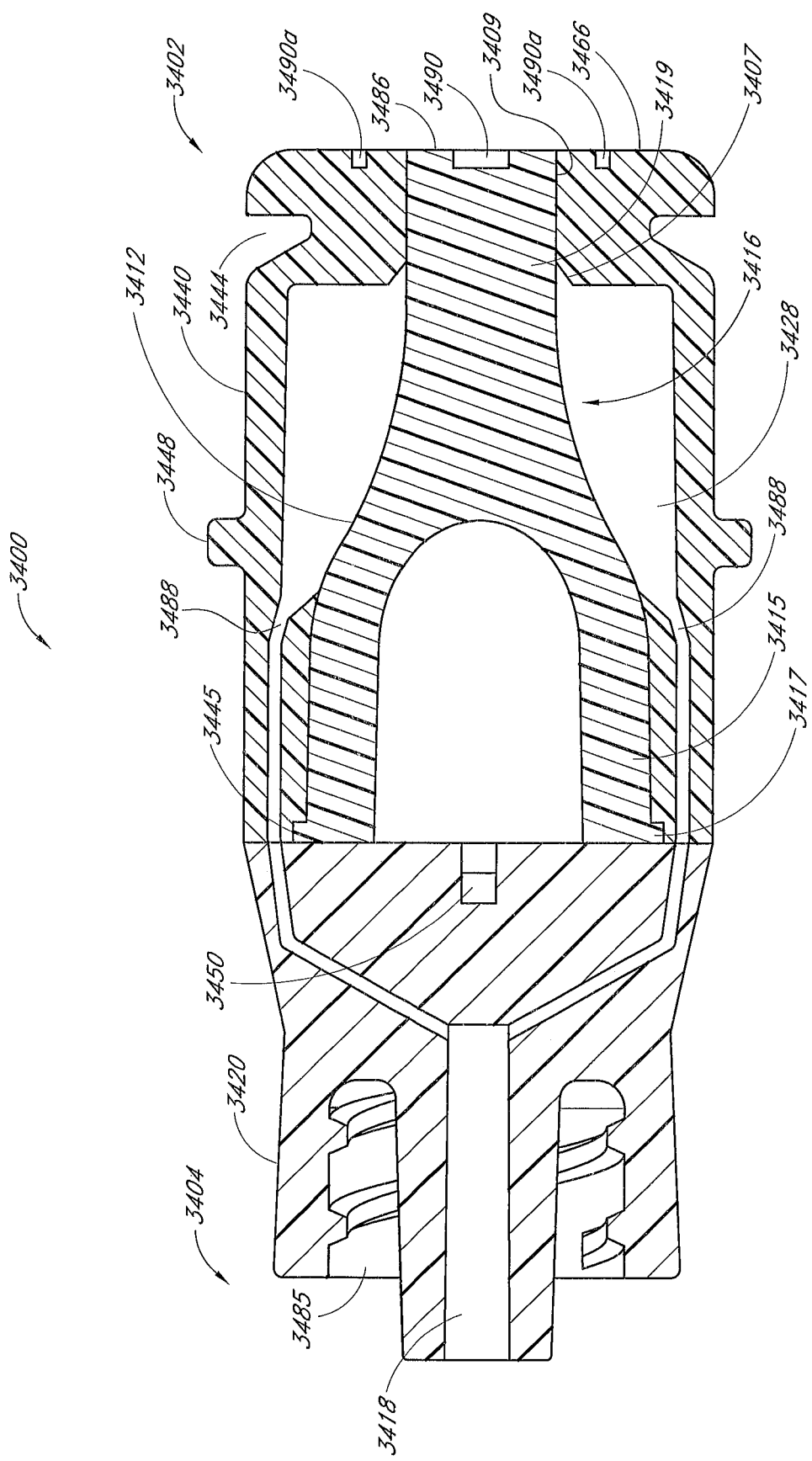
FIG. 75 shows a cross-sectional side view of another embodiment of a female connector.
Figure 77:
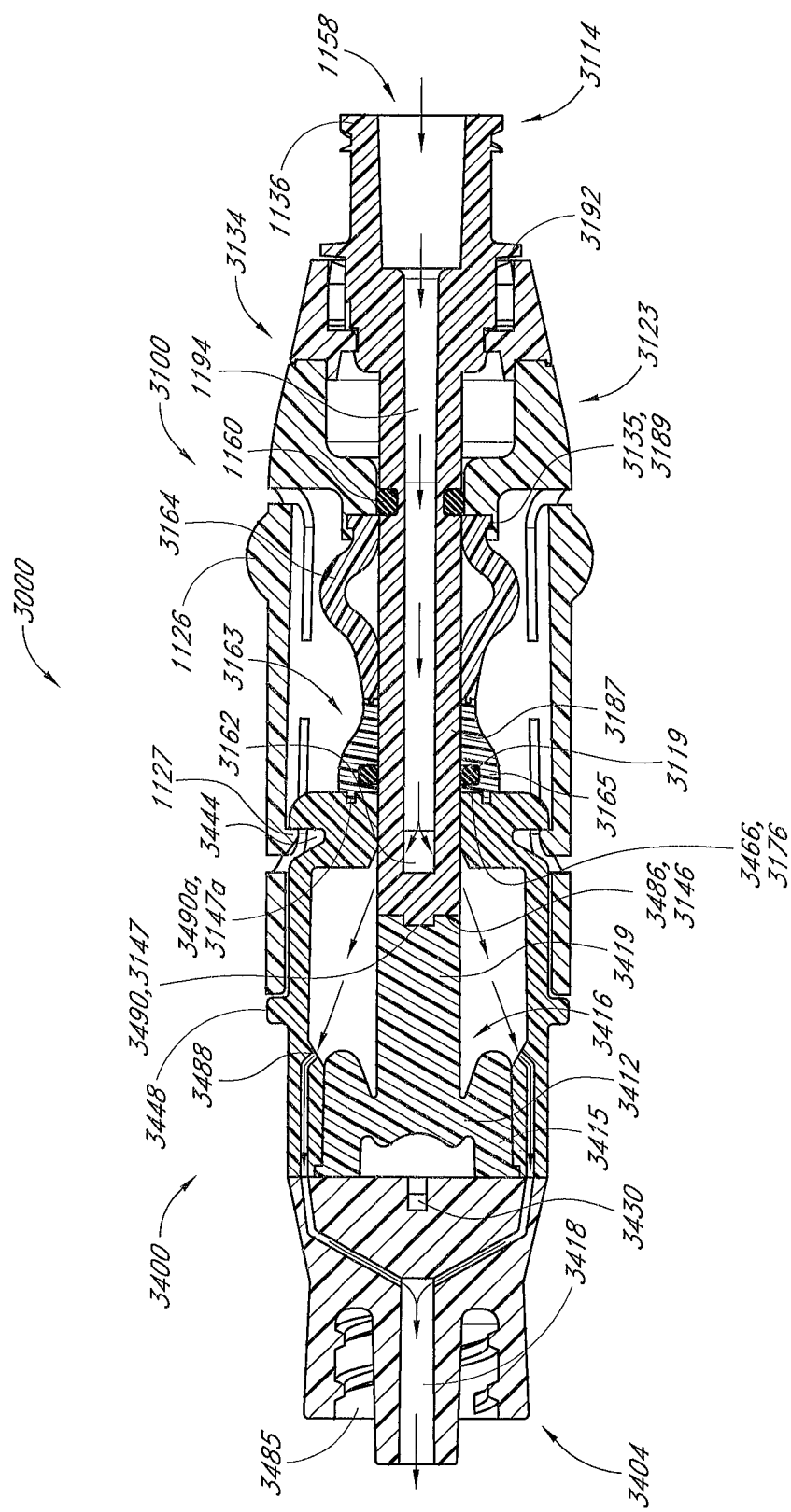
FIG. 77 shows a cross-sectional side view of the connector system of FIG. 76.

In some embodiments, the female connector 3400 includes a resilient or flexible valve member 3416, a female housing 3440, and a cap component 3420. In the illustrated example, there is no interior spike, port, or other rigid member within or supporting the valve member 3416. As illustrated in FIG. 75, the female connector 3400 can have a first end 3402 and a second end 3404 that is spaced from or opposite from the first end 3402. The valve member 3416 can be configured to transition between an opened configuration (e.g., as illustrated in FIG. 77) and a closed configuration (e.g., as illustrated in FIG. 75). In some embodiments, the valve member 3416 is constructed of rubber, silicone, or some other flexible or semi-flexible material. In some embodiments, a space between the valve member 3416 and the inner walls of the female housing 3440 provides a flow chamber 3428.

As illustrated, the distance or space between the outer surface of the valve member 3416 and the inner surface of the housing 3440 can be sufficiently large to provide a high-flow, low fluid-resistant passage in the region near the connection between the male and female connectors 3000, 3400. In some embodiments, the space between the outer surface of the valve member 3416 and the inner surface of the housing 3440 can be sufficiently small (e.g., less than or substantially less than the cross-sectional width of the valve member 3416 near its closing end, or less than or substantially less than the cross-sectional width of the inner surface of the fluid passageway 3418 near the second end 3404) to substantially eliminate or produce only a small amount of dead space within the female connector 3400. In some embodiments, the space between the outer surface of the valve member 3416 and the inner surface can be adjusted or configured so that the internal fluid volume within the female connector 3400 is generally the same when in both the opened and closed positions to produce a generally neutral-flow connector. As with all other disclosure herein, it is contemplated that this generally neutral-flow feature can be used in any other embodiment herein.

The valve member 3416 can include an elongate portion 3419. The elongate portion 3419 can have a substantially cylindrical shape, an axial centerline, an inner cross-section, and/or an outer cross-section. In some embodiments, the outer cross-section of the elongate portion 3419 is generally rectangular, generally triangular, generally oval shaped, generally hexagonal, any other suitable shape, or any combination thereof. In some embodiments, the shape of the outer-cross section of the elongate portion 3419 varies along the axial centerline of the elongate portion 3419. The female housing 3440 can have an opening 3409 adjacent the first end 3402 of the female connector 3402. The opening 3409 can have an inner cross-section. The inner cross-section of the opening 3409 can be sized and/or shaped to substantially match or correspond to the outer cross-section of the elongate portion 3419 of the valve member 3416. In some such embodiments, contact between the outer cross-section of the elongate portion 3419 and the inner cross-section of the opening 3409 creates a substantial fluid tight seal. Such a seal can inhibit fluid from passing between the flow chamber 3428 and the exterior of the female housing 3440 via the opening 3409 when the valve member 3416 is in the closed configuration.

The valve member 3416 can be resilient and/or can include a flexing and/or expanding portion 3415. In some embodiments, the portion 3415 has a substantially cylindrical shape, an axial centerline, an inner cross-section, and/or an outer cross-section. In some embodiments, the portion 3415 includes one or more flared and/or tapered portions along its axial length. The portion 3415 can be split into two or more regions via axial and/or radially-tangential openings in the portion 3415. For example, the portion 3415 can have two or more axial spaces that form two or more "legs" on the portion 3415. In some embodiments, the portion 3415 has no openings or spaces. In some embodiments, the valve member 3416 includes a transition portion 3412 between the elongate portion 3419 and the portion 3415. The transition portion 3412 can be configured to affect the overall stiffness of the valve member 3416. For example, the transition portion 3412 can be shaped such that the transition portion 3412 creates a collapsing point or region for the valve member 3416 when the elongate portion 3419 is pushed toward the portion 3415, as will be described in detail below.

In some embodiments, the portion 3415 can include a flange 3417. The flange 3417 can be configured to engage with a channel 3445 in the female housing 3440. In some embodiments, engagement between the flange 3417 and the channel 3445 inhibits the valve member 3416 moving away from the female housing 3440 toward the first end of the female housing 3440 in the axial direction. In some embodiments, the female housing 3440 includes a tapered portion 3407. The tapered portion 3407 can help guide the elongate portion 3419 toward the opening 3409 when the valve member 3416 transitions from the opened configuration to the closed configuration.

In some embodiments, the female connector 3400 can include one or more conduits or openings 3488. The conduits or openings 3488 can be in fluid communication with the flow chamber 3428. In some embodiments, the conduits are in fluid communication with a passageway 1418 in the female connector 3400. In some embodiments, the conduits or openings 3488 are in fluid communication with both the flow chamber 3428 and the passageway 1418. The conduits or openings 3488 can extend through the female housing 3440, through the cap component 3420, through both the female housing 3440 and the cap component 3420, or through neither the female housing 3440 nor the cap component 3420.

The first end 3402 of the female connector 3400 can include one or more alignment structures. In some embodiments, the one or more alignment structures can comprise protrusions, cavities, indentations or other surface features. For example, the valve member 3416 can include an indentation 3490. The indentation 3490 can be sized and shaped to releasably engage with an alignment structure on the first end 3112 of the male connector 3100. In some embodiments, the indentation 3490 is sized and shaped to releasably engage with a protrusion 3147 on the tube member 3187 of the male connector 3100. Furthermore, the valve member 3416 can include a mating surface 3486 generally proximate the indentation 3490.

In some embodiments, the female housing 3440 includes one or more indentations 3490a. The one or more indentations 3490a can be configured to releasably engage with one or more protrusions 3147a on the first sleeve portion 3165. In some embodiments, the female housing includes an annular indentation configured to releasably engage with an annular protrusion on the first sleeve portion 3165. The female housing 3440 can include a mating surface 3466 generally adjacent the mating surface 3486 of valve member 3416.

Figure 76:
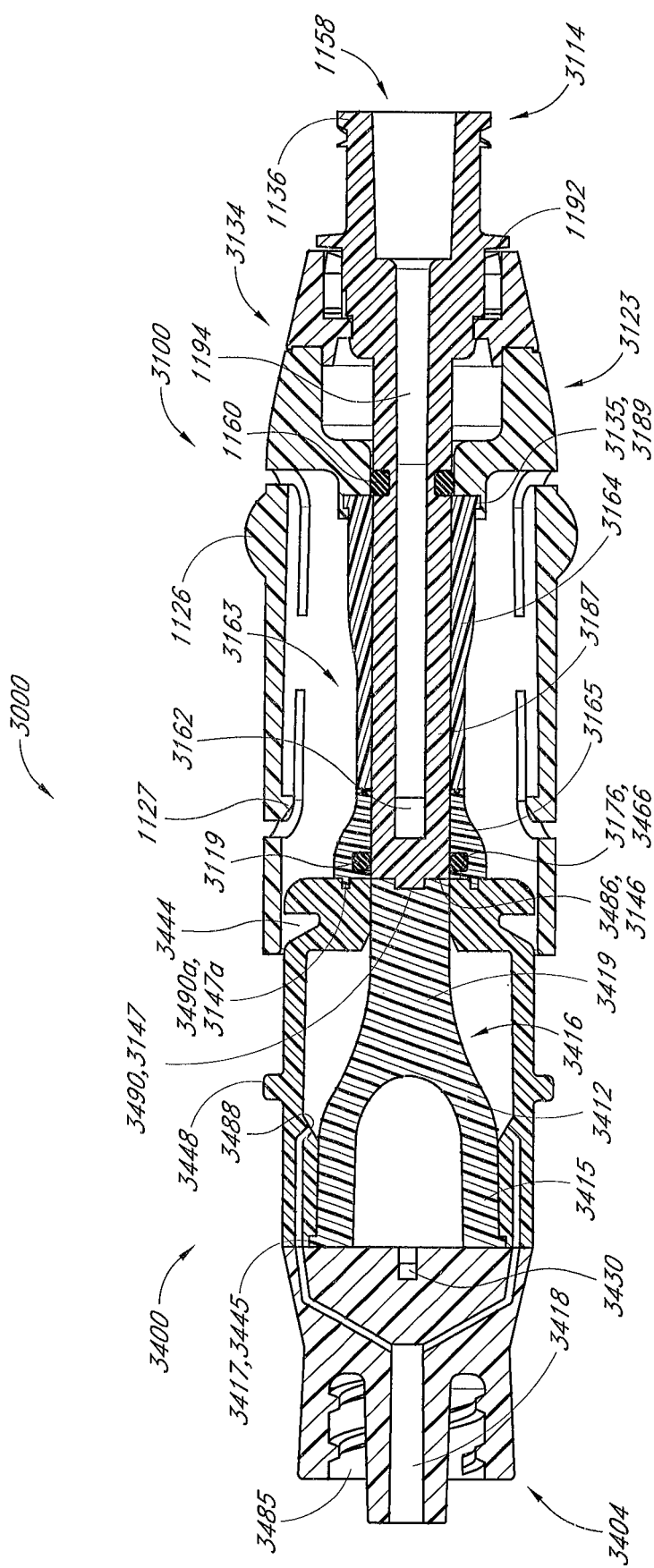
FIG. 76 shows a cross-sectional side view of the male connector of FIG. 74 adjacent to the female connector of FIG. 75.

As illustrated in FIGS. 76-77, the female connector 3400 and male connector 3100 can be mated together. In some embodiments, such mating can cause the valve member 3416 to transition to the opened configuration. At least a portion of the tube member 3187 can advance into the female connector 3400 and push the elongate portion 3419 of the valve member 3416 toward the second end 3404 of the female connector 3400. Engagement between the indentation 3490 on the tip of the elongate portion 3419 and the protrusion 3147 on the tube member 3187 can help inhibit radial movement or tilting (e.g., tilting with respect to an axial centerline of the female connector 3400) as the elongate portion 3419 is pushed toward the second end 3404 of the female connector 3400.

Pushing of the elongate portion toward the second end 3404 can cause the transition portion 3412 of the valve member 3416 to collapse. In some embodiments, collapse of the transition portion 3412 and/or portion 3415 can create an opposing spring force that can bias the elongate portion 3419 to the closed configuration. For example, as the female connector 3400 and the male connector 3100 are detached (e.g., pulled apart from each other), the transition portion 3412 and or portion 3415 can cause the elongate portion 3419 to maintain contact with the tube member 3187 until the valve member 3416 returns to the closed configuration. In some embodiments, the female housing 3440 is configured to wipe dry the outer side surfaces of tube member 3187 and the elongate portion 3419 of the valve member 3416 as the female connector 3400 and the male connector 3100 are disconnected. In some embodiments, the female connector 3400 can include a wiping surface, such as a narrow edge or a radially constraining O-ring to wipe down and remove fluid from one or more side surfaces within or outside of the connector.

In some embodiments, the female connector 3400 can include a vent 3430 that creates fluid communication between the interior of the female connector 3400 and the exterior of the female connector 3400. The vent 3430 can help prevent pressure buildup in the female connector 3400 when the elongate portion 3419 is pushed toward the second end 3404 of the female connector 3400. In some embodiments, as illustrated, a portion of the vent can be positioned at a location on the housing that is in communication with an interior space that is at least partially enclosed by, or generally surrounded by, a portion of the valve member 3416.

Mating of the female connector 3400 and the male connector 3100 can bring the mating surface 3466 of the female housing 3440 into contact with the mating surface 3176 of the first sleeve portion 3165. The female housing 3440 can push the first sleeve portion 3165 toward the second end 3114 of the male connector 3100. Pushing the first sleeve portion 3165 toward the second end 3114 of the male connector 3100 can cause the second sleeve portion 3164 to collapse. In some embodiments, collapse of the second sleeve portion 3164 can create a spring force within the second sleeve portion 3164 that can bias the first sleeve portion 3165 toward the first end 3112 of the male connector 3100. Such a biasing force can help to ensure that the first sleeve portion 3165 returns to the closed position as the male connector 3100 and the female connector 3400 are disconnected.

In some embodiments, as the first end 3402 of the female connector moves toward the second end 3114 of the male connector, the one or more ports 3162 near the closed end 3144 of the tube member 3187 are withdrawn from the first sleeve portion 3165. Withdrawing the one or more ports 3162 from the first sleeve portion 3165 can create fluid communication between the luer receiver 1158 and the flow chamber 3428 within the female connector 3400. Fluid within the flow chamber 3428 can flow through the one or more conduits or openings 3488 and through the fluid passageway 3418. In some embodiments, mating of the female connector 3400 with the male connector 3100 can create fluid communication between the luer receiver 1158 and the fluid passageway 3418. As shown in the example illustrated in FIG. 77, the central mating interface between the male and female connectors in the fully open configuration can be positioned in some embodiments within the female connector and outside of the sleeve portion 3163 of the male connector.

Figure 78:
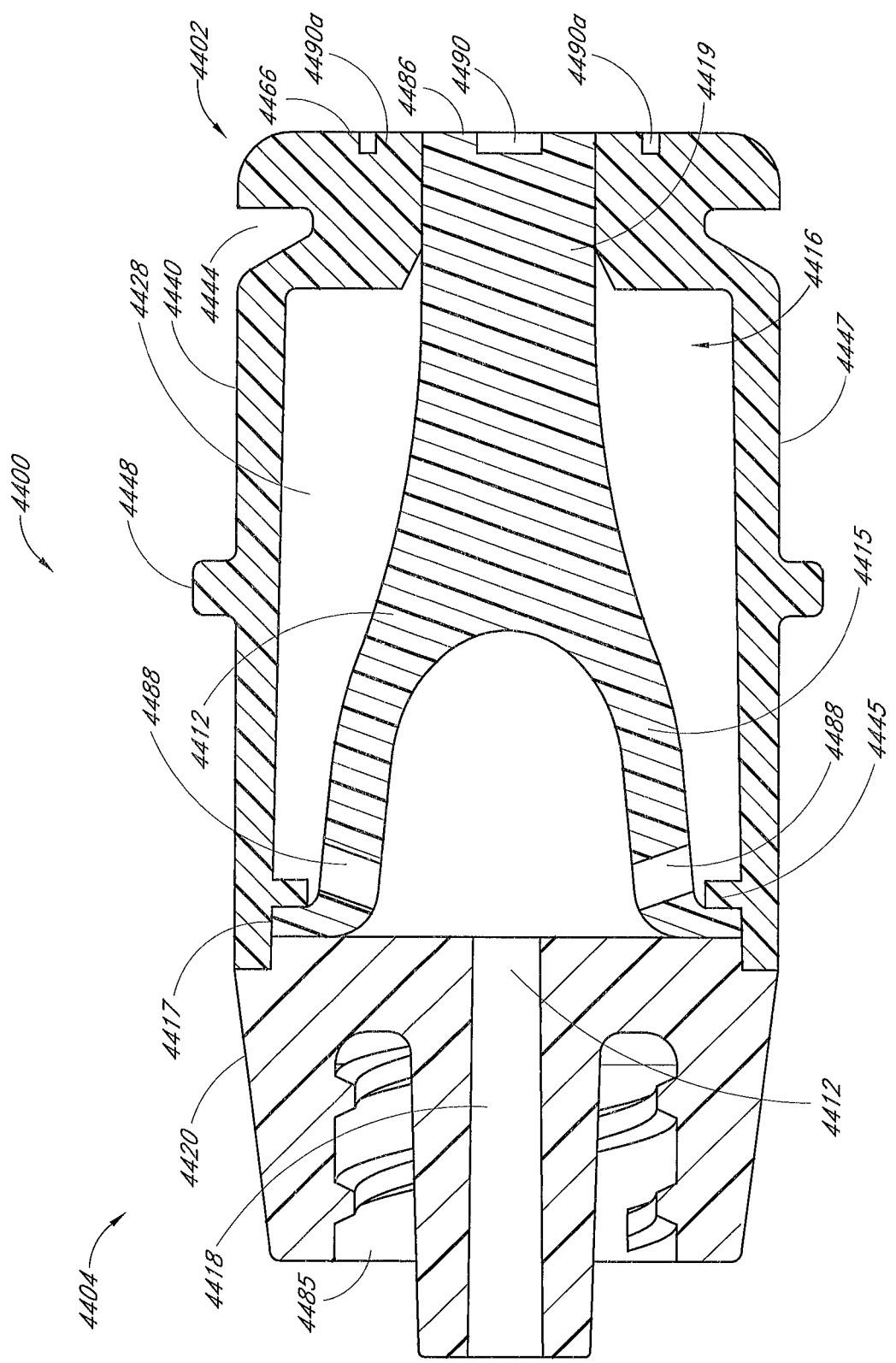
FIG. 78 shows a cross-sectional side view of another embodiment of a female connector.
Figure 79:
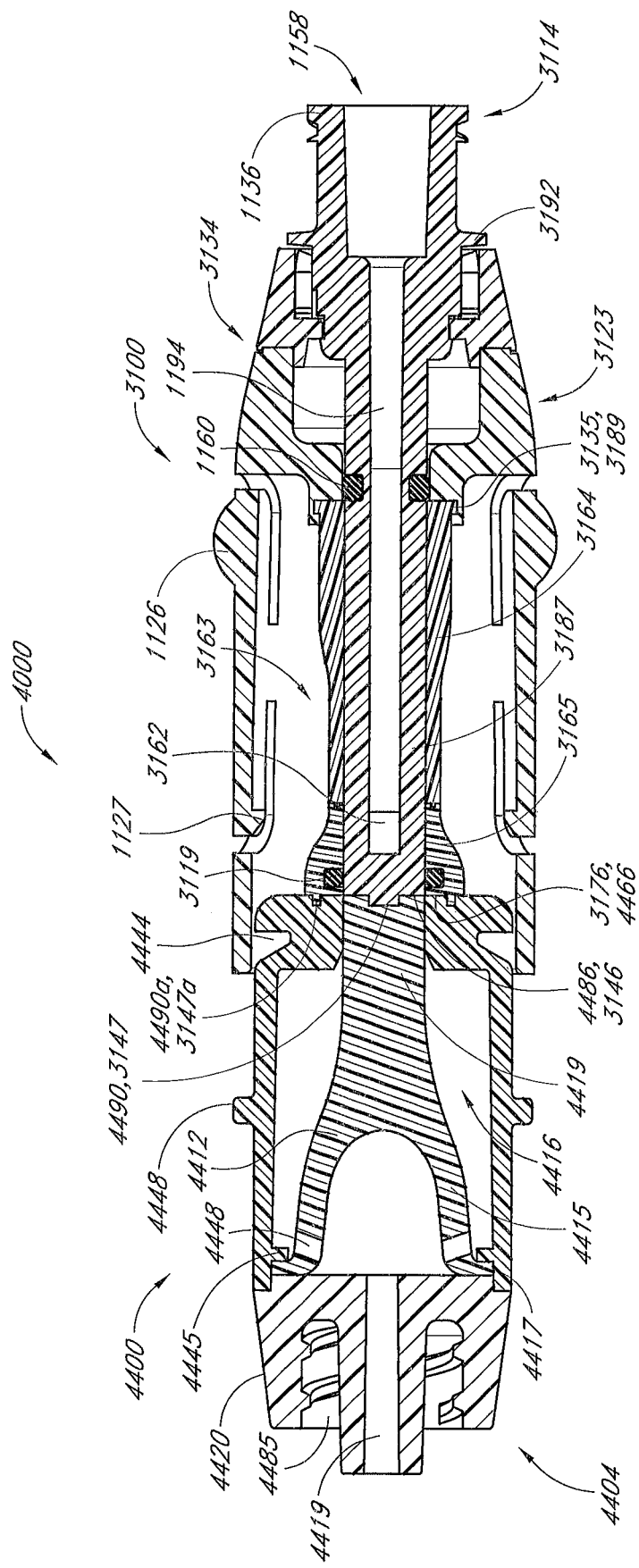
FIG. 79 shows a cross-sectional side view of the male connector of FIG. 74 adjacent the female connector of FIG. 78.
Figure 80:
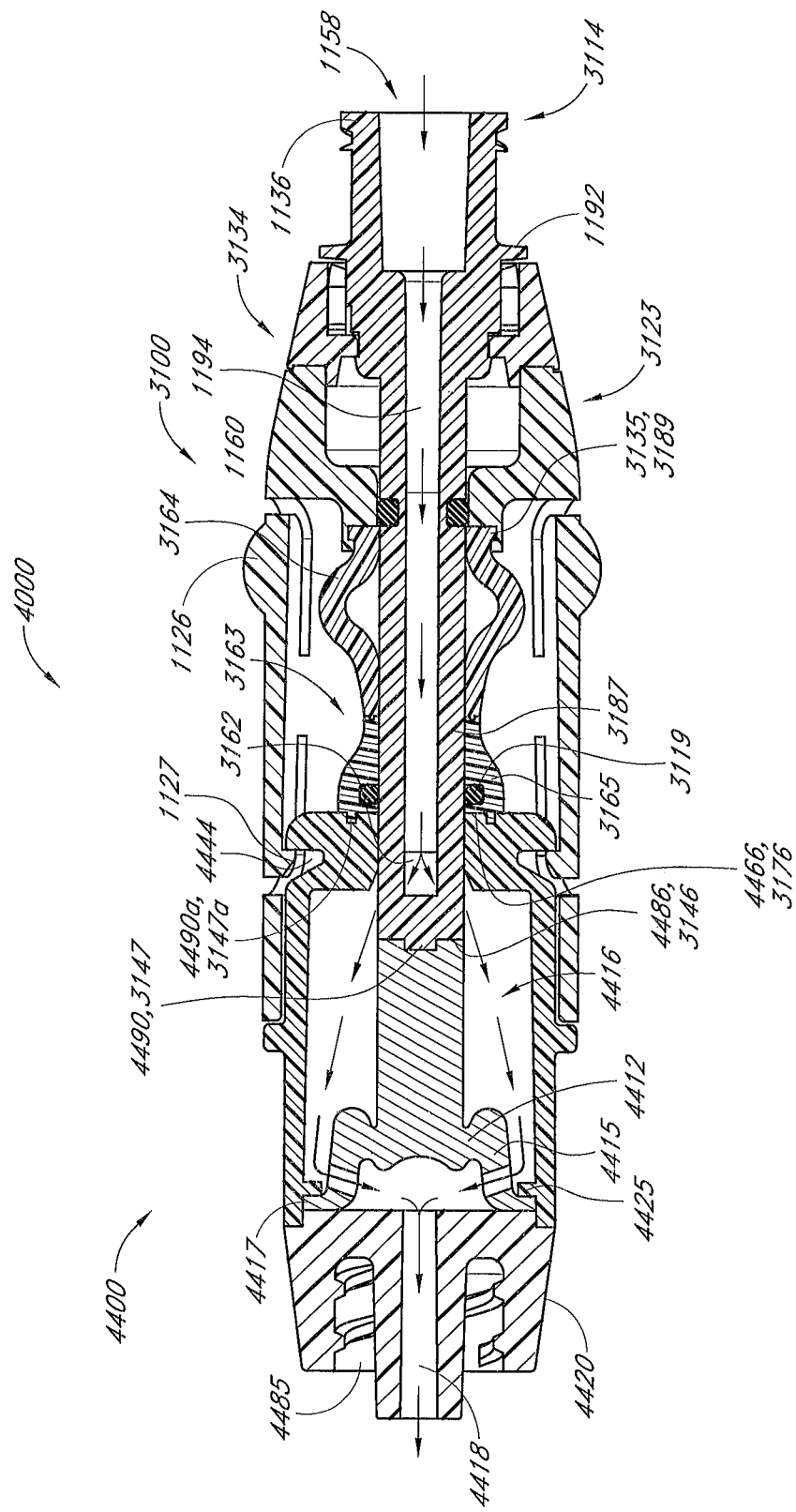
FIG. 80 shows a cross-sectional side view of the connector system of FIG. 79.

FIGS. 78-80 illustrate another embodiment of a connector system 4000 that comprises a male connector 3100 and a female connector 4400. Some numerical references to components in FIGS. 78-80 are the same as or similar to those previously described for the connector system 3000 and corresponding male connector 3100 and female connector 3400, (e.g. female connector 3400 v. female connector 4400). It is to be understood that the components can be the same in function or are similar in function to previously-described components. The connector system 4000 of FIGS. 78-80 shows certain variations to the connector system 3000 of FIGS. 74-77.

As illustrated in FIG. 78, the female connector 4400 can include a female housing 4400, a cap component 4420, and a valve member 4416. In some embodiments, the female connector has a first end 4402 and a second end 4404. The space between the inner walls of the female housing 4400 and the outer surface of the valve member 4416 can define a chamber 4428. In some embodiments, the cap component 4420 includes a passageway 4418 extending through the cap component 4420 from the second end 4404 through the cap component 4420 toward the first end 4402. In some embodiments, the valve member 4416 is configured to transition between an opened configuration (as shown in FIG. 80) and a closed configuration (as shown in FIG. 78). The valve member 4416 can include an elongate portion 4419 with many or all of the same characteristics as the elongate portion 3419. In some embodiments, the valve member 4416 includes an expanded portion 4415. The portion 4415 can include one or more ports 4488. The ports 4488 can be generally circular in shape, generally rectangular, generally triangular, or any other appropriate shape. In some embodiments, the ports 4488 are openings (e.g., slits or grooves) which open upon transition of the valve member 4416 from the closed configuration to the opened configuration. The ports 4488 can provide fluid communication between the chamber 4428 and the passageway 4418.

In some embodiments, the female connector 4400 mates with the male connector 3100 in a manner similar to that of the female connector 3400. Thus, performance of like components of the female connector 4400 and the female connector 3400 can be similar or the same. Entry of the tube member 3187 into the chamber 4428 of the female connector 4400 can push the elongate portion 4419 toward the second end 4404 of the female connector 4400. Movement of the elongate portion 4419 toward the second end 4404 of the female connector 4400 can cause the transition portion 4412 of the valve member 4416 to collapse. In some embodiments, movement of the elongate portion 4419 toward the second end 4404 of the female connector 4400 can cause the expanded portion 4415 of the valve member 4416 to collapse, compress, or otherwise move. Moving the expanded portion 4415 can open the one or more ports 4488 on the expanded portion. In some embodiments, the one or more ports 4488 are open when the expanded portion 4415 is compressed and when the expanded portion 4415 is uncompressed. Opening of the one or more ports 4488 can create fluid communication between the chamber 4428 and the passageway 4418. In some embodiments, mating between the female connector 4400 and the male connector 3400 can create fluid communication between the luer receiver 1158 and the fluid passageway 4418, as illustrated in FIG. 80. In some embodiments, the region within the valve member 4416 into which fluid flows can be sufficiently small, or sufficiently collapsible when in the closed configuration, to substantially eliminate negative inflow or negative pressure into the connector as the connector moves into a closed state.

FIGS. 81-84 illustrate another embodiment of a connector system 5000 that comprises a male connector 5100 and a female connector 5400. Some numerical references to components in FIGS. 81-84 are the same as or similar to those previously described for the connector system 20 and corresponding male connector 100 and female connector 400, (e.g. female connector 400 v. female connector 5400). It is to be understood that components or portions of the connector system 5000 can be the same in function or are similar in function to previously-described components or portions. The connector system 5000 of FIGS. 81-84 shows certain variations to the connector system 20 of FIGS. 1-32.

Figure 81:
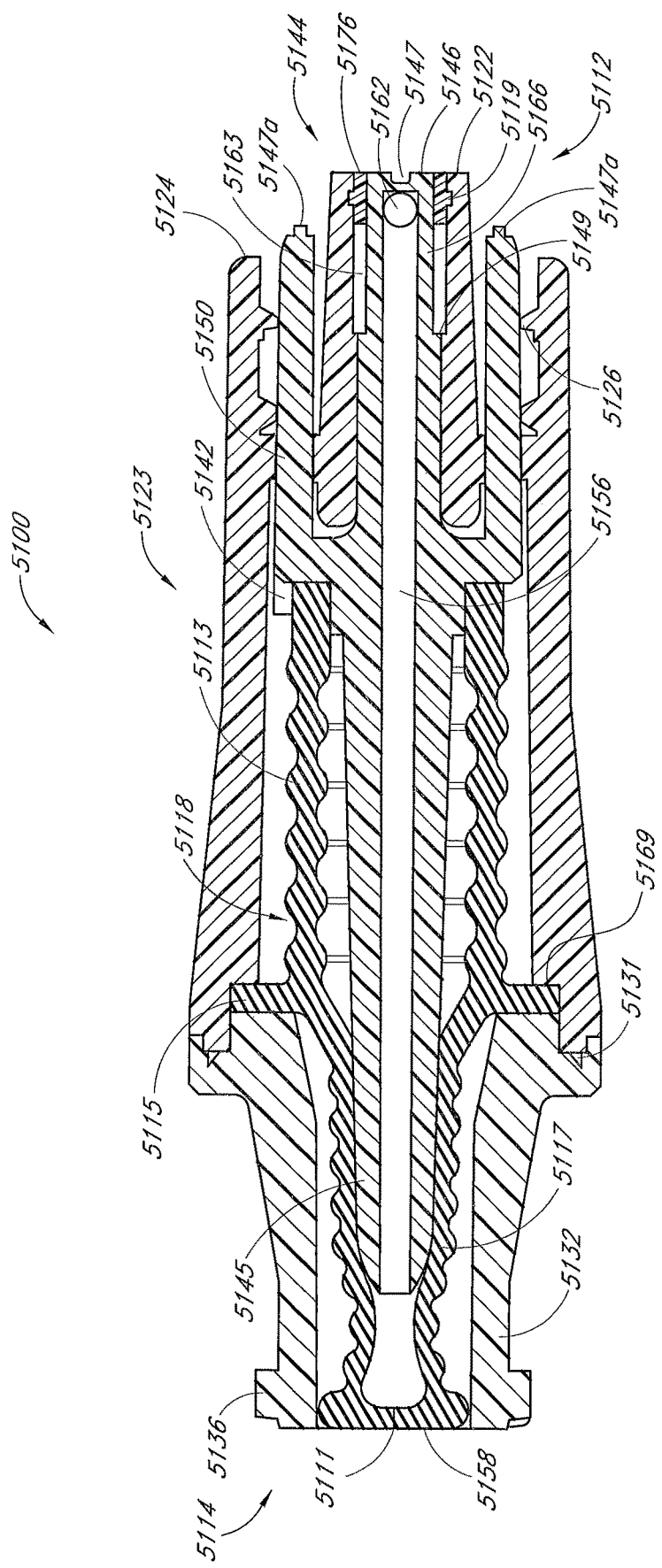
FIG. 81 shows a cross-sectional side view of another embodiment of a male connector.

As illustrated in FIG. 81, the male connector 5100 can have a first end 5112 and a second end 5114. The male connector 5100 can include a male housing 5123 generally proximate the first end 5112 and a cap component 5132 generally proximate the second end 5114. The cap component 5132 can be attached to the male housing 5123 via an adhesive, sonic welding, solvent bonding, any other suitable method of adhering or any combination thereof. In some embodiments, the second end 5114 of the male connector 5100 includes a female luer connection with external threads 5136. In some embodiments, the second end 5114 includes a luer receiver 5158.

In some embodiments, the first end 5112 of the male connector 5100 includes a male luer tip 5122. The male housing 5123 can include a shroud 5124 surrounding the male luer tip 5122. The shroud 5124 can have internal threads 5126. The male luer tip 5122 and/or the shroud 5124 can be integral with the male housing 5123. In some embodiments, the male luer tip 3122 and/or the shroud 5124 are removable from the male housing 5123. The internal threads 5126 and the luer tip 5122 can form a male luer engagement that conforms to ANSI specifications for male connectors. In some embodiments, the internal threads 5126 and/or the luer tip 5122 form a male luer engagement that is non-standard (e.g., it does not conform to ANSI specifications for male connectors). In some embodiments, non-conformity with standards can help reduce the likelihood of accidental connection of the male connector 5100 with other connectors which are not designed to be used in delivering the same type of medical fluids (e.g., potentially higher risk medical fluids can be delivered using non-standard connections). This can reduce the risk of accidental infusion of higher-risk fluids through connectors or accumulation of higher-risk residual liquid on the external ends of connectors, thereby reducing the risk of exposing patients and/or care providers to dangerous and/or toxic substances used in conjunction with the connector system 5000 As with all features disclosed herein, non-standard (e.g., non-ANSI-compliant) configurations can be used with any other embodiments disclosed herein, including, but not limited to, connector systems 02, 1000, 3000, 4000, 5000, 6000, 7000, 8000, and 9000.

Figure 83:
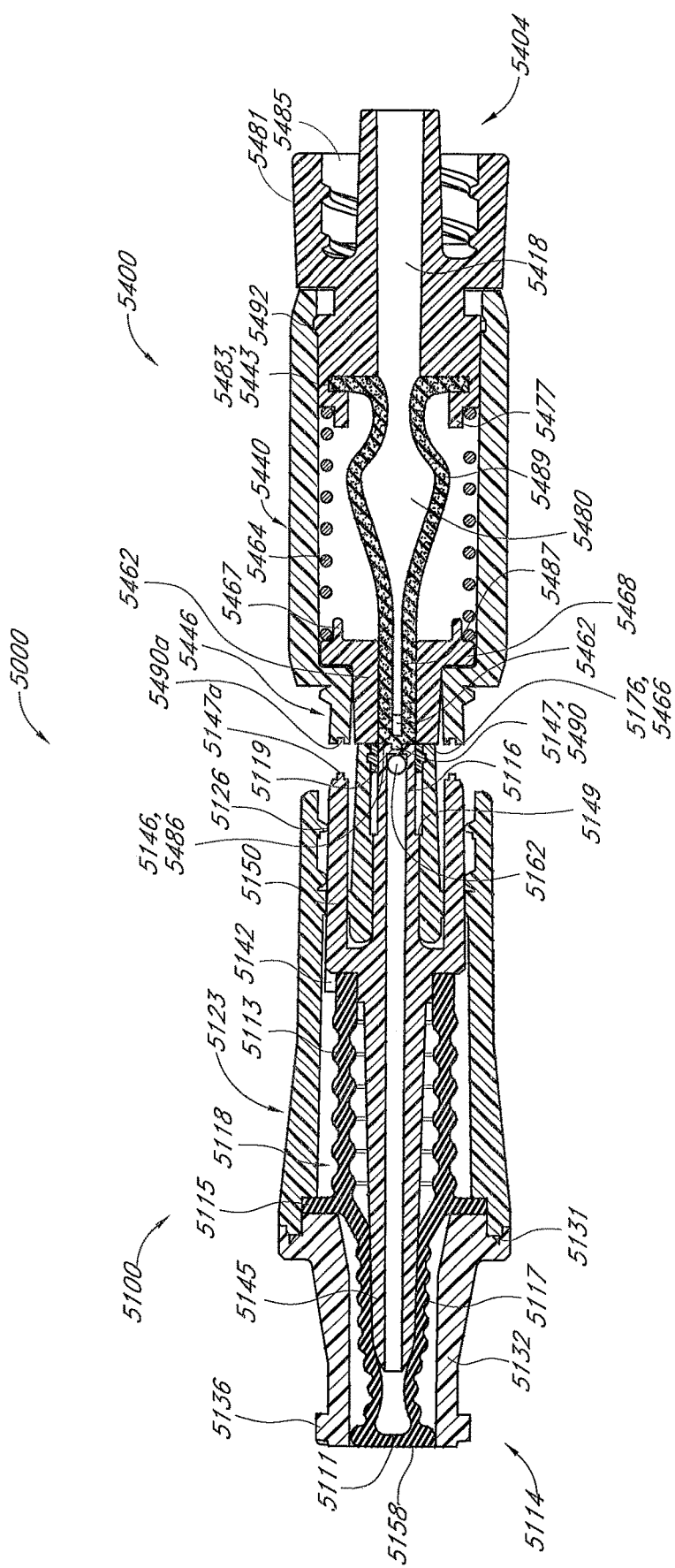
FIG. 83 shows a cross-sectional side view of the male connector of FIG. 81 adjacent the female connector of FIG. 82.
Figure 84:
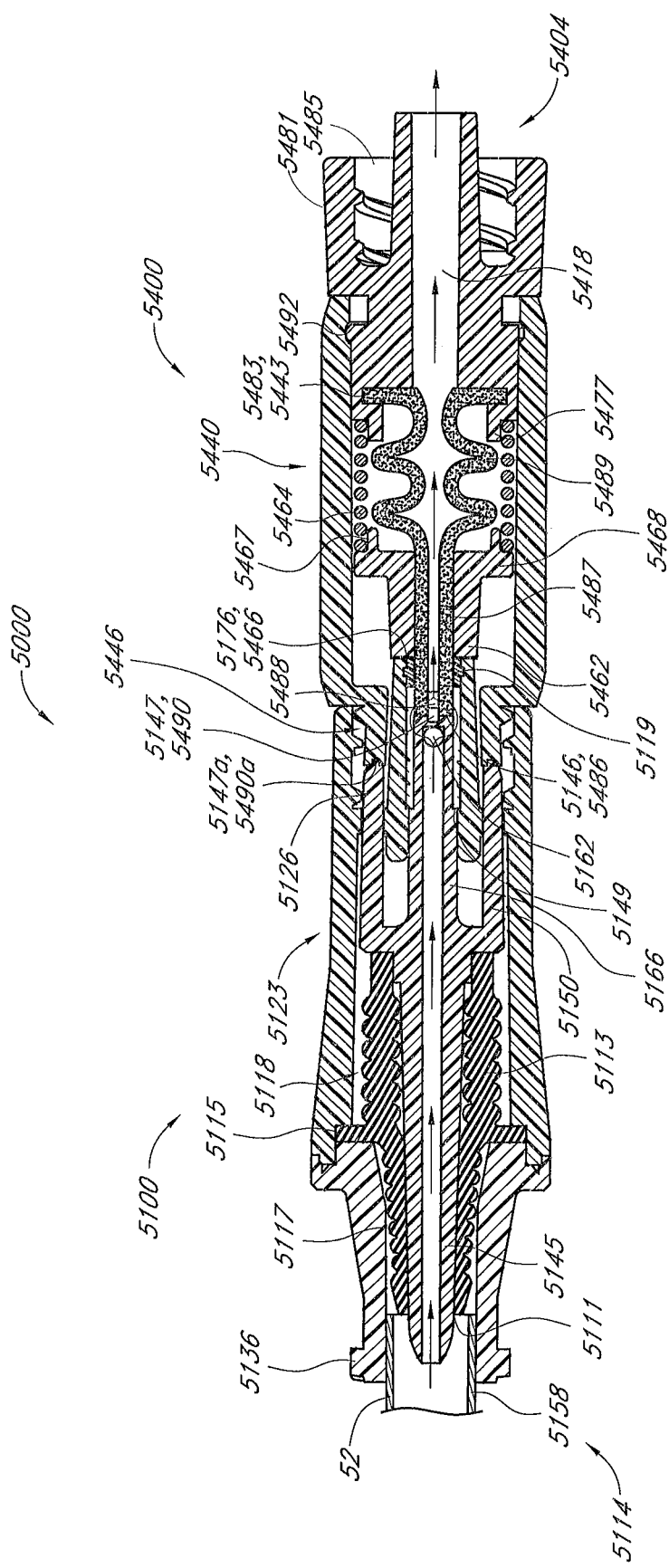
FIG. 84 shows a cross-sectional side view of the connector system of FIG. 83.

A valve member 5116 can be housed within the male housing 5123 and/or within the cap component 5132. In some embodiments, the valve member 5116 has a closed end 5144 and an opened end 5145. In some embodiments, both ends of the valve member 5116 are closed. In some embodiments, both ends of the valve member 5116 are opened. In some embodiments, the valve member 5116 can have an axial centerline, an inner cross-section, and an outer cross-section. The valve member 5116 can be configured to transition between an opened configuration (e.g., as illustrated in FIG. 84) and a closed configuration (e.g., as illustrated in FIGS. 81, 83).

The valve member 5116 can include a passageway 5156. The passageway 5156 can extend through both ends of the valve member 5116. In some embodiments, the passageway 5156 extends from an opening on the opened end 5145 of the valve member 5116 to one or more ports 5162 near the closed end 5144 of the valve member 5116. The male connector 5100 can include a sealing member 5119 configured to engage with a groove in the inner (e.g., toward the axial centerline of the valve member 5116) surface of the male luer tip 5122. The sealing member 5119 can be a flexible or semi-flexible O-ring or some other appropriate component for providing a fluid seal. In some embodiments, the sealing member 5119 creates a fluid seal around the outer cross-section of the valve member 5116 when the valve member 5116 is in a closed position, as illustrated in FIG. 81. The valve member 5116 can include a stepped portion 5149. In some embodiments, the stepped portion 5149 defines an axial location on the valve member 5116 where the outer cross-section of the valve member 5116 reduces. The reduced outer cross-section portion of the valve member 5116 can define an annular chamber 5163 between the outer cross-section of the valve member 5116 and the inner surface of the male luer tip 5122. The annular chamber 5163 can be bound in the axial direction between the stepped portion 5149 and the sealing member 5119.

In some embodiments, the valve member 5116 can include one or more struts 5150. The struts 5150 can be separate parts attached to the valve 5116. In some embodiments, the struts 5150 and the valve 5116 form a unitary part. The struts 5150 and/or valve member 5116 can include one or more alignment features. The alignment features can be protrusions, indentations, channels, or any other suitable feature or combination of features. For example, the valve member 5116 can include an indentation 5147. Furthermore, the struts 5150 can include one or more protrusions 5147*a*. In some embodiments, the valve member 5116 can include a mating surface 5146 generally adjacent the indentation 5147. Furthermore, in some embodiments, the sealing member 5119 includes a mating surface 5176 generally adjacent the mating surface 5146 of the valve member 5116.

In some embodiments, the male connector 5100 can include a resilient member 5118. The resilient member 5118 can be housed within the male housing 5123 and/or within the cap component 5132. In some embodiments, the resilient member 5118 is constructed of rubber, silicone, some other flexible/semi-flexible material, or some combination thereof. The resilient member 5118 can include a connection feature such as, for example, a flange 5115, configured to allow the resilient member to connect to the male housing 5123 and/or to the cap component 5132. The flange 5115 can be configured to fit within a receiving feature such as, for example, groove 5169 formed in the inner wall of the male housing 5123 and/or the cap component 5132. Engagement between the flange 5115 and the groove 5169 can inhibit a portion of the resilient member 5118 close to the flange 5115 from moving in the axial directions.

In some embodiments, the resilient member 5118 includes a first portion 5113 extending in the axial direction from the flange 5115 toward the first end 5112 of the male connector 5100. In some embodiments, the resilient member 5118 includes a second portion 5117 extending in the axial direction from the flange 5115 toward the second end 5114 of the male connector 5100. The first portion 5113 and/or second portion 5117 can have a generally cylindrical shape. In some embodiments, the first portion 5113 and/or the second portion 5117 are constructed of a series of O-rings connected together via portions of flexible or semi-flexible material. In some embodiments, the first portion 5113 and/or the second portion 5117 are constructed of a portion of flexible and/or semi-flexible material having a uniform thickness along its axial length. In some embodiments, the thickness of the first portion 5113 and/or the second portion 5117 varies along the axial length of the first portion 5113 and/or the second portion 5117.

In some embodiments, the valve member 5116 includes one or more retainer ridges 5142. The one or more retainer ridges 5142 can be configured to inhibit radial migration of the axial end of the first portion 5113 of the resilient member 5118. In some embodiments, the opened end 5145 of the valve member 5116 can extend into the cap component 5132. In some embodiments, the second portion 5117 of the resilient member 5118 can be configured to fit snugly, tightly, or closely around the opened end 5145 of the valve member 5116. In some embodiments, the end of the second portion 5117 furthest from the flange 5115 can form a sealed barrier around the opened end 5145 of the valve member 5116.

In some embodiments, the end of the second portion 5117 of the resilient member 5118 furthest from the flange 5115 can have a flexible, resilient, or expanding portion 5111. The portion 5111 can be configured to fill the luer receiver 5158 and substantially seal the second end 5114 of the male connector 5100. In some embodiments, the portion 5111 includes a valve. The valve can comprise, for example, one or more slits, one or more small apertures, or any combination thereof. In some embodiments, the valve in the portion 5111 is normally closed. In some embodiments, the valve in the portion 5111 is normally opened and is biased closed by the engagement between the portion 5111 and the luer received 5158. In some embodiments, the portion 5111 can be configured to allow the opened end 5145 of the valve member 5116 to pass through the valve in the portion 5111. According to some configurations, the portion 5111 is generally flush with and essentially completely fills the second end 5144 of the male connector 5100. In some embodiments, the portion 5111 extends beyond the second end 5144 of the male connector 5100. In some embodiments, the portion 5111 is swabable.

Figure 82:
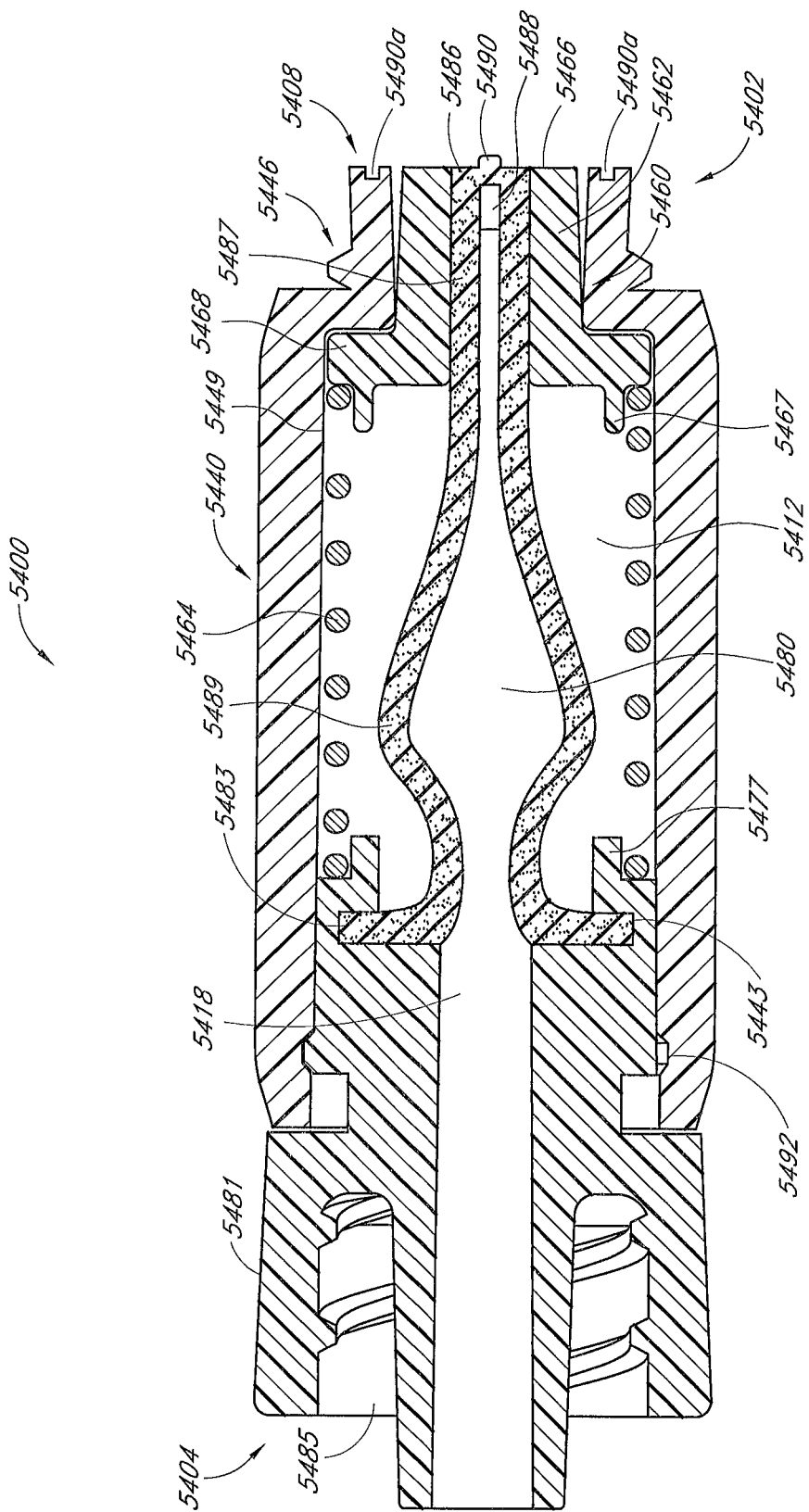
FIG. 82 shows a cross-sectional side view of another embodiment of a female connector.

As illustrated in FIG. 82, the female connector 5400 can have a first end 5402 and a second end 5404. In some embodiments, the female connector includes a female housing 5440 and a cap component 5481. The cap component 5481 can be connected to the female housing 5440 via snap-fit, adhesives, sonic welding, solvent bonding, other suitable methods of adhering, or any combination thereof. The cap component 5481 can include a male luer engagement 5485 on the second end 5404 of the female connector 5400. In some embodiments, the cap component 5481 includes a fluid passageway 5418 extending from the second end of the female connector 5400 to the interior of the female housing 5440. The female housing 5440 can include a female luer coupling portion 5446 on the first end 5402 of the female connector 5400. Furthermore, the female luer coupling portion 5446 can include an alignment portion. The alignment portion can be one or more indentations 5490*a*. The indentations 5490*a* can be configured to releasably engage with the one or more protrusions 5147*a* on the struts 5150, as illustrated in FIG. 83.

In some embodiments, the female connector 5400 includes a flexible tube member 5487. The flexible tube member 5487 can have a generally cylindrical shape, an inner cross-section, an outer cross-section, an axial centerline, one or more flared portions, and/or one or more tapered portions. The tube member 5487 can be housed within the female housing 5440 and/or within the cap component 5481. The tube member 5487 can have a closed end and an opened end. In some embodiments, the closed end is generally adjacent the first end 5402 of the female connector 5400. The closed end of the tube member 5487 can include an alignment member. In some embodiments, the alignment member on the tube member 5487 is a protrusion 5490. The protrusion 5490 can be configured to releasably engage with the indentation 5147 on the valve member 5116 of the male connector 5100. In some embodiments, both ends of the tube member 5487 are closed. In some embodiments, the tube member includes an expanded portion 5489. The expanded portion 5489 can be configured to affect the overall stiffness of the tube member 5487. For example, the width of the expanded portion 5489 can affect the amount of force required to displace the closed end of the tube member 5487 in the axial direction.

In some embodiments, the tube member 5487 can define a fluid conduit 5480. The fluid conduit 5480 can extend from the opened end of the tube member 5487 to the closed end of the tube member 5487. In some embodiments, the tube member 5487 includes one or more ports 5488 adjacent the closed end of the tube member 5487. The fluid conduit 5480 can extend from the opened end of the tube member to the one or more ports 5488. The fluid conduit 5480 can be in fluid communication with the fluid passageway 5418. In some embodiments, the tube member 5487 includes one or more engagement portions such as, for example, a flange 5483. The flange 5483 can be configured to engage with a receiving portion in the cap component 5481 and/or in the female housing 5440. The receiving portion, for example, can be a slot 5443 in the cap component 5481. Engagement between the flange 5483 and the slot 5443 can inhibit the tube member 5487 from moving out of the female connector 5400. In some embodiments, engagement between the flange 5483 and the slot 5443 helps stabilize the open end of the tube member 5487 and helps inhibit the open end of the tube member 5487 from moving toward the first end 5402 of the female connector 5400.

In some embodiments, the female connector 5400 can include a compressible seal element 5460. The compressible seal element 5460 can include a sealing portion 5462 and a compressible portion 5464. In some embodiments, the seal element 5460 is constructed of a plastic or some other rigid and/or semi-rigid polymer. In some embodiments, the seal element 5460 is constructed of rubber, silicone, some other flexible or semi-flexible material, or some combination thereof. The sealing portion 5462 can have a generally cylindrical shape, an inner cross-section, and an outer cross-section. The inner cross-section of the sealing portion 5462 can be substantially the same as the outer cross-section of the tube member 5487. In some embodiments, the inner cross-section of the sealing portion 5462 is substantially the same as the outer cross-section of the tube member 5487 near the first end 5402 of the female connector 5400. In some embodiments, engagement between the closed end of the tube member 5487 and the sealing portion 5462 can substantially seal the one or more ports 5488.

In some embodiments, the compressible portion 5464 is a compression spring. In some embodiments, the compressible portion 5464 is a solid compressible tube (e.g., a rubber tube), a braided compressible tube, or any other suitable compressible geometry and material. The sealing portion 5462 can include a retention feature such as, for example, an annular ridge 5467. In some embodiments, the inner wall 5449 of the female housing 5440 and the annular ridge 5467 can inhibit radial migration of the compressible portion 5464. In some embodiments, the cap component 5481 can include a retention feature such as, for example, an annular ridge 5477. The annular ridge 5477 and inner wall 5449 can inhibit radial migration of the compressible portion 5464. In some embodiments, the sealing portion 5463 can include a stop 5468 such as, for example, a shoulder. The stop 5468 can engage with the female housing 5440 and can limit the movement of the sealing portion 5462 toward the first end 5402 of the female connector 5400.

As illustrated in FIGS. 83-84, the female connector 5400 can be configured to mate with the male connector 5100. As illustrated in FIG. 83, the male connector 5100 can be configured such that the male luer tip 5122 comes into contact with the sealing portion 5462 of the compressible seal element 5460 before the struts 5150 come into contact with the female luer coupling portion 5446. In some configurations, at least a portion of the male luer tip 5122 can advance into the female connector 5400. Advancement of the male luer tip 5122 into the female connector 5400 can cause the compressible seal element 5460 to move toward the second end 5404 of the female connector 5400.

As the female connector 5400 is mated with the male connector 5100, the indentation 5147 of the closed end 5144 of the valve member 5116 can engage with the protrusion 5490 on the closed end of the flexible tube member 5487. In some embodiments, the closed end 5144 of the valve member 5116 can advance into the female connector 5400 as the male connector 5100 is mated with the female connector 5400. For example, the closed end 5144 of the valve member 5116 can enter the female connector at the same rate the male luer tip 5122 enters the female connector before the struts 5150 come into contact with the female luer coupling portion 5446. Movement of the closed end 5144 of the valve member 5116 into the female connector can cause the expanded portion 5489 of the flexible tube member 5487 to compress. Compression of the expanded portion 5489 can create a spring force within the expanded portion 5489 that can bias the closed end of the flexible tube member 5487 toward the first end 5402 of the female connector 5400. In some embodiments, the biasing force of the expanded portion 5489 can help ensure that the indentation 5147 of the closed end 5144 of the valve member 5116 remains engaged with the protrusion 5490 on the closed end of the flexible tube member 5487 as the male luer tip 5122 is advanced toward the second end 5404 of the female connector 5400. Such continued engagement between the closed end of the flexible tube member 5487 and the closed end 5144 of the valve member 5116 can inhibit fluid from contacting the mating surfaces 5176, 5466 of the valve member 5116 and flexible tube member 5487, respectively.

In some embodiments, the compression spring rate of the flexible tube member 5487 is less than the compression spring rate of the first portion 5113 of the resilient member 5118. For example, the amount of axial force (e.g., the force generally parallel to the axial centerline of the valve member 5116) required to push the valve member 5116 toward the second end 5114 of the male connector can be greater than the axial force required to push the closed end of the flexible tube member 5487 toward the second end 5404 of the female connector 5400.

In some embodiments, the male luer tip 5122 and valve member 5116 push the seal element 5460 and the closed end of the flexible tube member 5487, respectively, toward the second end of the female connector 5400 until the one or more protrusions 5147*a* of the struts 5150 engage with the one or more indentations 5490*a* on the female luer coupling portion 5446. Upon engagement between the one or more protrusions 5147*a* and the one or more indentations 5490*a*, the valve member 5116 can be inhibited from moving further toward the second end 5404 of the female connector 5400. The male luer tip 5122 can, however, continue to advance into the female connector 5400 and push the compressible seal element 5460 toward the second end 5404 of the female connector 5400. The further advancement of the male luer tip 5122 and compressible seal element 5460 toward the second end 5404 relative to the flexible tube member 5487 can cause the closed end of the flexible tube member 5487 to move at least partially into the annular chamber 5163 inside the male luer tip 5122.

In some embodiments, the further advancement of the male luer tip 5122 into the female connector 5400 can cause the male housing 5123 to move toward the second end 5404 of the female connector 5400 relative to the closed end 5144 of the valve member 5116. Movement of the male housing 5123 toward the second end 5404 of the female housing 5044 relative to the valve member 5116 can cause the first portion 5113 of the resilient member 5118 to compress. Compression of the first portion 5113 can create a spring force that can bias the valve member 5116 toward the first end 5112 of the male connector 5100. Such a biasing force can help ensure that the indentation 5147 of the closed end 5144 of the valve member 5116 remains engaged with the protrusion 5490 on the closed end of the flexible tube member 5487 as the male luer tip 5122 is advanced toward the second end 5404 of the female connector 5400.

In some embodiments, the sealing member 5119 is withdrawn from the one or more ports 5162 of the valve member 5116 as the male luer tip 5122 advances toward the second end 5404 of the female connector 5400 relative to the valve member 5116, thus creating fluid communication between the passageway 5156 and the annular chamber 5163 via the one or more ports 5162. Furthermore, in some embodiments, entry of the closed end of the flexible tube member 5487 into the annular chamber 5163 can withdraw the sealing portion 5462 of the compressible seal element 5460 from the one or more ports 5488. Entry of the one or more ports 5488 into the annular chamber 5163 can create fluid communication between the fluid conduit 5480 and the annular chamber 5163.

According to some configurations, movement of the male connector 5100 toward the female connector 5400 after the struts 5150 come into contact with the female luer coupling portion 5446 can cause the opened end 5145 of the valve member 5116 to move toward the second end 5144 of the male connector 5400, relative to the cap component 5132. In some embodiments, the valve member 5116 has an axial length such that opened end 5145 passes through the second end 5144 of the male connector 5100 when the male connector 5100 is fully connected with the female connector 5400 (e.g., when the internal threads 5126 of the male connector 5100 are fully engaged with the female luer coupling portion 5446). In some embodiments, the opened end 5145 of the valve member 5116 passes through the valve on the portion 5111 of the resilient member 5118 when the male connector 5100 and the female connector 5400 are fully connected with each other.

As illustrated in FIG. 84, the valve member 5116 can have an axial length such that the opened end 5145 remains within the male connector 5100 when the male connector 5100 is fully engaged with the female connector 5400. In some embodiments, the resilient member 5118 is configured such that, upon advancement of a male luer tip 5052 into the luer receiver 5158, the valve on the portion 5111 is opened and the portion 5111 is withdrawn from the opened end 5145 of the valve member 5116. In some embodiments, the interior of the male luer tip 5052 is brought into fluid communication with the fluid passage 5418 of the female connector 5400 via the passageway 5156, the one or more ports 5162, the annular chamber 5163, and the one or more ports 5488 and the fluid conduit 5480, when the male connector 5100 and female connector 5400 are fully connected and the male luer tip 5052 is advanced into the luer receiver 5158, as illustrated in FIG. 84.

In some embodiments, withdrawal of the portion 5111 from the opened end 5145 of the valve member 5116 can compress the second portion 5117 of the resilient member 5118. Compression of the second portion 5117 can create a spring force within the second portion 5117. Such spring force can bias the portion 5111 toward the second end 5114 such that the portion 5111 returns to the second end 5114 of the male connector 5100 upon removal of the male luer tip 5052 form the male connector 5100. Return of the portion 5111 to the second end 5114 of the male connector 5100 can cause the valve on the portion 5111 to close.

Figure 85:
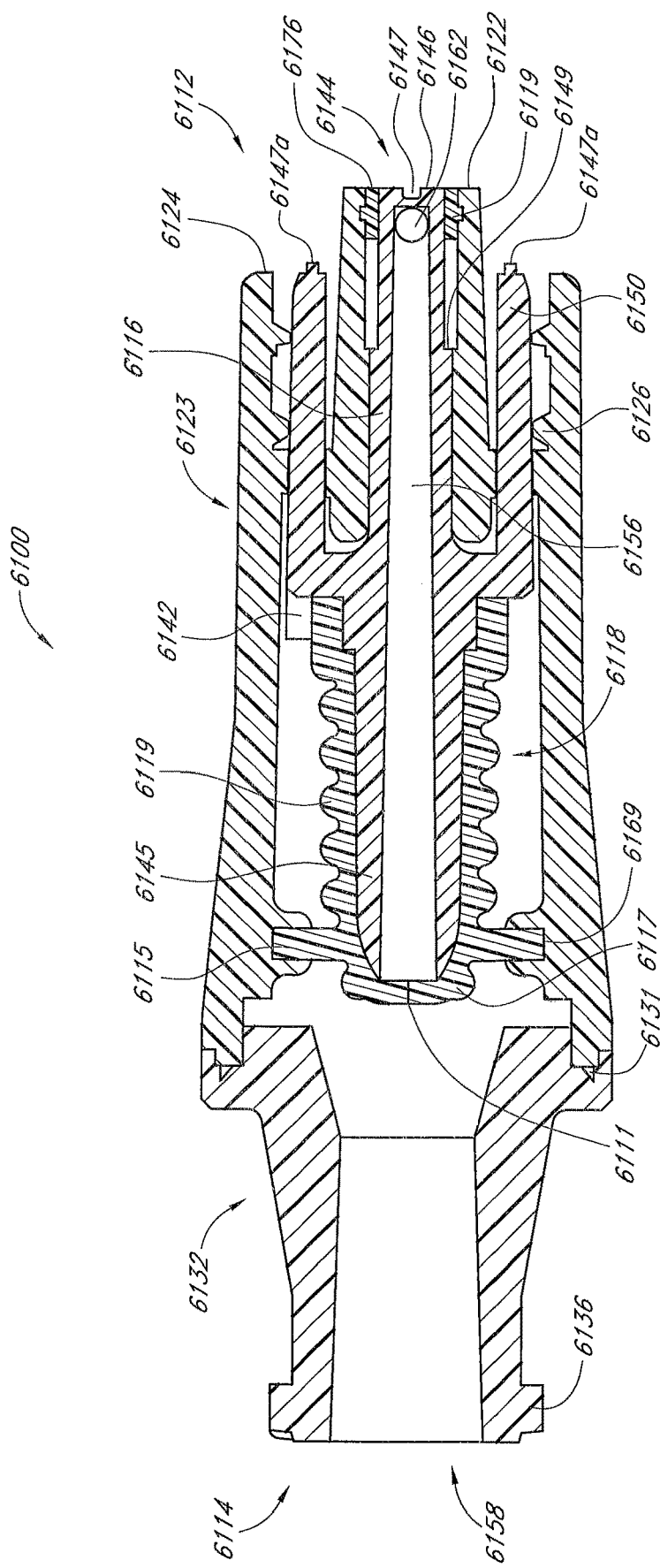
FIG. 85 shows a cross-sectional side view of another embodiment of a male connector.
Figure 86:
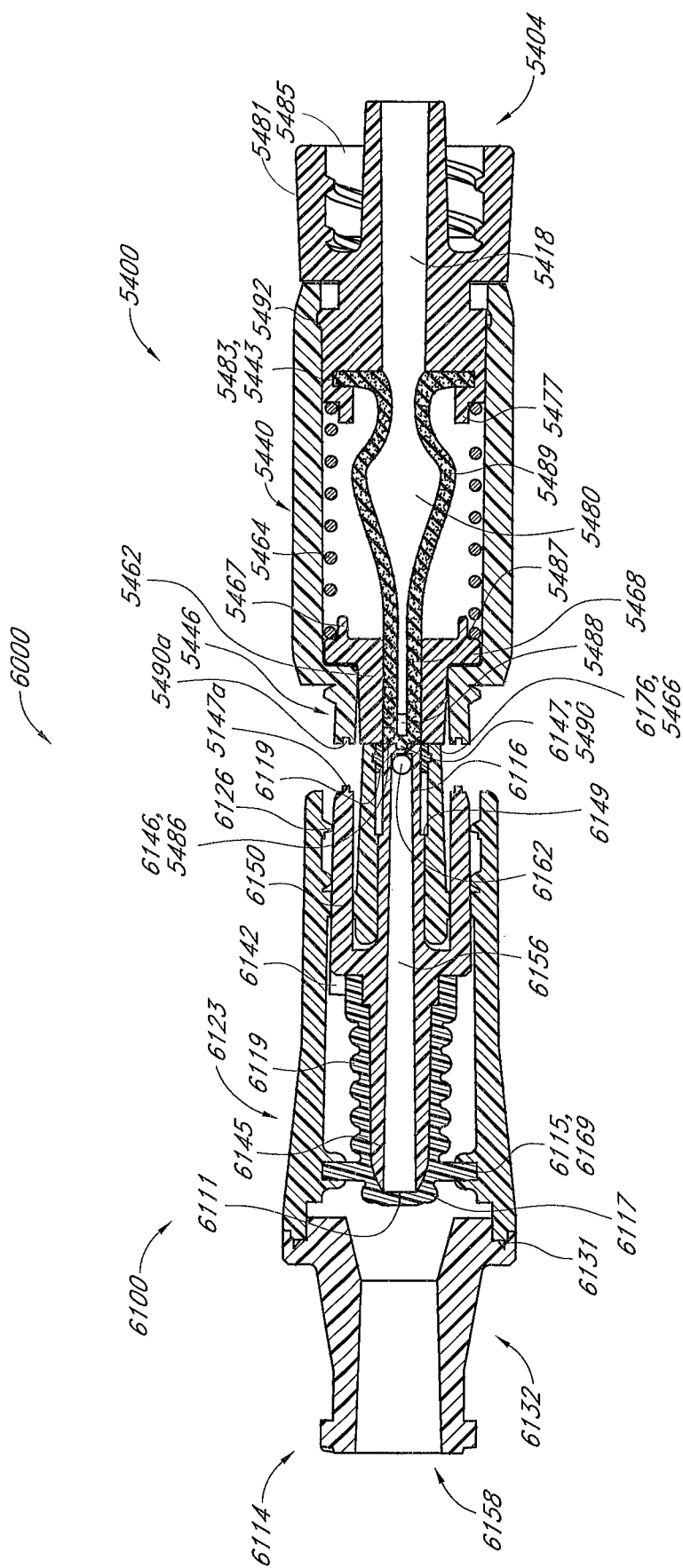
FIG. 86 shows a cross-sectional side view of the male connector of FIG. 85 adjacent the female connector of FIG. 82.
Figure 87:
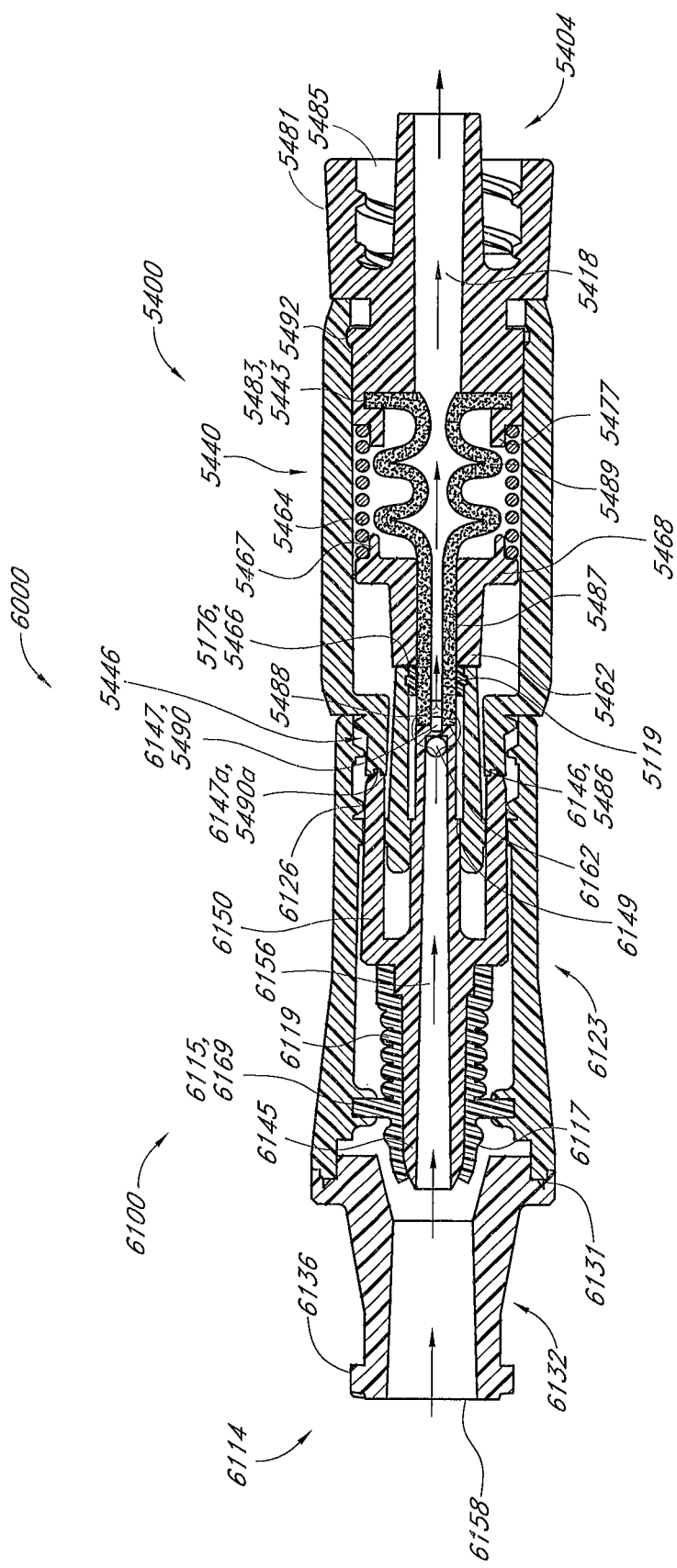
FIG. 87 shows a cross-sectional side view of the connector system of FIG. 86.

FIGS. 85-87 illustrate another embodiment of a connector system 6000 that comprises a male connector 6100 and a female connector 5400. Some numerical references to components in FIGS. 85-87 are the same as or similar to those previously described for the connector system 5000 and corresponding male connector 5100 and female connector 5400, (e.g. male connector 5100 v. male connector 6100). It is to be understood that components or portions of the connector system 6000 can be the same in function or are similar in function to previously-described components or portions. The connector system 6000 of FIGS. 85-87 shows certain variations to the connector system 5000 of FIGS. 81-84.

In some embodiments, the male connector 6100 can include a resilient member 6118. The resilient member 6118 can include a connection feature such as, for example an annular flange 6115. The flange 6115 can be configured to fit within a receiving feature such as, for example, a slot 6169. In some embodiments, the slot 6169 can be formed by two annular ridges on the inner wall of the male housing 6123. In some embodiments, the slot 6169 can be a slot cut into the inner wall of the male housing 6123. In some embodiments, the receiving feature can be a series coaxial ridge portions, similar to the retainer tabs 2171, 2173. The male connector 6100 is representative of certain aspects of the Texium® closed male luer connector sold by Carefusion Corporation, with some additions and modifications. The male connector 6100 is shown in this example being used with the female connector 5400, but any female connector disclosed herein, or any components thereof, or any other suitable female connector, can also be used with the male connector 6100.

In some embodiments, the resilient member 6118 includes an end portion 6111. In some embodiments, the male connector 6100 includes a valve member 6116. The valve member 6116 can have an opened end 6145 and a closed end 6144. In some embodiments, the end portion 6111 is configured to fit snugly, tightly, or snugly around the opened end 6154 of the valve member 6116. The end portion 6111 can include a valve. The valve can be, for example, one or more slits, one or more small apertures, or any combination thereof. In some embodiments, the valve is normally closed. The end portion 6111 and valve can be configured to allow the opened end 6145 of the valve member 6116 to pass through the valve.

As illustrated in FIG. 87, the valve member 6116 can be configured such that the opened end 6145 of the valve member 6116 advances toward the second end 6114 of the male connector 6100 relative to the resilient member 6118 when the male connector 6100 and female connector 5400 are fully connected (e.g., when the internal threads 6162 fully couple with the female luer coupling portion 5446 of the female connector 5400). Advancement of the opened end 6145 of the valve member 6116 can cause the opened end 6145 to open and pass through the valve on the end portion 6111. In some configurations, the luer receiver 6158 can be brought into fluid communication with the fluid passageway 5158, as illustrated in FIG. 87. In some embodiments, return of the opened end 6145 of the valve member 6116 toward the first end 6112 of the male connector 6100 can cause the opened end 6145 to pass back through the valve on the end portion 6111. In some such embodiments, the valve on the end portion 6111 can return to a closed position when the opened end 6145 passes back through the valve toward the first end 6112 of the male connector 6100.

Figure 88:
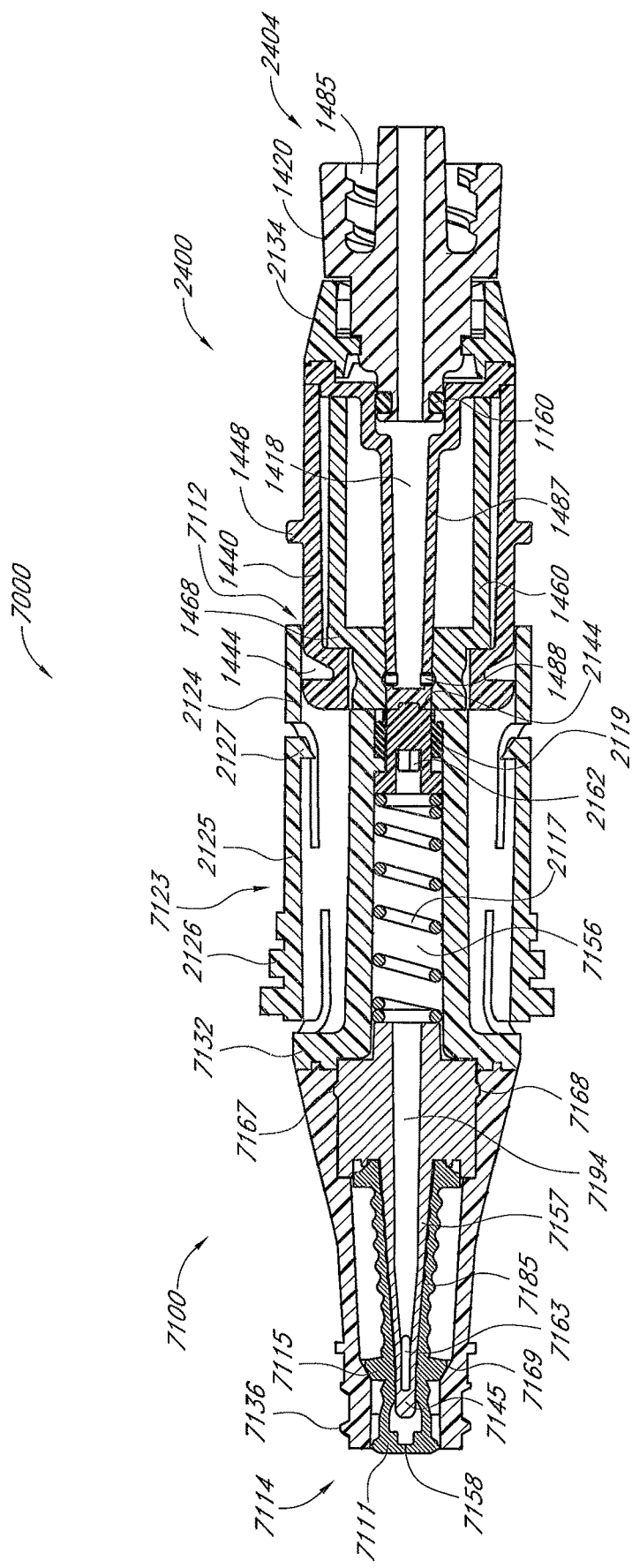
FIG. 88 shows a cross-sectional side view of a connector system.
Figure 89:
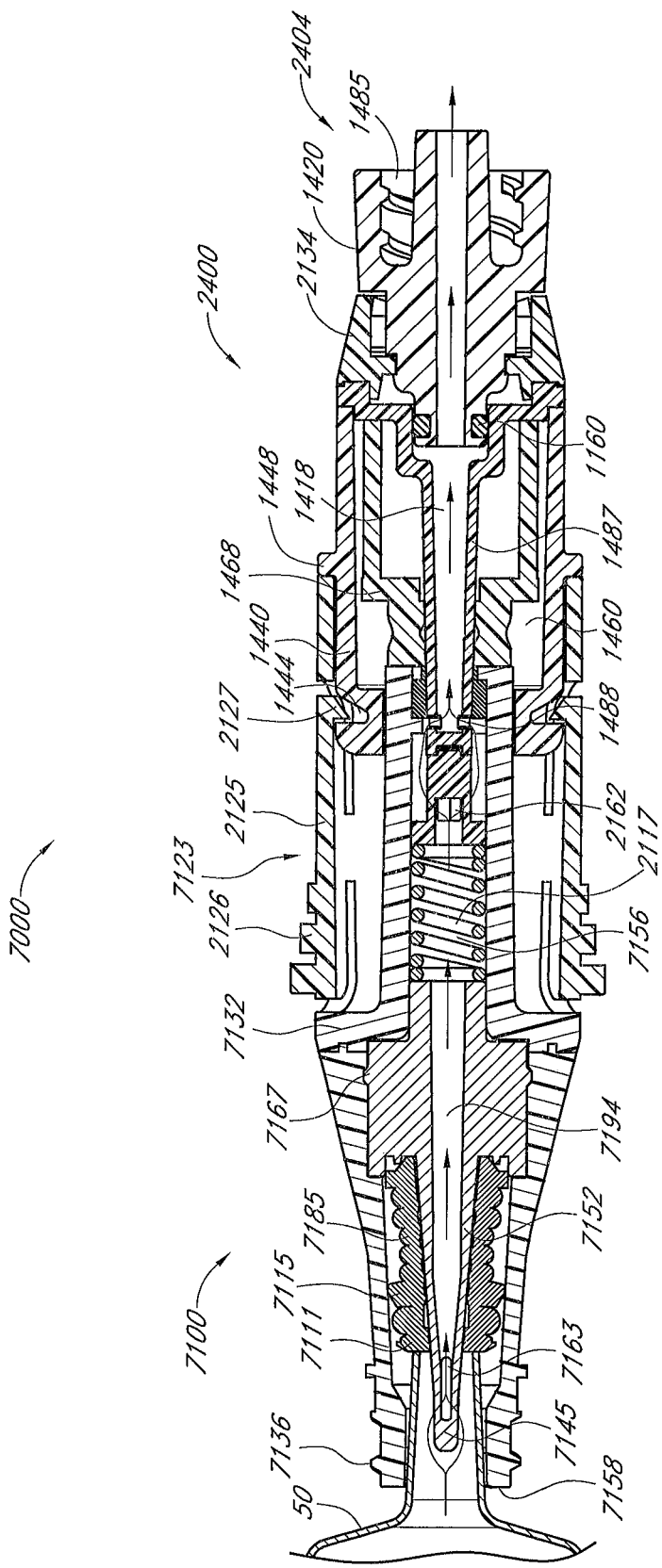
FIG. 89 shows a cross-sectional side view of the connector system of FIG. 88.

FIGS. 88-89 illustrate another embodiment of a connector system 7000 that comprises a male connector 7100 and a female connector 2400. Some numerical references to components in FIGS. 88-89 are the same as or similar to those previously described for the connector system 2000 and corresponding male connector 2100 and female connector 2400, (e.g. male connector 7100 v. male connector 2100). It is to be understood that components or portions of the connector system 7000 can be the same in function or are similar in function to previously-described components or portions. The connector system 7000 of FIGS. 88-89 shows certain variations to the connector system 2000 of FIGS. 53-65.

Male connector 7100 can include a first end 7112 and a second end 7114. The male connector 7100 can include a cap component 7132 and a male housing 7123. The cap component 7132 can be fixed to the male housing 7123 via adhesives, sonic welding, solvent bonding, snap-fitting, other suitable feature or means of adhering, or some combination thereof. The second end 7114 of the male connector 7100 can include a female luer engagement. The female luer engagement can include external threads 7136. In some embodiments, the female luer engagement includes a luer receiving port 7158. The luer receiving port 7158 can include an inner cross-section. The male connector 7100 can include one or more occluding features which selectively seal the receiving port 7158. In some embodiments, the occluding features can transition between a sealing configuration and an open configuration.

In some embodiments, the occluding feature can be a resilient seal 7185. The resilient seal 7185 can include sealing portion 7111 adjacent the second end 7114 of the male connector 7100. The sealing portion 7111 can substantially fill the inner cross-section of the luer receiving port 7158. In some embodiments, the sealing portion 7111 can include a valve. The valve can be, for example, one or more slits, one or more pin holes, or any combination thereof. In some embodiments, the valve in the sealing portion 7111 is normally closed. In some embodiments, the valve in the sealing portion 7111 is normally opened and is biased closed by the engagement between the sealing portion 7111 and the luer receiving port 7158. The resilient seal 7158 can be configured to transition between an opened configuration (e.g., when the valve in sealing portion 7111 is opened, as illustrated in FIG. 89) and a closed configuration (e.g., when the valve in the sealing portion 7111 is closed, as illustrated in FIG. 88).

In some embodiments, the resilient seal 7185 includes a restraining portion 7115. The restraining portion 7115 can be an annular projection, one or more radial projections, an annular flange, or any other suitable feature or combination of features. In some embodiments, the restraining portion 7115 is configured to engage with a retaining feature 7169 on the cap component 7123. The retaining feature 7169 can be a tapered portion, an inwardly-projecting feature (e.g., a flange or series of flange portions), or any feature suitable for retaining the restraining portion 7115 of the resilient seal 7185. In some embodiments, engagement between the restraining portion 7115 and the retaining feature 7169 inhibits movement of the resilient seal 7185 out of the cap component 7132. In some embodiments, engagement between the restraining portion 7115 and the retaining feature 7169 helps maintain the sealing portion 7111 in a fixed axial position when the resilient seal 7815 is in the closed configuration.

In some embodiments, the male connector 7100 includes a channel member 7157. The channel member 7157 can be at least partially contained within the resilient seal 7185. In some embodiments, the channel member 7157 can include a connecting portion 7168 configured to connect the channel member 7157 to the cap component 7132. In some embodiments, the connecting portion 7168 is an annular projection configured to engage with an engagement feature 7167 on the cap component 7132. The engagement feature can be an annular groove. In some embodiments, the channel member 7157 can be connected to the cap component 7132 via snap-fitting, adhesives, solvent bonding, sonic welding, other suitable means of adhering, or any combination thereof. In some embodiments, the channel member 7157 can be affixed to the male housing 7123 via snap-fitting, adhesives, solvent bonding, sonic welding, other suitable means of adhering, or any combination thereof.

The channel member 7157 can define a conduit 7194. The conduit 7194 can extend through the channel member 7157. In some embodiments, the channel member 7157 has a closed end 7145 and an opened end. The channel member 7157 can have one or more ports 7163 adjacent the closed end 7145. In some embodiments, the conduit 7194 extends from the opened end of the channel member 7157 to the one or more ports 7163. In some embodiments, the conduit 7194 is in fluid communication with a passageway 7156 within the male housing 7123. In some embodiments, the resilient seal 7185 is configured to inhibit fluid from passing from within the conduit 7194 out through the one or more ports 7163 when the resilient member 7185 is in the closed configuration.

The first end 7112 of the male connector 7100 can be configured to mate with the first end 2402 of the female connector 2100 in a same or similar manner as the male connector 2100. In some embodiments, the luer receiving port 7158 can be configured to receive a male luer tip 7052. The sealing portion 7111 of the resilient seal 7185 can be configured to withdraw from the one or more ports 7163 near the closed end 7145 of the channel member 7157 as the male luer tip 7052 is advanced into the luer receiving port 7158. Withdrawal of the sealing portion 7111 from the one or more ports 7163 can create a spring force in the resilient seal 7185. Such a spring force can bias the sealing portion 7111 toward the second end 7114 of the male connector 7100 such that the resilient seal 7185 returns to the closed configuration upon withdrawal of the male luer tip 7052 from the male connector 7100. Furthermore, withdrawal of the sealing portion 7111 from the one or more ports 7163 can bring the interior of the male luer tip 7052 into fluid communication with the fluid passageway 1418 of the female connector 2400 when the male connector 7100 is fully mated with the female connector 2400, as illustrated in FIG. 89.

A second end 7114 similar to or identical to the one illustrated in FIG. 88 (e.g., a second end including a resilient seal 7185 and a channel member 7157) can be used in combination with any of the male connectors 100, 1100, 2100, 3100, 5100, 6100, 8100, 9100 disclosed herein. The connector system 7000, in the illustrated example, or as modified, can provide a connector that is sealed on a plurality openings (e.g., one male and one female).

FIGS. 90-93 illustrate another embodiment of a connector system 8000 that comprises a male connector 8100 and a female connector 8400. Some numerical references to components in FIGS. 90-93 are the same as or similar to those previously described for the connector system 2000 and corresponding male connector 2100 and female connector 2400, (e.g. male connector 9100 v. male connector 2100). It is to be understood that components or portions of the connector system 8000 can be the same in function or are similar in function to previously-described components or portions. The connector system 8000 of FIGS. 90-93 shows certain variations to the connector system 2000 of FIGS. 53-65.

Figure 90:
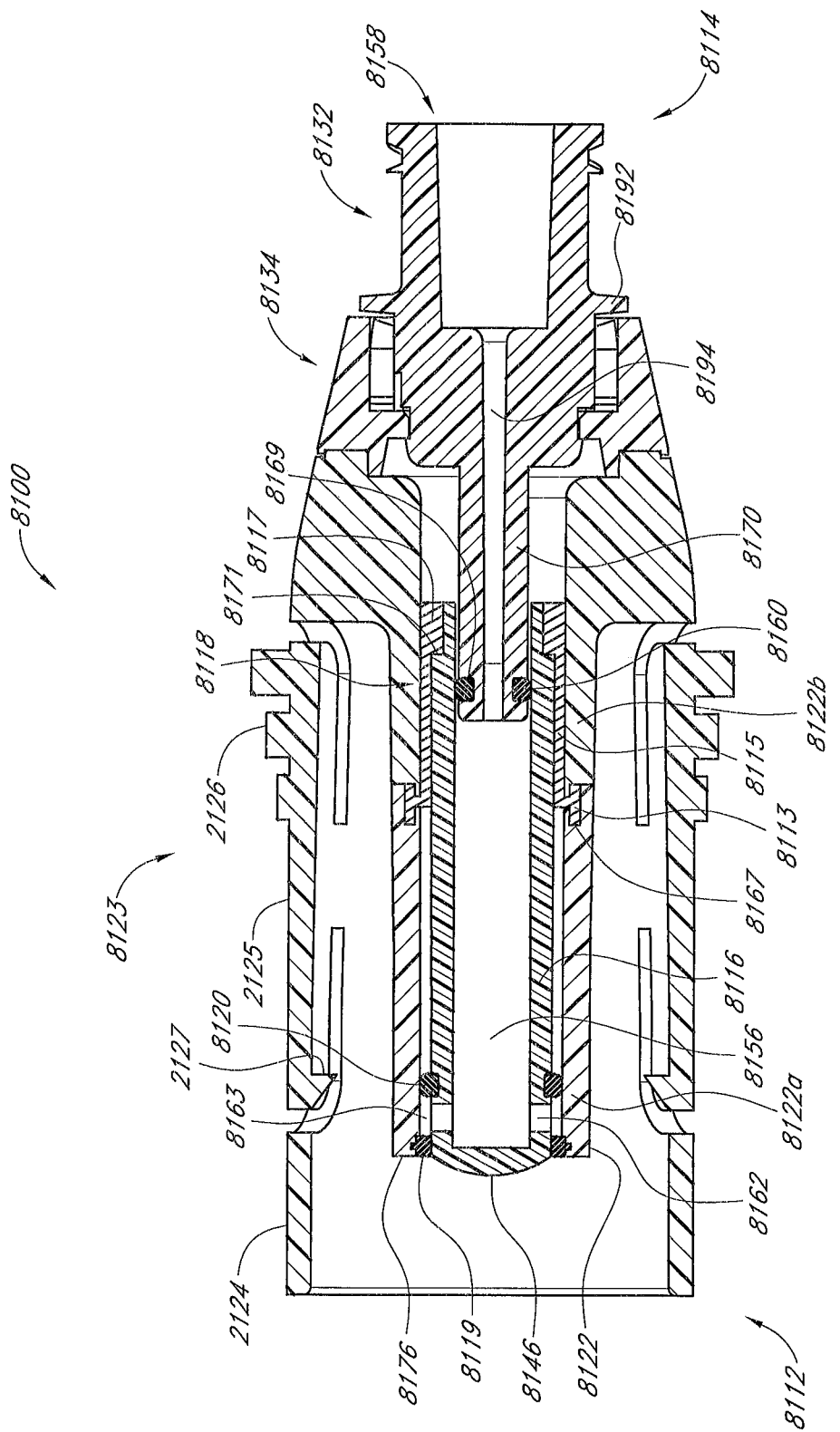
FIG. 90 shows a cross-sectional side view of another embodiment of a male connector.

As illustrated in FIG. 90, male connector 8100 can have a first end 8112 and a second end 8114. The male connector 8100 can include a first cap component 8132 and a second cap component 8134. The first cap component 8132 can be near the second end 8114 and can connect with the second cap component 8134 via adhesives, sonic welding, solvent bonding, snap-fitting, other suitable feature or means of adhering, or some combination thereof. In some embodiments, the first cap component 8132 and the second cap component 8134 form a unitary part. The male connector 8100 can include a male housing 8123 configured to connect to the second cap component 8134 via adhesives, sonic welding, solvent bonding, snap-fitting, other suitable feature or means of adhering, or some combination thereof. The male housing 8123 can include a shroud 2124. In some embodiments, the male connector 8100 has one or more coupling elements such as, for example, one or more tabs 2125 with hooks 2127.

In some embodiments, the male connector 8100 includes a male luer tip 8122. The male luer tip 8122 can have a first tip component 8122a connected to a second tip component 8122b via adhesives, sonic welding, solvent bonding, snap-fitting, other suitable feature or means of adhering, or some combination thereof. In some embodiments, the first tip component 8122a and the second tip component 8122b form a unitary part. The male luer tip 8122 can, in some embodiments, be housed within the shroud 2124. In some embodiments, the male luer tip 8122 extends outside the shroud 2124 toward the first end 8112 of the male connector 8100.

Figure 93:
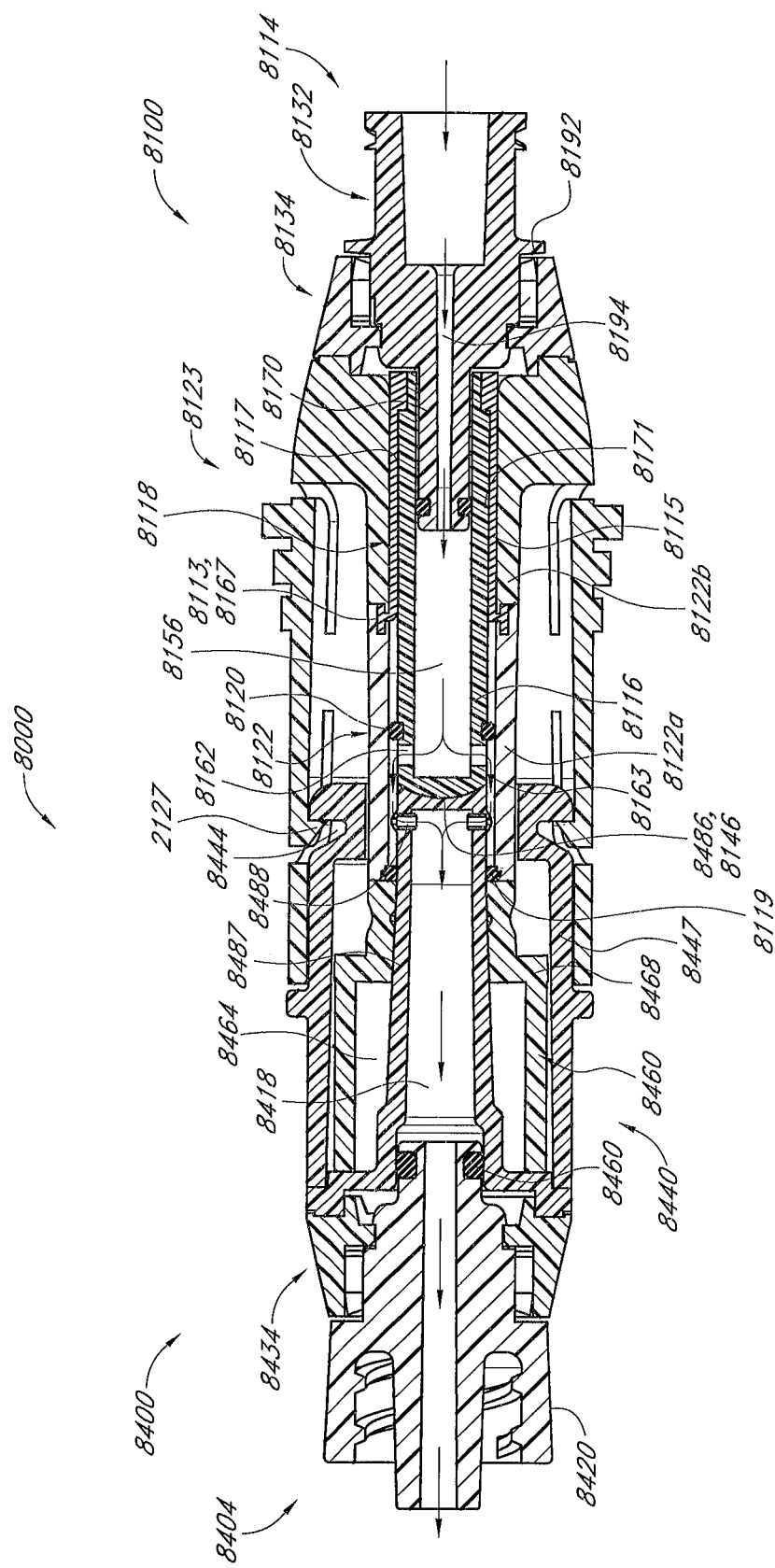
FIG. 93 shows a cross-sectional side view of the connector system of FIG. 93.

In some configurations, the male connector 8110 can include a valve member 8116. The valve member 8116 can have a generally cylindrical shape, an axial centerline, an axial length, an inner cross-section, and/or an outer cross-section. In some embodiments, the valve member 8116 is configured to transition between a closed configuration (e.g., as illustrated in FIG. 90) and an opened configuration (e.g., as illustrated in FIG. 93). The valve member 8116 can be housed at least partially within the male luer tip 8122. The valve member 8116 can have a closed end and an opened end. In some embodiments, the opened end of the valve member 8116 is on the end of the valve member 8116 closest to the second end 8114 of the male connector 8100. In some embodiments, the valve member has two closed ends. In some embodiments, the valve member has two opened ends. In some embodiments, as illustrated in FIG. 90, the closed end of the valve member 8116 has a mating surface 8146. The mating surface 8146 can be sized and shaped to be coupled in a manner that forms a tight, fluid-resistant interface with the mating surface 8486 on the female connector 8400. For example, the mating surface 8146 can include one or more alignment features such as, for example, one or more protrusions or indentations. In some embodiments, the mating surface 8146 has a non-planar shape (e.g., a convex shape, a concave shape, or a shape with multiple concavities and/or convexities) configured to generally match, compliment, or correspond to another non-planar shape on the mating surface 8486 on the female connector 8400. In some embodiments, either or both of the matching, complimenting, or corresponding surfaces 8146, 8486 can generally extend across the outer, leading, movable or pierceable surfaces of the valve members that are exposed to ambient when the connectors are closed.

The valve member 8116 can include a fluid passageway 8156. The valve member 8116 can include one or more ports 8162 near the closed end of the valve member 8116. In some embodiments, the fluid passageway 8156 extends between the one or more ports 8162 and the opened end of the valve member 8116. In some variants, the male luer tip 8122 can include a luer tip seal 8119. The luer tip seal 8119 can be sized to fit around the outer cross-section of the valve member 8116. In some embodiments, the luer tip seal 8119 is a flexible O-ring or some other appropriate component for providing a fluid-tight seal. The valve member 8116 can include a sealing member 8120. The sealing member can be a flexible O-ring or some other appropriate component for providing a fluid-tight seal. The sealing member 8120 can be configured to engage with a surface feature on the outer cross-section of the valve member 8116. For example, the outer surface of the valve member 8116 can include an annular groove 8169. The sealing member 8120 can be sized to engage with the annular groove 8169. In some embodiments, the sealing member 8120 is configured to engage with the inner cross-section of the male luer tip 8122 to create a substantially fluid-tight seal. In some embodiments, engagement between the sealing member 8120 and the inner cross-section of the male luer tip 8122 can inhibit fluid from leaking past the sealing member 8120 in either axial direction.

The space within the inner cross-section of the male luer tip 8122, the outer cross-section of the valve member 8116, the luer tip seal 8119, and the sealing member 8120 (e.g., the annular space 8163, illustrated in FIG. 90) can facilitate fluid communication between the fluid passageway 8156 and the female connector 8400 when the valve member 8116 is in the opened configuration. In some embodiments, the volume of the annular space 8163 can change as the valve member 8116 is translated in the axial direction. The sealing member 8120 can be configured to wipe the inner cross-sectional surface of the male luer tip 8122 as the valve member 8116 is moved in the axial direction. In some embodiments, the luer tip seal 8119 inhibits leakage of fluid from the annular space 8163 to the exterior of the male luer tip 8122 when the valve member 8116 is in the closed configuration.

In some embodiments, the male connector 8100 includes a plunger 8170. The plunger 8170 can have a generally cylindrical shape, an inner cross-section, an outer cross-section, an axial centerline, and an axial length. In some embodiments, the plunger 8170 includes a conduit 8194. The conduit 8194 can extend through the axial length of the plunger 8170. In some embodiments, the fluid passageway 8156 has a cross-section defined by the inner cross-section of the valve member 8116. The inner cross-section of the valve member 8116 can be configured to generally conform to the outer cross-section of the plunger 8170. In some embodiments, the plunger 8170 can include a seal such as, for example, an O-ring 8160. The O-ring 8160 can be configured to engage with a surface feature on the outer cross-section of the plunger 8170. For example, the O-ring 8160 can be configured to engage with an annular groove 8169. In some embodiments, the O-ring 8160 is configured to engage with the inner cross-section of the valve member 8116 to form a substantially fluid-tight seal. The O-ring 8160 can be configured to inhibit fluid from bypassing the conduit 8194 through the opened end of the valve member 8116.

The male connector 8100 can include a resilient or flexible closure member 8118. In some embodiments, the resilient member 8118 can be a flexible jacket configured to fit around the outer cross-section of the valve member 8116. The resilient member 8118 can include a first anchor portion 8113. The first anchor portion 8113 can be configured to engage with a cavity 8167 in the first tip component 8122a and/or the second tip component 8122b. In some embodiments, the resilient member 8118 can include a second anchor portion 8117. The second anchor portion 8117 can be an annular ring configured to engage with a shoulder 8171 on the valve member 8116. In some embodiments, the resilient member 8118 includes a rebound portion 8115. The rebound portion 8115 can be attached to the first anchor portion 8113 and/or to the second anchor portion 8117.

The female connector 8400 can be substantially the same as or similar to the female connector 2400. The female connector 8400 can have a first end 8402 and a second end 8404. In some embodiments, the female connector 8400 includes a female housing 8440 generally adjacent the first end 8402 of the female connector 8400. The female housing 8440 can have a generally cylindrical shape, an inner cross-section, an outer cross-section, an axial centerline, and an axial length. In some embodiments, the female housing 8440 includes a channel 8444 near the first end 8402 of the female connector 8400. In some embodiments, the channel 8444 is annular. In some embodiments, the channel 8444 includes a plurality of semi-annular channel portions.

In some embodiments, the female connector 8400 includes a fluid conduit portion 8480. The fluid conduit portion 8480 can be configured to connect to the female housing 8440 near the second end 8404 of the female connector 8400. In some embodiments, the fluid conduit portion 8480 and the female housing 8440 can form a unitary part. The fluid conduit portion 8480 can include a tube 8487 having a generally cylindrical shape, an inner cross-section, an outer cross-section, an axial centerline, and an axial length. In some embodiments, the tube 8487 has one or more tapered, flared, and/or stepped portions along its axial length. In some configurations, the axial length of the tube 8487 can be approximately the same as the axial length of the female housing 8440. In some embodiments, the axial length of the tube 8487 is greater than or equal to about 75% the axial length of the female housing 8440 and/or less than or equal to about 125% the axial length of the female housing 8440. In some embodiments, the axial length of the tube 8487 is approximately at least about 85% the axial length of the female housing 8440. As illustrated, the axial length of the tube 8487 can be longer than the axial length of the female housing 8440. In some embodiments, the tube 8487 has a mating surface 8486 near the first end 8402 of the female connector 8400. The mating surface 8486 can include one or more engagement features. For example, the mating surface can have one or more protrusions and/or indentations configured to engage with one or more protrusion and/or indentations on the first end 8112 of the male connector 8100. In some embodiments, the mating surface 8486 has a concave shape to correspond with the convex shape of the mating surface 8146.

The tube 8487 can include one or more ports 8488 near the first end 8402 of the female housing 8440. In some embodiments, the tube 8487 and/or fluid conduit portion 8480 can define a fluid passageway 8418. The fluid passageway 8418 can extend from the one or more ports 8488 to the second end 8404 of the female connector 8400.

Figure 91:
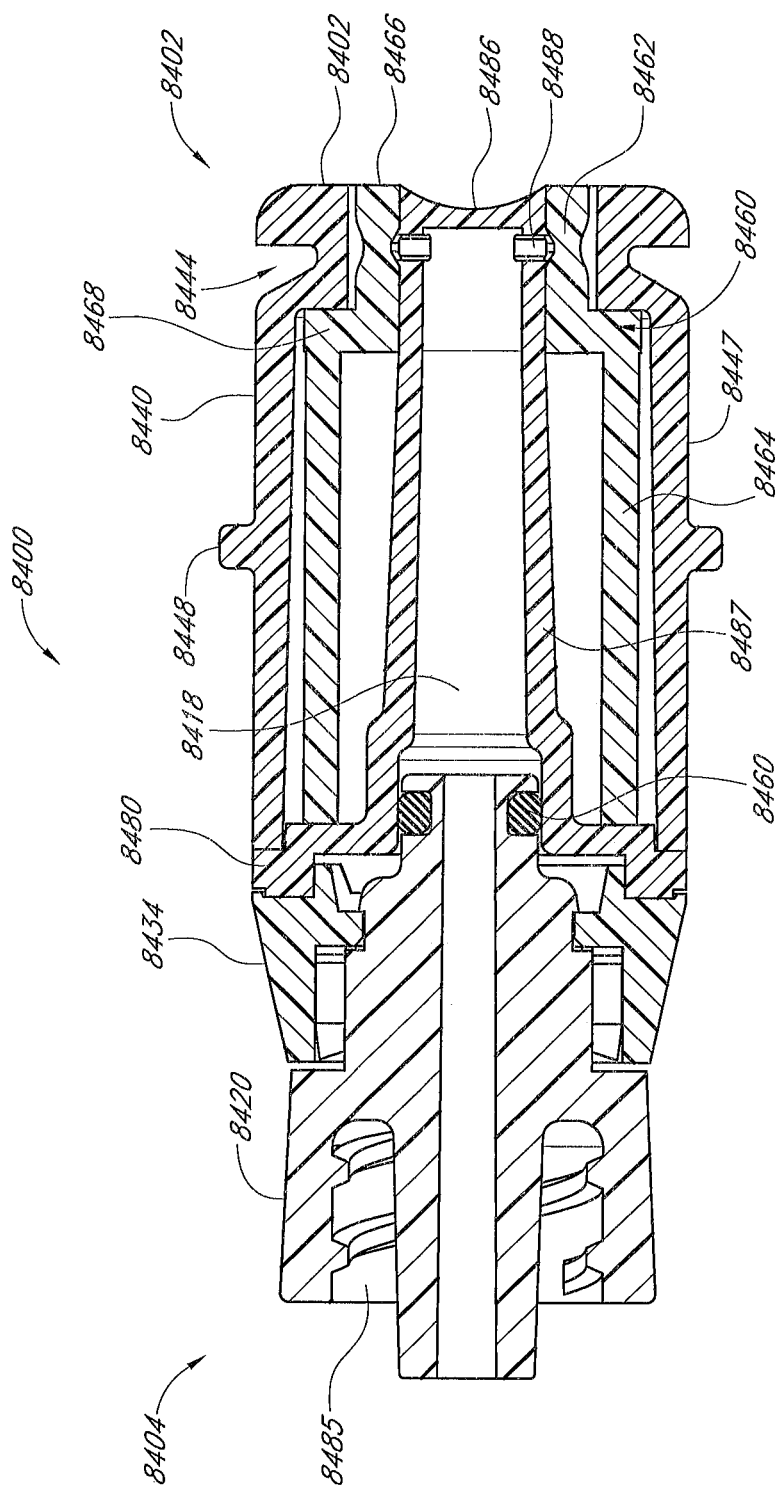
FIG. 91 shows a cross-sectional side view of another embodiment of a female connector.

The female connector 8400 can include a seal element 8460. The seal element can have a generally cylindrical shape, an inner cross-section, an outer cross-section, an axial centerline, and an axial length. In some embodiments, the axial length of the seal element 8460 is approximately the same as the axial length of the female housing 8440. The seal element 8460 can be configured to transition between an opened configuration (e.g., as illustrated in FIG. 93) and a closed configuration (e.g., as illustrated in FIG. 91). In some embodiments, the seal element 8460 is configured to be positioned at least partially within the female housing 8440. The seal element 8460 can include a shoulder 8468 configured to engage with the female housing 8440 and retain the seal element 8460 within the female housing 8440. The seal element 8460 can include a sealing portion 8462 near the first end 8402 of the female connector 8400. The inner cross-sectional size and/or shape of the sealing portion 8462 can be configured to match or generally correspond to size and/or shape of the outer cross-section of the tube 8487. In some embodiments, the sealing portion 8462 is configured to inhibit fluid flow through the one or more ports 8488 when the seal element 1460 is in the closed configuration.

In some embodiments, as illustrated, the outer cross-sectional width or outer diameter of the tube 8487 can be very large. For example, as shown, the area of the proximal mating surface 8486 of the tube 8487 that is exposed when the female connector 8400 is closed (or that is within the sealing element 8460) can comprise a majority or nearly a majority of the area within and bounded by the outer perimeter of the proximal end 8466 of the sealing element 8460. In some embodiments, as illustrated, the cross-sectional width of the proximal mating surface 8486 of the tube 8487 that is exposed when the female connector 8400 is closed (or that is within the sealing element 8460) can be about half as large as, or nearly about half as large as, the proximal opening in the female connector. As show, the cross-sectional width of the proximal mating surface 8486 of the tube 8487 can be about the same size as or larger than the inner diameter and/or outer diameter of the distal male tip of the female connector. As illustrated, in some embodiments, the difference between the outer diameter (or cross-sectional width) of the tube 8487 at the proximal end thereof, or in the region positioned within the neck of the housing in the closed position, and the inner diameter (or cross-sectional width) of the proximal opening on the housing is approximately the same size as, or slightly larger than, the thickness of the wall of the sealing element 8460 at or near the proximal end. In some embodiments, the outer cross-section of the tube 8487 can be greater than or equal to about 10% the size of the outer cross-section of the female housing 8440 and/or less than or equal to about 60% the size of the outer cross-section of the female housing 8440 at the first end 8402 of the female connector 8400. In some embodiments, the outer cross-section of the tube 8487 is approximately at least about 30% as great as the size of the outer cross-section of the female housing 8440 at the first end 8402 of the female connector 8400. The outer cross-section of the tube 8487 can be greater than or equal to about 20% the size of the outer cross-section of the sealing portion 8462 and/or less than or equal to about 80% the size of the outer cross-section of the sealing portion 8462. In some embodiments, the outer cross-section of the tube 8487 is approximately 55% or greater than the size of the outer cross-section of the sealing portion 8462. Many variations in the relative sizes of the outer cross-sections of the tube 8487, the female housing 8440 and the sealing portion 8462 are possible. In some embodiments, the outer cross-section of the tube 8487 at the first end 8402 of the female connector 8400 is configured to be substantially identical to the outer cross-section of the valve member 8116 at the first end 8112 of the male connector 8100. In some embodiments, the inner cross-section of the female housing 8440 at the first end 8402 of the female connector is configured to be greater than the outer cross-section of the male luer tip 8122 at the first end 8112 of the male connector 8100.

Figure 92:
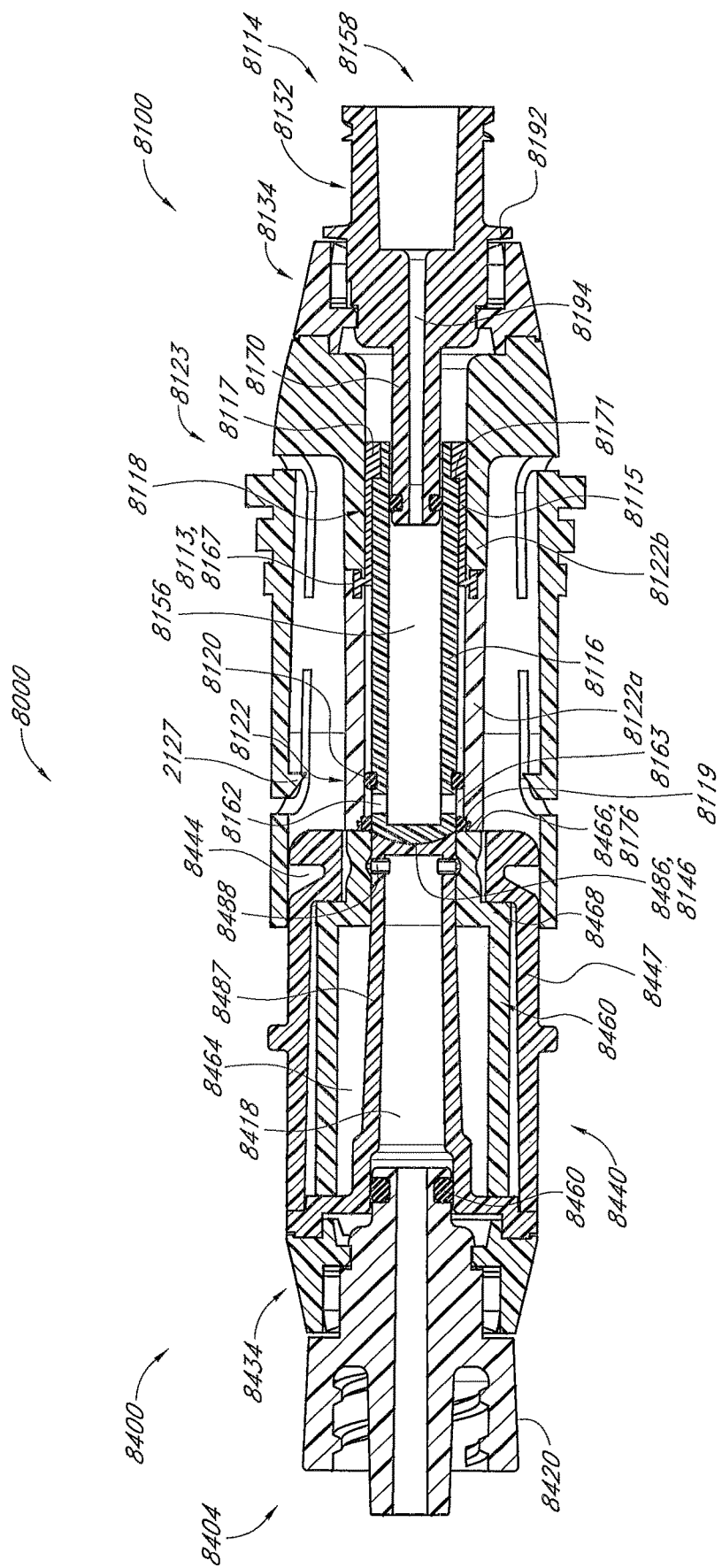
FIG. 92 shows a cross-sectional side view of the male connector of FIG. 90 adjacent the female connector of FIG. 91.

As illustrated in FIGS. 92 and 93, the female connector 8400 and the male connector 8100 can be configured to mate with each other. In some embodiments, advancement of the male luer tip 8122 into the female housing 8440 can push the sealing portion 8462 of the seal element 8460 toward the second end 8404 of the female connector 8400 relative to the one or more ports 8488. Withdrawal of the sealing portion 8462 from the one or more ports 8488 can create fluid communication between the fluid passageway 8418 and the annular space 8163. In some embodiments, the advancement of the male luer tip 8122 into the female housing 8440 can cause the tube 8487 to advance into the male luer tip 8122. Advancement of the tube 8487 into the male luer tip 8122 can push the valve member 8116 toward the second end 8114 of the male connector 8100 with respect to the male luer tip 8122. In some such embodiments, the sealing member 8120 moves toward the second end 8114 of the male connector 8100 with respect to the male luer tip 8122. Such movement of the sealing member 8120 can increase the axial length of the annular space 8163. In some embodiments, full engagement (e.g., engagement between the hooks 2127 and the channel 8444, as illustrated in FIG. 93) of the male connector 8100 with the female connector 8400 can facilitate fluid communication between the conduit 8194 and the fluid passageway 8418 via the one or more ports 8488, one or more ports 8162, and the annular space 8163.

In some embodiments, the rebound portion 8115 can be configured to stretch when the valve member 8116 is pushed toward the second end 8114 of the male connector 8100. In some embodiments, stretching of the rebound portion 8115 can cause the rebound portion 8115 to exert a returning force upon the valve member 8116. In some such embodiments, the returning force of the rebound portion 8115 can cause the valve member 8116 to move toward the first end 8112 of the male connector 8100 as the tube 8487 or other source of pushing is withdrawn from the male luer tip 8122. Such movement of the valve member 8116 toward the first end 8112 can return the valve member 8116 to the closed configuration. In some embodiments, the returning force of the rebound portion 8115 can help ensure that the mating surfaces 8486, 8186 remain in contact with each other as the tube member 8487 is advanced into and withdrawn from the male luer tip 8122. Such contact can help to inhibit fluid from contacting the mating surface 8486, 8186 while the valve member 8116 is in the opened configuration.

Figure 94:
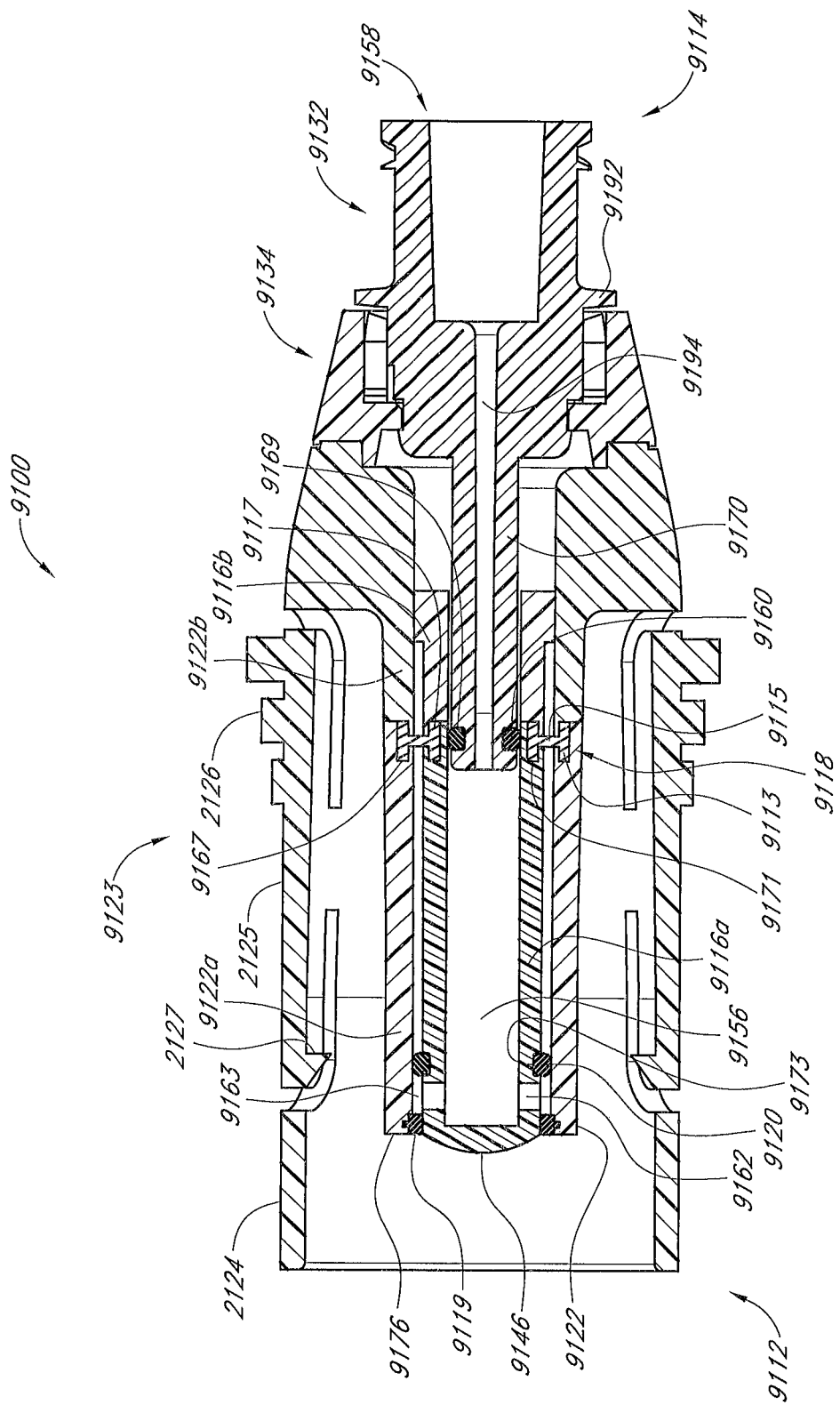
FIG. 94 shows a cross-sectional side view of another embodiment of a male connector.
Figure 95:
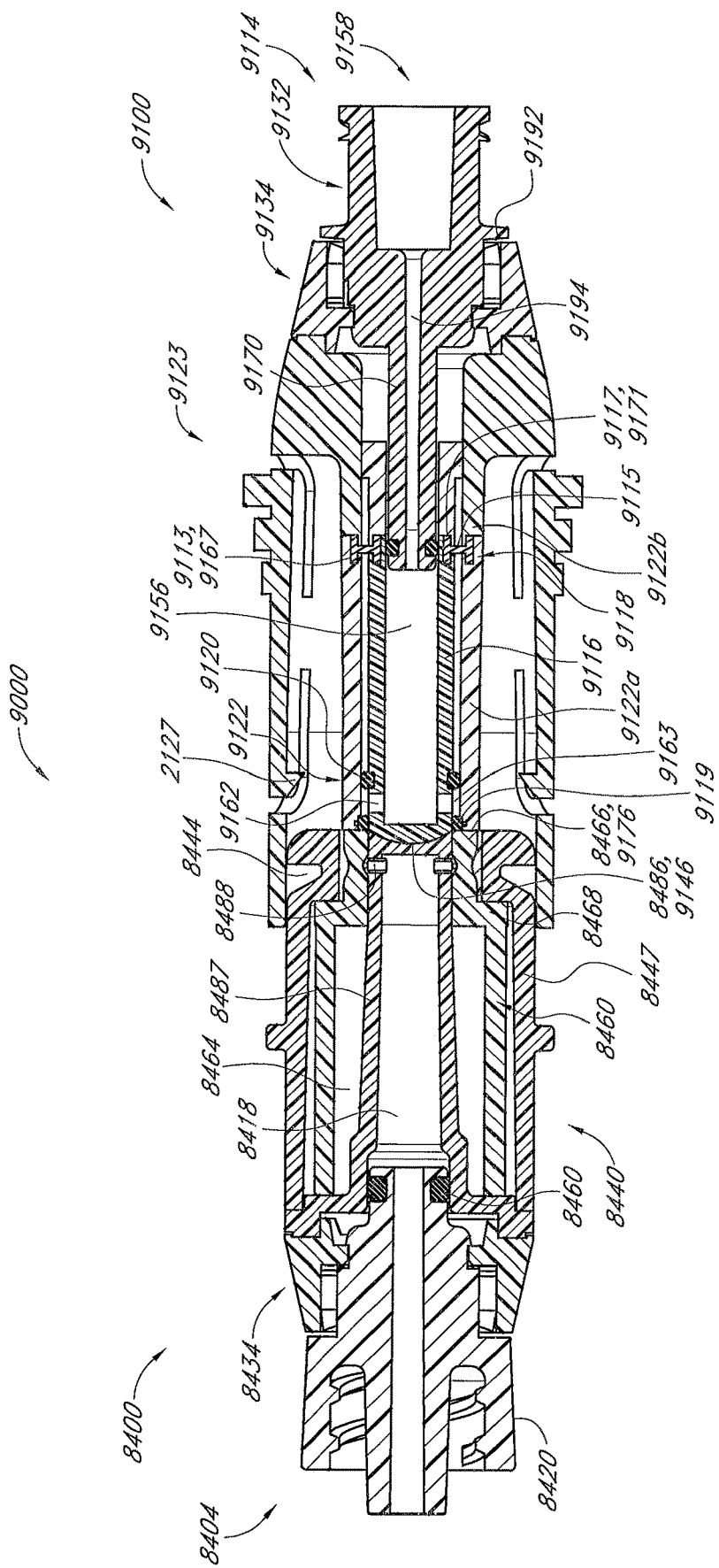
FIG. 95 shows a cross-sectional side view of the male connector of FIG. 94 adjacent the female connector of FIG. 91.
Figure 96:
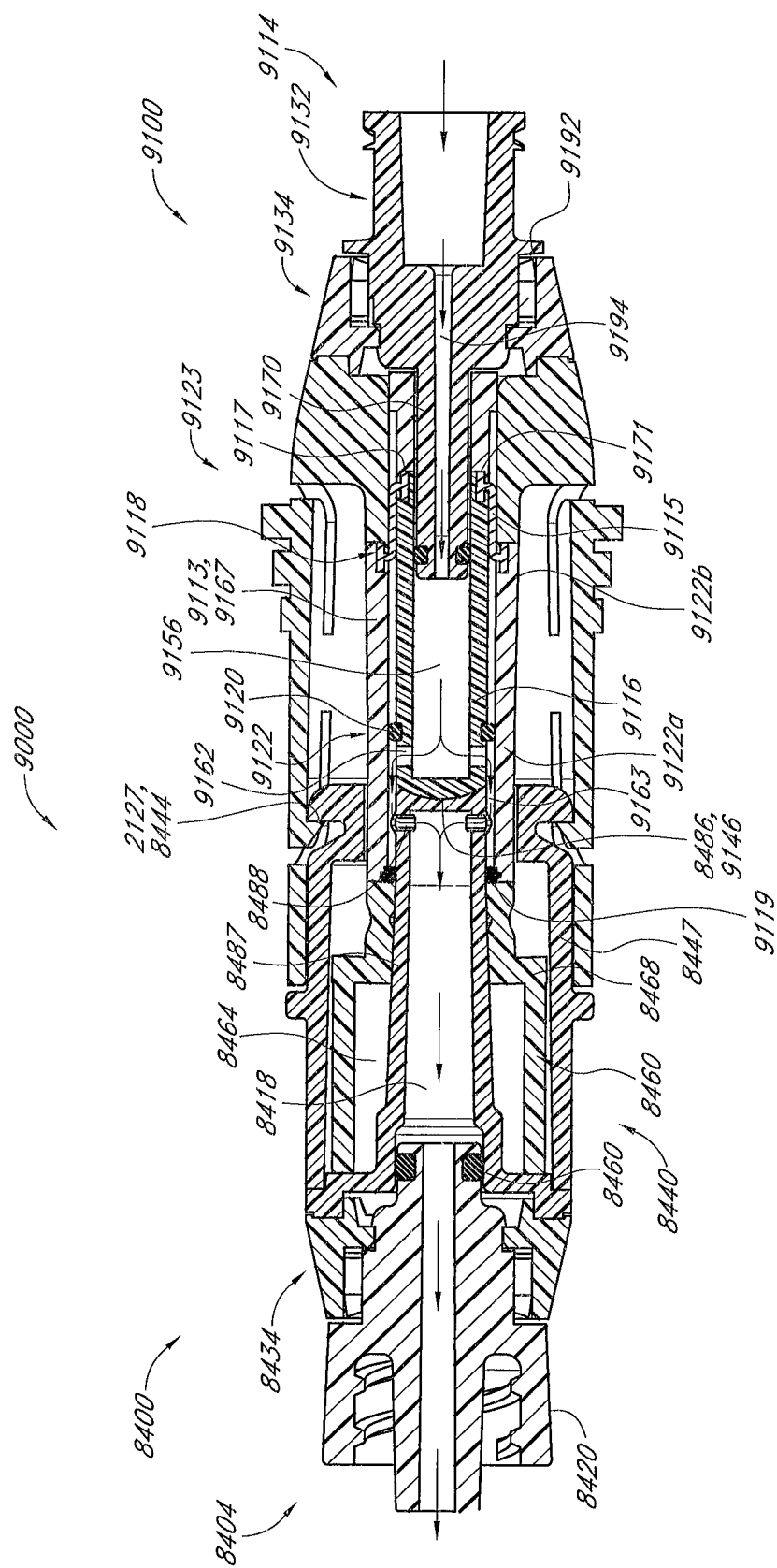
FIG. 96 shows a cross-sectional side view of the connector system of FIG. 95.

FIGS. 94-96 illustrate another embodiment of a connector system 9000 that comprises a male connector 9100 and a female connector 8400. Some numerical references to components in FIGS. 94-96 are the same as or similar to those previously described for the connector system 8000 and corresponding male connector 8100 and female connector 8400, (e.g. male connector 9100 v. male connector 8100). It is to be understood that components or portions of the connector system 9000 can be the same in function or are similar in function to previously-described components or portions. The connector system 9000 of FIGS. 94-96 shows certain variations to the connector system 8000 of FIGS. 90-93.

The male connector 9100 can be substantially similar to the male connector 8100. In some embodiments, the male connector 9100 includes a valve member 9116 which can be housed at least partially within a male luer tip 9122. In some embodiments, the valve member 9116 comprises a first valve portion 9116a and a second valve portion 9116b. In some embodiments, the first valve portion 9116a and the second valve portion 9116b are connected to each other via adhesives, sonic welding, solvent bonding, snap-fitting, other suitable feature or means of adhering, or some combination thereof. In some embodiments, the first valve portion 9116a and the second valve portion 9116b form a unitary part. Similarly, in some embodiments, the male luer tip 9122 comprises a first tip portion 9122a and a second tip portion 9122b. In some embodiments, the first tip portion 9122a and the second tip portion 9122b are connected to each other via adhesives, sonic welding, solvent bonding, snap-fitting, other suitable feature or means of adhering, or some combination thereof. In some embodiments, the first tip portion 9122a and the second tip portion 9122b form a unitary part. The valve member 9116 can include a stabilizing feature, such as, for example, an annular flange 9149. The annular flange 9149 can be configured to engage with the inner wall of the male luer tip 9122. In some embodiments, such engagement can help inhibit the valve member 9116 from tilting off axis within the male luer tip 9122.

In some embodiments, the male connector 9100 can include a resilient member 9118. The resilient member 9118 can include a first anchor portion 9113. In some embodiments, the first anchor portion 9113 is configured to engage with a cavity 9167 in the first tip portion 9122a and/or with a cavity in the second tip portion 9122b, such that the anchor portion 9113 is positioned between and held in place by at least two portions of the housing. The first anchor portion 9113 can be configured to inhibit the resilient member 9118 from disengaging from the male luer tip 9122 when the first anchor portion 9113 is installed in the male luer tip 9122. The resilient member 9118 can include a second anchor portion 9117. In some embodiments, the first and second anchor portions 9113, 9117 comprise portions of a generally continuous ring or ridge extending generally around the resilient member 9118. The rebound portion 9115 can, in some embodiments, also function as a fluid seal. In some embodiments, the second anchor portion 9117 is configured to engage with a slot or cavity 9171 in the first valve portion 9116a and/or with a slot or cavity in the second valve portion 9116b. The second anchor portion 9117 can be configured to inhibit the resilient member 9118 from disengaging from the valve member 9116 when the second anchor portion 9117 is installed in the valve member 9116.

The resilient member 9118 can include a rebound portion 9115 connecting the first anchor portion 9113 to the second anchor portion 9117. In some embodiments, the first and second anchor portion 9113, 9117 and the rebound portion 9115 each have an annular shape. In some embodiments, a plurality of first and second anchor portions 9113, 9117 and/or a plurality of rebound portions 9115 can be used.

In some embodiments, the rebound portion 9115 is configured to function in the same or a similar manner to the rebound portion 8115 described above. For example, the rebound portion 9115 can be configured to stretch when the valve member 9116 is pushed toward the second end 9114 of the male connector 9100, as illustrated in FIG. 96. In some embodiments, stretching of the rebound portion 9115 can cause the rebound portion 9115 to exert a returning force upon the valve member 9116. In some such embodiments, the returning force of the rebound portion 9115 can cause the valve member 9116 to move toward the first end 9112 of the male connector 9100 as the source of pushing is withdrawn from the male luer tip 9122.

Any features of the embodiments shown and/or described in the figures that have not been expressly described in this text, such as distances, proportions of components, etc. are also intended to form part of this disclosure. Additionally, although this invention has been disclosed in the context of various embodiments, features, aspects, and examples, it will be understood by those skilled in the art that the present invention extends beyond the specifically disclosed embodiments to other alternative embodiments and/or uses of the invention and obvious modifications and equivalents thereof. Accordingly, it should be understood that various features and aspects of the disclosed embodiments can be combined with, or substituted for, one another in order to perform varying modes of the disclosed inventions. For example, and without limitation, ANSI compliant and/or ANSI non-compliant connecting structures can be used to enable connection between the disclosed connector systems, connectors, and subcomponents. Moreover, any component or combination of components disclosed herein can be used in other structures or configurations of medical connectors. Thus, it is intended that the scope of the present invention herein disclosed should not be limited by the particular disclosed embodiments described above, but should be determined only by a proper reading of the claims.

The following is claimed:

1. A medical connector system comprising:
    a first medical connector comprising:
        a first region comprising a female portion;
        a second region comprising a male portion;
        a first engagement structure;
        a resilient seal disposed at a distal end of the male portion; and
        a valve member moveable within the male portion of the first medical connector between a closed position and an opened position; and
    a second medical connector comprising:
        a female region configured to receive the male portion of the first medical connector;
        a second engagement structure;
        a fluid conduit; and
        a resilient seal element disposed at a proximal end of the second medical connector, the seal element being moveable between a closed configuration and an opened configuration;
    wherein the first and second medical connectors are configured to be securely attached together by moving the first and second medical connectors toward each other in a substantially linear motion without requiring rotation;
    wherein, when the first and second medical connectors are attached, the resilient seal of the first medical connector is configured to sealingly contact the seal element of the second medical connector, and the engagement structures of the first medical connector and the second medical connector produce an audible sound; and
    wherein a size and shape of a distal end of the valve member of the first medical connector corresponds with a size and shape of a proximal end of the fluid conduit of the second medical connector to resist the accumulation of fluid remnants on mating ends of the connectors after disconnection.

2. The medical connector system of claim 1, wherein one of the valve member and the fluid conduit includes a protrusion and the other of the valve member and the fluid conduit includes a recess that corresponds in size and shape to the protrusion.

3. The medical connector system of claim 1 further comprising a release structure configured to release the engagement structure of the first medical connector from the engagement structure of the second medical connector, enabling the first medical connector to be decoupled from the second medical connector.

4. The medical connector system of claim 3 wherein the release structure is a button.

5. The medical connector system of claim 1, wherein after the first medical connector is decoupled from the second medical connector there is no residual fluid on the mating ends.

6. The medical connector system of claim 1, wherein any negligible amount of residual fluid remaining on an external surface of either of the first or second medical connectors after decoupling is small enough as to present no significant functional disadvantages or health hazards in the particular application in which the connector system is employed.

7. The medical connector system of claim 1, wherein the male portion is not a luer.

8. The medical connector system of claim 7, wherein a proximal opening in the female region of the second medical connector is not luer-compatible.

9. The medical connector system of claim 1, wherein the male portion is a luer.

10. The medical connector system of claim 9, wherein a proximal opening of a housing in the second medical connector is luer-compatible.

11. The medical connector system of claim 1, wherein the valve member has an internal fluid pathway configured to receive medical fluid.

12. The medical connector system of claim 1, further comprising a shroud on the first medical connector.

13. The medical connector system of claim 12, wherein the engagement structure of the first medical connector is part of the shroud.

14. The medical connector system of claim 13, wherein the shroud of the first medical connector extends completely around the male portion.

15. A medical connector system configured to facilitate medical fluid transfer and containment, the medical connector system comprising:
  a first medical connector comprising:
    a first region comprising a female portion;
    a second region comprising a shroud and a male portion;
    an engagement structure;
    a resilient seal disposed at a distal end of the male portion; and
    a valve member with a distal mating surface, the valve member being moveable within the male portion of the first medical connector between a closed position and an opened position, a portion of the valve member being disposed within the resilient seal in the closed position and the valve member being configured to be moved proximally within the male portion into the opened position, the valve member being biased toward the closed position; and
  a second medical connector comprising:
    a female region configured to receive the male portion of the first medical connector;
    an engagement portion on an external surface;
    a fluid conduit; and
    a resilient seal element disposed at a proximal end of the second medical connector, the seal element being moveable between a closed configuration and an opened configuration;

wherein the first and second medical connectors are configured to be securely attached together by moving the first and second medical connectors toward each other in a substantially linear motion without requiring rotation;
  wherein, when the first and second medical connectors are attached, the resilient seal of the first medical connector is configured to sealingly contact the seal element of the second medical connector, and the shroud of the first medical connector extends over the female region of the second medical connector until the engagement structure of the first medical connector engages with the engagement portion on the second medical connector, producing an audible sound; and
  wherein a size and shape of a distal end of the valve member of the first medical connector corresponds with a size and shape of a proximal end of the fluid conduit of the second medical connector to resist the accumulation of fluid remnants on mating ends of the connectors after disconnection.

16. The closed medical connector system of claim 15, wherein the engagement structure of the first medical connector comprises a movable hook, the engagement portion of the second medical connector comprises a channel, and wherein the medical connector system further comprises a release structure with a tab configured to release the hook from the channel.

17. The closed medical connector system of claim 15, wherein a proximal end of the fluid conduit is exposed to a region outside of the second medical connector when the first medical connector and the second medical connector are disconnected.

18. The closed medical connector system of claim 15, wherein the first medical connector and second medical connector can rotate with respect to each other while securely attached.

19. The closed medical connector system of claim 15, wherein the valve member of the first medical connector has an interior fluid passageway.

20. The closed medical connector system of claim 15, wherein the shroud of the first medical connector comprises a continuous circular band at a distal end of the first medical connector.

21. The closed medical connector system of claim 15, wherein the distal end of the male portion of the first medical connector is recessed proximally from a distal end of the shroud of the first medical connector.

22. The closed medical connector system of claim 21, wherein a proximal end of the seal element of the second medical connector is generally flush with the proximal end of the second medical connector in the closed configuration.

23. The closed medical connector system of claim 15, wherein the first region of the first medical connector in an initial stage of use does not rotate with respect to the second region of the first medical connector.

24. The closed medical connector system of claim 23, wherein the first medical connector transitions from the initial stage of use to a stage of use in which the first region and the second region rotate with respect to each other by breaking a tab.

* * * * *